(12) United States Patent
Bull et al.

(10) Patent No.: US 6,610,707 B1
(45) Date of Patent: Aug. 26, 2003

(54) HETEROCYCLIC COMPOUNDS AS INHIBITORS OF ROTOMASE ENZYMES

(75) Inventors: David John Bull, Sandwich (GB); Robert John Maguire, Sandwich (GB); Michael John Palmer, Sandwich (GB); Martin James Wythes, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/380,427

(22) PCT Filed: Feb. 15, 1999

(86) PCT No.: PCT/IB99/00259
§ 371 (c)(1),
(2), (4) Date: Sep. 1, 1999

(87) PCT Pub. No.: WO99/45006
PCT Pub. Date: Sep. 10, 1999

(30) Foreign Application Priority Data

Mar. 2, 1998 (GB) ............................................. 9804426

(51) Int. Cl.⁷ .................... A61K 31/445; C07D 413/04; C07D 413/14; C07D 417/04
(52) U.S. Cl. ....................... 514/326; 514/316; 514/322; 514/343; 514/442; 514/443; 514/235.5; 514/255; 514/256; 544/129; 544/242; 544/364; 546/187; 546/199; 546/210; 548/200; 548/201; 548/123; 548/124; 548/125; 548/128; 548/131
(58) Field of Search ................................ 548/200, 201, 548/123, 124, 125, 128, 131; 546/187, 199, 210; 544/129, 242, 364; 514/343, 316, 442, 322, 443, 326, 235.5, 255, 256

(56) References Cited

U.S. PATENT DOCUMENTS

| | | | | |
|---|---|---|---|---|
| 5,721,256 A | * | 2/1998 | Hamilton et al. | ............ 514/330 |
| 5,874,449 A | * | 2/1999 | Hamilton et al. | ............ 514/330 |
| 6,339,101 B1 | * | 1/2002 | Ross et al. | .................... 514/424 |
| 2002/0052510 A1 | * | 5/2002 | Hamilton et al. | ............ 548/200 |

FOREIGN PATENT DOCUMENTS

| | | | |
|---|---|---|---|
| JP | 55-153763 | * | 11/1980 |
| WO | 92/21313 | * | 12/1992 |
| WO | WO 9640633 A | | 12/1996 |
| WO | WO 9703973 A | | 2/1997 |

OTHER PUBLICATIONS

Hamilton et al. "Preparation of prolinylalkanediones . . . " CA 2000:30959, 2000.*
Zymalkowski et al. "aminoacylation products of nornicotine" CA 65:758g, 1964.*
Pfenninger et al. "N–phenylsulfonylpipecolinic acids their ester . . . " CA 70:87863, 1969.*
King "Bioiosostetes, conformational restriction and prodrugs . . . " med. Chem. Principle and Practice, p. 206–209, 1994.*
Patani et al. "Bioiososterism; a rational approach in drug design" Chem. Rev. v.96, p. 3147 and 3168, 1996.*
Kiyooka, Syun–Ichi et al.: "A short synthesis of pyrrole derivative having a chiral subsituent"; Synthesis (1988), (9), pp. 745–746, 1988.
Database Crossfire, Beilstein BRN=121325, XP002100247 & Vecchietti: Journal of Medicinal Chemistry., vol. 34, No. 1, 1991, pp. 397–403, Washington US.
Database Crossfire, Beilstein BRN=5814911, XP002100251 & Stolle: Journal of Organic Chemistry., vol. 57, No. 11, 1992, pp. 3000–3007, Easton US.
Database Crossfire, Beilstein BRN=6922736, XP002100252 & Mahboobi: Arch. Pharm., vol. 327, No. 7, 1994, pp. 417–428.
Database Crossfire, Beilstein BRN=958008, XP002100253 & Prokai–Tatrai: Tetrahedron. vol. 50, No. 33, 1994, pp. 9909–9918, Oxford GB.
Database Crossfire, Beilstein BRN=82637, XP002100254 & Sadykow: ZH. Obshch. KHIM., vol. 17, 1947, p. 1212.
Database Crossfire, Beilstein BRN=81965m XP002100255 & Alberici: Tetrahedron Letters., vol. 24, No. 18, 1983, pp. 1937–1940, Oxford GB.
Database Crossfire, Beilstein BRN=7587535, XP002100256 & Wabber: Journal of Organic Chemistry, vol. 61, No. 16, 1996, pp. 5581–5586, Easton US.
Database Crossfire, Beilstein BRN=5012306, XP002100257 & Tokuyama: Tetrahedron., vol. 39, No. 1, 1983, pp. 41–47, Oxford GB.

* cited by examiner

Primary Examiner—Ceila Chang
(74) Attorney, Agent, or Firm—P. C. Richardson; P. H. Ginsburg; I. Nissenbaum

(57) ABSTRACT

Compounds of the formula:

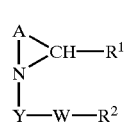

(I)

wherein $R^1$, Y, W, A and $R^2$ are as defined above are inhibitors of rotamase enzymes in particular FKBP-12 and FKBP-52. The compounds therefore moderate neuronal regeneration and outgrowth and can be used for treating neurological disorders arising from neurodegenerative diseases and nerve damage.

16 Claims, No Drawings

HETEROCYCLIC COMPOUNDS AS INHIBITORS OF ROTOMASE ENZYMES

This application is a 371 of PCT/IB99/00259 filed Feb. 15, 1999.

This invention relates to 2-heteroaryl-pyrrolidine, -piperidine and -homopiperidine derivatives and to processes for the preparation of, intermediates used in the preparation of, compositions containing and the uses of, such derivatives.

It has been reported that the immunosuppressant FK-506 promotes neurite outgrowth in vitro in neuronal cell line and culture models (see Lyons et al, Pro. Natl. Acad. Sci., 1994, 91, 3191–95 and Snyder et al, Nature Medicine, 1995, 1, 32–37). WO-A-96/40140, WO-A-96/40633 and WO-A-97/16190 disclose compounds that have neurotrophic activity but which lack inhibitory action at the protein phosphatase calcineurin and therefore which have no immunosuppressive activity.

It has been suggested in WO-A-96/40140 and WO-A-96/40633 that the neurotrophic effect of these compounds is mediated, at least in part, by a high affinity interaction with the FK-506 binding proteins, such as FKBP-12, or FKBP-52. However, the mechanism by which this interaction with FKBP-type immunophilins results in a neurotrophic effect is at present unknown. The range of neurotrophic activity that can be realised through this neurotrophic/non-immunosuppressant class of compounds has been explored and it has been found that axon regeneration can be promoted after facial nerve crush and sciatic nerve crush in the rat. It has also been observed that the functional regeneration of dopamine neurons damaged with the toxin MPTP was promoted by the compounds disclosed therein in mice. Additionally, it was reported that restoration of striatal innervation in the rat was promoted by the compounds disclosed therein following 6-hydroxydopamine lesioning of dopaminergic neurons (see Hamilton & Steiner, Current Pharmaceutical Design, 1997, 3, 405–428).

It has now been found that the present compounds are neurotrophic agents which have an affinity for FKBP-type immunophilins. In particular, they are potent inhibitors of the enzyme activity and especially of the cis-trans prolyl isomerase (rotamase) activity of FKBP-type immunophilins, particularly the immunophilin FKBP-12. The present compounds do not significantly inhibit the protein phosphatase calcineurin and therefore lack any significant immunosuppressive activity.

The present compounds therefore moderate neuronal degeneration and promote neuronal regeneration and outgrowth and can be used for treating neurological disorders arising from neurodegenerative diseases or other disorders involving nerve damage. The neurological disorders that may be treated include senile dementia (Alzheimer's disease) and other dementias, amyotrophic lateral sclerosis and other forms of motor neuron disease, Parkinson's disease, Huntington's disease, neurological deficits associated with stroke, all forms of degenerative disease affecting the central or peripheral nervous system (e.g. cerebellar-brainstem atrophies, syndromes of progressive ataxias), all forms of muscular dystrophy, progressive muscular atrophies, progressive bulbar muscular atrophy, physical or traumatic damage to the central or peripheral nervous system (e.g. spinal cord), hemiated, ruptured or prolapsed intervertebrae disc syndromes, cervical spondylosis, plexus disorders, thoracic outlet syndromes, all forms of peripheral neuropathy (both diabetic and non-diabetic), trigeminal neuralgia, glossopharyngeal neuralgia, Bell's Palsy, all forms of auto-immune related disease resulting in damage of the central or peripheral nervous system (e.g. multiple sclerosis, myasthenia gravis, Guillain-Barré syndrome), AIDS related disorders of the nervous system, dapsone ticks, bulbar and retrobulbar affections of the optic nerve (e.g. retinopathies and retrobulbar neuritis), hearing disorders such as tinnitus, and prion diseases.

Preferably, the present compounds can be used for treating senile dementia (Alzheimer's disease) or another dementia, amyotrophic lateral sclerosis or another form of motor neuron disease, Parkinson's disease, Huntingdon's disease, a neurological deficit associated with stroke, physical or traumatic damage to the central or peripheral nervous system (e.g. spinal cord), a peripheral neuropathy (either diabetic or non-diabetic), multiple sclerosis or a hearing disorder such as tinnitus.

The present invention provides a compound of the formula:

(I)

or a pharmaceutically acceptable salt or solvate thereof, wherein $R^1$ is a 5- or 6-membered ring heteroaryl group containing either 1, 2, 3 or 4 nitrogen heteroatoms, or 1 oxygen or sulphur heteroatom and, optionally, 1 or 2 nitrogen heteroatoms, said heteroaryl group being linked to the adjacent carbon atom by a ring carbon atom and optionally substituted by from 1 to 3 substituents each independently selected from $C_1$–$C_6$ alkyl, $C_2$–$C_6$ alkenyl, —X—($C_3$–$C_7$ cycloalkyl), —X-aryl, —X-het, —X—OH, —X—($C_1$–$C_4$ alkoxy), —X—$CO_2R^5$, —X—CN, and —X—$NR^3R^4$;

$R^2$ is H, phenyl or $C_3$–$C_7$ cycloalkyl, said phenyl or cycloalkyl being optionally benzo- or $C_3$–$C_7$ cycloalkyl-fused and optionally substituted, including in the benzo- or cycloalkyl-fused portion, by from 1 to 3 substituents each independently selected from $C_1$–$C_6$ alkyl, $C_1$–$C_6$ alkoxy, —OH, —($C_1$–$C_6$ alkylene)OH, halo and halo($C_1$–$C_6$ alkylene)—, or $R^2$ is a 5-, 6- or 7-membered ring heterocyclic group containing either 1, 2, 3 or 4 nitrogen heteroatoms, or 1 oxygen or sulphur heteroatom and, optionally, 1 or 2 nitrogen heteroatoms, said heterocyclic group being saturated or partially or fully unsaturated, optionally benzo-fused and optionally substituted, including in the benzo-fused portion, by from 1 to 3 substituents each independently selected from $C_1$–$C_6$ alkyl, $C_1$–$C_6$ alkoxy, halo, halo($C_1$–$C_6$ alkylene)— and —$CO_2R^5$; said $R^2$ group being attached to W by any mono- or bicyclic ring carbon atom or heteroatom;

$R^3$ and $R^4$ are either each independently selected from H, $C_1$–$C_6$ alkyl, $C_3$–$C_6$ cycloalkyl and —($C_1$–$C_6$ alkylene)($C_3$–$C_6$ cycloalkyl), or, when taken together, represent unbranched $C_3$–$C_6$ alkylene optionally containing O or $NR^5$;

$R^5$ is H, $C_1$–$C_6$ alkyl, $C_3$–$C_6$ cycloalkyl, —($C_1$–$C_6$ alkylene)($C_3$–$C_6$ cycloalkyl) or —($C_1$–$C_6$ alkylene)aryl;

A is unbranched $C_3$–$C_5$ alkylene optionally substituted by $C_1$–$C_6$ alkyl;

W is a direct link, $C_1$–$C_6$ alkylene or $C_2$–$C_6$ alkenylene;

X is a direct link, $C_1$–$C_6$ alkylene or —($C_0$–$C_6$ alkylene)—Z—($C_0$–$C_6$ alkylene)—;

Y is $SO_2$, carbonyl, —$CONR^5$—, —CO.CO—, —$CH_2CO$—, —CS.CO—, —CO.CS— or —CO.CH(OH)—;

Z is O, S, —$CR^5NR^3R^4$—, —$CR^5NR^5(CO_2R^5)$—, —$CR^5(aryl^1)$—, —$NR^5$—, —$NR^5CO_2$—, —$CONR^5$— or —$NR^5CO$—;

"aryl" is phenyl optionally substituted by from 1 to 3 substituents each independently selected from $C_1$–$C_6$ alkyl, —($C_1$–$C_6$ alkylene)OH, $C_1$–$C_6$ alkoxy, —($C_1$–$C_6$ alkylene)($C_1$–$C_6$ alkoxy), halo, halo($C_1$–$C_6$ alkylene)—, —$NR^3R^4$, —($C_1$–$C_6$ alkylene)$NR^3R^4$, —O($C_1$–$C_6$ alkylene)$NR^3R^4$ and —($C_1$–$C_6$ alkylene)(phthalimido);

"aryl" is phenyl optionally substituted by from 1 to 3 substituents each independently selected from $C_1$–$C_6$ alkyl, $C_1$–$C_6$ alkoxy, —($C_1$–$C_6$ alkylene)($C_1$–$C_6$ alkoxy), halo and halo($C_1$–$C_6$ alkylene)—; and "het" is a 5-, 6- or 7-membered ring heterocyclic group containing either 1, 2, 3 or 4 nitrogen heteroatoms, or 1 oxygen or sulphur heteroatom and, optionally, 1 or 2 nitrogen heteroatoms, said heterocyclic group being saturated or partially or fully unsaturated, or "het" is azetidinyl, said "het" being optionally substituted by from 1 to 3 substituents each independently selected from $C_1$–$C_6$ alkyl, —($C_1$–$C_6$ alkylene)($C_3$–$C_7$ cycloalkyl), $C_1$–$C_6$ alkoxy, $C_3$–$C_7$ cycloalkyl, —($C_1$–$C_6$ alkylene)($C_1$–$C_6$ alkoxy), halo, halo($C_1$–$C_6$ alkylene)—, —$NR^3R^4$, —$CO_2R^5$, —($C_1$–$C_6$ alkylene)aryl and —($C_1$–$C_6$ alkylene)$NR^3R^4$:

with the provisos that (a) the heteroaryl group of $R^1$ is not substituted by —($C_0$–$C_6$ alkylene)—Z—($C_0$ alkylene)(—OH or —$C_1$–$C_4$alkoxy or —CN or —$NR^3R^4$) when Z is O, S, —$NR^5$—, —$NR^5CO_2$— or —$CONR^5$—; and (b) when W is a direct link, $R^2$ is only H when Y is —$CONR^5$—;

(c) when A is $C_3$ alkylene, Y is sulphonyl, W is a direct link, and $R^2$ is para methyl substituted phenyl, then $R^1$ is not

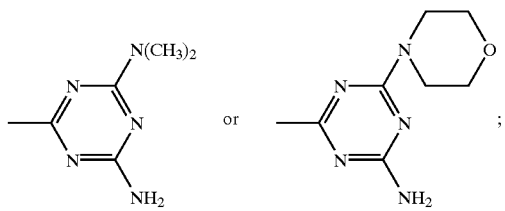

(d) when A is $C_4$ alkylene, Y is carbonyl, W is $C_1$ alkylene and $R^2$ is H, then $R^1$ is not

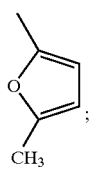

(e) when A is $C_4$ alkylene, Y is carbonyl, W is a direct link and $R^2$ is 3-hydroxy phenyl, then $R^1$ is not

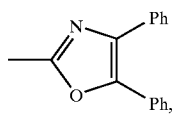

(f) when A is $C_3$ alkylene, Y is carbonyl, W is a direct link and $R^2$ is phenyl, then $R^1$ is not 2-furyl.

Disclaimers (c) to (f) are based on the following documents: Agr. Biol. Chem. (1971), 35(10), 1572–7; Tetrahedron Lett. (1981), 22(2), 141–4; WO-A-9703973 published Feb. 6, 1997 and Chemical Abstracts, vol. 56, no. 11, abstract no. 13001g.

With the aforementioned disclaimers (c ) to (f), the aforementioned compounds for formula (I) are novel. However, if one or more broader disclaimers are required for validity they may be based on the following disclaimers:

(c) wherein when A is $C_3$ alkylene and Y is sulphonyl, W is a direct link, and $R^2$ is substituted phenyl, then $R^1$ is not a diamino substituted triazine (relates to aforementioned disclaimer (c));

(d) wherein Y—W—$R^1$ does not represent a $C_1$–$C_4$ acyl group, when $R^1$ is an optionally substituted furanyl group (relates to aforementioned disclaimers (d) and (f)); and (e) wherein $R^1$ is not an oxazole disubstituted by aryl (relates to aforementioned disclaimer (e)).

Throughout the above definitions, "halo" means fluoro, chloro, bromo or iodo and alkyl, alkoxy, alkenyl, alkylene and alkenylene groups containing the requisite number of carbon atoms, except where indicated, can be unbranched- or branched-chain.

When $R^3$ and $R^4$, when taken together, represent unbranched $C_3$–$C_6$ alkylene optionally containing O or $NR^5$, the heteroatom may be positioned either at a terminal position of, or in an intermediate position in, the unbranched $C_3$–$C_6$ alkylene group. Examples of such —$NR^3R^4$ groups include piperazino and morpholino.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

Suitable base salts are formed from bases which form non-toxic salts and examples are the sodium, potassium, aluminium, calcium, magnesium, zinc and diethanolamine salts.

For a review on suitable salts see Berge et al, J. Pharm. Sci., 1977, 66, 1–19.

The pharmaceutically acceptable solvates of the compounds of the formula (I) include the hydrates thereof.

Also included within the present scope of the compounds of the formula (I) are polymorphs and radiolabelled derivatives thereof.

A compound of the formula (I) contains one or more asymmetric carbon atoms and therefore exists in two or more stereoisomeric forms. Where a compound of the formula (I) contains an alkenyl or alkenylene group, cis (E) and trans (Z) isomerism may also occur. The present invention includes the individual stereoisomers of the compounds of the formula (I) and, where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

Particularly preferred are compounds of the formula (I'):

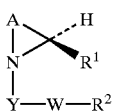

(I')

wherein $R^1$, $R^2$, A, W and Y are as previously defined for a compound of the formula (I).

In the above definitions of a compound of the formula (I) and (I'), the following definitions are preferred.

Preferably, $R^1$ is triazolyl, isoxazolyl, oxadiazolyl, tetraazolyl, thiazolyl or thiadiazolyl, that is linked to the adjacent carbon atom by a ring carbon atom and optionally substituted by 1, 2 or 3 substituents each independently selected from $C_1$–$C_6$ alkyl, —X-aryl, —X-het, —X—$CO_2R^5$ and —X—$NR^3R^4$.

More preferably, $R^1$ is triazolyl, isoxazolyl, oxadiazolyl, tetraazolyl, thiazolyl or thiadiazolyl, that is linked to the adjacent carbon atom by a ring carbon atom and optionally substituted by 1, 2 or 3 substituents each independently selected from $C_1$–$C_6$ alkyl, —X-aryl, —X-het, —X—$CO_2R^5$ and —X—$NR^3R^4$, wherein X is a direct link, $C_1$–$C_6$ alkylene or —($C_0$–$C_6$ alkylene)—Z—($C_0$–$C_6$ alkylene)—;

Z is O, —$CR^5NR^3R^4$, —$CR^5NR^5(CO_2R^5)$—, —$NR^5$— or —$NR^5CO_2$—;

"aryl" is phenyl optionally substituted by from 1 to 3 substituents each independently selected from —($C_1$–$C_6$ alkylene)$NR^3R^4$, —O—($C_1$–$C_6$ alkylene)$NR^3R^4$, —($C_1$–$C_6$ alkylene)(phthalimido) and —($C_1$–$C_6$ alkylene)OH;

"het" is piperidyl, pyrazinyl, furyl, piperazinyl, pyrimidinyl or morpholinyl, optionally substituted by from 1 to 3 —($C_1$–$C_6$ alkylene)aryl, —($C_1$–$C_6$ alkylene)($C_3$–$C_7$ cycloalkyl) substituents, or —$CO_2R^5$ where $R^5$ is —($C_1$–$C_6$ alkylene)aryl or $C_1$–$C_6$ alkyl; or —($C_1$–$C_6$ alkylene)$NR^3R^4$ where "het" is furyl;

$R^3$ and $R^4$ are either each independently selected from H and $C_1$–$C_6$ alkyl or, when taken together, represent unbranched $C_3$–$C_6$ alkylene; and $R^5$ is H or $C_1$–$C_6$ alkyl.

Yet more preferably, $R^1$ is 1,2,4-triazolyl, isoxazolyl, 1,2,4-oxadiazolyl, 1,3,4-oxadiazolyl or 1,3,4-thiadiazolyl, that is linked to the adjacent carbon atom by a ring carbon atom and optionally substituted by 1, 2 or 3 substituents each independently selected from methyl, benzyl, α-(amino) benzyl, α-(tert-butoxycarbonylamino)benzyl, benzylamino, benzylaminoethyl, aminomethylphenoxymethyl, methylaminomethylphenoxymethyl, dimethylaminomethylphenoxymethyl, pyrrolidinylmethylphenoxymethyl, aminoethoxybenzyl, phthalimidomethylphenoxymethyl, piperidyloxymethyl, benzylpiperidyloxymethyl, benzylpiperidyloxyethyl, morpholinomethyl, benzyloxycarbonylaminoethyl, amino, aminoethyl, R- -(amino)benzyl, S- -(amino)benzyl, pyrazinyl, benzyloxycarbonylpiperidinyloxymethyl, methylaminofuryl, cyclopropylmethylpiperidyloxymethyl, hydroxymethylphenoxymethyl, tertbutyloxycarbonylpiperazinylethyl, pyrimidinyl, benzylaminomethyl, (S)-α-(benzyloxycarbonylamino) benzyl, piperazinoethyl, phenylcarbonylaminoethyl, dimethylaminomethyl, hydrogen, phenyl, cyclohexylamino or (R)-α-(benzyloxycarbonylamino)benzyl.

More preferably still, $R^1$ is 5-benzyl-1,2,4-oxadiazol-3-yl, 5-(4-[phthalimidomethyl]phenoxymethyl)-1,2,4-oxadiazol-3-yl, 5-(4-aminomethylphenoxymethyl-1,2,4-oxadiazol-3-yl, 5-(4-dimethylaminomethylphenoxymethyl)-1,2,4-oxadiazol-3-yl, 5-(4-pyrrolidinomethylphenoxymethyl)-1,2,4-oxadiazol-3-yl, 5-(4-methylaminomethylphenoxymethyl)-1,2,4-oxadiazol-3-yl, 5-(1-benzylpiperid-4-yloxymethyl)-1,2,4-oxadiazol-3-yl, 5-(α-[tert-butoxycarbonylamino]benzyl)-1,2,4-oxadiazol-3-yl, 5-morpholinomethyl-1,2,4-oxadiazol-3-yl, 5-(2-[1-benzylpiperid-4-yloxy]ethyl)-1,2,4-oxadiazol-3-yl, 5-(1H-piperid-4-yloxymethyl)-1,2,4-oxadiazol-3-yl, 5-[α-[amino]benzyl)-1,2,4-oxadiazol-3-yl, 5-(2-[benzyloxycarbonylamino]ethyl)-1,2,4-oxadiazol-3-yl, 5-(2-aminoethyl)-1,2,4-oxadiazol-3-yl, 5-(2-[benzylamino]ethyl)-1,2,4-oxadiazol-3-yl, 5-(4-[2-aminoethoxy]benzyl)-1,2,4-oxadiazol-3-yl, 5-methyl-1,3,4-thiadiazol-2-yl, 1H-1,2,4-triazol-3-yl, 1-benzyl-1H-1,2,4-triazol-3-yl, 5-benzyl-4-methyl-4H-1,2,4-triazol-3-yl, 5-amino-1,3,4-oxadiazol-2-yl, 5-benzylamino-1,3,4-oxadiazol-2-yl, 3-methylisoxazol-5-yl, 5-(pyrazin-2-yl)-1,2,4-oxodiazol-3-yl, 5-(R)-[α-(amino)benzyl]-1,2,4-oxadiazol-3-yl, 5-(S)-[α-(amino)benzyl]-1,2,4-oxadiazol-3-yl, 5-(5-methylaminofuran-2-yl)-1,2,4-oxadiazol-3-yl, 5-(1-benzyloxycarbonylpiperid-4-yloxymethyl)-1,2,4-oxadiazol-3-yl, 5-(1-cyclopropylmethylpiperid-4-yloxymethyl)-1,2,4-oxadiazol-3-yl, 5-(4-hydroxymethylphenoxymethyl)-1,2,4-oxadiazol-3-yl, 5-[2-(4-tert-butoxycarbonylpiperazin-4-yl)ethyl]-1,2,4-oxadiazol-3-yl, 5-(pyrimidin-2-yl)-1,2,4-oxadiazol-3-yl, 5-methyl-1,2,4-oxadiazol-3-yl, 5-benzylaminomethyl-1,2,4-oxadiazol-3-yl, 5-(S)-(α-[benzyloxycarbonylamino]benzyl)-1,2,4-oxadiazol-3-yl, 5-(R)-(α-[benzyloxycarbonylamino]benzyl)-1,2,4-oxadiazol-3-yl,
5-[2-(4H-piperazin-1-yl)ethyl]-1,2,4-oxadiazol-3-yl,
5-[2-(phenylcarbonylamino)ethyl]-1,2,4-oxadiazol-3-yl,
5-[2-(dimethylamino)ethyl]-1,2,4-oxadiazol-3-yl,
1,2,4-oxadiazol-3-yl,
5-phenyl-1,2,4-oxadiazol-3-yl,
2-benzyl-2H-1,2,3,4-tetraazol-5-yl,
5-benzyl-1,3,4-oxadiazol-2-yl,
5-[2-(phenyl)ethyl]-1,3,4-oxadiazol-2-yl,
5-methyl-2H-1,2,3,4-tetraazol-5-yl,
5-cyclohexylamino-1,3,4-oxadiazol-2-yl,
5-methyl-1,3,4-oxadiazol-2-yl,
3-methyl-1,2,4-oxadiazol-3-yl,
5-methyl-1,3-thiazol-2-yl,
5-methyl-1H-1,2,4-triazol-3-yl,
5aminomethyl-1,2,4-oxadiazol-3-yl or
2H-1,2,3,4-tetraazol-5-yl.
Most preferably $R^1$ is
5-benzyl-1,2,4-oxadiazol-3-yl,
5-(4-[phthalimidomethyl]phenoxymethyl)-1,2,4-oxadiazol-3-yl,
5-(4-aminomethylphenoxymethyl)-1,2,4-oxadiazol-3-yl,
5-(4-dimethylaminomethylphenoxymethyl)-1,2,4-oxadiazol-3-yl,
5-(4-pyrrolidinomethylphenoxymethyl)-1,2,4-oxadiazol-3-yl,
5-(4-methylaminomethylphenoxymethyl)-1,2,4-oxadiazol-3-yl,
5-(1-benzylpiperid-4-yloxymethyl)-1,2,4-oxadiazol-3-yl,
5-(α-[tert-butoxycarbonylamino]benzyl)-1,2,4-oxadiazol-3-yl,
5-(2-[1-benzylpiperid-4-yloxy]ethyl)-1,2,4-oxadiazol-3-yl,
5-(1H-piperid-4-yloxymethyl)-1,2,4-oxadiazol-3-yl,
5-[α-[amino]benzyl]-1,2,4-oxadiazol-3-yl,
5-(2-[benzylamino]ethyl)-1,2,4-oxadiazol-3-yl,
5-(4-[2-aminoethoxy]benzyl)-1,2,4-oxadiazol-3-yl,
5-(pyrazin-2-yl)-1,2,4-oxodiazol-3-yl,
5-(R)-[α-(amino)benzyl]-1,2,4-oxadiazol-3-yl,
5-(S)-[α-(amino)benzyl]-1,2,4-oxadiazol-3-yl,
5-(5-methylaminofuran-2-yl)-1,2,4-oxadiazol-3-yl,
5-(1-benzyloxycarbonylpiperid-4-yloxymethyl)-1,2,4-oxadiazol-3-yl,
5-(1-cyclopropylmethylpiperid-4-yloxymethyl)-1,2,4-oxadiazol-3-yl,
5-(4-hydroxymethylphenoxymethyl)-1,2,4-oxadiazol-3-yl,
5-[2-(4-tert-butoxycarbonylpiperazin-4-yl)ethyl]-1,2,4-oxadiazol-3-yl,
5-(pyrimidin-2-yl)-1,2,4-oxadiazol-3-yl,
5-benzylaminomethyl-1,2,4-oxadiazol-3-yl,
5-(S)(α-[benzyloxycarbonylamino]benzyl)-1,2,4-oxadiazol-3-yl or
5-[2-(4H-piperazin-1-yl)ethyl]-1,2,4-oxadiazol-3-yl.

Preferably, $R^2$ is H, phenyl or $C_3$–$C_7$ cycloalkyl, said phenyl or cycloalkyl being optionally substituted by from 1 to 3 halo substituents, or $R^2$ is a 5- or 6-membered ring heterocyclic group containing either 1 or 2 nitrogen heteroatoms or 1 oxygen heteroatom, said heterocyclic group being saturated or partially or fully unsaturated, optionally benzo-fused and optionally substituted, including in the benzo-fused portion, by from 1 to 3 $C_1$–$C_6$ alkyl, arylalkoxycarbonyl (e.g. benzyloxycarbonyl), halo or halo ($C_1$–$C_6$) alkyl, substituents, said $R^2$ group being attached to W by any mono- or bicyclic ring carbon atom or heteroatom.

More preferably, $R^2$ is H, phenyl, cyclopentyl, cyclohexyl or cycloheptyl, said phenyl being optionally substituted by from 1 to 3 fluoro substituents, or $R^2$ is imidazoly, pyrrolidinyl, piperidinyl or tetrahydrofuranyl, said imidazolyl or tetrahydrofuranyl group being optionally benzo-fused and optionally substituted, including in the benzo-fused portion, by from by from 1 to 3 methyl or bromine or fluorine substituents, said $R^2$ group being attached to W by any mono- or bicyclic ring carbon atom.

Yet more preferably, $R^2$ is H, fluorophenyl, cyclohexyl, methylimidazolyl, benzimidazolyl, furanyl, cyclopentyl, cycloheptyl, bromobenzimidazolyl or fluorobenzimidazoyl.

Most preferably, $R^2$ is H, 4-fluorophenyl, cyclohexyl, 1-methyl-1H-imidazol-4-yl, 1H-benzo[d]imidazol-2-yl, tetrahydrofuran-3-yl, cyclopentyl, cycloheptyl or 5-bromo-1H-benzo[d]imidazol-2-yl.

Preferably, W is a direct link or $C_1$–$C_6$ alkylene.

More preferably, W is a direct link, methylene, ethylene or 2,2-dimethyl-1,3-propylene. Most preferably, W is a direct link or methylene.

Preferably, Y is $SO_2$ or —$CONR^5$—.
Most preferably, Y is $SO_2$ or —CONH—.
Preferred examples of —Y—W—$R^2$ include:
5-bromo1H-benzo[d]imidazol-2-ylsulphonyl,
1H-benzo[d]imidazol-2-ylsulphonyl,
1-methyl-1H-imidazol4-ylsulphonyl,
tetrahydrofuran-3-ylmethylsulphonyl,
cyclohexylmethylsulphonyl,
4-fluorophenylsulphonyl,
N-(2,2-dimethylprop-1-yl)aminocarbonyl,
cyclopentylmethyl sulphonyl,
cycloheptylmethyl sulphonyl,
1-(benzyloxycarbonyl)pyrrolidin-3-ylmethylsulphonyl,
1-(benzyloxycarbonyl)piperid-3-ylmethylsulphonyl,
benzylaminocarbonyl or
phenethylaminocarbonyl.

Highly preferred examples of —Y—W—$R^2$ include:
5-bromo1H-benzo[d]imidazol-2-ylsulphonyl,
1H-benzo[d]imidazol-2-ylsulphonyl,
cyclohexylmethylsulphonyl,
4-fluorophenylsulphonyl,
cyclopentylmethyl sulphonyl or
cycloheptylmethyl sulphonyl.

Preferably, A is unbranched $C_3$–$C_4$ alkylene (i.e. 1,3-propylene or 1,4-butylene). Most preferably A is $C_4$ alkylene.

In a preferred embodiment of the present invention $R^1$ is 1,2,4 or 1,3,4 oxadiazole, that is linked to the adjacent carbon atom by a ring carbon atom which is optionally preferably-mono-substituted by one of —X-aryl or —X-het wherein X is preferably selected from —($C_0$–$C_2$ alkylene)—Z—($C_0$–$C_2$ alkylene), more preferably —($C_1$ alkylene)—Z—($C_0$ alkylene) where Z is —O—; or X is a direct link or —($C_1$–$C_2$ alkylene); or X is —($C_0$ alkylene)—Z—($C_0$ alkylene) where Z is —CR$^5$NR$^3$R$^4$, or —CR$^5$NR$^5$(CO$_2$R$^5$) where R$^3$ and R$^4$ are selected from H, —(C$_1$–C$_3$ alkylene), more preferably H, —(C$_1$–C$_2$ alkylene) and R$^5$ is H or —(C$_1$–C$_4$ alkylene), or —(C$_1$–C$_2$ alkylene)aryl; or X is —(C$_1$–C$_2$ alkylene)—Z—(C$_1$–C$_2$ alkylene)(aryl) where Z is NR$^5$ and R$^5$ is H or —(C$_1$–C$_2$ alkylene)-;

wherein aryl of —X-aryl is phenyl optionally substituted by from 1 to 3 substituents independently selected from —(C$_1$–C$_3$ alkylene) NR$^3$ R$^4$, —(C$_1$–C$_6$ alkylene)(phthalimido); —O(C$_1$–C$_3$ alkylene) NR$^3$R$^4$ or —C$_{02}$R$^5$ wherein R$^3$ and R$^4$ are each independently selected from H, C$_1$–C$_3$ alkyl or, when taken together, represent unbranched C$_3$–C$_5$ alkylene; and R$^5$ is H, C$_1$–C$_4$ alkyl or —(C$_1$–C$_2$ alkylene)aryl;

wherein "het" of —X-het is piperidinyl, furyl, pyrazinyl, pyrimidinyl or piperazinyl optionally substituted by —(C$_1$–C$_3$ alkylene)(—C$_3$–C$_6$ cycloalkyl), —CO$_2$R$^5$, —(C$_1$–C$_3$ alkylene)NR$_3$R$_4$ or —(C$_1$–C$_2$ alkylene)aryl wherein aryl is phenyl and wherein R$^3$ and R$^4$ are selected from H, —(C$_1$–C$_3$ alkylene), more preferably H, —(C$_1$–C$_2$ alkylene) and R$^5$ is H or —(C$_1$–C$_4$ alkylene), or —(C$_1$–C$_2$ alkylene)aryl;

or X is —(C$_1$–C$_2$ alkylene)—Z—(C$_1$–C$_2$ alkylene)(aryl) where Z is NR$^5$ and R$^5$ is H or —(C$_1$–C$_2$ alkylene)—.

Further preferred embodiments of the present invention are as follows:

1H-Benzo[d]imidzol-2-yl[2S]-2-(5-benzyl-1,2,4-oxadiazol-3-yl)-1-piperidylsulphone, 2-[4-(3-[(2S)-1-(1H-Benzo[d]imidazol-2-ylsulfonyl)piperidyl-1,2,4-oxadiazol-5-ylmethoxy)benzyl]-1,3-isoindolinedione, 4-(3-[(2S)-1-(1H-Benzo[d]imidazol-2-ylsulfonyl)-2-piperidyl]-1,2,4-oxadiazol-5-ylmethoxy)benzylamine, N-[4-(3-[(2S)-1-(1H-Benzo[d]imidazol-2-ylsulfonyl)-2-piperidyl]-1,2,4-oxadiazol-5-ylmethoxy)benzyl]-N,N-dimethylamine, 3-[1-(1H-Benzo[d]imidazol-2-ylsulfonyl)-2-piperidyl]-5-[4-(1-pyrrolidylmethyl)phenoxy]methyl-1,2,4-oxadiazole, N-[4-(3-[1-(1H-Benzo[d]imidazol-2-ylsulfonyl)-2-piperidyl]-1,2,4-oxadiazol-5-ylmethoxy)benzyl]-N-methylamine, 4-[3-((2S)-1-[Cyclohexylmethylsulfonyl]-2-piperidyl)-1,2,4-oxadiazol-5-ylmethoxy]benzylamine, 5-[(1-Benzyl-4-piperidyl)oxymethyl]-3-[(2S)-1-cyclohexylmethylsulfonyl-2-piperidyl]-1,2,4-oxadiazole, 3-[(2S)-1-Cyclohexylmethylsulfonyl-2-piperidyl]-5-[4-piperidyloxymethyl]-1,2,4-oxadiazole, (3-[(2S)-1-Cyclohexylmethylsulfonyl-2-piperidyl]-1,2,4-oxadiazol-5-yl)(phenyl)methylamine, 5-(3-(2S)-1-[(Cyclohexylmethyl)sulfonyl]-2-piperidyl-1,2,4-oxadiazol-5-yl)-2-furyl]methylamine, N-(2-(3-[1-(1H-Benzo[d]imidazol-2-ylsulfonyl)-2-piperidyl]-1,2,4-oxadiazol-5-yl)ethyl)benzylamine, 2-[4-(3-[1-(1H-Benzo[d]imidazol-2-ylsulfonyl)-2-piperidyl]-1,2,4-oxadiazol-5-ylmethyl)phenoxy]ethylamine, N-(3-[1-(1H-benzo[d]imidazol-2-ylsulfonyl)-2-piperidyl]-1,2,4-oxadiazol-5-ylmethyl)-N-benzylamine, 2-[(2S)-2-5-[(4-Piperidyloxy)methyl]-1,2,4-oxadiazol-3-yl-1-piperidyl]sulfonyl-1H-benzo[d]imidazole, 2-[(2S)-2-[5-([1-(Cyclopropylmethyl)-4-piperidyl]oxymethyl)-1,2,4-oxadiazol-3-yl]-1-piperidyl]sulfonyl-1H-benzo[d]imidazole, 2-[(2S)-2-(5-Benzyl-1,2,4-oxadiazol-3-yl)-1-piperidyl]sulfonyl-5-bromo-1H-benzo[d]imidazole, 2-4-[(3-(2S)-1-[(5-Bromo-1H-benzo[d]imidazol-2-yl)sulfonyl]-2-piperidyl-1,2,4-oxadiazol-5-yl)methoxy]benzyl-1,3-isoindolinedione, 4-[(3-(2S)-1-[(5-Bromo-1H-benzo[d]imidazol-2-yl)sulfonyl]-2-piperidyl-1,2,4-oxadiazol-5-yl)methoxy]benzylamine, tert-Butyl 4-[2-(3-(1S)-2-[(cyclohexylmethyl)sulfonyl]-2-piperidyl-1,2,4-oxadiazol-5-yl)ethyl]-1-piperazinecarboxylate, (R)-(3-{(2S)-1-[(Cyclohexylmethyl)sulfonyl]-2-piperidyl}-1,2,4-oxadiazol-5-yl)(phenyl)methylamine, (S)-(3-{(2S)-1-[(Cyclohexylmethyl)sulfonyl]-2-piperidyl}-1,2,4-oxadiazol-5-yl)(phenyl)methylamine, 2-({2-[5-(2-pyrimidinyl)-1,2,4-oxadiazol-3-yl]-2-piperidyl}sulfonyl)-1H-benzo[d]imidazole, Benzyl 4-(3-[(2S)-1-(1H-benzo[d]imidazol-2-ylsulfonyl)-2-piperidyl]-1,2,4-oxadiazol-5-ylmethoxy)-1-piperidinecarboxylate, (2S)-2-(5-Benzyl-1,2,4-oxadiazol-3-yl)-1-[(cyclopentylmethyl)sulphonyl]piperidine, (2S)-2-(5-Benzyl-1,2,4-oxadiazol-3-yl)-1-[(cyclohexylmethyl)sulphonyl]piperidine, (2S)-2-(5-Benzyl-1,2,4-oxadiazol-3-yl)-1-[(cycloheptylmethyl)sulphonyl]piperidine, tert-Butyl-N-(3-{(2S)-1-(cyclohexylmethyl)sulphonyl-2-piperidyl}-1,2,4-oxadiazol 5-yl)(phenyl)methylcarbamate, (2S)-2-(5-{2-[(1-Benzyl-4-piperidyl)oxy]ethyl}-1,2,4-oxadiazol-3-yl)-1-(cyclohexylmethyl)sulphonyl]piperidine, {4-{3-{2S-1-[4-Fluorophenyl)sulphonyl]piperidyl}-1,2,4-oxadiazol-5-yl)methoxy]phenyl}methanol, 2-(3-{(2S)-1-[4-Fluorophenyl)sulphonyl]piperidyl}-1,2,4-oxadiazol-5-yl)pyrazine or 1-[2-(3-(1S)-2-[(Cyclohexylmethyl)sulphonyl]-2-piperidyl-1,2,4-oxadiazol-5-yl)ethyl]piperazine.

According to a further aspect of the invention there are provided compounds of formula (I) as defined herein before but wherein the optional substituent on R$^2$, where R$^2$ is a 5-, 6-, or 7-membered ring heterocyclic group, is not, CO$_2$R$^5$; or wherein the optional substituent on the "aryl" group of —X-aryl or R$^5$ is not —(C$_1$–C$_6$ alkylene)OH; or wherein the optional substituent on the —X-het group is not C$_3$–C$_7$ cycloalkyl or —(C$_1$–C$_6$ alkylene)(C$_3$–C$_7$ cycloalkyl).

Particularly preferred examples of the compounds of the formula (I) are as described in the Examples section hereafter.

The compounds of the formula (I) can be prepared using conventional procedures such as by the following illustrative methods.

1. All the compounds of the formula (I) can be prepared by
   (a) reaction of a compound of the formula:

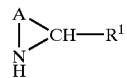

(II)

wherein R$^1$ and A are as previously defined for a compound of the formula (I), with a compound of the formula:

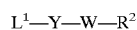

(III)

wherein R$^2$, W and Y are as previously defined for a compound of the formula (I) and L$^1$ is a suitable leaving group, e.g. fluoro, chloro or bromo; or (b) by ring formation or ring closure of a corresponding open ring structure, to formula (II), wherein the said open ring corresponds to an optionally substituted heterocycle $R^1$ followed by reaction with a compound of formula (III) as detailed herein before; or (c) by ring formation or ring closure of a corresponding open ring structure, to formula (I), wherein the said open ring corresponds to an optionally substituted heterocycle $R^1$.

If an acid addition salt of a compound of the formula (II) is used as the starting material, this may be converted to the free base in situ using a suitable acid acceptor, e.g. ethyldiisopropylamine.

For all definitions of Y, $L^1$ may be chloro and the reaction can be carried out in the presence of a suitable additional acid acceptor, e.g. ethyldiisopropylamine or triethylamine, and in a suitable solvent, e.g. dichloromethane. Where Y is $SO_2$, $L^1$ may be fluoro and the reaction can be carried out under similar conditions.

Where Y is carbonyl, —$CONR^5$—, —CO.CO—, —CO.CS— or —CO.CH(OH)—, $L^1$ may also be a group that forms an activated derivative of a carboxylic acid, e.g. an activated ester or imidazol-1-yl. The reaction may be carried out under conventional conditions.

The intermediate compounds of the formula (II) may be prepared by conventional methods, for example, where the heteroaryl group of $R^1$ is a 1,2,4-oxadiazol-3-yl group, by the route shown in Scheme 1.

Scheme 1

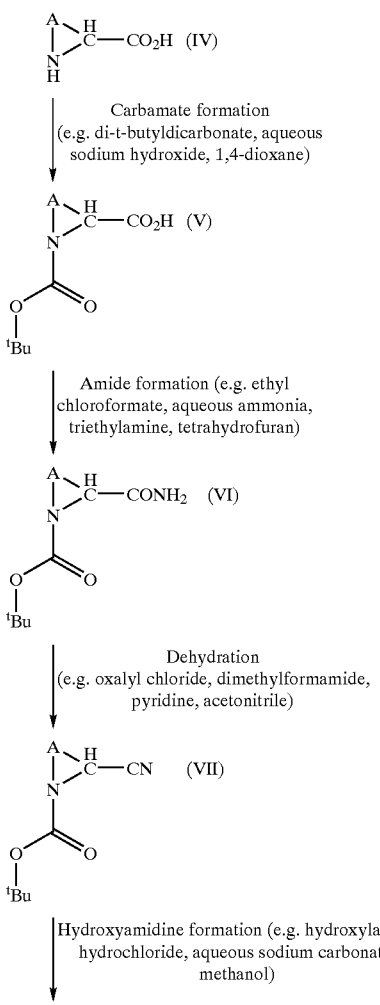

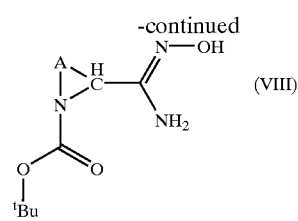

Coupling (e.g. $HO_2C$—$R^{1A}$, hydroxybenzotriazole, 1-(3-dimethylaminopropyl)-3-ethylcarbodiimide hydrochloride, 4-dimethylaminopyridine, N-methylmorpholine, dichloromethane)

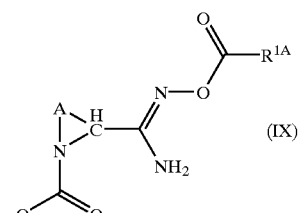

Ring closure (e.g. xylene, heat)

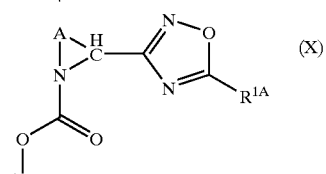

Deprotection (e.g. hydrogen chloride, dichloromethane)

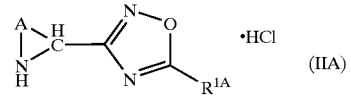

wherein A is as previously defined for a compound of the formula (I) and $R^{1A}$ is a relevant group corresponding to an optional substituent on the heteroaryl group as previously defined for $R^1$ for a compound of the formula (I).

A salt of the formula (IIA) is usually used directly in the reaction with a compound of the formula (III) where it may be converted to the corresponding free base of the formula (II) in situ using a suitable acid acceptor, e.g. ethyldiisopropylamine.

The intermediate compounds of the formula (III) may be prepared by conventional methods.

2. The compounds of the formula (I) wherein Y is —CONH— and $R^1$, $R^2$, A and W are as previously defined for a compound of the formula (I) can be prepared by reaction of a compound of the formula (II) wherein $R^1$ and A are as previously defined for a compound of the formula (I), with an isocyanate of the formula:

wherein $R^2$ and W are as previously defined for a compound of the formula (I).

The reaction may be carried out in a suitable solvent, e.g. dichloromethane.

The intermediate compounds of the formula (XI) can be prepared by conventional methods.

3. The compounds of the formula (I) wherein Y is —CONR$^5$— and R$^1$, R$^2$, R$^5$, A and W are as previously defined for a compound of the formula (I) can be prepared by reaction of a compound of the formula (II) wherein R$^1$ and A are as previously defined for a compound of the formula (I), first with a suitable carbonylation reagent, e.g. phosgene [or an equivalent thereof (e.g. triphosgene)] or 1,1'-carbonyldiimidazole, and then with a compound of the formula:

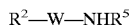

R$^2$—W—NHR$^5$ (XII)

wherein R$^2$, R$^5$ and W are as previously defined for a compound of the formula (I), the reaction being optionally carried out in the presence of a suitable acid acceptor, e.g. triethylamine.

The reaction may be carried out in a suitable solvent, e.g. dichloromethane.

The intermediate amines of the formula (XII) can be prepared by conventional methods.

4. The compounds of the formula (I) wherein R$^1$ is an optionally substituted 1,2,4-oxadiazol-3-yl heteroaryl group and R$^2$, A, W and Y are as previously defined for a compound of the formula (I) can be prepared by ring closure of a compound of the formula:

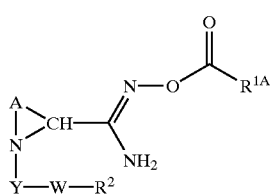

(XIIA)

wherein R$^2$, A, W and Y are as previously defined for a compound of the formula (I) and R$^{1A}$ is a relevant group corresponding to an optional substituent on the heteroaryl group as previously defined for R$^1$ for a compound of the formula (I).

The reaction may be carried out in a suitable solvent, e.g. xylene or pyridine, and at the reflux temperature thereof.

The intermediate compounds of the formula (XIIA) can be prepared by a similar method to that used to prepare a compound of the formula (IX) in Scheme 1 by initially converting a compound of the formula (IV) to a compound of the formula:

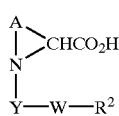

(XIII)

wherein R$^2$, A, W and Y are as previously defined for a compound of the formula (I), using a conventional method, and then by following the route indicated therein.

5. The compounds of the formula (I) wherein R$^1$ is an optionally substituted 1,3,4-oxadiazolyl heteroaryl group and R$^2$, A, W and Y are as previously 6. defined for a compound of the formula (I) can be prepared by ring closure of a compound of the formula:

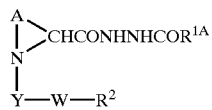

(XIV)

wherein R$^2$, A, W and Y are as previously defined for a compound of the formula (I) and R$^{1A}$ is a relevant group corresponding to an optional substituent on the heteroaryl group as previously defined for R$^1$ for a compound of the formula (I).

The reaction may be carried out under suitable conditions such as using a mixture of triphenylphosphine, iodine and triethylamine in dichloromethane. A compound of the formula (XIV) can be prepared by reaction of a compound of the formula (XIII) with a compound of the formula:

R$^{1A}$CONHNH$_2$ (XV)

under conventional dehydration conditions.

6. The compounds of the formula (I) wherein R$^1$ is a 1,3,4-oxadiazolyl heteroaryl group bearing an optionally substituted amino substituent (R$^{1B}$) (as previously defined for R$^1$) and R$^2$, A, W and Y are as previously defined for a compound of the formula (I) can be prepared by ring closure of a compound of the formula:

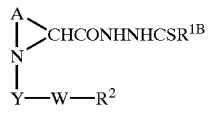

(XVI)

wherein R$^2$, A, W and Y are as previously defined for a compound of the formula (I) and R$^{1B}$ is a relevant optionally substituted amino substituent as defined above.

The reaction may be carried out using mercuric oxide in 1,4-dioxane and at the reflux temperature.

A compound of the formula (XVI) can be prepared by reaction of a compound of the formula (XIII) first with a carboxyl group activating reagent (e.g. 1,1'-carbonyldiimidazole) followed by a compound of the formula:

R$^{1B}$CSNHNH$_2$ (XVII)

wherein R$^{1B}$ is as previously defined for this method, under conventional conditions.

7. The compounds of the formula (I) wherein R$^1$ is an optionally substituted 1,3,4-thiadiazolyl heteroaryl group and R$^2$, A, W and Y are as previously defined for a compound of the formula (I) can be prepared by reaction of a compound of the formula (XIV) wherein R$^2$, A, W, Y and R$^{1A}$ are as previously defined for a compound of the formula (XIV) with a thionating agent, e.g. P$_4$S$_{10}$ or Lawesson's reagent (2,4-bis(4-methoxyphenyl)-1,3-dithia-2,4-diphosphetane-2,4-disulphide) in a suitable solvent, e.g. toluene, preferably at the reflux temperature thereof.

8. The compounds of the formula (I) wherein R$^1$ is an optionally substituted 1,2,4-triazol-3-yl heteroaryl group and R$^2$, A, W and Y are as previously defined for a compound of the formula (I) can be prepared by reaction of a compound of the formula:

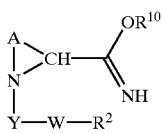

(XVIII)

where $R^2$, A, W and Y are as previously defined for a compound of the formula (I) and $R^{10}$ is $C_1$–$C_4$ alkyl, e.g. methyl or ethyl, with a compound of the formula:

$$R^{1A}NHNHCHO \quad (XIX)$$

wherein $R^{1A}$ is a relevant group corresponding to an optional substituent on the heteroaryl group as previously defined for $R^1$ for a compound of the formula (I).

The reaction may be carried out in a suitable solvent such as a mixture of toluene and 1,4-dioxane, and at the reflux temperature thereof. A compound of the formula (XVIII) can be prepared by reaction of a compound of the formula:

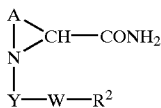

(XX)

wherein $R^2$, A, Y and W are as previously defined for a compound of the formula (I), with a tri($C_1$–$C_4$ alkyl) oxonium hexafluorophosphate in dichloromethane.

A compound of the formula (XX) can be prepared as described in Method (4) above or by treatment of a compound of the formula (XXIV) with ammonia.

9. The compounds of the formula:

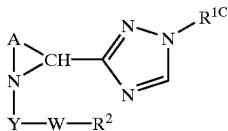

(IA)

wherein $R^2$, A, W and Y are as previously defined for a compound of the formula (I) and $R^{1C}$ is relevant group corresponding to a substituent on the heteroaryl group as previously defined for $R^1$ for a compound of the formula (I) that is linked to the ring nitrogen atom by a methylene group, can be prepared by alkylation of a compound of the formula:

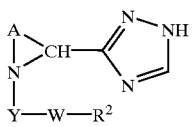

(IB)

wherein $R^2$, A, W and Y are as previously defined for a compound of the formula (I) (a compound of the formula (IB) is prepared by the route described in Method (8) above, i.e. where $R^{1A}$ is H) using an appropriate alkylating agent and under conventional conditions. Regioisomers may be formed in this reaction and they may be separated by chromatography.

10. The compounds of the formula (I) wherein $R^1$ is an optionally substituted 4-($C_1$–$C_6$ alkyl)-4H-1,2,4-triazol-3-yl heteroaryl group and $R^2$, A, W and Y are as previously defined for a compound of the formula (I) can be prepared by reaction of a compound of the formula:

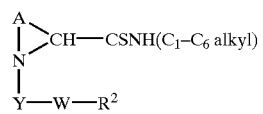

(XXI)

wherein $R^2$, A, W and Y are as previously defined for a compound of the formula (I), with a compound of the formula (XV) wherein $R^{1A}$ is as previously defined for a compound of the formula (XV), in the presence of mercuric oxide.

The reaction may be carried out in a suitable solvent, e.g. 1,4-dioxane or dimethylacetamide, and at the reflux temperature.

A compound of the formula (XXI) can be prepared under conventional conditions as shown in Scheme 2.

Scheme 2

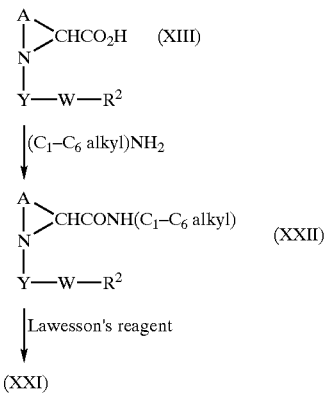

wherein $R^2$, A, W and Y are as previously defined for a compound of the formula (I).

11. The compounds of the formula (I) wherein $R^1$ is an optionally 3-substituted isoxazol-5-yl heteroaryl group and $R^2$, A, W and Y are as previously defined for a compound of the formula (I) can be prepared by ring closure of a compound of the formula:

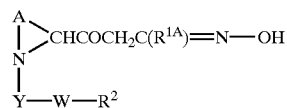

(XXIII)

wherein $R^2$, A, W and Y are as previously defined for a compound of the formula (I) and $R^{1A}$ is a relevant group corresponding to an optional substituent on the heteroaryl group as previously defined for $R^1$ for a compound of the formula (I).

The reaction may be carried out using mesyl chloride, triethylamine and dichloromethane as the solvent.

A compound of the formula (XXIII) can be prepared as shown in Scheme 3.

Scheme 3

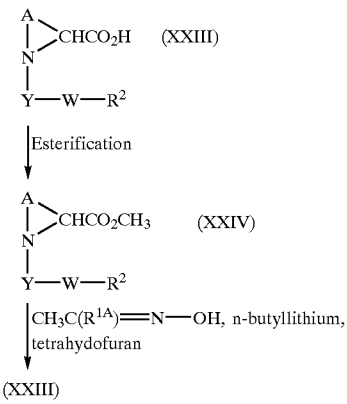

wherein $R^2$, A, W, Y and $R^{1A}$ are as previously defined for this method.

12. The compounds of the formula (I) wherein $R^1$ is an optionally substituted 1,2,3,4-tetraazol-5-yl heteroaryl group and $R^2$, A, W and Y are as previously defined for a compound of the formula (I) can be prepared by known methods such as, for example, by reaction of a compound of the formula (XXV):

where $R^2$, A, W and Y are as previously defined for a compound of the formula (I) with trimethylsilyl azide and dibutyltin oxide. The reaction may be carried out in a suitable solvent such as toluene and at the reflux temperature thereof. Compounds such as formula (XXV) can be N-alkylated using an appropriate alkylating agent and under conventional conditions regioisomers may be formed which can be separated be standard chromatogaphical methods.

13. The compounds of the formula (I) wherein $R^1$ is an optionally substituted 1,2,4-oxadiazol-5-yl heteroaryl group and $R^2$, A, W and Y are as previously defined for a compound of the formula (I) can be prepared by standard methods such as for example, by heat treatment of a compound of the formula (XXVI):

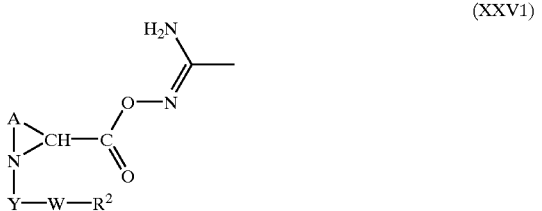

where $R^2$, A, W and Y are as previously defined for a compound of the formula (I), in a suitable solvent such as xylene at reflux temperature. The compound of the formula (XXVI) can be prepared by reacting a compound of the formula (XIII) with a $N^1$-hydroxyimidamide, such as $N^1$-hydroxyethanimidamide. Suitable reaction conditions would be for example, in the presence of hydroxybenzotriazole hydrate, N-methyl morpholine, and 1-(3-dimethylaminopropyl)-3-ethylcarbodiimide hydrochloride, in a solvent such as dichloromethane, at room temperature.

14. It will be appreciated that certain compounds of the formula (I) can be converted to other compounds of the formula (I) by conventional methods, e.g. using standard functional group interconversion techniques.

All of the above reactions and the preparations of novel starting materials using in the preceding methods are conventional and appropriate reagents and reaction conditions for their performance or preparation as well as procedures for isolating the desired products will be well-known to those skilled in the art with reference to literature precedents and the Examples and Preparations hereto.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The affinity of the compounds of the formula (I) for FKBP-12 can be determined in vitro in a coupled colorimetric PPlase assay using similar procedures to published methods (e.g. see Kofron, J. L., et al., Biochemistry, 1991, 30, 6127–6134, Zarnt, T., et al., Biochem. J. 1995, 305, 159–164, Holt, D. A., et al., J. Am. Chem. Soc., 1993,115, 9925–9938). In these methods, the cis-trans isomerisation of a hydrophobic amino acid-proline bond in a tetrapeptide substrate (e.g. the phenylalanine-proline bond in N-succinyl-ala-phepro-phe-p-nitroanilide [succinyl-AFPF-pNA]) can be determined by monitoring cleavage of pNA from the transPro-containing peptide by an excess of chymotrypsin.

The $IC_{50}$ (the concentration of the compound of the formula (I) producing 50% inhibition) values were determined using the following assay methodology. Assay buffer (2.175 ml) (50 mM 4-(2-hydroxyethyl)-1-piperazineethanesulphonic acid (HEPES), 100 mM NaCl, 1 mM dithiothreitol (DTT), pH 8.0) is equilibrated to 10° C. in a cuvette. 12.5 µl of a solution of the present compound in DMSO, 250 µl of a 60 mg/ml solution of a-chymotrypsin in 1 mM aqueous hydrochloric acid and then 50 µl of a solution of human recombinant FKBP-12 (4.5 µM) in assay buffer are added and mixed. The reaction is initiated by addition of 12.5 µl of a solution of 20 mM succinyl-AFPF-pNA in DMSO. The absorbance at 390 nM is monitored for one minute collecting data every 0.25 second. Data are fitted with a first order rate equation with offset and the rate constant obtained corrected for the rate of uncatalysed isomerisation of the substrate. The rate constant determined at different inhibitor concentrations (10 nM to 100 µM) is expressed as % inhibition of the control rate constant. The $IC_{50}$ is estimated using a nonlinear least squares curve fitting routine of the sigmoidal dose response data.

$K_{i,app}$ (the apparent inhibition constant) was determined for the present compounds using the assay procedure described below. Assay buffer (2.175 ml) (50 mM HEPES, 100 mM NaCl, 1 mM DTT, pH 8.0) is equilibrated to 10° C. in a cuvette. 12.5 µl of a solution of the present compound in DMSO, 250 µl of a 60 mg/ml solution of α-chymotrypsin in 1 mM aqueous hydrochloric acid and then 50 µL of a solution of human recombinant FKBP-12 (1.5 µM) in assay buffer are added and mixed. The reaction is initiated by adding 12.5 µl of a solution of anhydrous succinyl-ALPF-pNA (100 µM final concentration) in a 400 mM solution of LiCl in trifluoroethanol. The absorbance at 390 nM is monitored for 3 minutes collecting data every 0.5 second. Data are fitted with a first order rate equation with offset and the initial velocity (v) is calculated from the concentration of cis (re leu-pro bond)succinyl-ALPF-pNA at $t_0$ and the first order rate constant at different inhibitor concentrations (I). Data in the form $v_{inh}/v_{control}$ v. [I] are fitted with an equation for reversible tight binding inhibition to generate values for $K_{i,app}$ (see Morrison, J. F., et al, Comments Mol. Cell Biophys., 1985, 2, 347–368). This analysis is used when the $K_{i,app}$ approaches the concentration of FKBP-12 in the assay (30 nM). Dixon analysis (see Dixon, M., Biochem. J.,1953, 55, 170–171) is used for generating values of $K_{i,app}$ for less potent compounds.

The same methodology is used to generate $K_{i,app}$ for FKBP52 with the following modifications: Forty microliters human recombinant FKBP52 (5.2 $\mu$M) is substituted for FKBP12 and 2.185 ml assay buffer are used in the assay.

The compounds of the invention have inhibitory activity against the FKBP-12 enzyme. Early experimentation suggests that the compounds of the invention also have inhibitory activity against the FKPB-52 enzyme.

The neurite outgrowth promoting activity of the compounds of the formula (I) can be determined in explant cultures of embryonic chick dorsal root ganglia. Dorsal root ganglia (DRG) are isolated aseptically according to the method of Bray (see "Culturing Nerve Cells", Ed. G. Banker and K. Goslin, MIT Press, Cambridge, Mass., 1991, p.119). The individual ganglia were kept in $Ca^{2+}/Mg^{2+}$-free Tyrodes buffer on ice until a number of ganglia had been collected. Individual ganglia were then transferred into collagen-coated 24-well culture plates containing Neurobasal medium plus B27 supplements and incubated at 37° C. in a 5% $CO_2$ atmosphere. The present compound was added after allowing 4 hours for the ganglia to attach. The explants were fixed and stained with Coomassie blue after 24 or 48 hours in culture. For each treatment 4 to 6 ganglia were analysed and scored by estimating the extent of neurite outgrowth relative to the diameter of the explant using image analysis. The present compounds were tested with and without 10 ng/ml nerve growth factor (NGF) present and compared to outgrowth in the presence of 10 ng/ml nerve growth factor alone.

An alternative system for measuring neurite outgrowth promoting activity of FKBP-12 PPlase inhibitors is the SH-SY-5Y neuroblastoma model described by Gold, B. G., et al, in Exp. Neurol., 1997, 147(2), 269–278. Cells are maintained in Dulbecco's Modified Eagle's Medium (DMEM) supplemented with 10% Fetal calf serum (FCS), 50 U/ml penicillin, 50 $\mu$g/ml streptomycin at 37° C. in a 7% $CO_2$ atmosphere. Cells are plated at $1 \times 10^6$ cells per well and treated for 5 days with 400 nM aphidicolin. Cells are then washed and treated with NGF at 10 ng/ml±various compound concentrations for 7 days to determine if the compounds promote neurite outgrowth in the presence of suboptimal NGF concentrations (and/or in the absence of NGF). Neurite outgrowth is determined by using image analysis to measure neurite lengths in 20 random fields.

The neurotrophic activity of the present compounds can be evaluated in vivo using the sciatic nerve crush model in rat as a model for peripheral nerve regeneration (see Bridge, P. M., et al., Experimental Neurology, 1994, 127, 284–290, Medinaceli, L., et al., Expl. Neurology, 1982, 77, 634–643, Gold, B. G.,et al., Restorative Neurology and Neuroscience, 1994, 6, 287–296), the 1-methyl-4-phenyl-1,2,3,6-tetrahydropyridine (MPTP) and 6-hydroxydopamine models in various species as a model for regeneration in Parkinson's disease (see Mokry, J., Physiol. Res., 1995, 44(3), 143–150) and fimbria-fornix lesions as a model for regeneration in Alzheimer's disease (see Cassel, J. C., Duconseille, E., Jeltsch, H. and Will, B., Prog. Neurol., 1997, 51, 663–716).

The compounds of the formula (I) can be administered alone but will generally be administered in admixture with a suitable pharmaceutical excipient diluent or carrier selected with regard to the intended route of administration and standard pharmaceutical practice.

For example, the compounds of the formula (I) can be administered orally or sublingually in the form of tablets, capsules, ovules, elixirs, solutions or suspensions, which may contain flavouring or colouring agents, for immediate or controlled release applications.

Such tablets may contain excipients such as microcrystalline cellulose, lactose, sodium citrate, calcium carbonate, dicalcium phosphate and glycine, disintegrants such as starch (preferably corn, potato or tapioca starch), alginic acid and certain complex silicates, and granulation binders such as polyvinylpyrrolidone, sucrose, gelatin and acacia. Additionally, lubricating agents such as magnesium stearate, sodium lauryl sulfate and talc may be included.

Solid compositions of a similar type may also be employed as fillers in gelatin capsules. Preferred excipients in this regard include lactose or milk sugar as well as high molecular weight polyethylene glycols. For aqueous suspensions and/or elixirs, the compounds of the formula (I) may be combined with various sweetening or flavouring agents, colouring matter or dyes, with emulsifying and/or suspending agents and with diluents such as water, ethanol, propylene glycol and glycerin, and combinations thereof.

The compounds of the formula (I) can also be injected parenterally, for example, intravenously, intraperitoneally, intrathecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the formula (I) will usually be from 1 microgram/kg to 25 mg/kg (in single or divided doses).

Thus tablets or capsules of the compound of the formula (I) may contain from 0.05 mg to 1.0 g of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of formula (I) can also be administered intranasally or by inhalation and are conveniently delivered in the form of a dry powder inhaler or an aerosol spray presentation from a pressurised container or a nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark] or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the formula (I) and a suitable powder base such as lactose or starch.

Aerosol or dry powder formulations are preferably arranged so that each metered dose or "puff" contains from 20 μg to 20 mg of a compound of the formula (I) for delivery to the patient. The overall daily dose with an aerosol will be in the range of from 20 μg to 20 mg which may be administered in a single dose or, more usually, in divided doses throughout the day.

Alternatively, the compounds of the formula (I) can be administered in the form of a suppository or pessary, or they may be applied topically in the form of a lotion, solution, cream, ointment or dusting powder. The compounds of the formula (I) may also be transdermally administered by the use of a skin patch. They may also be administered by the ocular route, particularly for treating neurological disorders of the eye.

For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the formula (I) can also be administered together with other neutrophic agents such as neurotrophic growth factor (NGF), glial derived growth factor, brain derived growth factor, ciliary neurotrophic factor and/or neurotrophin-3. The dosage level of the neurotrophic agent will depend upon the neurotrophic effectiveness of the combination and the route of administration used.

It is to be appreciated that all references herein to treatment include curative, palliative and prophylactic treatment.

Thus the invention further provides:

(i) a pharmaceutical composition comprising a compound of the formula (I) or a pharmaceutically acceptable salt or solvate thereof, together with a pharmaceutically acceptable excipient, diluent or carrier;

(ii) a compound of the formula (I) or a pharmaceutically acceptable salt, solvate or composition thereof, for use as a medicament;

(iii) the use of a compound of the formula (I) or of a pharmaceutically acceptable salt, solvate or composition thereof, for the manufacture of a medicament for the treatment of neuronal degeneration;

(iv) the use of a compound of the formula (I) or of a pharmaceutically acceptable salt, solvate or composition thereof, for the manufacture of a medicament for the promotion of neuronal regeneration and outgrowth;

(v) the use of a compound of the formula (I) or of a pharmaceutically acceptable salt, solvate or composition thereof, for the manufacture of a medicament for the treatment of a neurological disease or disorder such as a neurodegenerative disease;

(vi) use as in (v) where the neurological disease or disorder is selected from the group consisting of senile dementia (Alzheimer's disease) and other dementias, amyotrophic lateral sclerosis and other forms of motor neuron disease, Parkinson's disease, Huntington's disease, neurological deficits associated with stroke, all forms of degenerative disease affecting the central or peripheral nervous system (e.g. cerebellar-brainstem atrophies, syndromes of progressive ataxias), all forms of muscular dystrophy, progressive muscular atrophies, progressive bulbar muscular atrophy, physical or traumatic damage to the central or peripheral nervous system (e.g. spinal cord), herniated, ruptured or prolapsed intervertebrae disc syndromes, cervical spondylosis, plexus disorders, thoracic outlet syndromes, all forms of peripheral neuropathy (both diabetic and non-diabetic), trigeminal neuralgia, glossopharyngeal neuralgia, Bell's Palsy, all forms of autoimmune related disease resulting in damage of the central or peripheral nervous system (e.g. multiple sclerosis, myasthenia gravis, Guillain-Barré syndrome), AIDS related disorders of the nervous system, dapsone ticks, bulbar and retrobulbar affections of the optic nerve (e.g. retinopathies and retrobulbar neuritis), hearing disorders such as tinnitus, and prion diseases;

vii) use as (vi) where the neurological disease or disorder is senile dementia (Alzheimer's disease) or another dementia, amyotrophic lateral sclerosis or another form of motor neuron disease, Parkinson's disease, Huntington's disease, a neurological deficit associated with stroke, physical or traumatic damage to the central or peripheral nervous system (e.g. spinal cord), a peripheral neuropathy (either diabetic or non-diabetic), multiple sclerosis or a hearing disorder such as tinnitus;

(viii) a method of treatment of a human to treat neuronal degeneration which comprises treating said human with an effective amount of a compound of the formula (I) or with a pharmaceutically acceptable salt, solvate or composition thereof;

(ix) a method of treatment of a human to promote neuronal regeneration and outgrowth which comprises treating said human with an effective amount of a compound of the formula (I) or with a pharmaceutically acceptable salt, solvate or composition thereof;

(x) a method of treatment of a human to treat a neurological disease or disorder such as a neurodegenerative disease which comprises treating said human with an effective amount of a compound of the formula (I) or with a pharmaceutically acceptable salt, solvate or composition thereof;

(xi) a method as in (x) where the neurological disease or disorder is selected from the group consisting of senile dementia (Alzheimer's disease) and other dementias, amyotrophic lateral sclerosis and other forms of motor neuron disease, Parkinson's disease, Huntington's disease, neurological deficits associated with stroke, all forms of degenerative disease affecting the central or peripheral nervous system (e.g. cerebellar-brainstem atrophies, syndromes of progressive ataxias), all forms of muscular dystrophy, progressive muscular atrophies, progressive bulbar muscular atrophy, physical or traumatic damage to the central or peripheral nervous system (e.g. spinal cord), herniated, ruptured or prolapsed intervertebrae disc syndromes, cervical spondylosis, plexus disorders, thoracic outlet syndromes, all forms of peripheral neuropathy (both diabetic and non-diabetic), trigeminal neuralgia, glossopharyngeal neuralgia, Bell's Palsy, all forms of autoimmune related disease resulting in damage of the central or peripheral nervous system (e.g. multiple sclerosis, myasthenia gravis, Guillain-Barré syndrome), AIDS related disorders of the nervous system, dapsone ticks, bulbar and retrobulbar affections of the optic nerve (e.g. retinopathies and retrobulbar neuritis), hearing disorders such as tinnitus, and prion diseases;

(xii) a method as in (xi) where the neurological disease or disorder is senile dementia (Alzheimer's disease) or another dementia, amyotrophic lateral sclerosis or another form of motor neuron disease, Parkinson's disease, Huntington's disease, a neurological deficit associated with stroke, physical or traumatic damage to the central or peripheral nervous system (e.g. spinal cord), a peripheral neuropathy (either diabetic or non-diabetic), multiple sclerosis or a hearing disorder such as tinnitus; and (xiii) any novel intermediates described herein.

The following Examples illustrate the preparation of the compounds of the formula (I). The ACD/IUPAC Pro software programme was used as the basis for naming the prepared compounds.

EXAMPLE 1

1H-Benzo[d]imidazol-2-yl[(2S)-2-(5-benzyl-1,2,4-oxadiazol-3-yl)-1-piperidyl]sulfone

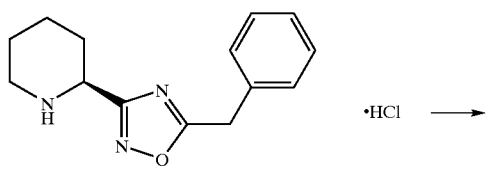

·HCl ⟶

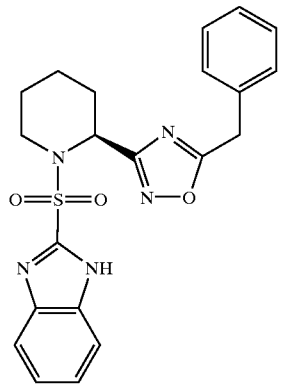

Ethyldiisopropylamine (383 μl) was added to a mixture of 5-benzyl-3-[(2S)-2-piperidyl-1,2,4-oxadiazole hydrochloride (279.8 mg) [see Preparation 7] and 1H-benzo[d]imidazole-2-sulfonyl chloride (325 mg) [see Preparation 8] in dichloromethane (5 ml). The reaction mixture was stirred at room temperature for 18 hours after which time the mixture was diluted with dichloromethane and washed with aqueous sodium hydrogen carbonate solution. The organic layer was separated, dried over magnesium sulphate, and the solvent removed under reduced pressure. The residue was chromatographed on silica gel eluting with a solvent gradient of 0:100 changing to 20:80, by volume, ethyl acetate-:hexane to give the product as a white solid. This solid was dissolved in dichloromethane and the solvent was removed under reduced pressure to give 1H-benzo[d]imidazol-2-yl [(2S)-2-(5-benzyl-1,2,4-oxadiazol-3-yl)-1-piperidyl]sulfone (245 mg) as a white solid. $^1$H-NMR (CDCl$_3$) δ: 10.80 (1H, s), 7.80 (1H, s), 7.40–7.10 (8H, m), 5.50 (1H, m), 3.95 (1H, d), 3.85 (2H, q), 3.20 (1H, m), 2.25 (1H, d), 2.05 (1H, m), 1.80–150 (4H, m) ppm. MS (mass spectrometry): 424 (MH$^+$). Analysis: Found C, 58.07; H, 4.97; N, 15.81; C$_{21}$H$_{21}$N$_5$O$_3$S.0.6H$_2$O requires C, 58.08; H, 5.15; N, 16.13%. Rotation: $[\alpha]_D^{25}$=−56.37° (c=0.1, methanol).

EXAMPLES 2–8

The compounds of the following tabulated Examples (Table 1) of the general formula:

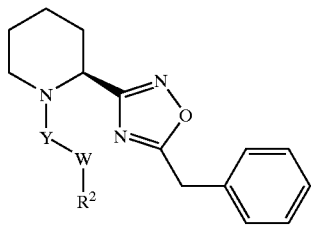

were prepared by a similar method to that of Example 1 using the appropriate sulphonyl chloride and 5-benzyl-3-[(2S)-2-piperidyl]-1,2,4-oxadiazole hydrochloride [see Preparation 7].

TABLE 1

| Example no. | Starting material prep. no. | Y—W—R² | Analytical data |
|---|---|---|---|
| 2 | | (1-methylimidazol-4-yl)sulfonyl group | ¹H-NMR (CDCl₃) δ: 7.40–7.2 (6H, m), 7.15 (1H, s), 5.40(1H, m), 4.20(2H, s), 3.90(1H, d), 3.60(3H, s), 3.45(1H, m), 2.00 (2H, m), 1.60(4H, m). Analysis: Found C, 55.61; H, 5.50; N, 17.87, $C_{18}H_{21}N_5O_3S$ requires C, 55.80; H, 5.46; N, 18.07%. |
| 3 | 11 | (tetrahydrofuran-3-yl)methylsulfonyl group | ¹H-NMR (CDCl₃) δ: 7.40–7.20 (5H, m), 5.25(1H, s), 4.20(2H, s), 3.95(1H, m), 3.80–3.60(3H, m), 3.45(1H, m), 3.20–3.00(3H, m), 2.70(1H, m), 2.25(1H, m), 2.10(1H, m), 1.95(1H, m), 1.80–1.40(5H, m). Analysis: Found C, 56.98; H, 6.39; N, 10.21; $C_{19}H_{25}N_3O_4S$ 0.1 $CH_2Cl_2$ requires C, 57.17; H, 6.33; N, 10.46%. |
| 4 | 58 | (1-benzyloxycarbonylpyrrolidin-3-yl)methylsulfonyl group | ¹H-NMR (CDCl₃) δ: 7.40–7.20 (10H, m), 5.30(1H, m), 5.15 (2H, s), 4.20(2H, s), 3.80(2H, m), 3.55(1H, m), 3.35(1H, m), 3.20–3.00(4H, m), 2.70(1H, m), 2.40(1H, d), 2.00(1H, m), 1.80–1.50(6H, m). Analysis: Found C, 61.52; H, 6.11; N, 10.61; $C_{27}H_{32}N_4O_5S$ requires C, 61.81; H, 6.15; N, 10.68%. |
| 5 | 62 | (1-benzyloxycarbonylpiperidin-3-yl)methylsulfonyl group | ¹H-NMR (d6-DMSO) δ: 7.40–7.20(10H, m), 5.15(1H, m), 5.00(2H, s), 4.30(2H, s), 4.15 (1H, d), 4.05(1H, m), 3.80(1H, m), 3.60(1H, m), 3.00(3H, m), 2.80(1H, m), 2.60(1H, m), 2.05 (1H, d), 1.80(3H, m), 1.55(3H, m), 1.40–1.10(3H, m). Analysis: Found C, 62.11; H, 6.34; N, 10.27; $C_{28}H_{34}N_4O_5S$ requires C, 62.43; H, 6.36; N, 10.40%. |
| 6 | 65 | cyclopentylmethylsulfonyl group | MS: 390(MH⁺). Analysis: Found C, 61.40; H, 6.96; N, 10.76; $C_{20}H_{27}N_3O_3S$ requires C, 61.67; H, 6.99; N, 10.79%. $[\alpha]_D = -41.93°$ (C = 0.1, methanol). |
| 7 | | cyclohexylmethylsulfonyl group | ¹H-NMR (CDCl₃) δ: 7.40–7.20 (5H, m), 5.35(1H, m), 4.25(2H, s), 3.80(1H, d), 3.20(1H, m), 2.90(2H, m), 2.25(1H, d), 2.00 (3H, m), 1.80–1.40(8H, m), 1.30–1.10(3H, m), 1.00(2H, m). Analysis: Found C, 62.47; H, 7.29; N, 10.33; $C_{21}H_{29}N_3O_3S$ requires C, 62.50; H, 7.24; N, 10.41% |

TABLE 1-continued

| Example no. | Starting material prep. no. | Y—W—R² | Analytical data |
|---|---|---|---|
| 8 | 68 | (cycloheptylmethyl sulfonyl group) | ¹H-NMR (CDCl₃) δ: 7.40–7.20 (5H, m), 5.25(1H, d), 4.20(2H, m), 3.75(1H, d), 3.20(1H, t), 2.90(2H, m), 2.25(1H, d), 2.10 (1H, m), 2.00–1.80(3H, m), 1.70–1.40(12H, m), 1.25(2H, m). Analysis: Found C, 62.97; H, 7.42; N, 9.99; $C_{22}H_{31}N_3O_3S$ requires C, 63.28; H, 7.48; N, 10.06% |

EXAMPLE 9

N1-Neopentyl-((2S)-2-(5-benzyl-1,2,4-oxadiazol-3-yl))-1-piperidinecarboxamide

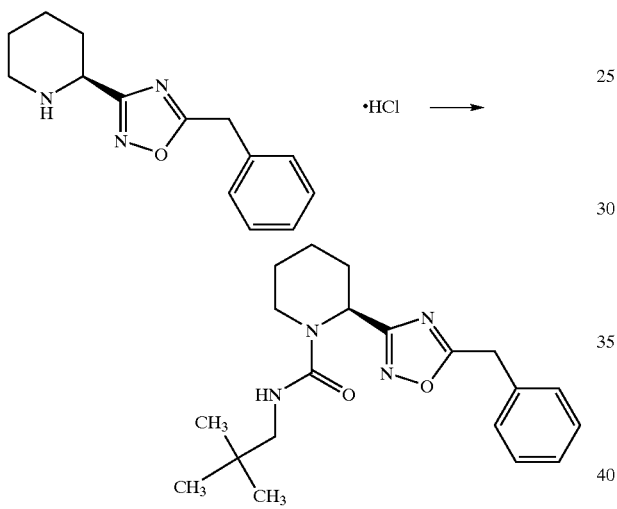

Triphosgene (45 mg) in dichloromethane (2 ml) was added dropwise to a solution of 5-benzyl-3-[(2S)-2-piperidyl]-1,2,4-oxadiazole hydrochloride (140 mg) [see Preparation 7] and triethylamine (139 ml) in dichloromethane (2 ml). The reaction mixture was stirred at room temperature for 1 hour. A solution of neopentylamine (78 mg) and triethylamine (70 μl) in dichloromethane was added to the mixture and stirred for 18 hours. The reaction mixture was then diluted with dichloromethane and water, the organic phase was separated, dried over magnesium sulphate and the solvent removed under reduced pressure. The crude product was purified by column chromatography on silica gel eluting with a solvent gradient of 90:10 changing to 83:17, by volume, hexane:ethyl acetate to afford N1-neopentyl-((2S)-2-(5-benzyl-1,2,4-oxadiazol-3-yl))-1-piperidinecarboxamide (66 mg) as a clear oil.

¹H-NMR (CDCl₃) δ: 7.30 (5H, m), 5.50 (1H, s), 4.80 (1H, s), 4.20 (2H, s), 3.70 (1H, d), 3.20–3.00 (3H, m), 2.25 (1H, d), 1.90 (1H, m), 1.70–1.40 (4H, m), 0.90 (9H, s). Rotation: $[\alpha]_D^{25} = -43.41°$ (c=0.1, methanol). Analysis: Found C, 66.95; H, 7.99; N, 15.18; $C_{20}H_{28}N_4O_2 \cdot 0.2H_2O$ requires C, 66.71; H, 7.95; N, 15.56%.

EXAMPLE 10

2-[4-(3-[((2S)-1-(1H-Benzo[d]imidazol-2-ylsulfonyl)-2-piperidyl]-1,2,4-oxadiazol-5-ylmethoxy)benzyl]-1,3-isoindolinedione

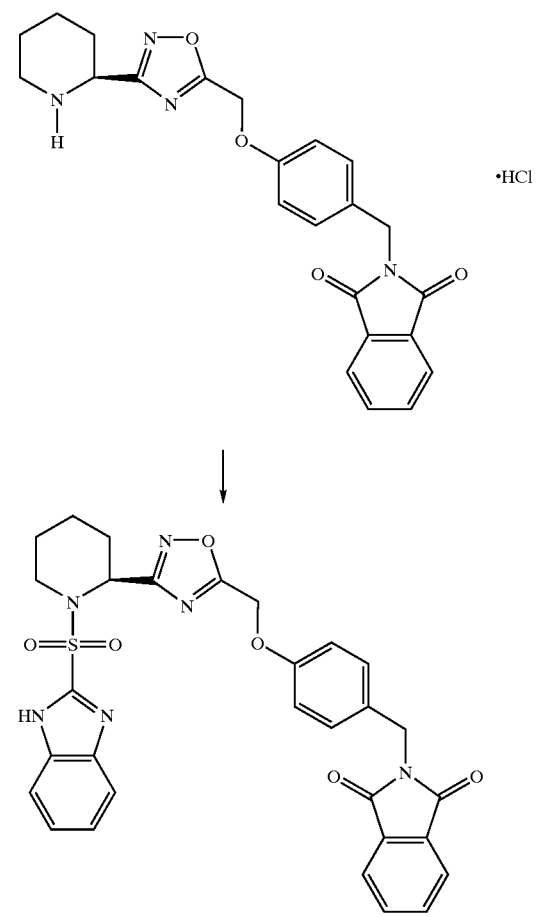

The title compound was prepared by a similar method to Example 1 from 2-[4-(3-[(2S)-2-piperidyl]-1,2,4-oxadiazol-5-ylmethoxy)benzyl]-1,3-isoindolinedione hydrochloride [see Preparation 15] and 1H-benzo[d]imidazole-2-sulfonyl chloride [see Preparation 8] to afford 2-[4-(3-[(2S)-1-(1H-benzo[d]imidazol-2-ylsulfonyl)-2-piperidyl]-1,2,4-oxadiazol-5-ylmethoxy)benzyl]-1,3-isoindolinedione (956 mg).

¹H-NMR (CDCl₃) δ: 7.85 (2H, m), 7.75 (2H, m), 7.70 (2H, bs), 7.40 (2H, d), 7.30 (2H, d), 6.80 (2H, d), 5.60 (1H, d), 4.80 (4H, 2×d), 4.00 (1H, d), 3.20 (1H, t), 2.30 (1H, d), 2.10 (1H, m), 1.80–1.40 (4H, m). Analysis: Found C, 59.04; H, 4.60; N, 13.24; $C_{30}H_{26}N_6O_6S.0.3EtOAc.0.5H_2O$ requires C, 59.10; H, 4.67; N, 13.25% (EtOAc=ethyl acetate). $[\alpha]_D^{25}=-46°$ (c=0.1, methanol).

EXAMPLE 11

4-(3-[(2S)-1-(1H-Benzo[d]imidazol-2-ylsulfonyl)-2-piperidyl]-1,2,4-oxadiazol-5-ylmethoxy)benzylamine

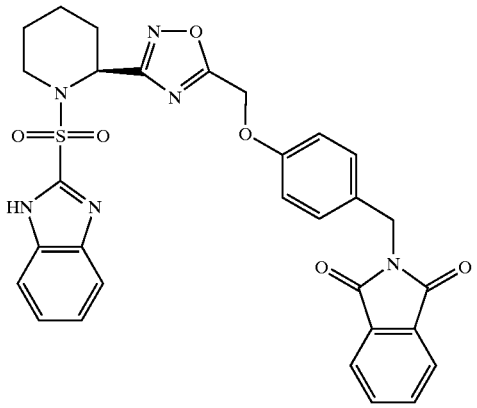

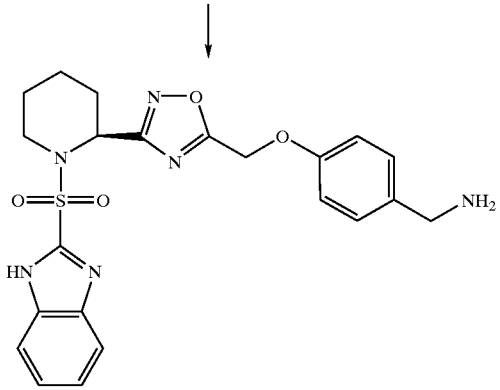

2-[4-(3-[(2S)-1-(1H-benzo[d]imidazol-2-ylsulfonyl)-2-piperidyl]-1,2,4-oxadiazol-5-ylmethoxy)benzyl]-1,3-isoindolinedione (885 mg) [see Example 10] was added to a solution of 33% w/w methylamine in ethanol (2.2 ml). The reaction mixture was stirred at room temperature for 5 hours after which time the solvent was removed under reduced pressure. The resulting solid was dissolved in 1N aqueous hydrochloric acid solution and dichloromethane. The aqueous layer was then separated and basified to pH 12 with 0.88 aqueous ammonia solution. The mixture was then extracted with ethyl acetate, the organic layer dried over magnesium sulphate and the solvent removed under reduced pressure to afford 4-(3-[(2S)-1-(1H-benzo[d]imidazol-2-ylsulfonyl)-2-piperidyl]-1,2,4-oxadiazol-5-ylmethoxy)benzylamine (369 mg) as a white solid.

$^1$H-NMR (d$_6$-DMSO) δ: 7.60 (2H, d), 7.35 (2H, d), 7.20 (2H, d), 7.00 (2H, d), 5.40 (1H, s), 5.20 (2H, q), 3.90 (1H, d), 3.80 (2H, s), 3.20 (3H, bs), 1.90 (1H, d), 1.80 (1H, m), 1.50 (2H, t), 1.30 (2H, m). Analysis: Found C, 55.91; H, 5.10; N, 17.68; $C_{22}H_{24}N_6O_4S.0.1H_2O$ requires C, 56.18; H, 5.19; N, 17.87%. $[\alpha]_D^{25}=-54°$ (c=0.1, methanol).

EXAMPLE 12

N-[4-(3-[(2S)-1-(1H-Benzo[d]imidazol-2-ylsulfonyl)-2-piperidyl]-1,2,4-oxadiazol-5-ylmethoxy)benzyl]-N,N-dimethylamine

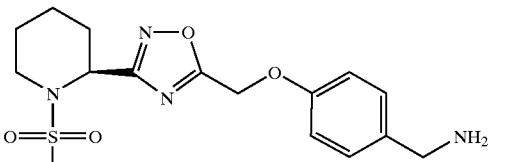

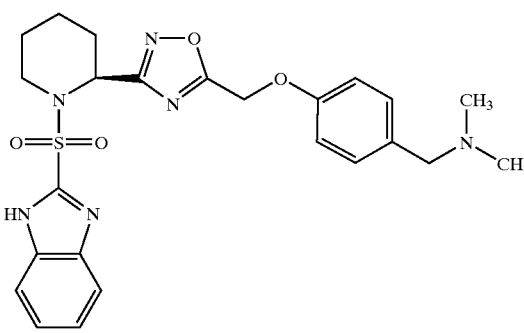

Formaldehyde (37% w/w aqueous solution) (65 μl) was added to a solution of 4-(3-[(2S)-1-(1H-benzo[d]imidazol-2-ylsulfonyl)-2-piperidyl]-1,2,4-oxadiazol-5-ylmethoxy)benzylamine (75 mg) [see Example 11] in acetonitrile (2 ml), followed by sodium triacetoxyborohydride (170 mg). The reaction mixture was stirred at room temperature for 18 hours, after which time glacial acetic acid was added until the solution was at pH 7.0. The mixture was then diluted with dichloromethane and washed with saturated aqueous sodium hydrogen is carbonate solution. The organic layer was separated, dried over magnesium sulphate and the solvent removed under reduced pressure. The crude product was purified by column chromatography on silica gel eluting with a solvent $^1$H-NMR (CDCl$_3$) δ: 7.70 (2H, m), 7.40 (2H, d), 7.25 (2H, d), 6.80 (2H, d), 5.60 (1H, d), 4.90 (2H, q), 4.00 (1H, d), 3.40 (2H, s), 3.20 (1H, m), 2.40 (1H, d), 2.20 (6H, s), 2.16 (1H, m), 1.80 (1H, m), 1.30 (1H, m), 0.90 (2H, m). Rotation: $[\alpha]_D^{25}=-48.41°$ (c=0.1, methanol). Analysis: Found C, 58.15; H, 6.01; N, 16.02; $C_{24}H_{28}N_6O_4S.0.2hexane.0.5H_2O$ requires C, 58.07; H, 5.84; N, 16.12%.

EXAMPLE 13

3-[1-(1H-Benzo[d]imidazol-2-ylsulfonyl)-2-piperidyl]-5-[4-(1-pyrrolidylmethyl)phenoxy]methyl-1,2,4-oxadiazole

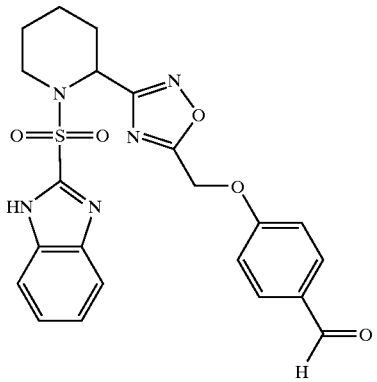

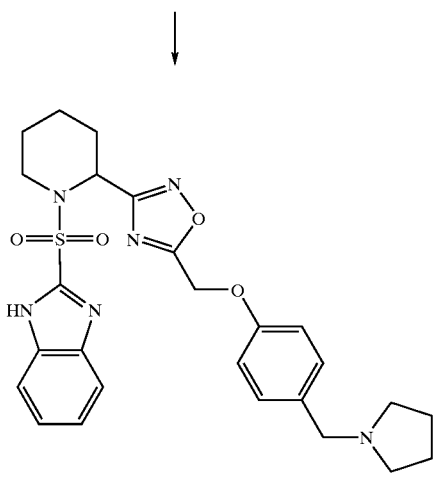

Pyrrolidine (19 μl) was added to a solution of 4-(3-[1-(1H-benzo[d]imidazol-2-ylsulfonyl)-2-piperidyl]-1,2,4-oxadiazol-5-ylmethoxy)benzaldehyde (85 mg) [see Preparation 22] in tetrahydrofuran (10 ml). Sodium triacetoxyborohydride (64 mg) was added followed by glacial acetic acid (11.5 μl). The reaction mixture was stirred under an atmosphere of nitrogen for 6 hours. Sodium triacetoxyborohydride (21 mg) was added and the mixture was stirred for 56 hours after which time the solvent was removed under reduced pressure. The crude product was purified by column chromatography on silica gel eluting with a solvent gradient of 97.5:2.5:0.25 changing to 95:5:0.5, by volume, dichloromethane:methanol:0.88 aqueous ammonia solution to afford 3-[1-(1H-benzo[d]imidazol-2-ylsulfonyl)-2-piperidyl]-5-[4-(1-pyrrolidylmethyl)phenoxy]methyl-1,2,4-oxadiazole (90 mg) as a white solid.

$^1$H-NMR (CDCl$_3$) δ: 7.70 (2H, s), 7.40 (2H, m), 7.30 (2H, m), 6.80 (2H, m), 5.60 (1H, d), 4.90 (2H, q), 4.00 (1H, d), 3.60 (2H, s), 3.20 (1H, m), 2.60 (4H, bs), 2.30 (1H, d), 2.00–0.95 (8H, m). Analysis: Found C, 59.24; H, 5.94; N, 15.10; C$_{26}$H$_{30}$N$_6$O$_4$S.H$_2$O.0.3hexane requires C, 59.20; H, 6.04; N, 14.90%.

EXAMPLE 14

N-[4-(3-[1-(1H-Benzo[d]imidazol-2-ylsulfonyl)-2-piperidyl]-1,2,4-oxadiazol-5-ylmethoxy)benzyl]-N-methylamine

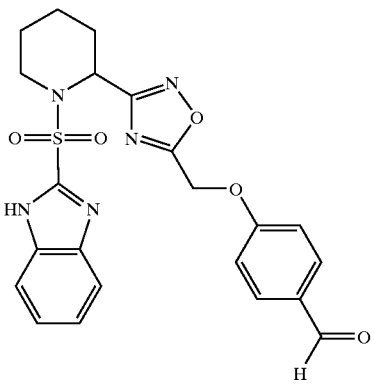

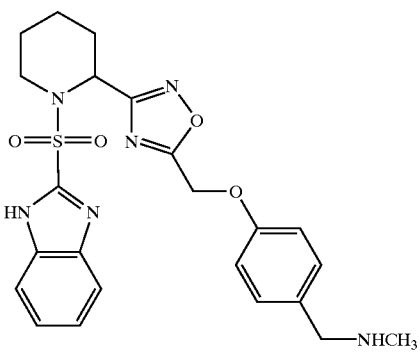

The title compound was prepared by a similar method to Example 13 from 4-(3-[1-(1H-benzo[d]imidazol-2-ylsulfonyl)-2-piperidyl]-1,2,4-oxadiazol-5-ylmethoxy)benzaldehyde [see Preparation 22] and methylamine hydrochloride to afford N-[4-(3-[1l-(1H-benzo[d]imidazol-2-ylsulfonyl)-2-piperidyl]-1,2,4-oxadiazol-5-ylmethoxy)benzyl]-N-methylamine as a white solid.

$^1$H-NMR (CDCl$_3$) δ: 7.70 (2H, bs), 7.40 (2H, m), 7.30 (2H, m), 6.80 (2H, m), 5.60 (1H, d), 4.90 (2H, q), 4.00 (1H, d), 3.75 (2H, s), 3.20 (1H, m), 2.50 (3H, s), 2.40–2.00 (4H, m), 1.80 (2H, m). Analysis: Found C, 54.74; H, 5.50; N, 15.56; C$_{23}$H$_{26}$N$_6$O$_4$S.H$_2$O.0.2CH$_2$Cl$_2$. 0.2 hexane requires C, 54.97; H, 5.60; N, 15.76%.

EXAMPLE 15

4-[3-((2S)-1-[Cyclohexylmethylsulfonyl]-2-piperidyl)-1,2,4-oxadiazol-5-ylmethoxy]benzylamine

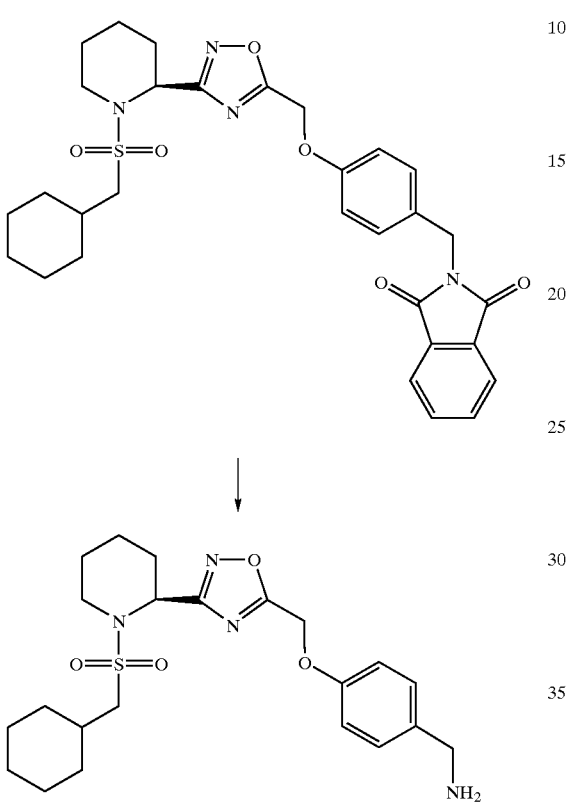

The title compound was prepared by a similar method to Example 11 from 2-[4-(3-[(2S)-1-cyclohexylmethylsulfonyl-2-piperidyl]-1,2,4-oxadiazol-5-ylmethoxy)benzyl]-1,3-isoindolinedione [see Preparation 23] and methylamine. The crude product was purified by column chromatography on silica gel eluting with a solvent gradient of 100:0:0 changing to 90:10:1, by volume, dichloromethane:methanol:0.88 aqueous ammonia solution to afford 4-[3-((2S)-1-[cyclohexylmethylsulfonyl]-2-piperidyl)-1,2,4-oxadiazol-5-ylmethoxy]benzylamine as a colourless oil.

$^1$H-NMR (CDCl$_3$) δ: 7.30 (2H, d), 7.00 (2H, d), 5.40 (1H, d), 5.30 (2H, s), 3.85 (2H, s), 3.80 (1H, d), 3.20 (1H, m), 2.90 (2H, m), 2.30 (1H, d), 2.00–1.00 (18H, m). Accurate MS: 449.2216 (MH$^+$).

EXAMPLE 16

5-[(1-Benzyl-4-piperidyl)oxymethyl]-3-[(2S)-1-cyclohexylmethylsulfonyl-2-piperidyl]-1,2,4-oxadiazole

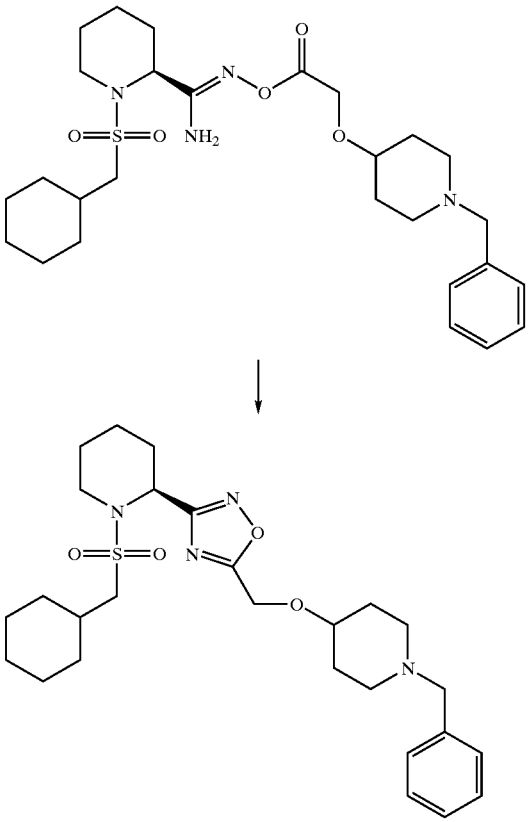

The compound of Preparation 29 (464 mg) was dissolved in pyridine (5 ml) and heated under reflux for 18 hours. The reaction mixture was then cooled and the solvent removed under reduced pressure. The residue was partitioned between ethyl acetate and water, the organic layer was separated, dried over magnesium sulphate and the solvent removed under reduced pressure. The crude product was purified by column chromatography on silica gel eluting with a solvent gradient of 99:0.4:0.2 changing to 93:7:1, by volume, dichloromethane:methanol:0.88 aqueous ammonia solution to afford 5-[(1-benzyl-4-piperidyl)oxymethyl]-3-[(2S)-1-cyclohexylmethylsulfonyl-2-piperidyl]-1,2,4-oxadiazole (357 mg) as a yellow oil.

$^1$H-NMR (CDCl$_3$) δ: 7.30 (5H, m), 5.30 (1H, d), 4.80 (2H, s), 3.80 (1H, d), 3.55 (1H, m), 3.50 (2H, s), 3.20 (1H, m), 2.90 (2H, m), 2.75 (2H, m), 2.20 (3H, m), 2.00 (6H, m), 1.70 (8H, m), 1.50–1.00 (6H, m). Analysis: Found C, 62.53; H, 7.84; N, 10.82; C$_{27}$H$_{40}$N$_4$O$_4$S requires C, 62.76; H, 7.80; N, 10.84%.

EXAMPLES 17–22

The compounds of the following tabulated Examples (Table 2) of the general formula:

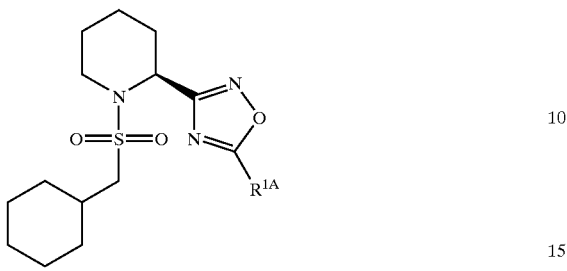

were prepared by a similar method to Example 16 from the corresponding hydroxyamidine derivatives and pyridine.

TABLE 2

| Example no. | Starting material prep. no. | $R^{1A}$ | Analytical data |
|---|---|---|---|
| 17 | 31 | [CH₃)₃C-O-C(O)-NH-CH(Ph)-] | $^1$H-NMR (CDCl$_3$) δ: 7.40(5H, m), 6.10(1H, bs), 5.50(1H, s), 5.35(1H, s), 3.80(1H, d), 3.20 (1H, q), 2.90(2H, m), 2.25(1H, d), 2.00(4H, m), 1.80–1.00(21H, m). Analysis: Found C, 58.53; H, 7.33; N, 10.18; C$_{26}$H$_{38}$N$_4$O$_5$S. 0.8 H$_2$O requires C, 58.58; H, 7.48; N, 10.51%. |
| 18 | 32 | [morpholinomethyl] | $^1$H-NMR (CDCl$_3$) δ: 5.35(1H, d), 3.80(2H, m), 3.75(4H, m), 3.25 (1H, t), 2.90(2H, m), 2.60(4H, t), 2.25(1H, d), 2.00(4H, m), 1.70(6H, m), 1.40–1.00(7H, m). Analysis: Found C, 54.67; H, 7.82; N, 13.23; C$_{19}$H$_{32}$N$_4$O$_4$S. 0.1 CH$_2$Cl$_2$ requires C, 54.49; H, 7.71; N, 13.31%. |
| 19 | 36 | [1-benzyl-4-piperidinyloxyethyl] | $^1$H-NMR (CDCl$_3$) δ: 7.30(5H, m), 5.30(1H, s), 3.90(2H, m), 3.80(1H, d), 3.45(2H, s), 3.40 (1H, m), 3.20(1H, m), 3.15(2H, m), 2.95(2H, m), 2.70(2H, m), 2.25(1H, d), 2.10(2H, t), 2.00–1.00(20H, m). Analysis: Found C, 61.49; H, 7.82; N, 10.07; C$_{28}$H$_{42}$N$_4$O$_4$S. 0.75 H$_2$O requires C, 61.79; H, 8.06; N, 10.29%. |
| 20 | 69 | [-CH₂-N(CH₃)₂ ethyl] | $^1$H-NMR (CDCl$_3$) δ: 5.30(1H, d), 3.80(1H, d), 3.20(1H, t), 3.05 (2H, t), 2.90(2H, m), 2.80(2H, t), 2.25(6H, s), 2.20(1H, s), 2.00–1.85(4H, m), 1.70(6H, m), 1.50(1H, m), 1.30–1.00(5H, m). Analysis: Found C, 56.13; H, 8.44; N, 14.44; C$_{18}$H$_{32}$N$_4$O$_3$S requires C, 56.22; H, 8.39; N, 14.57%. Rotation: [α]$_D$ = −25.81° (c = 0.1, methanol). |
| 21 | 70 | H | $^1$H-NMR (CDCl$_3$) δ: 8.70(1H, s), 5.40(1H, d), 3.80(1H, d), 3.25 (1H, t), 2.95(2H, m), 2.30(1H, d), 2.00(4H, m), 1.80–1.60(6H, |

TABLE 2-continued

| Example no. | Starting material prep. no. | $R^{1A}$ | Analytical data |
|---|---|---|---|
| | | | m), 1.50(1H, m), 1.35–1.05(5H, m). Analysis: Found C, 53.61; H, 7.43; N, 13.09; $C_{14}H_{23}N_3O_3S$ requires C, 53.65; H, 7.40; N, 13.41%. Rotation: $[\alpha]_D = -27.60°$ (c = 0.1, methanol). |
| 22 | 71 | $CH_3$ | $^1$H-NMR (CDCl$_3$) δ: 5.30(1H, d), 3.80(1H, d), 3.25(1H, t), 2.95 (2H, m), 2.60(3H, s), 2.25(1H, d), 2.00(4H, m), 1.80–1.60(6H, m), 1.50(1H, m), 1.40–1.05(5H, m). Analysis: Found C, 55.19; H, 7.80; N, 12.40; $C_{15}H_{25}N_3O_3S$.0.1EtOAc requires C, 55.01; H, 7.73; N, 12.50%. Rotation: $[\alpha]_D = -26.70°$ (c = 0.1, methanol). |

EXAMPLE 23

3-[(2S)-1-Cyclohexylmethylsulfonyl-2-piperidyl]-5-[4-piperidyloxymethyl]-1,2,4-oxadiazole

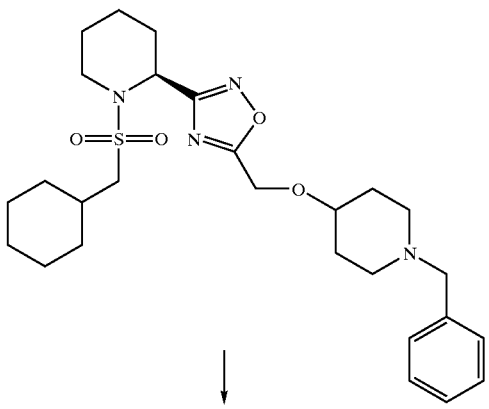

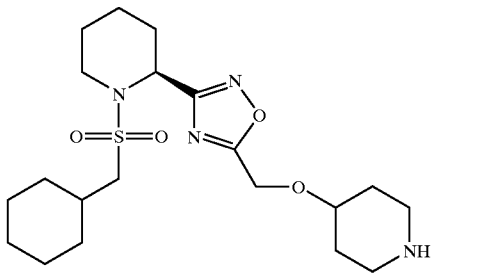

α-Chloroethyl chloroformate (95 μl) was added to a solution of 5-[(1-benzyl-4-piperidyl)oxymethyl]-3-[(2S)-1-cyclohexylmethylsulfonyl-2-piperidyl]-1,2,4-oxadiazole (325 mg) [see Example 16] in dichloromethane (20 ml) at 0° C. The reaction mixture was stirred for 1.5 hours after which time the dichloromethane was removed under reduced pressure and the residue dissolved in methanol. The mixture was then heated under reflux for 2 hours, the solvent removed under reduced pressure and the residue partitioned between diethyl ether and 2N aqueous hydrochloric acid solution. The aqueous layer was washed twice with diethyl ether and then neutralised (pH7) with sodium hydrogen carbonate. The aqueous layer was extracted with ethyl acetate, dried over magnesium sulphate and the solvent removed under reduced pressure to afford 3-[(2S)-1-cyclohexylmethylsulfonyl-2-piperidyl]-5-[4-piperidyloxymethyl]-1,2,4-oxadiazole (170 mg) as a brown oil.

$^1$H-NMR (CDCl$_3$) δ: 5.30 (1H, d), 4.80 (2H, s), 3.80 (1H, d), 3.60 (1H, m), 3.25 (1H, m), 3.15 (2H, m), 2.90 (2H, m), 2.75 (2H, m), 2.30 (1H, d), 2.00 (6H, m), 1.80–1.00 (15H, m). Analysis: Found C, 54.69; H, 8.06; N, 12.71; $C_{20}H_{34}N_4O_4S.0.2CH_2Cl_2$ requires C, 54.70; H, 7.82; N, 12.63%.

EXAMPLE 24

(3-[(2S)-1-Cyclohexylmethylsulfonyl-2-piperidyl]-1,2,4-oxadiazol-5-yl)(phenyl)methylamine

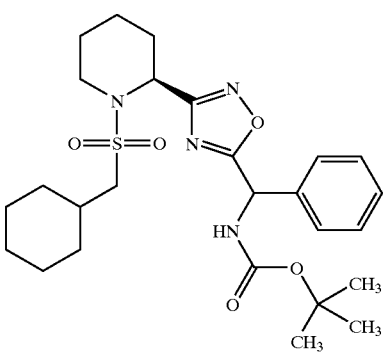

-continued

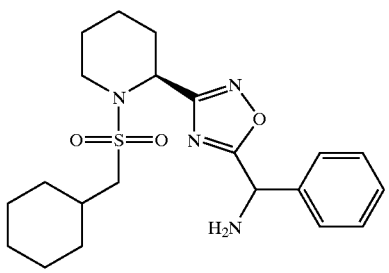

The title compound was prepared by the method of Preparation 7 from tert-butyl N-[(3-[(2S)-1-cyclohexylmethylsulfonyl-2-piperidyl]-1,2,4-oxadiazol-5-yl)(phenyl)methyl]carbamate [see Example 17]. The crude product was purified by high pressure liquid chromatography eluting with 30:70:0.1, by volume, acetonitrile:water:trifluoroacetic acid to afford (3-[(2S)-1-cyclohexylmethylsulfonyl-2-piperidyl]-1,2,4-oxadiazol-5-yl)(phenyl)methylamine as a colourless oil.

$^1$H-NMR (d$_4$-CH$_3$OH) δ: 7.50–7.30 (5H, m), 5.45 (1H, s), 5.25 (1H, s), 3.75 (1H, d), 3.30 (1H, m), 2.90 (2H, d), 2.25 (1H, d), 2.00–1.00 (18H, m). Accurate MS: 419.2123 (MH$^+$).

EXAMPLE 25

[5-(3-(2S)-1-[(Cyclohexylmethyl)sulfonyl]-2-piperidyl-1,2,4-oxadiazol-5-yl)-2-furyl]methylamine

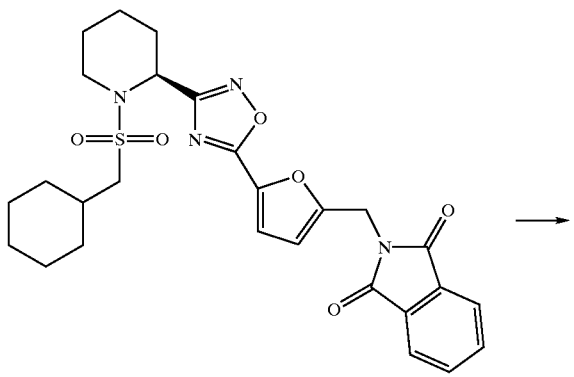

The title compound was prepared by a similar method to Example 11 from 2-[5-(3-(2S)-1-[(cyclohexylmethyl)sulfonyl]-2-piperidyl-1,2,4-oxadiazol-5-yl)-2-furyl]methyl-1,3-isoindolinedione [see Preparation 100] and methylamine. The crude product was purified by column chromatography on silica gel eluting with 95:5:0.5, by volume, dichloromethane:methanol:0.88 ammonia to afford [5-(3-(2S)-1-[(cyclohexylmethyl)sulfonyl]-2-piperidyl-1,2,4-oxadiazol-5-yl)-2-furyl]methylamine as a solid.

$^1$H-NMR (d4-MeOH) δ: 7.40 (1H, d), 6.60 (1H, d), 5.30 (1H, d), 3.90 (2H, s), 3.80 (1H, d), 3.30 (1H, m), 3.05 (2H, m), 2.30 (1H, d), 2.00–1.90 (4H, m), 1.80–1.60 (7H, m), 1.40–1.00 (5H, m). Accurate MS: Found 409.1928 (MH$^+$). C$_{19}$H$_{28}$N$_4$O$_4$S requires 409.1910 (MH$^+$).

EXAMPLE 26

Benzyl N-(2-(3-[1-(1H-Benzo[d]imidazol-2-ylsulfonyl)-2-piperidyl]-1,2,4-oxadiazol-5-yl)ethyl) carbamate

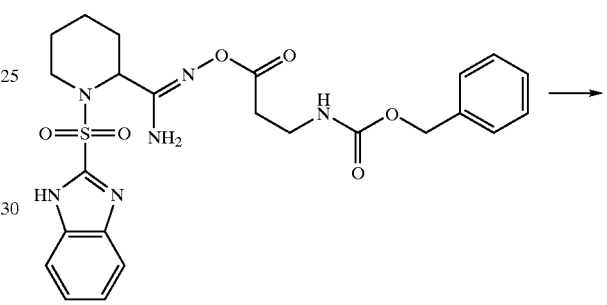

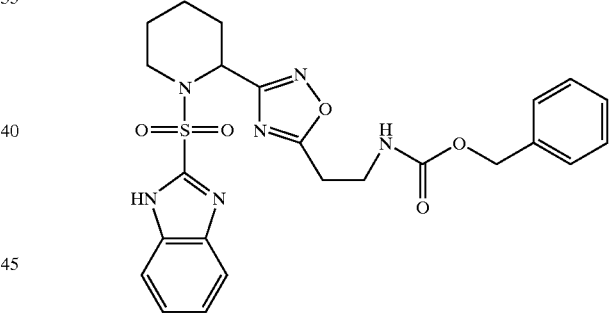

The title compound was prepared by a similar method to Example 16 from the compound of Preparation 37 and pyddine. The crude product was purified by column chromatography on silica gel eluting with a 'solvent gradient of 70:30 changing to 60:40, by volume, hexane:ethyl acetate to afford benzyl N-(2-(3-[1-(1H-benzo[d]imidazol-2-ylsulfonyl)-2-piperidyl]-1,2,4-oxadiazol-5-yl)ethyl) carbamate as a colourless oil.

$^1$H-NMR (d$_6$-DMSO) δ: 13.60 (1H, bs), 7.80 (1H, bs), 7.60 (1H, bs), 7.30 (7H, m), 5.40 (1H, d), 5.00 (2H, s), 3.90 (2H, d), 3.140 (1H, d), 3.20 (2H, t), 2.75 (2H, m), 2.00 (1H, d), 1.80 (1H, m), 1.60 (1H, d), 1.50–1.20 (2H, m). Analysis: Found C, 55.48; H, 5.22; N, 15.57; C$_{24}$H$_{26}$N$_6$O$_5$S.0.1EtOAc.0.5H$_2$O requires C, 55.46; H, 5.30; N, 15.90%. (EtOAc=ethyl acetate).

EXAMPLE 27

2-(3-[1-(1H-Benzo[d]imidazol-2-ylsulfonyl)-2-piperidyl]-1,2,4-oxadiazol-5-yl)ethylamine

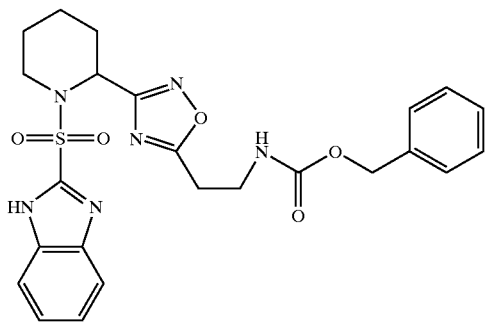

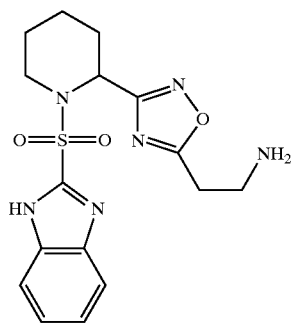

Benzyl N-(2-(3-[1-(1H-benzo[d]imidazol-2-ylsulfonyl)-2-piperidyl]-1,2,4-oxadiazol-5-yl)ethyl)carbamate (1.88 g) [see Example 26] was dissolved in 45% w/w hydrogen bromide in glacial acetic acid (30 ml). The reaction mixture was stirred at room temperature for 3.5 hours after which time the mixture was diluted with water and washed with diethyl ether. The aqueous layer was then basified with potassium carbonate and then extracted with ethyl acetate. The organic layer was dried over magnesium sulphate, and the solution was left to stand for 18 hours after which time a solid had formed. This was filtered off to afford 2-(3-[1-(1H-benzo[d]imidazol-2-ylsulfonyl)-2-piperidyl]-1,2,4-oxadiazol-6-yl)ethylamine (0.71g) as a white solid.

$^1$H-NMR (CDCl$_3$) δ: 11.50 (1H, s), 7.80 (4H, d), 5.60 (1H, s), 4.00 (1H, d), 3.80 (2H, d), 3.45 (3H, m), 3.30 (1H, m), 2.60 (1H, d), 2.20 (1H, m), 1.90–1.60 (3H, m), 1.40 (1H, m). Analysis: Found C, 48.93; H, 5.25; N, 21.09; C$_{16}$H$_{20}$N$_6$SO$_3$.0.9H$_2$O requires C, 48.94; H, 5.60; N, 21.40%.

EXAMPLE 28

N-(2-(3-[1-(1H-Benzo[d]imidazol-2-ylsulfonyl)-2-piperidyl]-1,2,4-oxadiazol-5-yl)ethyl)benzylamine

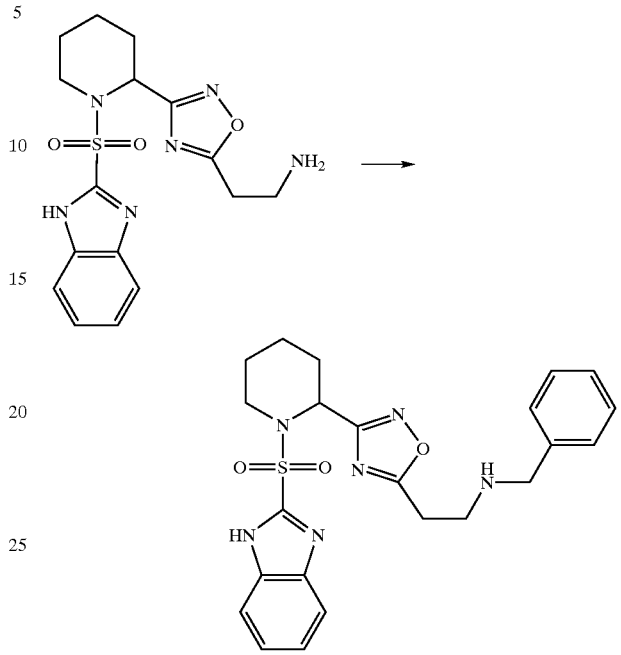

The title compound was prepared by a similar method to Example 13 from 2-(3-[1-(1H-benzo[d]imidazol-2-ylsulfonyl)-2-piperidyl]-1,2,4-oxadiazol-5-yl)ethylamine [see Example 27] and benzaldehyde. The crude product was purified by column chromatography on silica gel eluting with a solvent gradient of 99:1 changing to 98:2, by volume, dichloromethane:methanol to afford N-(2-(3-[1-(1H-benzo[d]imidazol-2-ylsulfonyl)-2-piperidyl]-1,2,4-oxadiazol-5-yl)ethyl)-benzylamine.

$^1$H-NMR (d$_4$-CH$_3$OH) δ: 7.60 (2H, d), 7.40–7.20 (7H, m), 5.45 (1H, d), 4.10 (1H, d), 3.60 (2H, s), 3.40 (1H, t), 2.60 (4H, m), 2.10 (1H, d), 2.00 (1H, m), 1.70 (1H, m), 1.50 (3H, m). Analysis: Found C, 57.42; H, 5.61; N, 17.43; C$_{23}$H$_{26}$N$_6$O$_3$S.0.8H$_2$O requires C, 57.44; H, 5.78; N, 17.47%.

EXAMPLE 29

2-[(2S)-1-[(4-Fluorophenyl)sulfonyl]-2-piperidyl]-5-methyl-1,3,4-thiadiazole

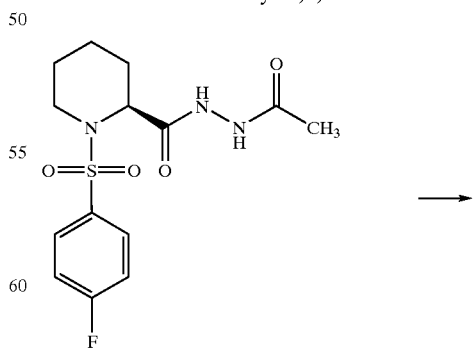

43

-continued

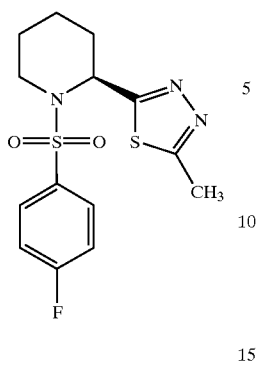

Lawesson's reagent (2,4-bis(4-methoxyphenyl)-1,3-dithia-2,4-diphosphetane-2,4-disulphide] (271 mg) was added to a solution of N'2-acetyl-(2S)-1-[(4-fluorophenyl)sulfonyl]-2-piperidinecarbohydrazide (192 mg) [see Preparation 39] in toluene (10 ml). The reaction mixture was heated under reflux for 3 hours and the cooled mixture was then purified by column chromatography on silica gel eluting with a solvent gradient of 0:100 changing to 30:70 (in 10% increments), by volume, hexane:ethyl acetate, to afford 2-[(2S)-1-[(4-fluorophenyl)sulfonyl]-2-piperidyl]-5-methyl-1,3,4-thiadiazole (106 mg) as a clear oil.

$^1$H-NMR (CDCl$_3$) δ: 7.85 (2H, m), 7.20 (2H, m), 5.60 (1H, s), 3.90 (1H, d), 3.20 (1H, t), 2.80 (3H, s), 2.40 (1H, d), 1.80–1.40 (5H, m). Analysis: Found C, 48.07; H, 4.63; N, 11.60; C$_{14}$H$_{16}$N$_3$O$_2$S.0.5H$_2$O requires C, 47.98; H, 4.89; N, 11.99%. Rotation: [α]$_D^{25}$=−64.01°. (c=0.1, methanol).

EXAMPLE 30

(2S)-2-(1-Benzyl-1H-1,2,4-triazol-3-yl)-1-[(4-fluorophenyl)sulfonyl]piperidine

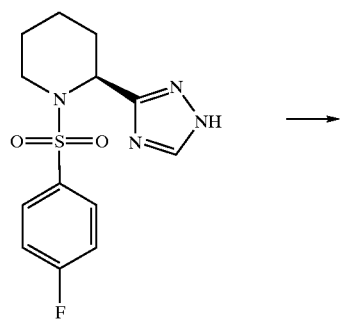

44

-continued

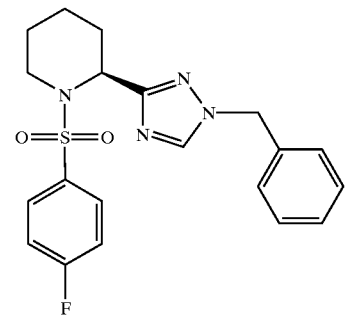

Benzyl bromide (40 μl) was added to a solution of (2S)-1-[(4-fluorophenyl)sulfonyl]-2-(1H-1,2,4-triazol-3-yl)piperidine (95 mg) [see Preparation 42] and potassium carbonate (47 mg) in dimethylformamide (5 ml). The reaction mixture was stirred at 50° C. for 7 hours, after which time the solvent was removed under reduced pressure and the residue diluted with ethyl acetate. The organic solution was washed with water, dried over magnesium sulphate and the solvent removed under reduced pressure. The crude product was purified by column chromatography on silica gel eluting with 100:0 changing to 50:50, by volume, hexane:ethyl acetate (in 10% increments), to afford (2S)-2-(1-benzyl-1H-1,2,4-triazol-3-yl)-1-[(4-fluorophenyl)sulfonyl]piperidine (35 mg) as a white solid.

$^1$H-NMR (CDCl$_3$) δ: 7.70 (1H, s), 7.60 (2H, t), 7.40 (2H, d), 7.20 (3H, m), 6.80 (2H, t), 5.40 (1H, s), 5.10 (2H, s), 3.80 (1H, d), 3.40 (1H, t), 2.05 (1H, m), 1.90 (1H, m), 1.70–1.50 (4H, m). Analysis: Found C, 59.42; H, 5.25; N, 13.66; C$_{20}$H$_{21}$N$_4$O$_2$S.0.05CH$_2$Cl$_2$ requires C, 59.50; H, 5.25; N, 13.84%.

EXAMPLE 31

(2S)-2-(5-Benzyl-4-methyl-4H-1,2,4-triazol-3-yl)-1-[(4-fluorophenyl)sulfonyl]piperidine

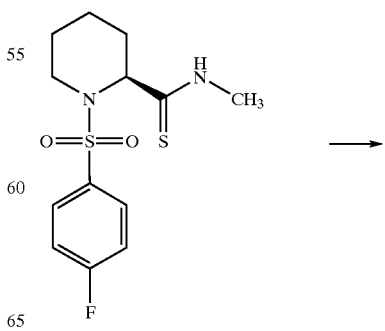

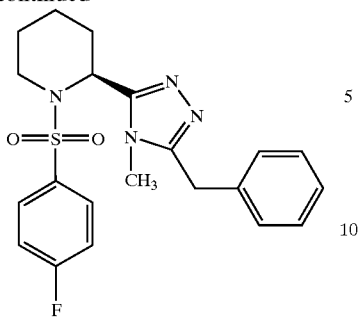

Phenylacetic hydrazide (180 mg) was added to a solution of N2-methyl-(2S)-1-[(4-fluorophenyl)sulfonyl]-2-piperidinecarbothioamide (270 mg) [see Preparation 44] and mercuric oxide (202 mg) in 1,4-dioxane (10 ml). The reaction mixture was heated under reflux and stirred for 18 hours. The dioxane was then removed under reduced pressure and dimethylacetamide (10 ml) added followed by phenylacetic hydrazide (180 mg) and mercuric oxide (202 mg). The reaction mixture was heated to 140° C. and stirred for 18 hours. After this time the solvent was removed under reduced pressure and the residue partitioned between ethyl acetate and water. The organic layer was separated and washed with 1N aqueous hydrochloric acid solution, dried over magnesium sulphate and the solvent was removed under reduced pressure. The crude product was purified by column chromatography on silica gel eluting with a solvent gradient of 100:0 changing to 0:100, by volume, hexane-:ethyl acetate (in 10% increments). The product was further purified on a MCI (trade mark) reverse phase gel column eluting with a solvent gradient of 50:50 changing to 0:100 (in 5% increments), by volume, water: methanol. This gave (2S)-2-(5-benzyl-4-methyl-4H-1,2,4-triazol-3-yl)-1-[(4-fluorophenyl)sulfonyl]piperidine (57 mg) as a yellow solid.

$^1$H-NMR (CDCl$_3$) δ: 7.60 (2H, d), 7.30 (2H, m), 7.25 (1H, m), 7.20 (2H, d). 7.10 (2H, t), 5.10 (1H, s), 4.10 (2H, s), 3.60 (1H, d), 3.50 (3H, s), 3.40 (1H, t), 2.25 (1H, m), 2.00 (1H, d), 1.75 (1H, m), 1.50 (2H, m), 1.25 (1H, m). Rotation: $[\alpha]_D^{25}$=0.21° (c=0.1, methanol). Analysis: Found C, 60.44; H, 5.56; N, 13.33; C$_{21}$H$_{23}$FN$_4$O$_2$S requires C, 60.85; H, 5.59; N, 13.52%.

EXAMPLE 32

2-Amino-5-[(2S)-1-[(4-fluorophenyl)sulfonyl]-2-piperidyl]-1,3,4-oxadiazole

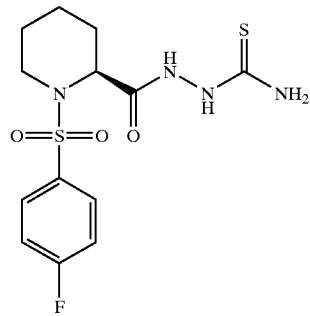

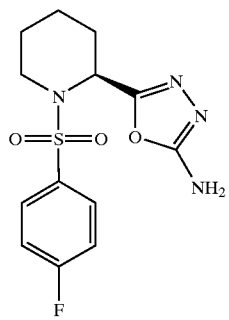

Mercuric oxide (204 mg) was added to a solution of 2-((2S)-1-[(4-fluorophenyl)sulfonyl]-2-piperidylcarbonyl)-1-hydrazinecarbothioamide (170 mg) [see Preparation 45] in 1,4-dioxane (5 ml). The reaction mixture was heated under reflux and stirred for 4 hours. The resulting suspension was filtered through a plug of ARBOCEL (trade mark) filter aid, washing with dichloromethane:methanol (90:10, by volume). The filtrate was evaporated under reduced pressure and purified by column chromatography on silica gel eluting with, 100:0 changing to 90:10 (in 5% increments), by volume, dichloromethane:methanol. The product was further purified by column chromatography on silica gel eluting with 0:100 changing to 60:40, by volume, ethyl acetate:hexane, to afford 2-amino-5-[(2S)-1-[(4-fluorophenyl)sulfonyl]-2-piperidyl]-1,3,4-oxadiazole (64 mg) as a white solid.

$^1$H-NMR (CDCl$_3$) δ: 7.80 (2H, m), 7.10 (2H, m), 5.30 (1H, s), 5.00 (2H, s), 3.80 (1H, d), 3.10 (1H, t), 2.10 (1H, d), 1.90–1.60 (5H, m). Rotation: $[\alpha]_D^{25}$=−39.21° (c=0.1, methanol). Analysis: Found C, 47.49; H, 4.59; N, 16.79; C$_{13}$H$_{15}$FN$_4$O$_3$S.0.2H$_2$O requires C, 47.32; H, 4.70; N, 16.98%.

EXAMPLE 33

2-Benzylamino-5-[(2S)-1-[(4-fluorophenyl)sulfonyl]-2-piperidyl]-1,3,4-oxadiazole

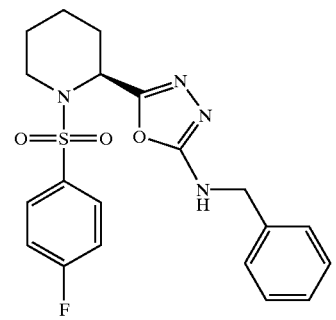

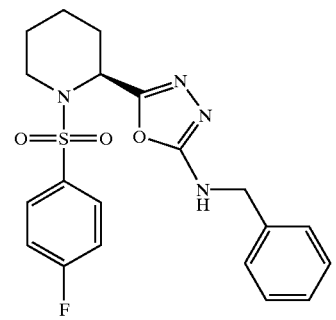

Benzaldehyde (101 μl) was added to a solution of 2-amino-5-[(2S)-1-[(4-fluorophenyl)sulfonyl]-2-piperidyl]-

1,3,4-oxadiazole (163 mg) [see Example 32] in tetrahydrofuran (2 ml), followed by acetic acid (172 μl) and sodium triacetoxyborohydride (297 mg). The reaction mixture was stirred at room temperature for 18 hours, after which time the solvent was removed under reduced pressure and the residue partitioned between dichloromethane and saturated aqueous sodium hydrogen carbonate solution. The organic layer was separated, dried over magnesium sulphate and the solvent removed under reduced pressure. The crude product was purified by column chromatography on silica gel eluting with a solvent gradient of 0:100 changing to 40:60 (in 10% increments), by volume, ethyl acetate:hexane, to afford 2-benzylamino-5-[(2S)-1-[(4-fluorophenyl)sulfonyl]-2-piperidyl]-1,3,4-oxadiazole (6 mg) as a white solid.

$^1$H-NMR (CDCl$_3$) δ: 7.80 (2H, m), 7.35 (5H, m), 7.05 (2H, t), 5.25 (1H, s), 5.00 (1H, s), 4.40 (2H, s), 3.70 (1H, d), 3.10 (1H, t), 2.05 (1H, t), 1.80 (1H, m), 1.50–1.35 (4H, m). MS: 417 (MH$^+$).

EXAMPLE 34

5-[(2S)-1-[(4-Fluorophenyl)sulfonyl]-2-piperidyl]-3-methylisoxazole

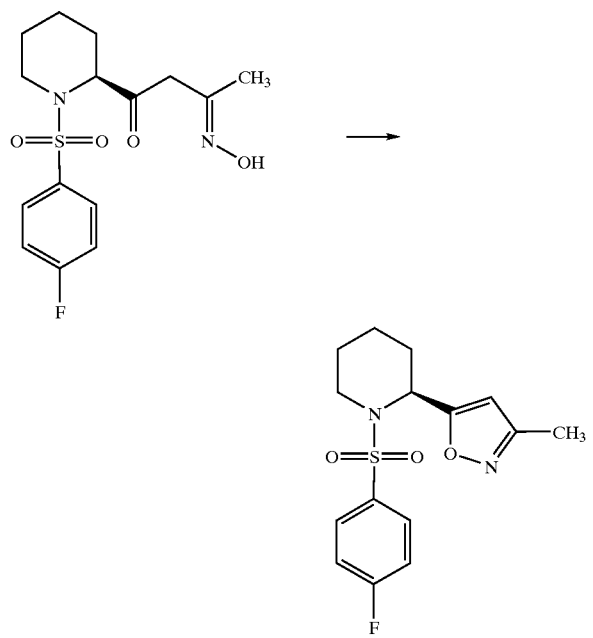

Mesyl chloride (57 μl) was added to a solution of the compound of Preparation 47 (211 mg) and triethylamine (111 μl) in dichloromethane (4 ml) at 0° C. The reaction mixture was stirred at room temperature for 18 hours. After this time the mixture was purified by column chromatography on silica gel eluting with a solvent gradient of 0:100 changing to 10:90 (in 5% increments), by volume, ethyl acetate:hexane. The product was further purified by column chromatography on silica gel as above to afford 5-[(2S)-1-[(4-fluorophenyl)sulfonyl]-2-piperidyl]-3-methylisoxazole (26 mg) as a clear oil.

$^1$H-NMR (CDCl$_3$) δ: 7.80 (2H, t), 7.10 (2H, t), 5.80 (1H, s), 5.30 (1H, d), 3.75 (1H, d), 3.05 (1H, t), 2.20 (3H, s), 2.10 (1H, d), 1.80 (1H, m), 1.60 (2H, m), 1.40 (2H, m). Rotation: [α]$_D^{25}$=−49.61 ° (c=0.1, methanol). MS: 325 (MH$^+$).

EXAMPLE 35

5-Benzyl-3-[(2S)-1-[(4-fluorophenyl)sulfonyl]-2-pyrrolidyl]-1,2,4-oxadiazole

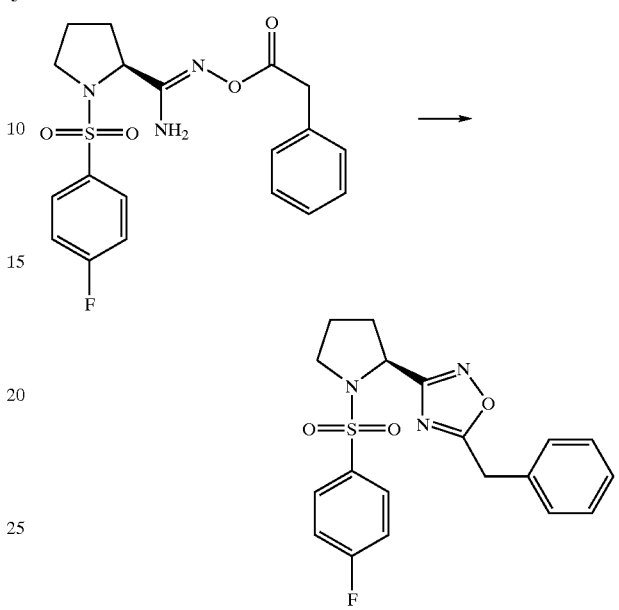

The title compound was prepared by a similar method to Preparation 6 from the compound of Preparation 53 and xylene. The crude product was purified by column chromatography on silica gel eluting with a solvent gradient of 0:100 changing to 30:70, by volume, ethyl acetate:hexane. This gave 5-benzyl-3-[(2S)-1-[(4-fluorophenyl)sulfonyl]-2-pyrrolidyl]-1,2,4-oxadiazole as a colourless oil.

$^1$H-NMR (CDCl$_3$) δ: 7.80 (2H, t), 7.40 (5H, m), 7.05 (2H, t), 5.00 (1H, d), 4.15 (2H, s), 3.50 (2H, m), 2.20 (3H, m), 1.90 (1H, m). Rotation: [α]$_D^{25}$=−100.22° (c=0.1, methanol). Analysis: Found C, 58.24; H, 4.65; N, 10.64; C$_{19}$H$_{18}$N$_3$FO$_3$S.0.05CH$_2$Cl$_2$ requires C, 58.42; H, 4.66; N, 10.73%.

EXAMPLE 36 TO 39

The compounds of the following tabulated Examples (Table 3) of the general formula:

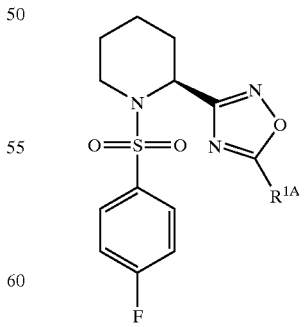

were prepared by a similar method to Preparation 6, either from the corresponding hydroxyamidine derivative and xylene (Examples 36,38) or from the corresponding hydroxyamidine derivative and pyridine (Examples 37,39).

TABLE 3

| Example No. | Starting material prep. No. | R¹ᴬ | Analytical data |
|---|---|---|---|
| 36 | 74 | 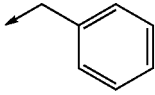 | ¹H-NMR (CDCl₃) δ: 7.70(2H, m), 7.40–7.20(5H, m), 6.90(2H, t), 5.40(1H, d), 4.10(2H, s), 3.80(1H, d), 3.30(1H, t), 2.00(2H, m), 1.80–1.60(4H, m). Analysis: Found C, 59.72; H, 4.83; N, 10.34; $C_{20}H_{20}N_3O_3SF$ requires C, 59.84; H, 5.02; N, 10.47%. |
| 37 | 75 | 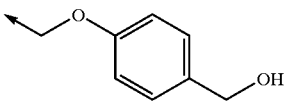 | ¹H-NMR (CDCl₃) δ: 7.70(2H, m), 7.30(2H, d), 7.00(2H, t), 6.95(2H, d), 5.40(1H, d), 5.15(2H, s), 4.60 (2H, d), 3.80(1H, d), 3.25(1H, t), 2.10(1H, m), 2.00(1H, m), 1.70–1.40(4H, m). Analysis: Found C, 55.22; H, 4.88; N, 8.98; $C_{21}H_{22}N_3O_5SF.0.5\ H_2O$ requires C, 55.25; H, 5.08; N, 9.20%. |
| 38 | 76 | 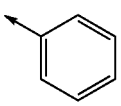 | ¹H-NMR (CDCl₃) δ: 8.00(2H, d), 7.75(2H, m), 7.55(1H, m), 7.50 (2H, m), 7.00(2H, m), 5.45(1H, d), 3.80(1H, d), 3.40(1H, t), 2.20(1H, d), 2.00(1H, m), 1.80–1.50(4H, m). Analysis: Found C; 58.87; H, 4.60; N, 10.72; $C_{19}H_{18}N_3O_3SF$ requires C, 58.90; H, 4.68; N, 10.85%. Rotation: $[\alpha]_D = -33.21°$ (c = 0.1, methanol). |
| 39 | 97 | 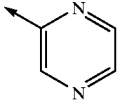 | ¹H-NMR (CDCl₃) δ: 9.25(1H, s), 8.80(2H, m), 7.80(2H, m), 7.00 (2H, m), 5.50(1H, d), 3.85(1H, d), 3.40(1H, t), 2.20(1H, d), 2.00(1H, m), 1.80–1.40(4H, m). Analysis: Found C, 52.50; H, 4.09; N, 17.85; $C_{17}H_{16}N_5O_3SF$ requires C, 52.44; H, 4.14; N, 17.98%. Rotation: $[\alpha]_D = -55.61°$ (c = 0.1, methanol). |

EXAMPLE 40

2-(1S)-2-[(4-Fluorophenyl)sulfonyl]cyclohexyl-5-methyl-1,3,4-oxadiazole

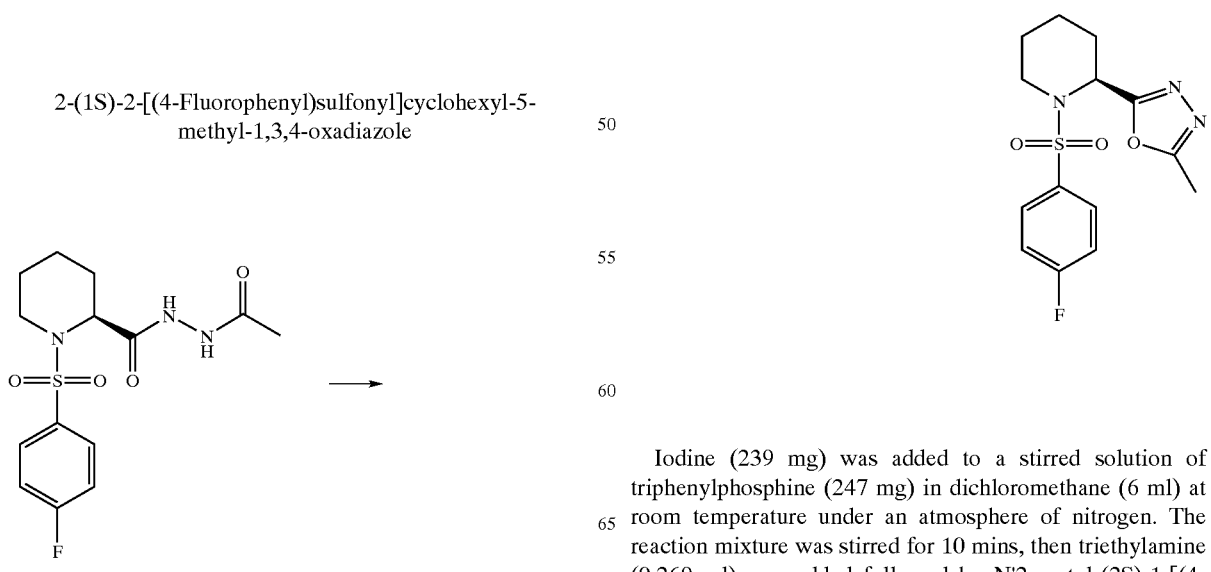

Iodine (239 mg) was added to a stirred solution of triphenylphosphine (247 mg) in dichloromethane (6 ml) at room temperature under an atmosphere of nitrogen. The reaction mixture was stirred for 10 mins, then triethylamine (0.269 ml) was added followed by N'2-acetyl-(2S)-1-[(4- fluorophenyl)sulfonyl]-2-piperidinecarbohydrazide (160 mg) [see Preparation 39] in dichloromethane (2 ml). The reaction mixture was stirred for 18 hrs, after which time the solvent was removed under reduced pressure. The crude product was pre-absorbed onto silica gel and purified by column chromatography on silica gel eluting with a solvent gradient of 0:100 changing to 30:70, by volume, ethyl acetate:hexane, to afford 2-(1S)-2-[(4-fluorophenyl) sulfonyl]cyclohexyl-5-methyl-1,3,4-oxadiazole (87 mg) as an oil.

$^1$H-NMR (CDCl$_3$) δ: 7.80 (2H, m), 7.20 (2H, m), 5.40 (1H, m), 3.80 (1H, d), 3.20 (1H, t), 2.40 (3H, s), 2.15 (1H, d), 2.00 (1H, m), 1.80–1.50 (4H, m). Analysis: Found C, 51.52; H, 4.97; N, 12.57; C$_{14}$H$_{16}$N$_3$O$_3$SF requires C, 51.68; H, 4.96; N, 12.91%. Rotation: [α]$_D^{25}$=−71.41° (c=0.1, methanol).

EXAMPLE 41 AND 42

The compounds of the following tabulated Examples (Table 4) of the general formula:

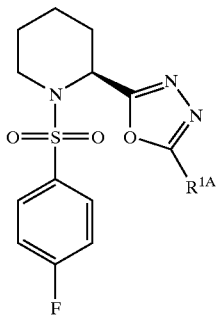

were prepared by a similar method to Example 40 from the corresponding hydrazide, iodine, triphenylphosphine and triethylamine.

EXAMPLE 43 AND 44

The compounds of the following tabulated Examples (Table 5) of the general formula:

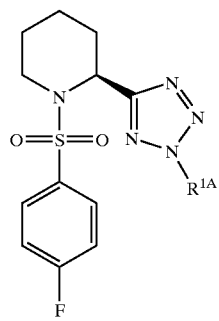

were prepared by a similar method to Example 30. Example 43 was prepared from (2S)-1-[(4-Fluorophenyl)sulfonyl]-2-(2H-1,2,3,4-tetraazol-5-yl)piperidine [see Preparation 79] and benzyl bromide. Example 44 was prepared from (2S)-1-[(4-Fluorophenyl)sulfonyl]-2-(2H-1,2,3,4-tetraazol-5-yl) piperidine [see Preparation 79] and methyl iodide.

Purification of both Examples was achieved by chromatography on silica, eluting with 100:0, changing to 75:25, by volume, ethyl acetate:hexane, with desired product isolated as the less polar regioisomer

TABLE 4

| Example No. | Starting material prep. No. | R$^{1A}$ | Analytical data |
|---|---|---|---|
| 41 | 77 | benzyl | $^1$H-NMR (CDCl$_3$) δ: 7.75(2H, m), 7.45–7.20(5H, m), 7.00(2H, t), 5.40(1H, d), 4.10(2H, d), 3.80(1H, d), 3.20(1H, t), 2.20–1.90(2H, m), 1.80–1.50(4H, m), Analysis: Found C, 58.43; H, 4.98; N, 10.06; C$_{20}$H$_{20}$N$_3$O$_3$SF.0.15 CH$_2$Cl$_2$ requires C, 58.43; H, 4.94; N, 10.14%. Rotation: [α]$_D$ = −42.01° (c = 0.1, methanol). |
| 42 | 78 | phenethyl | $^1$H-NMR (CDCl$_3$) δ: 7.75(2H, m), 7.30–7.10(7H, m), 5.40(1H, s), 3.80(1H, d), 3.20–3.00(5H, m), 2.10(1H, d), 2.00(1H, m), 1.70–1.50(4H, m). Analysis: Found C, 58.40; H, 5.18; N, 9.57; C$_{21}$H$_{22}$N$_3$O$_3$SF.0.1CH$_2$Cl$_2$.0.5H$_2$O requires C, 58.53; H, 5.40; N, 9.70%. Rotation: [α]$_D$ = −49.41° (c = 0.1, methanol). |

TABLE 5

| Example No. | Starting material Prep. No. | $R^{1A}$ | Analytical data |
|---|---|---|---|
| 43 | 79 | benzyl (CH₂-phenyl) | $^1$H-NMR (CDCl$_3$) δ: 7.60(2H, m), 7.40–7.30(5H, m), 6.80(2H, t), 5.60(3H, m), 3.85(1H, d), 3.35(1H, t), 2.05(2H, m), 1.80–1.60(4H, m). Analysis: Found C, 56.64; H, 4.98; N, 17.34; C$_{19}$H$_{20}$N$_5$O$_2$SF requires C, 56.84; H, 5.02; N, 17.44%. Rotation: $[\alpha]_D = -37.3°$ (c = 0.1, methanol). |
| 44 | 79 | CH$_3$ | $^1$H-NMR (CDCl$_3$) δ: 7.70(2H, m), 7.05 (2H, t), 5.60(1H, s), 4.20(3H, s), 3.85 (1H, d), 3.35(1H, t), 2.05(2H, m), 1.80–1.60(4H, m). Analysis: Found C, 47.69; H, 4.89; N, 21.27; C$_{13}$H$_{16}$N$_5$O$_2$SF requires C, 47.99; H, 4.96; N, 21.52%. Rotation: $[\alpha]_D = -54.34°$ (c = 0.1, methanol). |

EXAMPLE 45

(2S)-1-[(4-Fluorophenyl)sulfonyl]-2-(5-methyl-4H-1,2,4-triazol-3-yl)piperidine

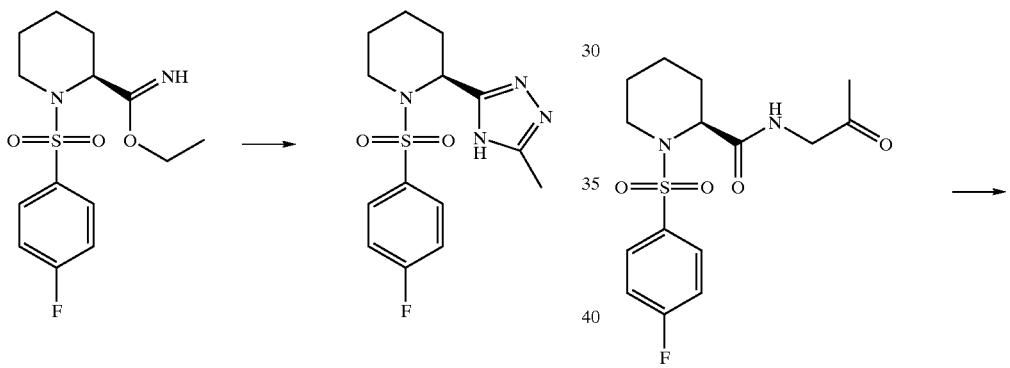

Acetyl chloride (91 ml) was added to a stirred solution of ethyl (2S)-1-[(4-fluorophenyl)sulfonyl]-2-piperidinecarboximidate (288 mg) [see Preparation 41] and triethylamine (178 ml) in toluene (5 ml). The reaction mixture was stirred at room temperature for 1 hr after which time hydrazine hydrate (62 ml) was added. The mixture was stirred for 18 hrs and then poured into a column containing silica gel, and the product eluted with a solvent gradient of 1:1, by volume, ethyl acetate: hexane followed by 95:5 ethyl acetate:methanol. The fractions containing the product were combined and the solvent removed under reduced pressure, the remaining residue was dissolved in toluene (10 ml) and the reaction mixture was heated to reflux for 1 hr. Tosic acid (5 mg) was then added and the mixture was heated to reflux for a further 18 hrs. The cooled reaction mixture was then purified by column chromatography on silica gel eluting with a solvent gradient of 1:1, changing to 0:100, by volume, hexane:ethyl acetate, in 10% increments, to afford (2S)-1-[(4-fluorophenyl)sulfonyl]-2-(5-methyl-4H-1,2,4-triazol-3-yl)piperidine (60 mg) as a white solid.

$^1$H-NMR (CDCl$_3$) δ: 7.80 (2H, m), 7.15 (2H, t), 5.30 (1H, s), 3.80 (1H, d), 3.30 (1H, bs), 2.40 (3H, s), 2.30 (1H, d), 1.80 (1H, bs), 1.50 (3H, m), 1.45 (1H, m). Analysis: Found C, 51.53; H, 5.25; N, 17.15; C$_{14}$H$_{17}$N$_4$O$_2$SF requires C, 51.84; H, 5.28; N, 17.27%. Rotation: $[\alpha]_D^{25} = -136.76°$ (c=1.0, methanol).

EXAMPLE 46

(2S)-1-[(4-Fluorophenyl)sulfonyl]-2-(5-methyl-1,3-thiazol-2-yl)piperidine

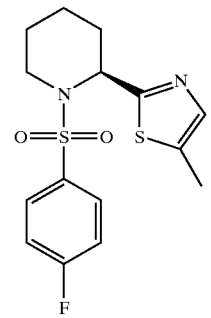

The title compound was prepared by a similar method to Example 29 from (2S)-1-[(4-fluorophenyl)sulfonyl]-N$^2$-(2-oxopropyl)-2-piperidinecarboxamide [see Preparation 81] and Lawesson's reagent. The crude product was purified by column chromatography on silica gel eluting with a solvent gradient of 100:0 changing to 75:25, by volume, hexane-:ethyl acetate, in 5% increments, to afford (2S)-1-[(4-fluorophenyl)sulfonyl]-2-(5-methyl-1,3-thiazol-2-yl) piperidine as a white solid.

¹H-NMR (CDCl₃) δ: 7.85 (2H, m), 7.25 (1H, s), 7.20 (2H, t), 5.40 (1H, d), 3.90 (1H, d), 3.25 (1H, t), 2.45 (3H, s), 2.40 (1H, d), 1.80 (1H, m), 1.60 (3H, m), 1.40 (1H, m). Analysis: Found C, 52.78; H. 5.03; N, 8.12; $C_{15}H_{17}N_2O_2S_2F$ requires C, 52.92; H, 5.03; N, 8.23%. Rotation: $[\alpha]_D^{25}$=−47.32° (c=0.1, methanol).

EXAMPLE 47

(2S)-1-[(4-Fluorophenyl)sulfonyl]-2-(3-methyl-1,2,4-oxadiazol-5-yl)piperidine

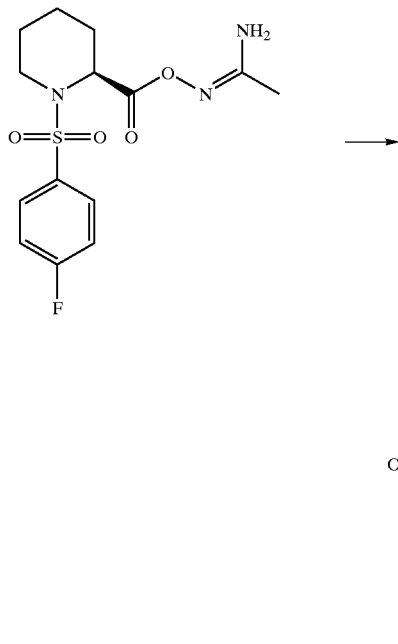

The title compound was prepared by a similar method to Preparation 6 from N'¹-[((2S)-1-[(4-fluorophenyl)sulfonyl]-2-piperidylcarbonyl)oxy]ethanimidamide [see Preparation 82] and xylene. The crude product was purified by column chromatography on silica gel eluting with a solvent gradient of 100:0 changing to 80:20, by volume, hexane:ethyl acetate in 10% increments, to afford (2S)-1-[(4-fluorophenyl) sulfonyl]-2-(3-methyl-1,2,4-oxadiazol-5-yl)piperidine as an oil.

¹H-NMR (CDCl₃) δ: 7.75 (2H, m), 7.10 (2H, t), 5.50 (1H, d), 3.85 (1H, d), 3.30 (1H, t), 2.25 (3H, s), 2.05 (2H, m), 1.80–1.60 (3H, m), 1.50 (1H, m). Analysis: Found C, 51.30; H, 4.89; N, 12.38; $C_{14}H_{16}N_3O_3SF.0.25H_2O$ requires C, 50.98; H, 5.04; N, 12.74%. Rotation: $[\alpha]_D^{25}$=−71.01° (c=0.1, methanol).

EXAMPLE 48

N²-Cyclohexyl-5-(2S)-1-[(4-fluorophenyl)sulfonyl]-2-piperidyl-1,3,4-oxadiazol-2-amine

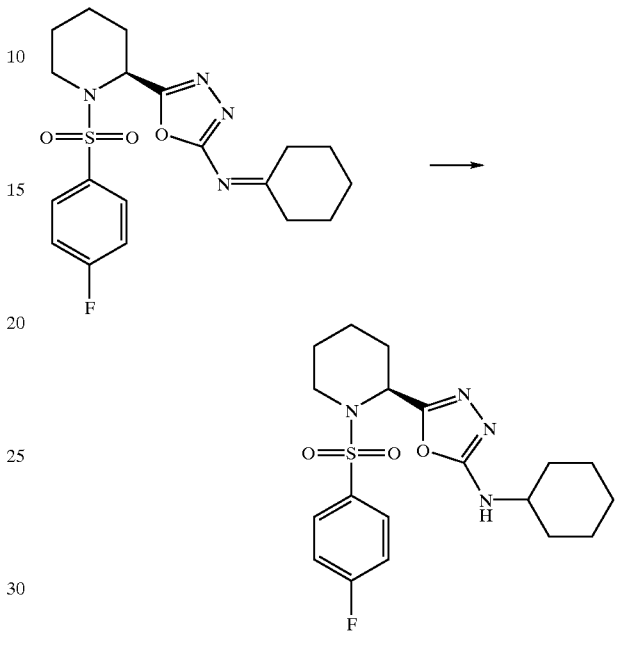

Sodium borohydride (71 mg) was added to a stirred solution of N²-cyclohexyliden-5-(2S)-1-[(4-fluorophenyl) sulfonyl]-2-piperidyl-1,3,4-oxadiazol-2-amine [see Preparation 83] in ethanol (15 ml) and methanol (5 ml). The reaction mixture was stirred for 3 hrs after which time further sodium borohydride (30 mg) was added to the mixture. The mixture was stirred for a further 18 hrs and then the solvent was removed under reduced pressure, the residue was partitioned between dichloromethane and 1N aqueous hydrochloric acid. The aqueous layer was separated and basified to pH 8 with 0.88 aqueous ammonia, the product was re-extracted with dichloromethane, dried over magnesium sulphate and the solvent was removed under reduced pressure. The crude product was purified by column chromatography on silica gel eluting with a solvent gradient of 100:0 changing to 50:50, by volume, hexane:ethyl acetate, in 5% increments, to afford N²-cyclohexyl-5-(2S)-1-[(4-fluorophenyl) sulfonyl]-2-piperidyl-1,3,4-oxadiazol-2-amine (59 mg) as a white gum.

¹H-NMR (CDCl₃) δ: 7.75 (2H, m), 7.10 (2H, t), 5.25 (1H, d), 4.30 (1H, d), 3.75 (1H, d), 3.40 (1H, m), 3.10 (1H, t), 2.00 (3H, m), 1.85 (1H, m), 1.70–1.60 (5H, m), 1.40 (2H, m), 1.25 (4H, m), 0.95 (1H, m). Analysis: Found C, 55.28; H, 6.35; N, 12.22; $C_{19}H_{25}N_4O_3SF0.3hexane.H_2O$ requires C, 55.52; H, 6.45; N, 12.45%. Rotation: $[\alpha]_D^{25}$=−13.00° (c=0.1, methanol).

EXAMPLE 49

2-[4-(3-[1-(1H-Benzo[d]imidazol-2-ylsulfonyl)-2-piperidyl]-1,2,4-oxadiazol-5-ylmethyl)phenoxy]ethylamine

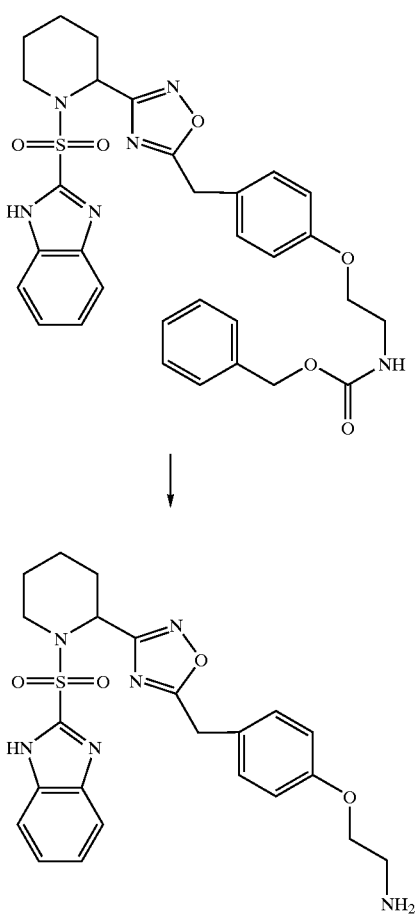

The title compound was prepared by a similar method to Example 27 from benzyl N-(2-[4-(3-[1-(1H-benzo[d]imidazol-2-ylsulfonyl)2-piperidyl]-1,2,4-oxadiazol-5-ylmethyl)phenoxy]ethyl)carbamate [see Preparation 56] and 45% w/w hydrogen bromide in glacial acetic acid to afford 2-[4-(3-[1-(1H-benzo[d]imidazol-2-ylsulfonyl)-2-piperidyl]-1,2,4-oxadiazol-5-ylmethyl)phenoxy]ethylamine as a white solid.

$^1$H-NMR (CDCl$_3$) δ: 7.40 (2H, m), 7.25 (2H, m), 7.10 (2H, d), 6.85 (2H, d), 5.55 (1H, d), 4.00 (3H, m), 3.90 (2H, s), 3.20 (1H, m), 3.10 (2H, m), 2.30 (1H, d), 2.10 (1H, m), 1.80–1.40 (7H, m). Analysis: Found C, 55.33; H, 5.49; N, 15.84; C$_{23}$H$_{26}$N$_6$O$_4$S.0.6EtOAc.0.7H$_2$O requires C, 55.67; H, 5.92; N, 15.33%. (EtOAc=ethyl acetate).

EXAMPLE 50

N$^1$-(2-3-[1-(1H-Benzo[d]imidazol-2-ylsulfonyl)-2-piperidinyl]-1,2,4-oxadiazol-5-ylethyl)benzamide

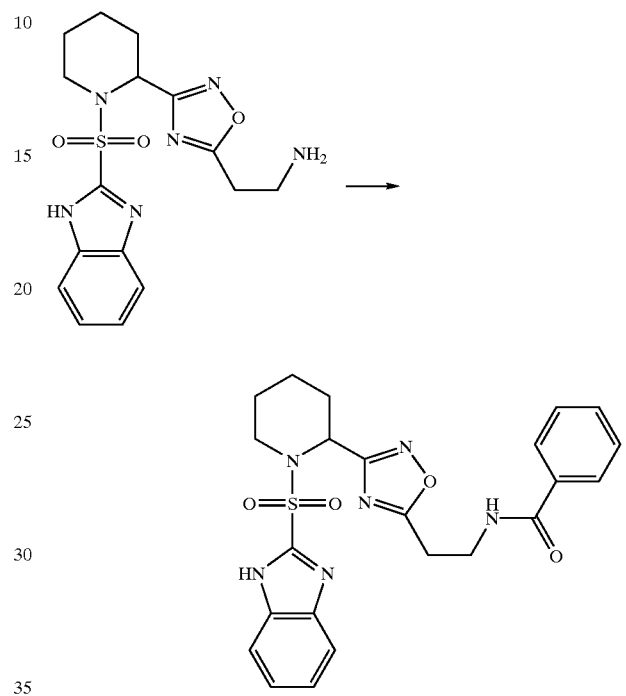

Benzoyl chloride (0.07 ml) was added to a solution of 2-3-[1-(1H-benzo[d]imidazol-2-ylsulfonyl)-2-piperidyl]-1,2,4-oxadiazol-5-ylethylamine (0.2 g) [see Example 27] and triethylamine (0.11 ml) in dichloromethane (5 ml). The reaction mixture was stirred at room temperature for 18 hrs, after which time a white solid was filtered off, and the filtrate concentrated under reduced pressure. The remaining residue was dissolved in ethyl acetate and washed with water and 1N aqueous hydrochloric acid. The organic layer was then dried over magnesium sulphate and the solvent removed under reduced pressure. The crude product was purified by column chromatography on silica gel eluting with 1:1, by volume, ethyl acetate:hexane, to afford N$^1$-(2-3-[1-(1H-benzo[d]imidazol-2-ylsulfonyl)-2-piperidinyl]-1,2,4-oxadiazol-5-ylethyl)benzamide (63 mg) as a white solid.

$^1$H-NMR (d6-DMSO) δ: 13.60 (1H, bs), 8.60 (1H, bs), 7.80 (2H, d), 7.70 (2H, m), 7.60–7.20 (5H, m), 5.40 (1H, m), 3.90 (1H, d), 3.50 (2H, m), 3.30 (1H, m), 2.90 (2H, m), 2.00 (1H, m), 1.80 (1H, m), 1.50 (1H, d), 1.40 (1H, m), 1.35–1.10 (2H, m). Analysis: Found C, 57.23; H, 5.03; N, 17.15; C$_{23}$H$_{24}$N$_6$O$_4$S requires C, 57.49; H, 5.03, 17.49%.

EXAMPLE 51

N-(3-[1-(1H-Benzo[d]imidazol-2-ylsulfonyl)-2-piperidyl]-1,2,4-oxadiazol-5-ylmethyl)-N-benzylamine

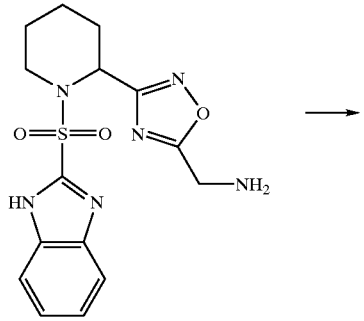

Benzaldehyde (0.06 ml) was added to a solution of 3-[1-(1H-benzo[d]imidazol-2-ylsulfonyl)-2-piperidyl]-1,2,4-oxadiazol-5-ylmethylamine (0.2 g) [see Preparation 86] in tetrahydrofuran (5 ml). The reaction mixture was stirred at room temperature for 30 mins, after which time sodium triacetoxyborohydride (0.16 g) and glacial acetic acid (0.03 ml) were added, and the mixture was then stirred for 18 hrs. The mixture was then diluted with water and basified with saturated sodium hydrogen carbonate, and the product was extracted with ethyl acetate.

The organic layer was separated, dried over magnesium sulphate and the solvent removed under reduced pressure. The crude product was purified by column chromatography on silica gel eluting with a solvent gradient of 80:20 changing to 50:50, by volume, hexane:ethyl acetate, in 10% increments, to afford N-(3-[1-(1H-benzo[d]imidazol-2-ylsulfonyl)-2-piperidyl]-1,2,4-oxadiazol-5-ylmethyl)-N-benzylamine (0.08g) as a white solid.

$^1$H-NMR (d6-DMSO) δ: 7.75 (1H, bs), 7.55 (1H, bs), 7.40–7.20 (9H, m), 5.40 (1H, d), 3.90 (1H, d), 3.60 (4H, m), 3.40 (1H, m), 2.00 (1H, m), 1.80 (1H, m), 1.65 (1H, m), 1.55 (1H, m), 1.40 (2H, m). Analysis: Found C, 57.38; H, 5.45; N, 17.91; $C_{22}H_{24}N_6O_3S.0.5\ H_2O$ requires C, 57.25; H, 5.46; N, 18.21%.

EXAMPLE 52

2-[(2S)-2-5-[(4-Piperidyloxy)methyl]-1,2,4-oxadiazol-3-yl-1-piperidyl]sulfonyl-1H-benzo[d]imidazole

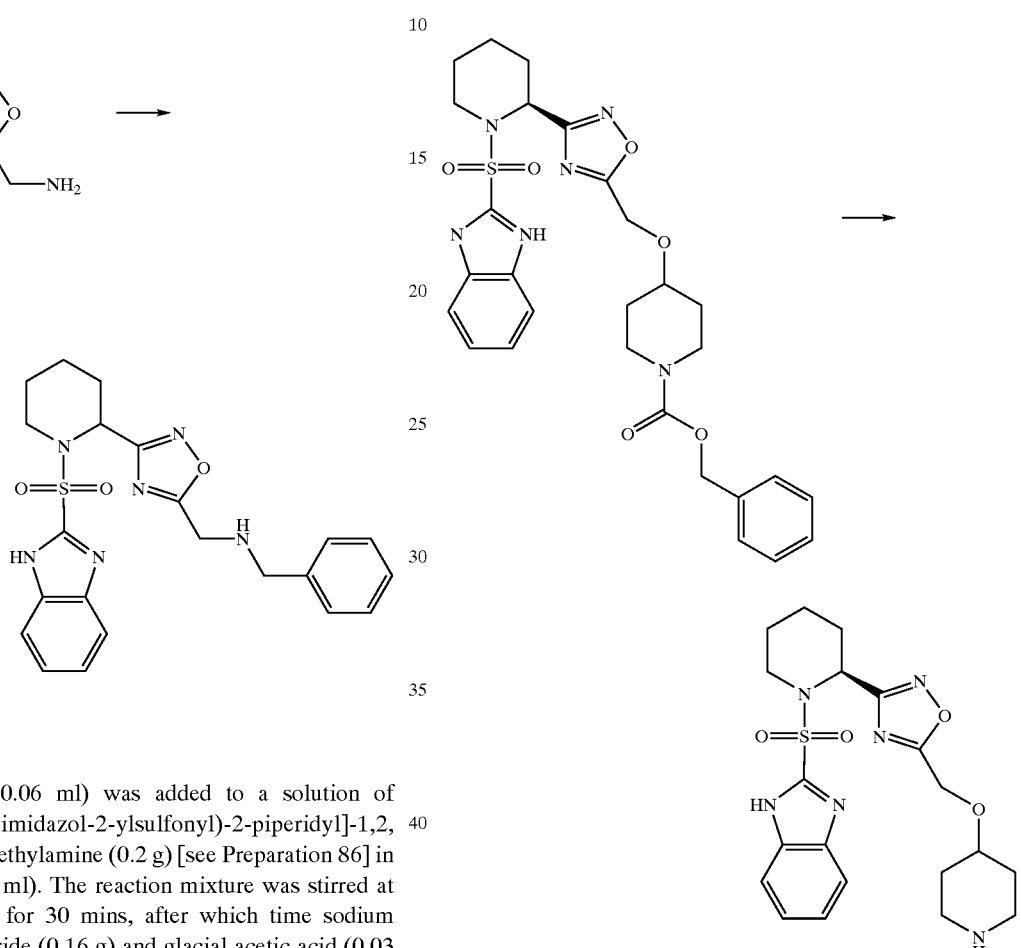

The title compound was prepared by the method of Example 27 from benzyl 4-(3-[(2 S)-1-(1H-benzo[d]imidazol-2-ylsulfonyl)-2-piperidyl]-1,2,4-oxadiazol-5-ylmethoxy)-1-piperidinecarboxylate [see Preparation 96] and hydrogen bromide in glacial acetic acid. The crude product was recrystallised from isopropanol to afford 2-[(2S)-2-5-[(4-piperidyloxy)methyl]-1,2,4-oxadiazol-3-yl-1-piperidyl]sulfonyl-1H-benzo[d]imidazole as an off-white solid.

$^1$H-NMR (d6-DMSO) δ: 7.65 (2H, m), 7.35 (2H, m), 5.40 (1H, d), 4.50 (2H, s), 3.95 (1H, d), 3.60 (1H, m), 3.35 (1H, t), 3.15 (2H, m), 2.95 (2H, m), 2.00–1.80 (4H, m), 1.75–1.30 (6H, m). Rotation: $[\alpha]_D^{25}=-19.10°$ (c=0.05, methanol).

EXAMPLE 53

2-[(2S)-2-[5-([1-(Cyclopropylmethyl)-4-piperidyl]
oxymethyl)-1,2,4-oxadiazol-3-yl]-1-piperidyl]
sulfonyl-1H-benzo[d]imidazole

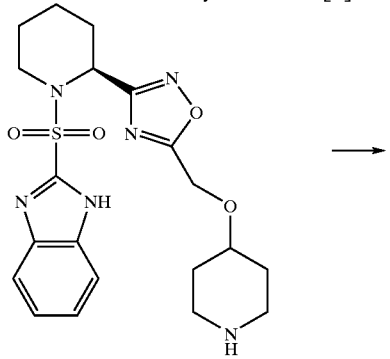

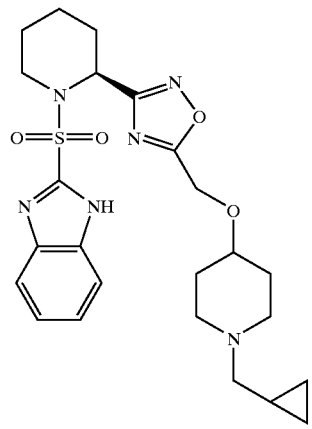

Cyclopropyl methyl bromide (21.4 ml) was added to a solution of 2-[(2S)-2-5-[(4-piperidyloxy)methyl]-1,2,4-oxadiazol-3-yl-1-piperidyl]sulfonyl-1H-benzo[d]imidazole (100 mg) [see Example 52], sodium hydrogen carbonate (18.8 mg) and sodium iodide (33.6 mg) in acetonitrile (2 ml). The reaction mixture was stirred for 18 hrs at room temperature under an atmosphere of nitrogen, after which time the mixture was diluted with ethyl acetate and water. The organic layer was separated and washed with saturated sodium hydrogen carbonate, brine, dried over magnesium sulphate and the solvent removed under reduced pressure. The crude product was purified by column chromatography on silica gel eluting with a solvent gradient of 98:1.75:0.25, changing to 80:20:3, by volume dichloromethane:methanol:0.88 aqueous ammonia to afford 2-[(2S)-2-[5-([1-(cyclopropylmethyl)-4-piperidyl]oxymethyl)-1,2,4-oxadiazol-3-yl]-1-piperidyl]sulfonyl-1H-1,3-benzo[d]imidazole (35 mg) as a white solid.

$^1$H-NMR (CDCl$_3$) δ: 7.75 (2H, m), 7.40 (2H, m), 5.60 (1H, d), 4.45 (2H, s), 3.95 (1H, d), 3.40 (1H, m), 3.15 (1H, m), 2.85 (2H, m), 2.35 (1H, d), 2.20–2.00 (4H, m), 1.90 (1H, m), 1.80–1.60 (7H, m), 0.90 (1H, m), 0.50 (2H, d), 0.10 (2H, d). Analysis: Found C, 57.30; H, 6.54; N, 16.13; C$_{24}$H$_{32}$N$_6$O$_4$S.0.5CH$_3$OH requires C, 56.96; H, 6.63; N, 16.27%. Rotation: [α]$_D^{25}$=−52.00° (c=0.05, methanol).

EXAMPLE 54

2-[(2S)-2-(5-Benzyl-1,2,4-oxadiazol-3-yl)-1-piperidyl]sulfonyl-5-bromo-1H-benzo[d]imidazole

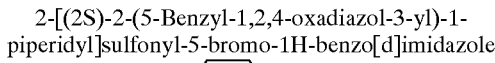

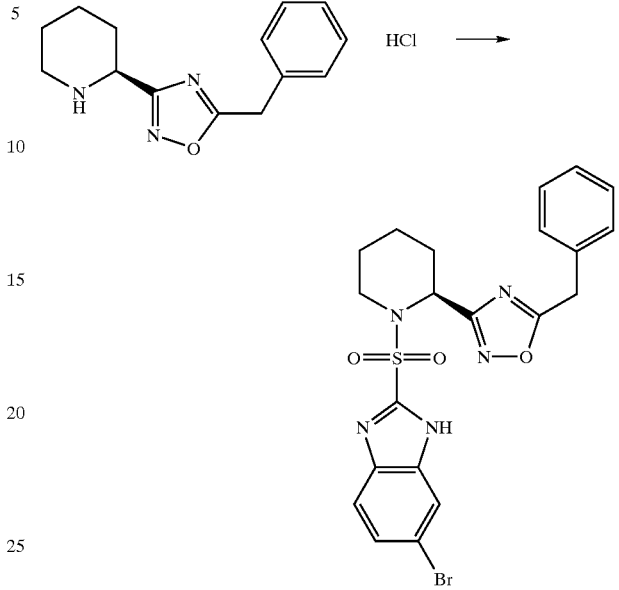

The title compound was prepared by a similar method to Example 1 from 5-benzyl-3-[(2S)-2-piperidyl]-1,2,4-oxadiazole hydrochloride [see-Preparation 7] and 5-bromo-1H-benzo[d]imidazole-2-sulfonyl chloride [see Preparation 88]. The crude product was purified by column chromatography on silica gel eluting with a solvent gradient of 90:10 changing to 70:30, by volume, hexane:ethyl acetate, in 10% increments, to afford 2-[(2S)-2-(5-benzyl-1,2,4-oxadiazol-3-yl)-1-piperidyl]sulfonyl-5-bromo-1H-benzo[d]imidazole as a white solid.

$^1$H-NMR (d6-DMSO) δ: 7.85 (1H, s), 7.60 (1H, d), 7.45 (1H, m), 7.30 (3H, m), 7.20 (2H, m), 5.35 (1H, d), 4.05 (2H, s), 3.95 (1H, d), 3.20 (1H, d), 2.00 (1H, d), 1.80 (1H, m), 1.60 (1H, d), 1.55 (1H, m), 1.40–1.20 (2H, m). Analysis: Found C, 50.17; H, 4.16; N, 13.75; C$_{21}$H$_{20}$N$_5$O$_3$SBr requires C, 50.21; H, 4.01; N, 13.94%. Rotation: [α]$_D^{25}$=−29.41° (c=0.1, methanol).

EXAMPLE 55

2-4-[(3-(2S)-1-[(5-Bromo-1H-benzo[d]imidazol-2-yl)sulfonyl]-2-piperidyl-1,2,4-oxadiazol-5-yl)methoxy]benzyl-1,3-isoindolinedione

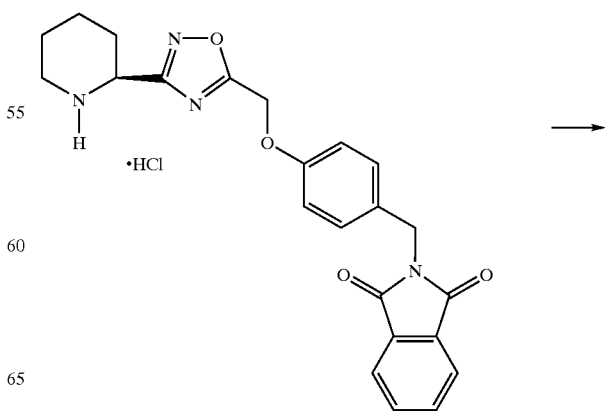

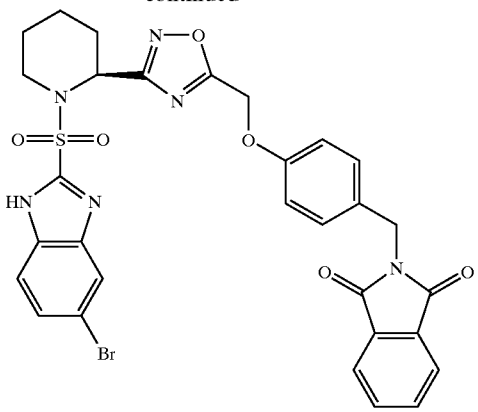

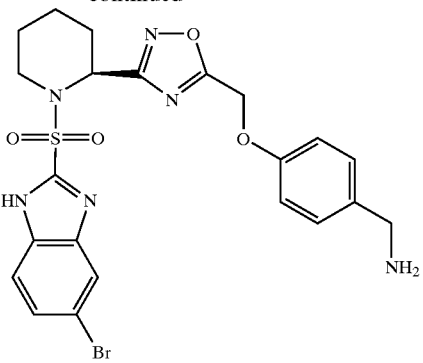

The title compound was prepared by a similar method to Example 1 from 2-[4-(3-[(2S)-2-piperidyl]-1,2,4-oxadiazol-5-ylmethoxy)benzyl]-1,3-isoindolinedione hydrochloride [see Preparation 15] and 5-bromo-1H-benzo[d]imidazole-2-sulfonyl chloride [see Preparation 88]. The crude product was purified by column chromatography on silica gel eluting with a solvent gradient of 90:10 changing to 40:60, by volume, hexane:ethyl acetate, in 10% increments, to afford 2-4-[(3-(2S)-1-[(5-bromo-1H-benzo[d]imidazol-2-yl)sulfonyl]-2-piperidyl-1,2,4-oxadiazol-5-yl)methoxy]benzyl-1,3-isoindolinedione as a white solid.

$^1$H-NMR (d6-DMSO) δ: 7.85 (5H, m), 7.60 (1H, d), 7.40 (1H, d), 7.20 (2H, m), 6.90 (2H, d), 5.40 (1H, d), 5.20 (2H, d), 4.70 (2H, s), 3.90 (1H, d), 3.20 (1H, m), 2.00 (1H, d), 1.80 (1H, m), 1.60 (2H, m), 1.40–1.20 (2H, m). Analysis: Found C, 52.20; H, 3.54; N, 11.92; $C_{30}H_{25}N_6O_6SBr·0.6H_2O$ requires C, 52.21; H, 3.86; N, 12.18%.

EXAMPLE 56

4-[(3-(2S)-1-[(5-Bromo-1H-benzo[d]imidazol-2-yl)sulfonyl]-2-piperidyl-1,2,4-oxadiazol-5-yl)methoxy]benzylamine

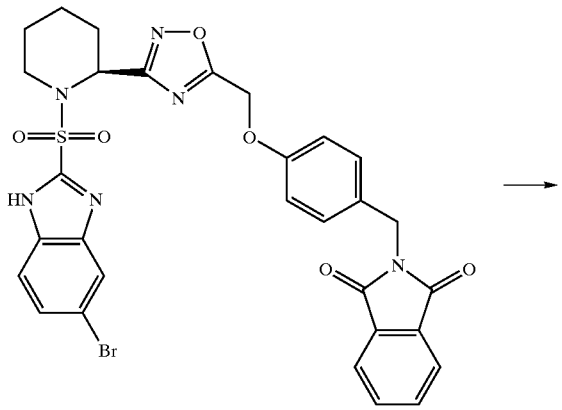

→

The title compound was prepared by a similar method to Example 11 from 2-4-[(3-(2S)-1-[(5-bromo-1H-benzo[d]imidazol-2-yl)sulfonyl]-2-piperidyl-1,2,4-oxadiazol-5-yl)methoxy]benzyl-1,3-isoindolinedione [see Example 55] and 33% methylamine in ethanol. The crude product was purified by recrystallisation from methanol and diethyl ether, to afford 4-[(3-(2S)-1-[(5-bromo-1H-benzo[d]imidazol-2-yl)sulfonyl]-2-piperidyl-1,2,4-oxadiazol-5-yl)methoxy]benzylamine as a white solid.

$^1$H-NMR (d4-CH$_3$OH) δ: 7.75 (1H, m), 7.50 (1H, m), 7.40–7.30 (3H, m), 6.95 (2H, m), 5.50 (1H, m), 4.80 (2H, s), 4.10 (1H, m), 3.95 (2H, m), 3.35 (1H, m), 2.05 (1H, m), 1.95 (1H, m), 1.60 (1H, m), 1.40 (3H, m). Analysis: Round C, 47.83; H, 3.98; N, 14.97; $C_{22}H_{23}N_6O_4SBr$ requires C, 48.27; H, 4.23; N, 15.35%.

EXAMPLE 57 tert-Butyl 4-[2-(3-(1S)-2-[(Cyclohexylmethyl)sulfonyl]-2-piperidyl-1,2,4-oxadiazol-5-yl)ethyl]-1-piperazinecarboxylate

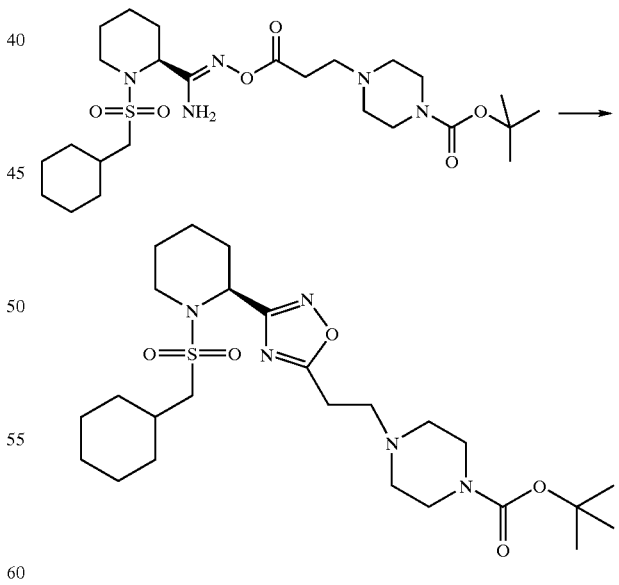

The title compound was prepared by a similar method to Example 16 from tert-butyl 4-(3-[((Z)-amino(1S)-2-[(cyclohexylmethyl)sulfonyl]-2-piperidylmethylidene)amino]oxy-3-oxopropyl)-1-piperazinecarboxylate [see Preparation 91] and pyridine. The crude product was purified by column chromatography on silica gel eluting with a solvent gradient of 90:10 changing to 50:50, by volume, hexane:ethyl acetate, to afford tert-butyl 4-[2-(3-(1S)-2-[(cyclohexylmethyl)sulfonyl]-2-piperidyl-1,2,4-oxadiazol-5-yl)ethyl]-1-piperazinecarboxylate as a gum.

$^1$H-NMR (CDCl$_3$) δ: 5.30 (1H, d), 3.80 (1H, d), 3.40 (4H, m), 3.20 (1H, m), 3.10 (2H, m), 3.00–2.80 (4H, m), 2.45 (4H, m), 2.25 (1H, d), 2.00 (4H, m), 1.80–1.60 (6H, m), 1.50 (9H, s), 1.40–1.00 (6H, m). MS=527.7 (MH$^+$).

EXAMPLE 58

1-[2-(3-1S)-2-[(Cyclohexylmethyl)sulfonyl]-2-piperidyl-1,2,4-oxadiazol-5-yl)ethyl]piperazine

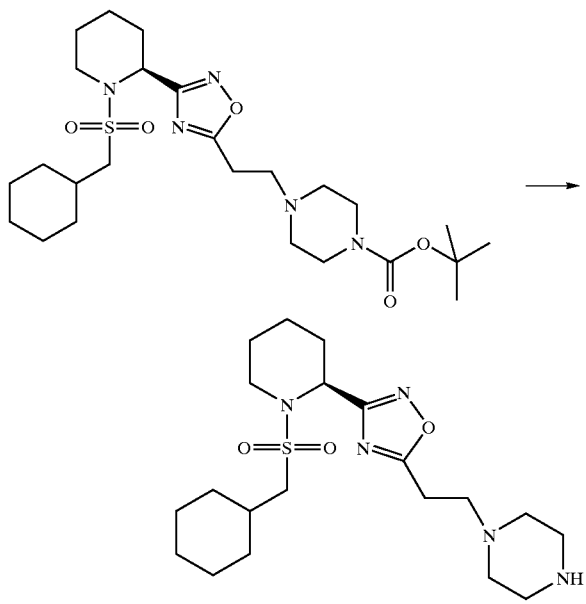

Trifluoroacetic acid (10 ml) was added to a solution of tert-butyl 4-[2-(3-(1S)-2-[(cyclohexylmethyl)sulfonyl]-2-piperidyl-1,2,4-oxadiazol-5-yl)ethyl]-1-piperazinecarboxylate (265 mg) [see Example 57] in dichloromethane (10 ml). The reaction mixture was stirred at room temperature for 3 hrs, after which time the solvent was removed under reduced pressure and the residue partitioned between ethyl acetate and saturated sodium hydrogen carbonate. The organic layer was separated and washed with brine, dried over magnesium sulphate and the solvent removed under reduced pressure to afford 1-[2-(3-(1S)-2-[(cyclohexylmethyl)sulfonyl]-2-piperidyl-1,2,4-oxadiazol-5-yl)ethyl]piperazine (136 mg) as a brown oil.

$^1$H-NMR (CDCl$_3$) δ: 5.30 (1H, d), 3.80 (1H, d), 3.25 (1H, t), 3.10 (2H, m), 3.00–2.80 (8H, m), 2.55 (4H, s), 2.25 (1H, d), 2.00 (5H, m), 1.80–1.60 (5H, m), 1.50 (1H, m), 1.40–1.00 (5H, m). Analysis: Found C, 53.50; H, 8.08; N, 14.97; C$_{20}$H$_{35}$N$_5$O$_3$S.1.5H$_2$O requires C, 53.07; H, 8.46; N, 15.47%.

EXAMPLE 59

(2S)-N$^1$-Benzyl-2-(5-benzyl-1,2,4-oxadiazol-3-yl)-1-piperidinecarboxamide

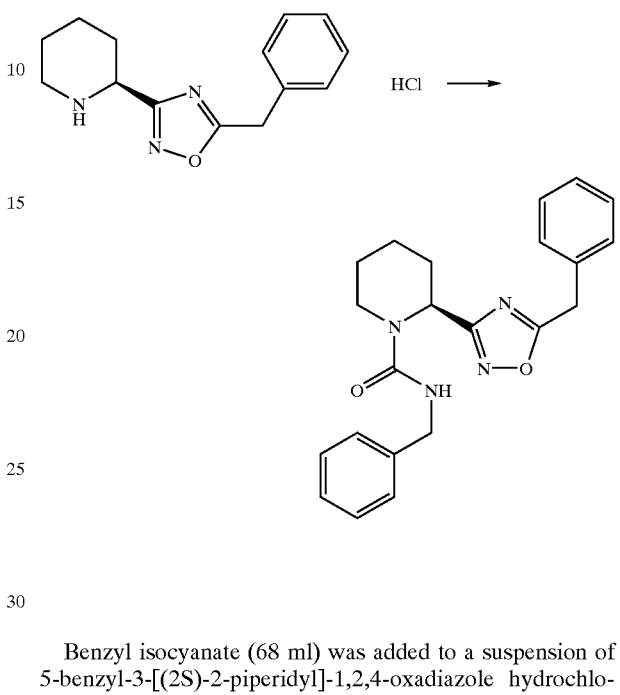

Benzyl isocyanate (68 ml) was added to a suspension of 5-benzyl-3-[(2S)-2-piperidyl]-1,2,4-oxadiazole hydrochloride (279.8 mg) [see Preparation 7] (140 mg) and triethylamine (70 ml) in dichloromethane (5 ml). The reaction mixture was stirred for 2 hrs, the crude product was then purified by column chromatography on silica gel eluting with a solvent gradient of 100:0 changing to 50:50, by volume, hexane:ethyl acetate, to afford a solid which was triturated with diethylether to afford (2S)-M-benzyl-2-(5-benzyl-1,2,4-oxadiazol-3-yl)-1-piperidinecarboxamide (150 mg) as a white solid.

$^1$H-NMR (CDCl$_3$) δ: 7.25 (10H, m), 5.60 (1H, d), 4.95 (1H, bs), 4.40 (2H, s), 4.20 (2H, s), 3.70 (1H, d), 3.10 (1H, t), 2.25 (1H, d), 1.85 (1H, t), 1.65 (2H, m), 1.45 (2H, m). Analysis: Found C, 70.02; H, 6.44; N, 14.87; C$_{22}$H$_{24}$N$_4$O$_2$ requires C, 70.19; H, 6.43; N, 14.88%.

EXAMPLE 60

(2S)-2-(5-Benzyl-1,2,4-oxadiazol-3-yl)-N$^1$-phenethyl-1-piperidinecarboxamide

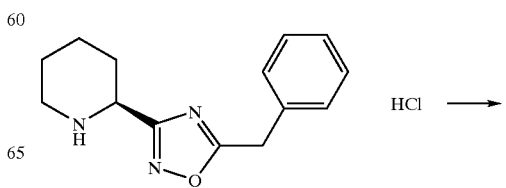

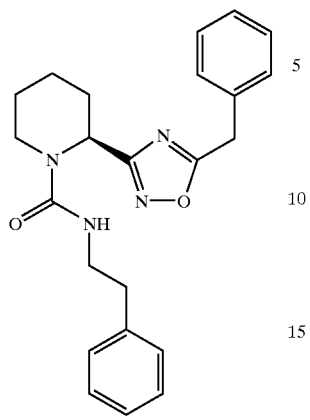

The title compound was prepared and purified by a similar method to Example 59 from 5-benzyl-3-[(2S)-2-piperidyl]-1,2,4-oxadiazole hydrochloride [see Preparation 7] and phenethyl isocyanate to afford (2S)-2-(5-benzyl-1,2,4-oxadiazol-3-yl)-$N^1$-phenethyl-1-piperidinecarboxamide as a gum.

$^1$H-NMR (CDCl$_3$) δ: 7.35–7.15 (10H, m), 5.55 (1H, d), 4.65 (1H, bs), 4.20 (2H, s), 3.45 (3H, m), 3.10 (1H, t), 2.80 (2H, m), 2.20 (1H, d), 1.85 (1H, m), 1.65 (2H, m), 1.50–1.35 (2H, m). Analysis: Found C, 70.43; H, 6.77; N, 14.22; C$_{23}$H$_{26}$N$_4$O$_2$ requires C, 70.75; H, 6.71; N, 14.35%.

EXAMPLE 61

Benzyl N-[(R)-(3-{(2S)-1-(Cyclohexylmethyl)sulfonyl-2-piperidyl}-1,2,4-oxadiazol-5-yl)(phenyl)methyl]carbamate

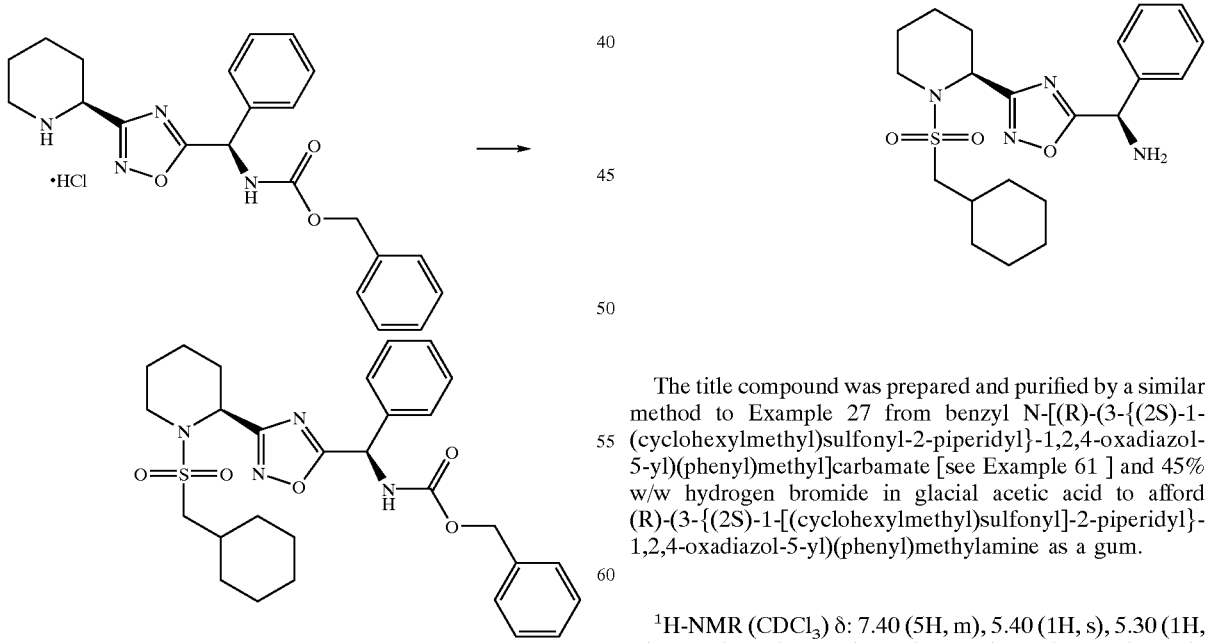

The title compound was prepared and purified by a similar method to Example 1 from benzyl N-[(R)-phenyl{3-[(2S)-2-piperidyl]-1,2,4-oxadiazol-5-yl}methyl]carbamate hydrochloride [see Preparation 103] and cyclohexylmethylsulphonyl chloride to afford benzyl N-[(R)-(3-{(2S)-1-(cyclohexylmethyl)sulfonyl-2-piperidyl}-1,2,4-oxadiazol-5-yl)(phenyl)methyl]carbamate as a gum.

$^1$H-NMR (CDCl$_3$) δ: 7.35 (10H, m), 6.20 (1H, d), 5.75 (1H, d), 5.30 (1H, m), 5.05 (2H, m), 3.75 (1H, d), 3.20 (1H, m), 2.80 (2H, m), 2.10 (1H, d), 1.90 (4H, m), 1.60 (6H, m), 1.40 (1H, m), 1.10 (2H, m), 1.05 (1H, m), 0.95 (2H, m). Analysis: Found C, 62.66; H, 6.55; N, 9.91; C$_{29}$H$_{36}$N$_4$SO$_5$.0.2H$_2$O requires C, 62.61; H, 6.60; N, 10.07%. Rotation: [α]$_D^{25}$=−30° (C=0.1, methanol).

EXAMPLE 62

(R)-(3-{(2S)-1-[(Cyclohexylmethyl)sulfonyl]-2-piperidyl}-1,2,4-oxadiazol-5-yl)(phenyl)methylamine

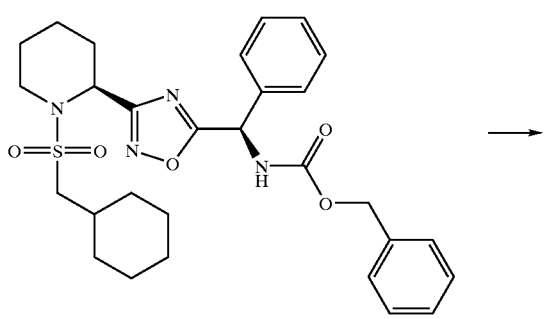

The title compound was prepared and purified by a similar method to Example 27 from benzyl N-[(R)-(3-{(2S)-1-(cyclohexylmethyl)sulfonyl-2-piperidyl}-1,2,4-oxadiazol-5-yl)(phenyl)methyl]carbamate [see Example 61 ] and 45% w/w hydrogen bromide in glacial acetic acid to afford (R)-(3-{(2S)-1-[(cyclohexylmethyl)sulfonyl]-2-piperidyl}-1,2,4-oxadiazol-5-yl)(phenyl)methylamine as a gum.

$^1$H-NMR (CDCl$_3$) δ: 7.40 (5H, m), 5.40 (1H, s), 5.30 (1H, m), 3.75 (1H, d), 3.20 (1H, m), 2.85 (2H, m), 2.30 (1H, m), 1.95 (6H, m), 1.65 (6H, m), 1.50 (1H, m), 1.20 (3H, m), 0.95 (2H, m). Analysis: Found C, 59.97; H, 7.21; N, 13.00; C$_{21}$H$_{30}$N$_4$SO$_3$ requires C, 60.26; H, 7.22; N, 13.39%. Rotation: [α]$_D^{25}$=−49° (c=0.1, methanol).

EXAMPLE 63

Benzyl N-[(S)-(3-{(2S)-1-(Cyclohexylmethyl)sulfonyl-2-piperidyl}-1,2,4-oxadiazol-5-yl)(phenyl)methyl]carbamate

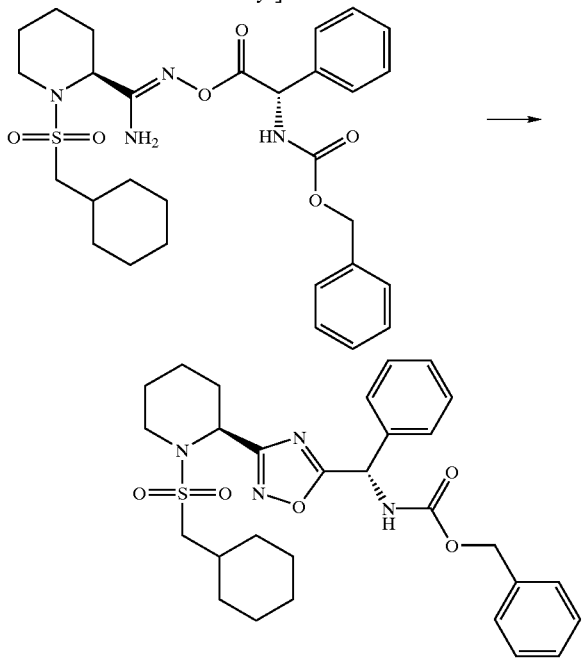

The title compound was prepared and purified by a similar method to Example 16 from benzyl-N-[(1S)-2{[((Z)-amino{(2S)-1-[(cyclohexylmethyl)sulfonyl]-2-piperidyl}methylidene)amino]oxy}-2-oxo-1-phenylethyl]carbamate [see Preparation 104] and toluene to afford benzyl N-[(S)-(3-{(2S)-1-(cyclohexylmethyl)sulfonyl-2-piperidyl}-1,2,4-oxadiazol-5-yl)(phenyl)methyl]carbamate as a gum.

¹H-NMR (CDCl₃) δ: 7.40 (10H, m), 6.20 (1H, d), 5.70 (1H, s), 5.30 (1H, m), 5.15 (2H, m), 3.75 (1H, d), 3.20 (1H, m), 2.80 (2H, m), 2.15 (1H, m), 1.90 (4H, m), 1.60 (6H, m), 1.40 (1H, m), 1.20 (3H, m), 0.95 (2H,m). Analysis: Found C, 62.92; H, 6.59; N, 10.05; C₂₉H₃₆N₄SO₅. requires C, 63.02; H, 6.57; N, 10.14%. Rotation: [α]$_D^{25}$=−20° (c=0.1, methanol).

EXAMPLE 64

(S)-(3-{(2S)-1-[(Cyclohexylmethyl)sulfonyl]-2-piperidyl}-1,2,4-oxadiazol-5-yl)(phenyl)methylamine

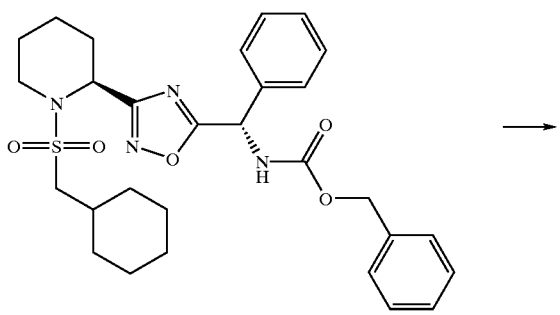

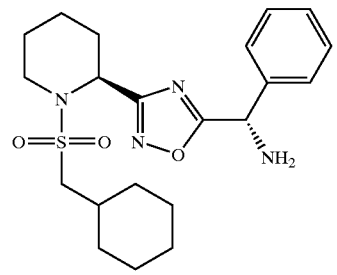

The title compound was prepared and purified by a similar method to Example 27 from benzyl N-[(S)-(3-{(2S)-1-(cyclohexylmethyl)sulfonyl-2-piperidyl}-1,2,4-oxadiazol-5-yl)(phenyl)methyl]carbamate [see Example 63 ] to afford (S)-(3-{(2S)-1-[(cyclohexylmethyl)sulfonyl]-2-piperidyl}-1,2,4-oxadiazol-5-yl)(phenyl)methylamine as a gum.

¹H-NMR (CDCl₃) δ: 7.30 (5H, m), 5.40 (1H, s), 5.30 (1H, d), 3.75 (1H, d), 3.20 (1H, m), 2.85 (2H, m), 2.25 (1H, m), 2.10 (2H, m), 1.90 (4H, m), 1.60 (6H, m), 1.45 (1H, m), 1.20 (3H, m), 0.95 (2H, m). Analysis: Found C, 60.07; H, 7.21; N, 13.04; C₂₁H₃₀N₄SO₃. requires C, 60.26; H, 7.22; N, 13.39%. Rotation: [α]$_D^{25}$=−46.2° (c=0.1, methanol).

EXAMPLE 65

2-({2-[5-(2-Pyrimidinyl)-1,2,4-oxadiazol-3-yl]-2-piperidyl}sulfonyl)-1H-benzo[d]imidazole

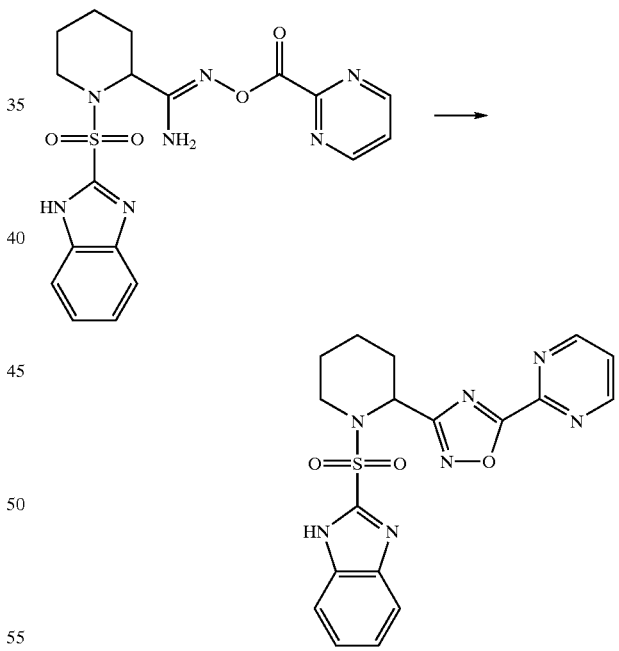

The title compound was prepared by the method of Preparation 13 from 1-(1H-benzo[d]imidazol-2-ylsulfonyl)-N'²-[(2-pyrimidinylcarbonyl)oxy]-2-piperidinecarboximidamide [see Preparation 105] and pyridine, to afford 2-({(2-[5-(2-pyrimidinyl)-1,2,4-oxadiazol-3-yl]-2-piperidyl}sulfonyl)-1H-benzo[d]imidazole as a solid.

¹H-NMR (CDCl₃) δ: 9.10 (2H, s), 7.85 (1H, d), 7.65 (2H, m), 7.35 (2H, m), 5.80 (1H, s), 3.90 (1H, d), 3.00 (1H, t), 2.55 (1H, d), 2.15 (1H, m), 1.90–1.60 (4H, m). Analysis:

Found C, 52.12; H, 4.13; N, 23.09; $C_{18}H_{17}N_7SO_3 \cdot 0.1CH_2Cl_2$ requires C, 51.77; H, 4.13; N, 23.35%.

It should be noted that Preparations 21, 23, 42, 79, 86 and 96 in the following Preparations section also illustrate the syntheses of compounds of the formula (I).

The following Preparations describe the preparation of certain intermediates used in the preceding Examples.

PREPARATION 1

(2S)-1-tert-Butoxycarbonyl)-2-piperidinecarboxylic Acid

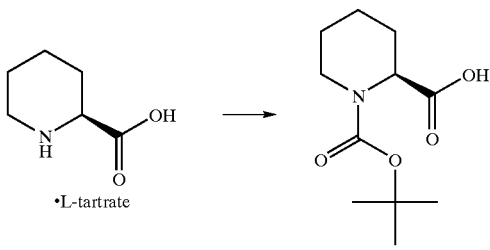

•L-tartrate (2S)-2-Piperidinecarboxylic acid L-tartrate (55.0g) (see WO-A-96/11185) was dissolved in water (200 ml). The resulting solution was cooled to 0° C. and di-t-butyldicarbonate (86g) in 1,4-dioxane (203 ml) was added followed by 1N aqueous sodium hydroxide solution (610 ml) over a period of 20 mins. The reaction mixture was stirred at 0° C. for 1 hour and then at room temperature for 56 hours. The solvent was then removed under reduced pressure and the resulting solid was dissolved in water (100 ml) and washed with diethyl ether (1000 ml). The aqueous layer was acidified to pH 2.0 with 1M aqueous citric acid solution (500 ml) and the product was extracted with ethyl acetate (4×500 ml). The combined organic layers were dried over magnesium sulphate and the solvent was removed under reduced pressure to afford (2S)-1-(tert butoxycarbonyl)-2-piperidinecarboxylic acid (19.55 g) as a white solid.

$^1$H-NMR ($d_6$-DMSO) δ: 12.7 (1H, bs), 4.55 (1H, d), 3.80 (1H, s), 2.90–2.60 (1H, m), 2.05 (1H, m), 1.60 (3H, m), 1.30 (1OH, d), 1.10 (1H, m).

PREPARATION 2 tert-Butyl (2S)-2-(Aminocarbonyl)-1-piperidinecarboxylate

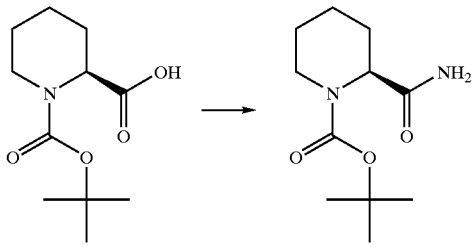

Triethylamine (14.46 ml) was added to a solution of (2S)-1-(tert-butoxycarbonyl)-2-piperidinecarboxylic acid (18.3 g) [see Preparation 1] in tetrahydrofuran (240 ml) at −20° C. under an atmosphere of nitrogen. Ethyl chlorofor- mate (7.52 ml) was then added to the mixture and the resulting solution was stirred for 40 mins. at −10° C. and then 0.88 aqueous ammonia solution (32 ml) added. The reaction mixture was stirred for 10 mins. after which time the solvent was removed under reduced pressure and the residue diluted with ethyl acetate and water. The organic layer was separated and dried over magnesium sulphate and the solvent was removed under reduced pressure to afford tert-butyl (2S)-2-(aminocarbonyl)-1-piperidinecarboxylate (18.65 g) as a white solid. $^1$H-NMR (CDCl$_3$) δ: 6.0 (1H, bs), 5.40 (1H, bs), 4.80 (1H, s), 4.00 (1H, m), 2.85 (1H, t), 2.30 (1H, d), 1.80–1.40 (14H, m).

PREPARATION 3 tert-Butyl (2S)-2-Cyano-1-piperidinecarboxylate

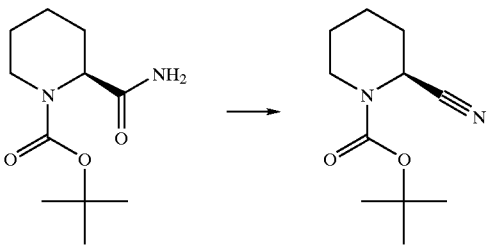

Oxalyl chloride (8.54 ml) was added to a stirred solution of dimethylformamide (7.57 ml) in acetonitrile (440 ml) at −5° C. under an atmosphere of nitrogen. The mixture was stirred for 15 mins., after which time a solution of tert-butyl (2S)-2-(aminocarbonyly)-1-piperidinecarboxylate (18.63 g) [see Preparation 2] and pyridine (16.50 ml) in acetonitrile (100 ml) was added and the resulting solution was stirred for 10 mins. The mixture was then reduced to low volume under reduced pressure and diluted with ethyl acetate (1000 ml) and water (1000 ml). The organic layer was separated, dried over magnesium sulphate and the solvent removed under reduced pressure to afford tert-butyl (2S)-2-cyano-1-piperidinecarboxylate (13.7g) as a white solid.

$^1$H-NMR (CDCl$_3$) δ: 5.20 (1H, s), 4.00 (1H, m), 2.90 (1H, t), 1.90 (1H, d), 1.80–1.60 (4H, m), 1.40 (9H, s), 1.40 (1H, m). Rotation: $[\alpha]_D^{25} = -136.83°$ (c=0.1, methanol).

PREPARATION 4 tert-Butyl (Z)-(2S)-2-[Amino(hydroxyimino) methyl]-1-piperidinecarboxylate

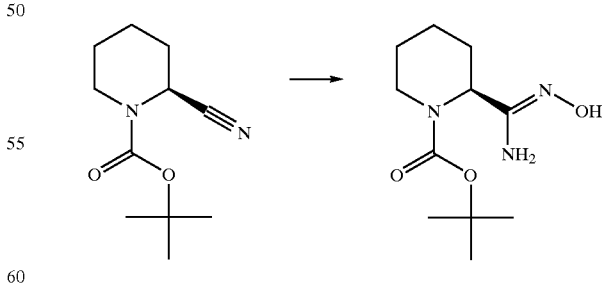

A solution of tert-butyl (2S)-2-cyano-1-piperidinecarboxylate (13.10 g) [see Preparation 3] in methanol (500 ml) was added to a solution of hydroxy- lamine hydrochloride (21.6 g) and sodium carbonate (33.0 g) in water (600 ml). The reaction mixture was warmed to the reflux temperature and stirred for 8 hours after which time the methanol was removed under reduced pressure and the product extracted from the aqueous layer with ethyl acetate (3×500 ml). The combined organic layers were washed with water (500 ml), dried over magnesium sulphate and the solvent removed under reduced pressure to afford tert-butyl (Z)-(2S)-2-[amino(hydroxyimino)methyl]-1-piperidinecarboxylate (14.1 g) as a white solid.

$^1$H-NMR (CDCl$_3$) δ: 7.10 (1H, bs), 4.95 (1H, s), 4.70 (2H, bs), 4.00 (1H, d), 2.90 (1H, t), 2.15 (1H, d), 1.80 (1H, t), 1.60–1.30 (13H, m). MS: 244 (MH$^+$).

PREPARATION 5 tert-Butyl (Z)-2S)-2-(Amino[(2-phenylacetyl)oxy]iminomethyl)-1-piperidinecarboxylate

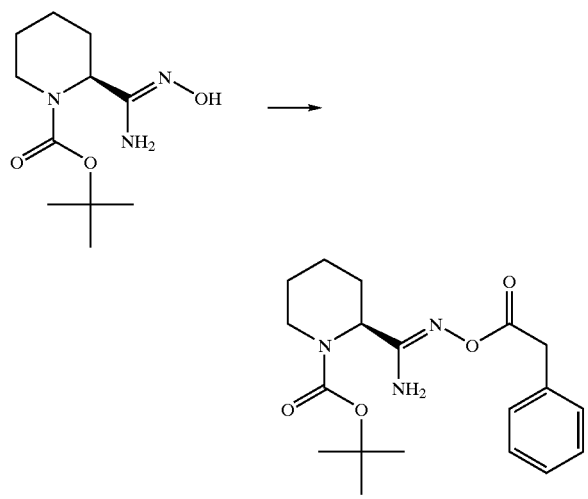

1-Hydroxybenzotriazole hydrate (8.67 g), phenylacetic acid (8.0 g), N-methylmorpholine (14.69 ml), 4-dimethylaminopyridine (3.3 g) and 1-(3-dimethylaminopropyl)-3-ethylcarbodiimide hydrochloride (12.29 g) were added to a solution of tert-butyl (Z)-(2S)-2-[amino(hydroxyimino)methyl]-1-piperidinecarboxylate (13.0 g) [see Preparation 4] in dichloromethane (180 ml). The reaction mixture was stirred for 2 hours under an atmosphere of nitrogen, after which time the mixture was diluted with dichloromethane and 1N aqueous citric acid solution. The organic layer was separated, washed with saturated aqueous sodium hydrogen carbonate solution, dried over magnesium sulphate and the solvent was removed under reduced pressure to afford tert-butyl (Z)-(2S)-2-(amino[(2-phenylacetyl)oxy]iminomethyl)-1-piperidinecarboxylate (17.63 g) as a white solid.

$^1$H-NMR (CDCl$_3$) δ: 7.30 (5H, m), 4.90 (1H, s), 4.80 (2H, bs), 4.00 (1H, d), 3.75 (2H, s), 2.75 (1H, t), 2.20 (1H, d), 1.80 (1H, m), 1.60–1.30 (13H, m). Rotation: $[\alpha]_D^{25}$=−64.0° (c=0.1, methanol).

PREPARATION 6 tert-Butyl (2S)-2-(5-Benzyl-1,2,4-oxadiazol-3-yl)-1-piperidinecarboxylate

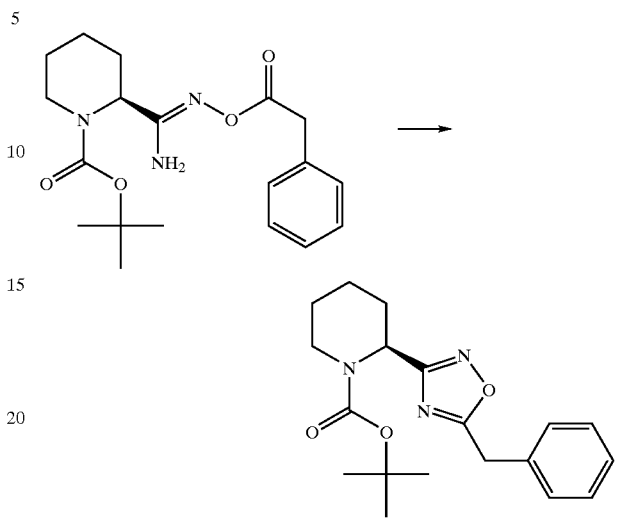

tert-Butyl (Z)-(2S)-2-(amino[(2-phenylacetyl)oxy[iminomethyl)-1-piperidinecarboxylate (17.5 g) [see Preparation 5] was dissolved in xylene (500 ml) and heated under reflux for 17 hours. The crude reaction mixture was chromatographed on silica gel eluting with a solvent gradient of 0:100 changing to 20:80, by volume, ethyl acetate: hexane to afford tert-butyl (2S)-2-(5-benzyl-1,2,4-oxadiazol-3-yl)-1-piperidinecarboxylate (10.56 g) as a yellow oil.

$^1$H-NMR (CDCl$_3$) δ: 7.30 (5H, m), 5.40 (1H, s), 4.20 (2H, s), 4.00 (1H, d), 3.00 (1H, t), 2.20 (1H, d), 1.80 (1H, m), 1.60–1.30 (13H, m).

PREPARATION 7

5-Benzyl-3-[(2S)-2-piperidyl]-1,2,4-oxadiazole Hydrochloride

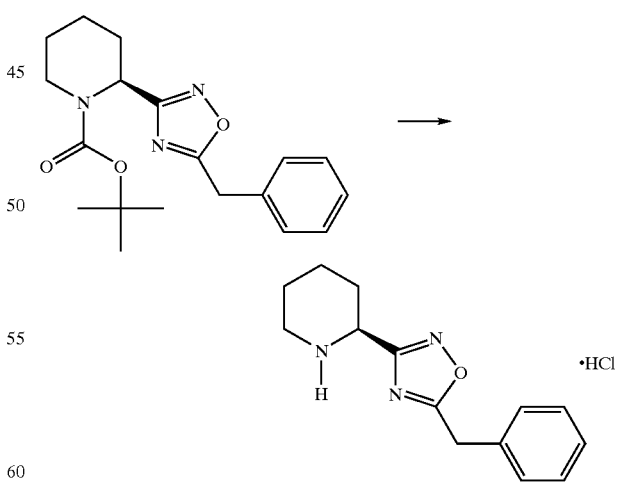

tert-Butyl (2S)-2-(5-benzyl-1,2,4-oxadiazol-3-yl)-1-piperidinecarboxylate (10.59 g) [see Preparation 6] was dissolved in dichloromethane (150 ml) and cooled to 0° C. Hydrogen chloride gas was then bubbled through until the point of saturation. The reaction mixture was then stirred for 30 mins. at 0° C., the solvent was removed under reduced pressure and the product azeotroped with dichloromethane to afford 5-benzyl-3-[(2S)-2-piperidyl]-1,2,4-oxadiazole hydrochloride (8.3 g) as a yellow solid.

$^1$H-NMR (CDCl$_3$): δ10.00 (1H, bs), 7.30 (5H, m), 4.45 (1H, s), 4.20 (2H, s), 3.65 (1H, m), 3.20 (1H, m), 2.40 (1H, m), 2.10 (1H, m), 2.00 (1H, m), 1.90–1.60 (3H, m). Rotation: $[\alpha]_D^{25}$=−15.20° (c=0. 1, methanol). Analysis: Found C, 59.38; H, 6.47; N, 14.76; C$_{14}$H$_{17}$N$_3$O.HCl.0.05CH$_2$Cl$_2$ requires C, 59.42; H, 6.42; N, 14.79%.

PREPARATION 8

1H-Benzo[d]imidazole-2-sulfonyl Chloride

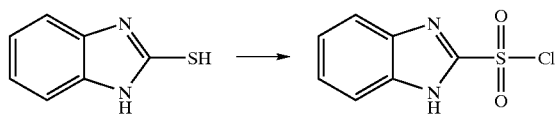

1H-2-Benzo[d]imidazolethiol (1.5 g) was suspended in 20% v/v acetic acid/water (60 ml) and cooled to 0° C. Chlorine gas was bubbled through the mixture until a point of saturation. The reaction mixture was stirred for 1 hour after which time it was filtered and the resulting solid was washed with ice-cold water and dried under reduced pressure to afford 1H-benzo[d]imidazole-2-sulfonyl chloride (2.38 g) as a light brown solid.

$^1$H-NMR (d$_6$-DMSO) δ: 7.70 (2H, d), 7.55 (2H, d).

PREPARATION 9

3-(Bromomethyl)tetrahydrofuran

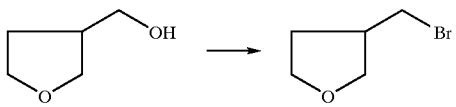

A solution of triphenylphosphine (7.34 g) in dichloromethane (65 ml) was added to a solution of 3-(hydroxymethyl)tetrahydrofuran (1.93 ml) and carbon tetrabromide (7.95 g) in dichloromethane (55 ml) at 0° C. The solution was warmed to room temperature and the reaction mixture was stirred for 3.5 hours after which time the solvent was removed under reduced pressure. The residue was chromatographed on silica gel eluting with a solvent gradient of 15:1 changing to 10:1, by volume, hexane:ethyl acetate to afford 3-(bromomethyl)tetrahydrofuran (2.49 g) as a colourless oil.

$^1$H-NMR (CDCl$_3$) δ: 3.85 (2H, m), 3.75 (1H, q), 3.58 (1H, m), 3.40 (2H, q), 2.65 (1H, m), 2.10 (1H, m), 1.65 (1H, m).

PREPARATION 10

Sodium Tetrahydrofuran-3-ylmethanesulfonate

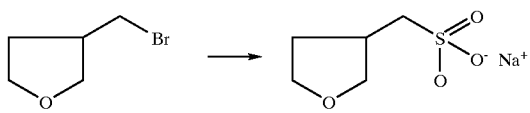

Sodium sulfite heptahydrate (6.10 g) was added to a solution of 3-(bromomethyl)tetrahydrofuran (2.0 g) [see Preparation 9] in 1,4-dioxane (9 ml) and water (9 ml). The reaction mixture was then heated under reflux and stirred for 18 hours, cooled and the solvent removed under reduced pressure. The resulting solid was dissolved in water and concentrated to a low volume. The solid formed was then collected to afford sodium tetrahydrofuran-3-ylmethanesulfonate (1.30 g) as a white solid.

$^1$H-NMR (D$_2$O) δ: 3.95 (1H, m), 3.80–3.60 (2H, m), 3.45 (1H, m), 3.00 (2H, m), 2.60 (1H, m), 2.20 (1H, m), 1.65 (1H, m).

PREPARATION 11

Tetrahydrofuran-3-ylmethanesulfonyl Chloride

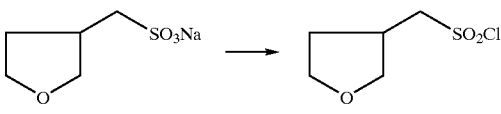

Sodium tetrahydrofuran-3-ylmethanesulfonate (1.0 g) [see Preparation 10] was dissolved in dimethylformamide (0.05m)) and thionyl chloride (5.3 ml) was added. The reaction mixture was heated under reflux for 5 hours, cooled and toluene (10 ml) added. The solvent was removed under reduced pressure. The residue was partitioned between ethyl acetate and water, the organic layer was separated, washed with brine, dried over magnesium sulphate and the solvent removed under reduced pressure to afford tetrahydrofuran-3-ylmethanesulfonyl chloride (0.22 g) as a yellow oil.

$^1$H-NMR (CDCl$_3$) δ: 3.95 (1H, m), 3.90–3.60 (2H, m), 3.45 (1H, m), 3.00 (2H, m), 2.30 (1H, m), 2.10 (1H, m), 1.80 (1H, m).

PREPARATION 12 tert-Butyl (Z)-(2S)-2-Amino[(2-[4-(hydroxymethyl) phenoxy]acetyloxy)imino]methyl-1-piperidinecarboxylate

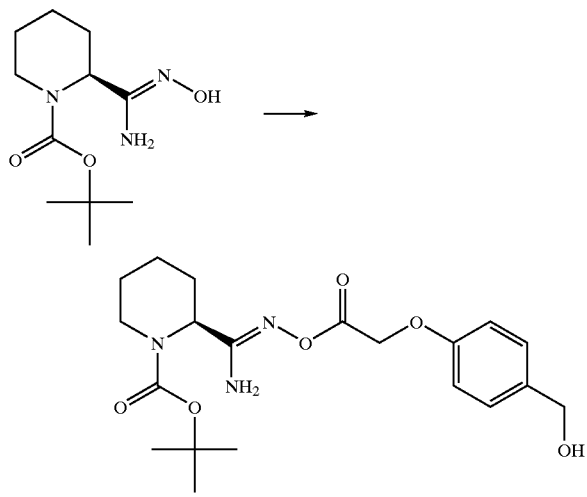

To a stirred solution of tert-butyl (Z(2S)-2-[amino (hydroxyimino)methyl]-1-piperidinecarboxylate [see Preparation 4] (2.43 g) in dichloromethane (75 ml) was added 4-(hydroxymethyl)phenoxyacetic acid (2.19 g), 1-(3-dimethylaminopropyl)-3-ethylcarbodimide hydrochloride (2.30 g), 4-dimethylaminopyridine (0.611 g) and N-methylmorpholine (1.30 ml). The reaction mixture was stirred for 56 hours, after which time it was diluted with dichloromethane (200 ml) and washed with 1M aqueous hydrochloric acid solution (50 ml) followed by saturated aqueous sodium hydrogen carbonate solution (50 ml). The organic layer was separated, dried over magnesium sulphate and the solvent was removed under reduced pressure to afford tert-butyl (Z)-(2S)-2-amino[(2-[4-(hydroxymethyl)phenoxy]acetyloxy)imino]methyl-1-piperidinecarboxylate (2.94 g).

$^1$H-NMR (CDCl$_3$) δ: 7.30 (2H, m), 7.00 (2H, m), 6.85 (1H, d), 5.55 (1H, bs), 5.30 (2H, s), 5.20 (1H, s), 4.60 (3H, m), 4.00 (1H, d), 3.00 (1H, d), 2.30 (1H, d), 1.90 (1H, m), 1.80–1.30 (13H, m).

PREPARATION 13 tert-Butyl (2S)-2-(5-[4-(hydroxymethyl)phenoxymethyl]-1,2,4-oxadiazol-3-yl)-1-piperidinecarboxylate

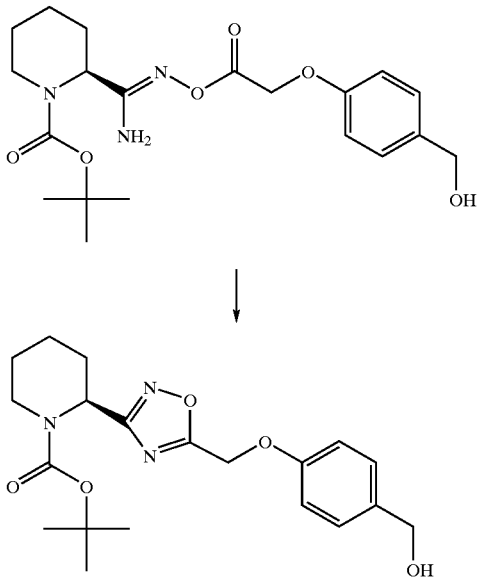

tert-Butyl (Z)-(2S)-2-amino[(2-[4-(hydroxymethyl)phenoxy]acetyloxy)imino]methyl-1-piperidinecarboxylate (see Preparation 12) (2.94 g) was dissolved in pyridine (30 ml) and heated under reflux for 18 hours. The reaction mixture was cooled and the solvent removed under reduced pressure. The residue was partitioned between ethyl acetate and water, the organic layer was separated, dried over magnesium sulphate and the solvent removed under reduced pressure. The crude product was purified by column chromatography on silica gel eluting with a solvent gradient of 50:50 changing to 0:100 (in 10% increments), by volume, hexane:ethyl acetate to afford tert-butyl (2S)-2-(5-[4-(hydroxymethyl)phenoxymethyl]-1,2,4-oxadiazol-3-yl)-1-piperidinecarboxylate (1.06 g).

$^1$H-NMR (CDCl$_3$) δ: 7.30 (2H, d), 7.00 (2H, d), 5.50 (1H, bs), 5.25 (2H, s), 4.65 (2H, d), 4.00 (1H, d), 3.00 (1H, t), 2.25 (1H, d), 1.90 (1H, m), 1.75–1.40 (13H, m).

PREPARATION 14 tert-Butyl (2S)-2-[5-(4-[(1,3-Dioxo-2,3-dihydro-1H-2-isoindolyl)methyl]phenoxymethyl)-1,2,4-oxadiazol-3-yl]-1-piperidinecarboxylate

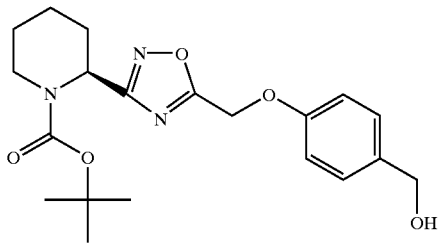

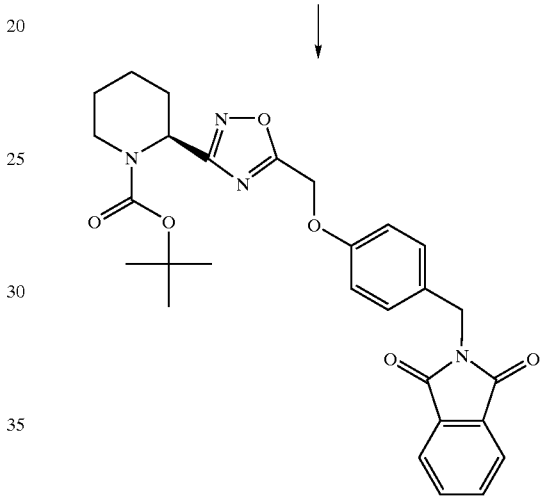

Phthalimide (480 mg) was added to a solution of tert-butyl (2S)-2-(5-[4-(hydroxymethyl)phenoxymethyl]-1,2,4-oxadiazol-3-yl)-1-piperidinecarboxylate [see Preparation 13] (1.06 g) in tetrahydrofuran (10 ml). The mixture was cooled to 0° C. and triphenylphosphine (1.07 g) was added followed by diethylazodicarboxylate (0.642 ml). The resulting yellow solution was stirred at 0° C. for 10 mins. and then at room temperature for 1 hour. The mixture was evaporated to a low volume under reduced pressure and partitioned between dichloromethane and water. The organic layer was separated, washed with brine, dried over magnesium sulphate and the solvent was removed under reduced pressure. The crude product was purified by column chromatography on silica gel eluting with a solvent gradient of 90:10 changing to 70:30, by volume, hexane:ethyl acetate to afford tert-butyl (2S)-2-[5-(4-[(1,3-dioxo-2,3-dihydro-1H-2-isoindolyl)methyl]phenoxymethyl)-1,2,4-oxadiazol-3-yl]-1-piperidinecarboxylate (1.09 g) as a white solid.

$^1$H-NMR (CDCl$_3$) δ: 7.90 (2H, s), 7.70 (2H, s), 7.40 (2H, m), 6.90 (2H, m), 5.45 (1H, bs), 5.20 (2H, d), 4.80 (2H, d), 4.00 (1H, m), 3.00 (1H, bs), 2.25 (1H, m), 1.80 (1H, bs), 1.70–1.30 (13H, m). Analysis: Found C, 63.85; H, 5.91; N, 10.03; $C_{28}H_{30}N_4O_6 \cdot 0.5$EtOAc requires C, 64.04; H, 6.09; N, 9.96%. (EtOAc=ethyl acetate).

PREPARATION 15

2-[4-(3-[(2S)-2-Piperidyl]-1,2,4-oxadiazol-5-ylmethoxy)benzyl]-1,3-isoindolinedione Hydrochloride

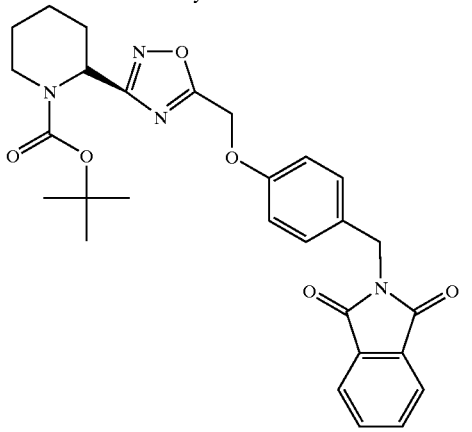

↓

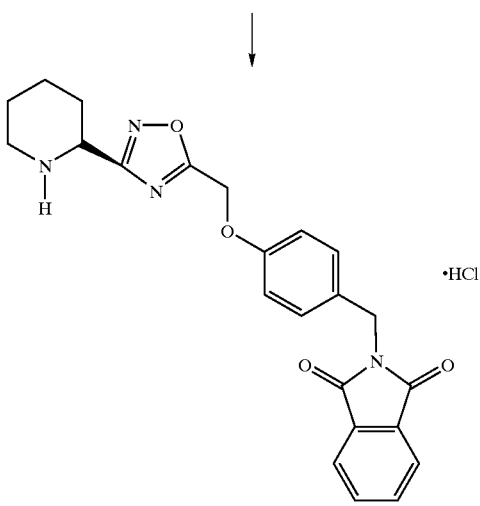

The title compound was prepared by the method of Preparation 7 from tert-butyl (2S)-2-[5-(4-[(1,3-dioxo-2,3-dihydro-1H-2-isoindolyl)methyl]-phenoxymethyl)-1,2,4-oxadiazol-3-yl]-1-piperidinecarboxylate [see Preparation 14] and hydrogen chloride gas to afford 2-[4-(3-[(2S)-2-piperidyl]-1,2,4-oxadiazol-5-ylmethoxy)benzyl]-1,3-isoindolinedione hydrochloride as a white solid.

$^1$H-NMR (d$_6$-DMSO) δ: 7.85 (4H, m), 7.30 (2H, d), 7.00 (2H, d), 5.60 (2H, s), 4.70 (3H, d), 3.05 (1H, t), 2.20 (1H, d), 1.90–1.50 (6H, m).

PREPARATION 16

1-(1H-Benzo[d]imidazol-2-ylsulfonyl)-2-piperidinecarboxylic Acid

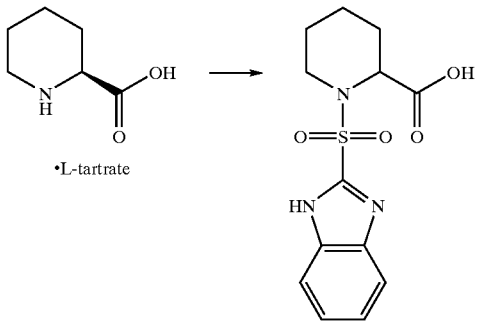

(2S)-2-Piperidinecarboxylic acid L-tartrate (42 g) [see Preparation 1] was dissolved in 10% w/w aqueous sodium hydroxide solution (600 ml) and 1H-benzo[d]imidazole-2-sulfonyl chloride (39 g) [see Preparation 8] was added. The reaction mixture was stirred at room temperature for 56 hours after which time the product was extracted with ethyl acetate. The organic layer was separated, 2N aqueous hydrochloric acid solution added and the acidic aqueous layer extracted twice with ethyl acetate. The combined organic layers were dried over magnesium sulphate and the solvent removed under reduced pressure. The crude product was purified by column chromatography on silica gel eluting with 95:5:0.5, by volume, dichloromethane:methanol:glacial acetic acid to afford 1-(1H-benzo[d]imidazol-2-ylsulfonyl)-2-piperidinecarboxylic acid (17.5 g).

$^1$H-NMR (d$_6$-DMSO) δ: 7.25 (2H, m), 7.10 (2H, m), 4.65 (1H, s), 3.85 (1H, d), 3.20 (1H, t), 2.30 (1H, d), 1.50 (3H, m), 1.20 (2H, m).

PREPARATION 17

1-(1H-Benzo[d]imidazol-2-ylsulfonyl)-2-piperidinecarboxamide

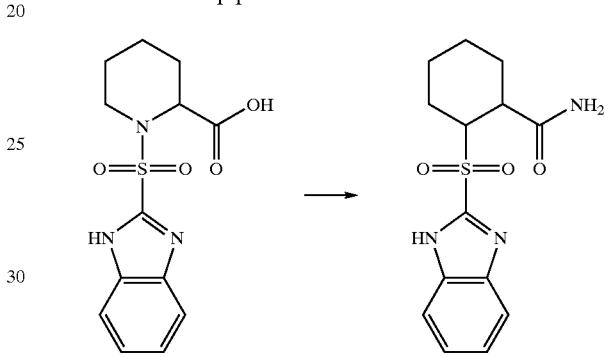

1-(1H-Benzo[d]imidazol-2-ylsulfonyl)-2-piperidinecarboxylic acid (17.5 g) [see Preparation 16] was dissolved in tetrahydrofuran (180 ml) and cooled to −20° C. Triethylamine (10.2 ml) was added to the mixture followed by ethyl chloroformate (5.4 ml). The reaction mixture was stirred for 1 hour at −20° C. and 0.88 aqueous ammonia solution (25 ml) was added. The mixture was then stirred for a further 2 hours at room temperature. The organic solvent was removed under reduced pressure and ethyl acetate added. The organic layer was separated, washed with water, dried over magnesium sulphate and the solvent removed under reduced pressure to afford 1-(1H-benzo[d]imidazol-2-ylsulfonyl)-2-piperidinecarboxamide (14.73 g).

$^1$H-NMR (CDCl$_3$) δ: 8.80 (1H, s), 7.70 (2H, m), 7.40 (2H, m), 6.00 (1H, bs), 5.00 (1H, s), 3.80 (1H, d), 3.20 (1H, t), 2.60 (1H, d), 1.80–1.50 (5H, m).

PREPARATION 18

1-(1H-Benzo[d]imidazol-2-ylsulfonyl)-2-piperidinecarbonitrile

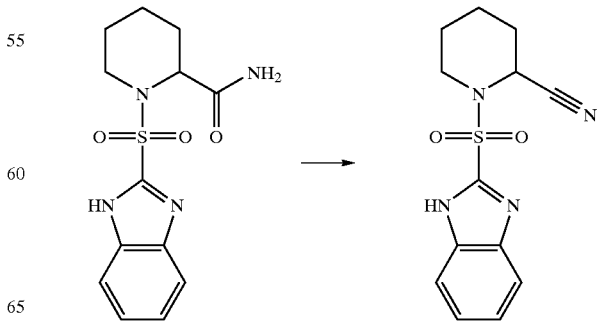

Oxalyl chloride (5.00 ml) was added dropwise to a solution of dimethylformamide (4.43 ml) in acetonitrile (200 ml) at 0° C. The mixture was stirred for 20 mins. and a suspension of pyridine (9.66 ml) and 1-(1H-benzo[d]imidazol-2-ylsulfonyl-2-piperidinecarboxamide (14.73 g) [see Preparation 17] in acetonitrile (100 ml) was added over a period of 10 mins. The reaction mixture was stirred for a further 20 mins. after which time the solvent was removed under reduced pressure. The residue was diluted with diethyl ether and washed with water, brine, dried over magnesium sulphate and the solvent was removed under reduced pressure. The crude product was purified by column chromatography on silica gel eluting with 70:30, by volume, hexane:ethyl acetate to afford 1-(1H-benzo[d]imidazol-2-ylsulfonyl)-2-piperidinecarbonitrile (4.9 g).

$^1$H-NMR (CDCl$_3$) δ: 7.80 (1H, m), 7.60 (1H, m), 7.30 (2H, m), 5.20 (1H, s), 4.00 (1H, d), 3.00 (1H, t), 2.00 (1H, m), 1.80 (2H, m), 1.40 (3H, m).

PREPARATION 19

(Z)-1-(1H-Benzo[d]imidazol-2-ylsulfonyl)-N'$^2$-hydroxy-2-piperidinecarboximidamide

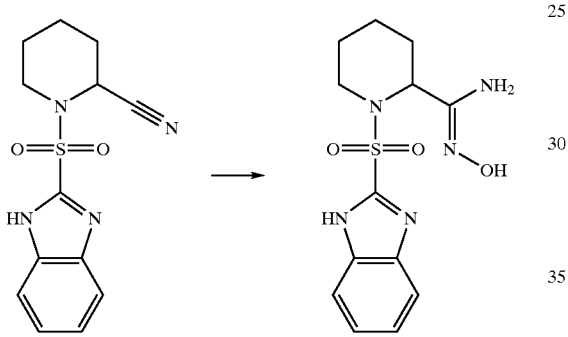

The title compound was prepared by a similar method to Preparation 4 from 1-(1H-benzo[d]imidazol-2-ylsulfonyl)-2-piperidinecarbonitrile [see Preparation 18] to afford the title compound as an oil.

$^1$H-NMR (d$_6$-DMSO) δ: 9.40 (1H, bs), 7.70 (2H, s), 7.40 (2H, m), 5.60 (2H, bs), 4.80 (1H, s), 3.80 (1H, d), 3.20 (1H, t), 2.00 (1H, d), 1.60–1.30 (5H, m).

PREPARATION 20

(Z)-1-(1H-Benzo[d]imidazol-2-ylsulfonyl)-N'$^2$-(2-[4-(hydroxymethyl)phenoxy]acetyloxy)-2-piperidinecarboximidamide

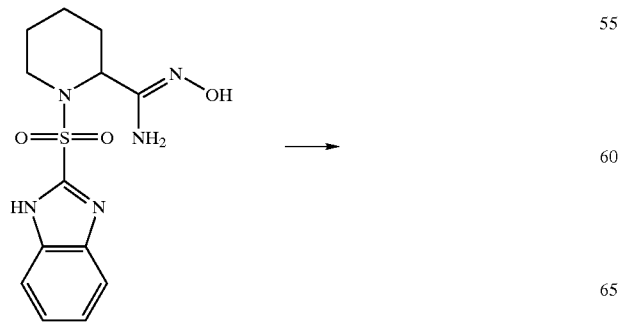

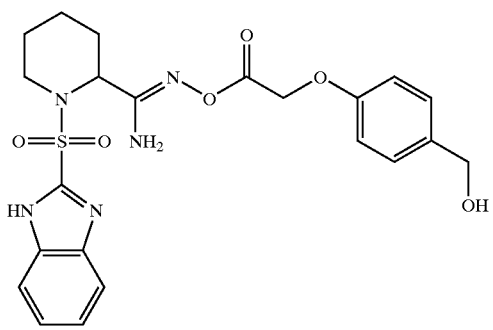

The title compound was prepared by a similar method to Preparation 12 from the compound of Preparation 19 and 4-(hydroxymethyl)phenoxyacetic acid. The crude title compound was used without purification in Preparation 21.

PREPARATION 21

4-(3-[1-(1H-Benzo[d]imidazol-2-ylsulfonyl)-2-piperidyl]-1,2,4-oxadiazol-5-ylmethoxy)phenylmethanol

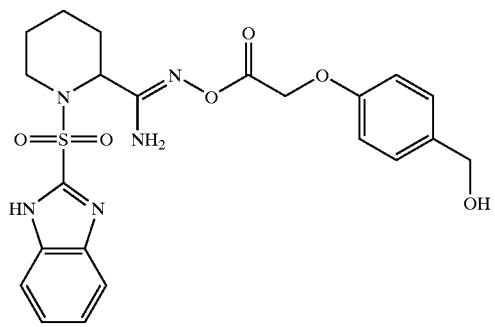

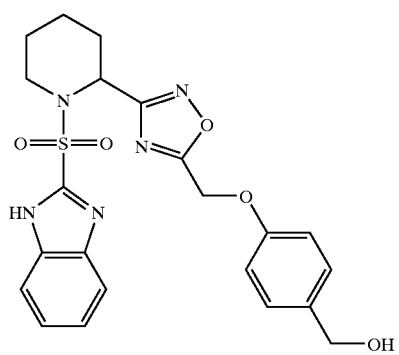

PREPARATION 22

The title compound was prepared by a similar method to Preparation 13 from the compound of Preparation 20 and pyridine to afford 4-(3-[1-(1H-benzo[d]imidazol-2-ylsulfonyl)-2-piperidyl]-1,2,4-oxadiazol-5-ylmethoxy)phenylmethanol as an oil.

¹H-NMR (CDCl₃) δ: 7.80 (1H, m), 7.50 (1H, m), 7.30 (4H, m), 6.80 (2H, m), 5.60 (1H, d), 4.80 (2H, d), 4.60 (2H, s), 4.00 (1H, d), 3.20 (1H, m), 2.30 (1H, d), 2.10 (1H, m), 1.80 (4H, m).

4-(3-[1-(1H-Benzo[d]imidazol-2-ylsulfonyl)-2-piperidyl]-1,2,4-oxadiazol-5-ylmethoxy)benzaldehyde

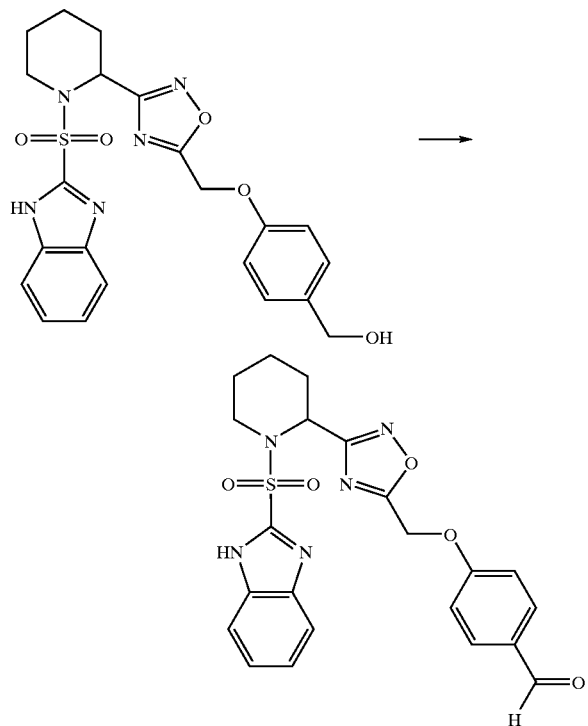

Tetrapropylammonium perruthenate (14.4 mg) was added to a stirred suspension of 4-(3-[1-(1H-benzo[d]imidazol-2-ylsulfonyl)-2-piperidyl]-1,2,4-oxadiazol-5-ylmethoxy)phenylmethanol (384 mg) [see Preparation 21], N-methylmorpholine oxide (166 mg) and 4 Å molecular sieves in 10% v/v acetonitrile/dichloromethane (4 ml). The reaction mixture was stirred for 1 hour after which time the solvent was removed under reduced pressure. The crude product was purified by column chromatography on silica gel eluting with ethyl acetate to afford 4-(3-[1-(1H-benzo[d]imidazol-2-ylsulfonyl)-2-piperidyl]-1,2,4-oxadiazol-5-ylmethoxy)benzaldehyde (342 mg).

¹H-NMR (CDCl₃) δ: 10.40 (1H, bs), 9.95 (1H, s), 7.85 (2H, d), 7.50–7.20 (4H, m), 7.00 (2H, d), 5.50 (1H, d), 4.80 (2H, q), 4.05 (1H, d), 3.25 (1H, t), 2.25 (1H, m), 2.10 (1H, m),1.80 (4H, m).

PREPARATION 23

2-[4-(3-[(2S)-1-Cyclohexylmethylsulfonyl-2-piperidyl]-1,2,4-oxadiazol-5-ylmethoxy)benzyl]-1,3-isoindolinedione

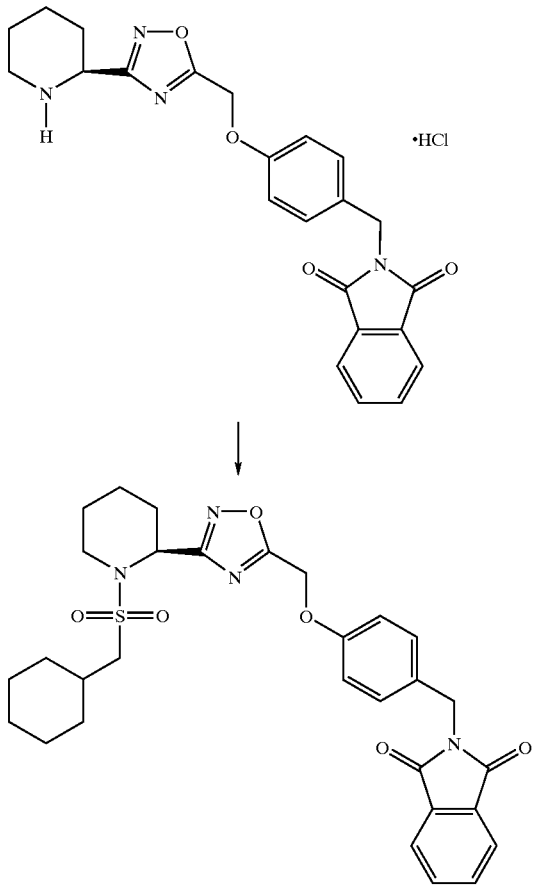

Cyclohexylmethanesulfonyl chloride (359 mg) [King. J. F. et al., J. Am. Chem. Soc., 1992, 114(5), 1743–9] was added to a solution of 2-[4-(3-[(2S)-2-piperidyl]-1,2,4-oxadiazol-5-ylmethoxy)benzyl]-1,3-isoindolinedione hydrochloride (627 mg) [see Preparation 153 and triethylamine (0.4 ml) in dichloromethane (2 ml). The reaction mixture was stirred at room temperature for 18 hours after which time it was heated to 30° C. and stirred for a further 56 hours. The mixture was diluted with dichloromethane and washed with dilute aqueous hydrochloric acid solution, the organic layer dried over magnesium sulphate and the solvent removed under reduced pressure. The crude product was purified by column chromatography on silica gel eluting with a solvent gradient of 100:0 changing to 75:25, by volume, hexane:ethyl acetate to afford 2-[4-(3-[(2S)-1-cyclohexylmethylsulfonyl-2-piperidyl]-1,2,4-oxadiazol-5-ylmethoxy)benzyl]-1,3-isoindolinedione (192 mg).

¹H-NMR (CDCl₃) δ: 7.85 (2H, d), 7.70 (2H, d), 7.40 (2H, d), 6.95 (2H, d), 5.40 (1H, d), 5.20 (2H, s), 4.80 (2H, s), 3.80 (1H, d), 3.20 (1H, t), 2.90 (2H, m), 2.20 (1H, d), 2.00–1.00 (16H, m).

PREPARATION 24

(2S)-2-(Methoxycarbonyl)piperidine Hydrochloride

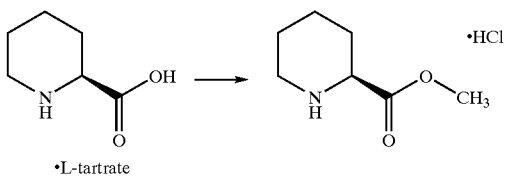

·L-tartrate

Thionyl chloride (161 ml) was added dropwise to a suspension of (2S)-2-piperidinecarboxylic acid L-tartrate (60 g) [see Preparation 1] in methanol (800 ml) at 0° C. The reaction mixture was stirred for 18 hours at room temperature after which time the solvent was removed under reduced pressure and the product azeotroped with toluene, precipitated out using methanol and filtered to afford (2S)-2-(methoxycarbonyl)piperidine hydrochloride (37.7 g) as a white solid.

$^1$H-NMR (D$_2$O) δ: 3.95 (1H, d), 3.70 (3H, s), 3.40 (1H, d), 3.00 (1H, t), 2.20 (1H, d), 1.80 (2H, d), 1.70–1.40 (3H, m).

PREPARATION 25

Methyl (2S)-1-[(Cyclohexylmethyl)sulfonyl]-2-piperidinecarboxylate

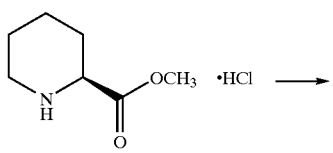

Triethylamine (22.15 ml) was added to a solution of (2S)-2-(methoxycarbonyl)piperidine hydrochloride (10 g) [see Preparation 24] and cyclohexylmethanesulfonyl chloride (16.42 g) [King. J. F. et al,. J. Am. Chem. Soc., 1992, 114(5), 1743–9] in dichloromethane (100 ml). The reaction mixture was stirred for 18 hours after which time the solvent was removed under reduced pressure and the residue diluted with ethyl acetate. The organic layer was washed with water, brine, dried over magnesium sulphate and the solvent was removed under reduced pressure. The crude product was purified by column chromatography on silica gel eluting with a solvent gradient of 95:5 changing to 80:20, by volume, hexane:ethyl acetate to afford methyl (2S)-1-[(cyclohexylmethyl)sulfonyl]-2-piperidinecarboxylate (11.9 g) as a white solid.

$^1$H-NMR (CDCl$_3$) δ: 4.70 (1H, d), 3.75 (3H, s), 3.70 (1H, d), 3.20 (1H, t), 2.80 (2H, d), 2.20 (1H, d), 2.00–1.00 (16H, m).

PREPARATION 26

(2S)-1-[(Cyclohexylmethyl)sulfonyl]-2-piperidinecarboxamide

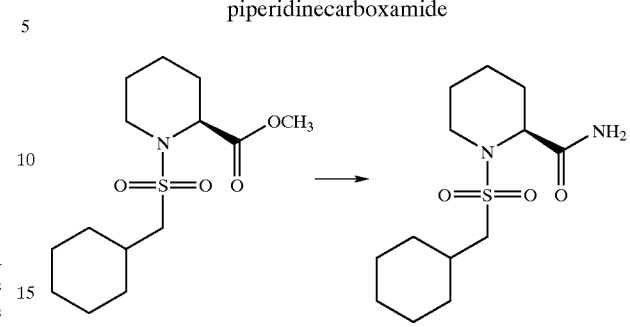

Methyl (2S)-1-[(cyclohexylmethyl)sulfonyl]-2-piperidinecarboxylate (3.0 g) [see Preparation 25] was dissolved in 1,4-dioxane (30 ml) and 0.88 aqueous ammonia solution (25 ml) was added. Ammonia gas was bubbled through the mixture for 20 mins. and the reaction mixture was heated to 100° C. in a sealed vessel for 56 hours. After this time the mixture was cooled and the solvent removed under reduced pressure. The residue was taken up in ethyl acetate and washed with saturated aqueous sodium hydrogen carbonate solution, brine, dried over magnesium sulphate and the solvent was removed under reduced pressure to afford (2S)-1-[(cyclohexylmethyl)sulfonyl]-2-piperidinecarboxamide (1.77 g) as a colourless oil.

$^1$H-NMR (CDCl$_3$) δ: 4.80 (1H, d), 3.70 (1H, d), 3.20 (1H, t), 2.95 (2H, d), 2.30 (1H, d), 2.00–1.00 (16H, m). Rotation: $[\alpha]_D^{25}$=−15.8° (c=0.1, methanol).

PREPARATION 27

(2S)-1-[(Cyclohexylmethyl)sulfonyl]-2-piperidinecarbonitrile

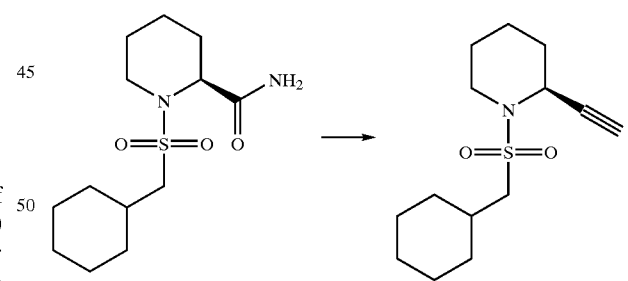

The title compound was prepared by a similar method to Preparation 3 from (2S)-1-[(cyclohexylmethyl)sulfonyl]-2-piperidinecarboxamide [see Preparation 26], oxalyl chloride, dimethylformamide and pyridine. The crude product was purified by column chromatography on silica gel eluting with a solvent gradient of 80:20 changing to 20:80, by volume (in 10% increments), hexane:ethyl acetate to afford (2S)-1-[(cyclohexylmethyl)sulfonyl]-2-piperidinecarbonitrile as an oil.

$^1$H-NMR (CDCl$_3$) δ: 4.90 (1H, s), 3.80 (1H, d), 3.00–2.80 (3H, m), 2.00–1.00 (17H, m).

PREPARATION 28

(Z)-(2S)-1-[Cyclohexylmethylsulfonyl]-N'2-hydroxy-2-piperidinecarboximidamide

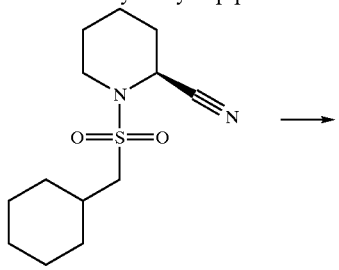

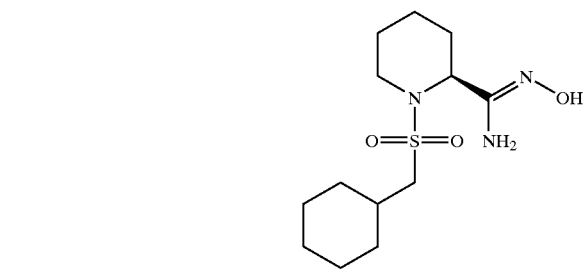

The title compound was prepared by a similar method to Preparation 4 from (2S)-1l-[(cyclohexylmethyl)sulfonyl]-2-piperidinecarbonitrile [see Preparation 27], hydroxy]amine hydrochloride and sodium carbonate. The title compound was obtained as a white solid.

$^1$H-NMR (CDCl$_3$) δ: 7.00 (1H, bs), 5.00 (2H, bs), 4.50 (1H, s), 3.75 (1H, d), 3.05 (1H, d), 2.85 (2H, d), 2.20 (1H, d), 2.00–1.00 (16H, m).

PREPARATION 29

(Z)-(2S)-N'2-(2-[(1-Benzyl-4-piperidinyl)oxy]acetyloxy)-1-[(cyclohexylmethyl)sulfonyl]-2-piperidinecarboximidamide

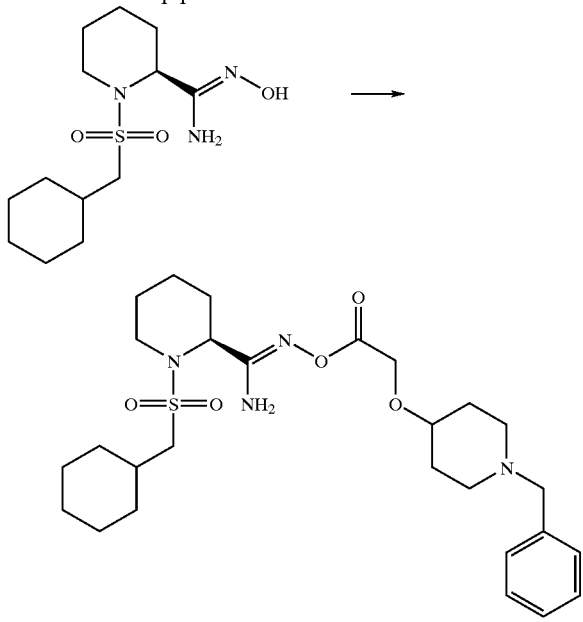

The title compound was prepared by a similar method to Preparation 5 from the compound of Preparation 28, sodium 2-[(1-benzyl-4-piperidyl)oxy]acetate [J. Med. Chem., 1987, 30(8), 999–1003], N-methylmorpholine, 1-hydroxybenzotriazole hydrate and 1-(3-dimethylaminopropyl)-3-ethylcarbodiimide hydrochloride. The title compound was obtained as a brown liquid.

$^1$H-NMR (CDCl$_3$) δ: 7.30 (5H, m), 5.20 (1H, d), 4.60 (1H, d), 4.30 (2H, s), 3.80 (1H, d), 3.55 (3H, s), 3.10 (1H, m), 2.95 (2H, d), 2.75 (2H, m), 2.35 (1H, d), 2.15 (2H, t), 2.00–1.00 (20H, m).

PREPARATION 30

Alpha-[(tert-Butoxycarbonyl)amino]phenylacetic Acid

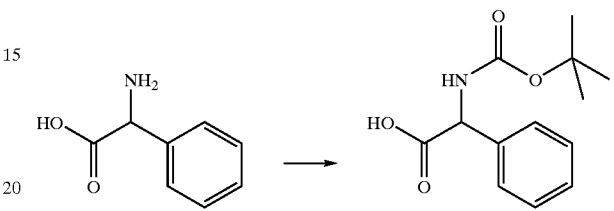

The title compound was prepared by a similar method to Preparation 1 from alpha-aminophenylacetic acid and di-t-butyldicarbonate to afford alpha-[(tert-butoxycarbonyl)amino]phenylacetic acid as a white solid.

$^1$H-NMR (CDCl$_3$) δ: 7.40 (5H, m), 5.40–5.10 (1H, bs), 1.50–1.20 (9H, bs).

PREPARATION 31 tert-Butyl N-(2-[((Z)-Amino(2S)-1-[(cyclohexylmethyl)sulfonyl]-2-piperidylmethylidene)amino]oxy-2-oxo-1-phenylethyl)carbamate

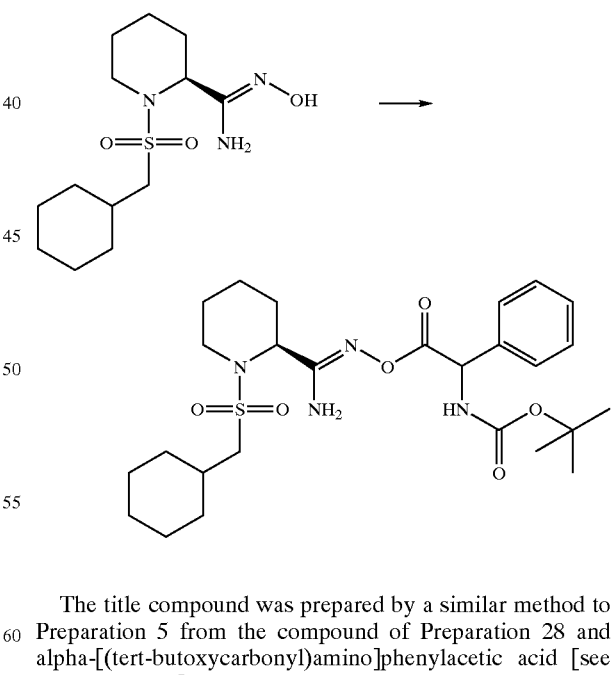

The title compound was prepared by a similar method to Preparation 5 from the compound of Preparation 28 and alpha-[(tert-butoxycarbonyl)amino]phenylacetic acid [see Preparation 30]. The crude product was purified by column chromatography on silica gel eluting with 80:20, by volume, hexane:ethyl acetate to afford the title compound as an oil.

$^1$H-NMR (CDCl$_3$) δ: 7.50 (5H, m), 5.50 (2H, m), 5.20 (2H, bs), 4.60 (1H, s), 3.75 (1H, d), 3.05 (1H, m), 2.90 (2H, s), 2.30 (1H, t), 2.00–1.00 (25H, m).

PREPARATION 32

(Z)-(2S)-1-[(Cyclohexylmethyl)sulfonyl]-N'²-[(2-morpholinoacetyl)oxy]-2-piperidinecarboximidamide

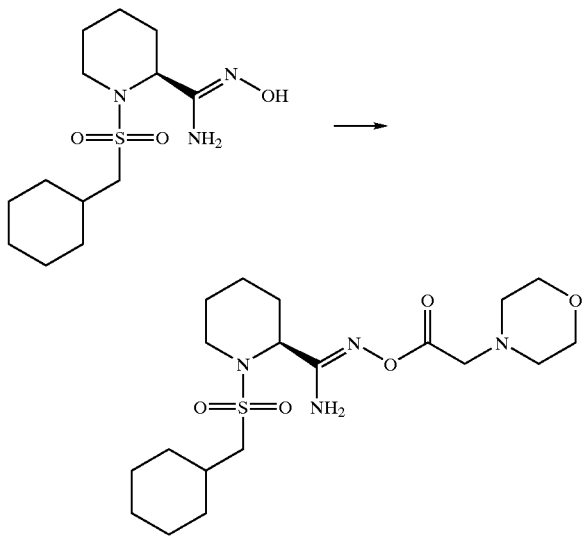

The title compound was prepared by a similar method to Preparation 5 from the compound of Preparation 28 and 2-morpholinoacetic acid [J. Med. Chem., 1993, 36(3), 320] to afford the title compound (240 mg) as a clear oil.

¹H-NMR (CDCl₃) δ: 5.25 (2H, s), 4.60 (1H, s), 3.80 (5H, m), 3.40 (2H, s), 3.10 (1H, t), 2.95 (2H, d), 2.65 (4H, m), 2.40 (1H, d), 2.00–1.00 (16H, m).

PREPARATION 33

2-[(1-Benzyl-4-piperidyl)oxy]ethyl Cyanide

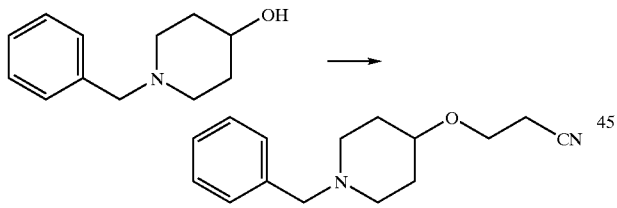

Sodium hydride [50% w/w in mineral oil] (2.0 g) was added to a slurry of 1-benzyl-4-piperidinol (400 g) and acrylonitrile (530 g) at 0° C. over 1 hour. The reaction mixture was warmed slowly to room temperature and stirred for 18 hours after which time the acrylonitrile was removed under reduced pressure and the residue taken up in isopropanol (1 L). The resulting yellow precipitate was filtered off. The filtrate was evaporated under reduced pressure to afford an orange oil which was dissolved in dichloromethane and washed with water. The organic layer was separated, dried over magnesium sulphate and the solvent removed under reduced pressure. The crude product was purified by distillation to afford 2-[(1-benzyl-4-piperidyl)oxy]ethyl cyanide (308 g), b.p. 150–160° C. @ 0.2 mmHg.

¹H-NMR (CDCl₃) δ: 7.70 (2H, m), 7.45 (3H, m), 4.10 (2H, m), 3.80 (1H, s), 3.65 (2H, t), 3.25 (2H, m), 3.00 (2H, m), 2.60 (4H, m), 2.00 (2H, d).

PREPARATION 34

Methyl 3-[(1-Benzyl-4-piperidyl)oxy]propanoate

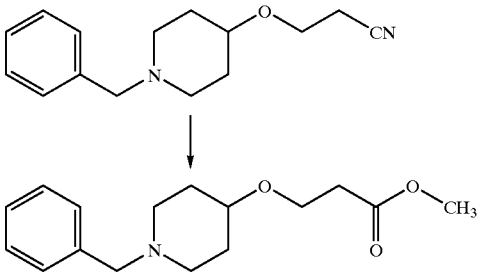

2-[(1-Benzyl-4-piperidyl)oxy]ethyl cyanide (10 g) [see Preparation 33] was dissolved in a 20% w/w solution of hydrogen chloride in methanol (100 ml). The reaction mixture was then heated under reflux for 3 hours. After this time the mixture was cooled and the white precipitate was filtered off. The filtrate was evaporated under reduced pressure and the residue was dissolved in dichloromethane and washed with aqueous sodium carbonate solution. The organic layer was separated, dried over magnesium sulphate and the solvent was removed under reduced pressure to afford methyl 3-[(1-benzyl-4-piperidyl)oxy]propanoate (7.8 g) as an oil.

¹H-NMR (CDCl₃) δ: 7.30–7.20 (5H, m), 3.75 (5H, m), 3.50 (2H, s), 3.30 (1H, m), 2.75 (2H, m), 2.60 (2H, m), 2.20 (2H, m), 1.90 (2H, m), 1.60 (2H, m).

PREPARATION 35

3-[(1-Benzyl-4-piperidyl)oxy]propanoic Acid

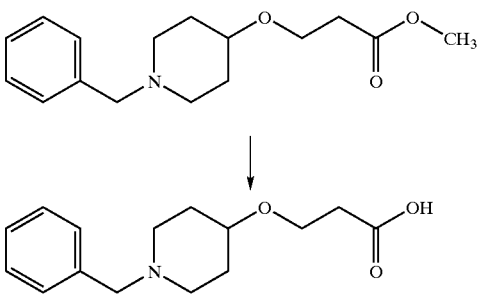

Lithium hydroxide (7.21 ml of a 1N aqueous solution) was added to a solution of methyl 3-[(1-benzyl-4-piperidyl)oxy]propanoate (1.00 g) [see Preparation 34) in methanol (43.3 ml). The reaction mixture was stirred for 36 hours at room temperature after which time the methanol was evaporated under reduced pressure. The crude product was dissolved in a small amount of water and purified on a Dowex 50WX8-200 (trade mark) ion-exchange resin eluting with 0:100 changing to 50:50 (in 10% increments), by volume, water: 0.88 aqueous ammonia solution. The aqueous eluted solution was concentrated under reduced pressure and the residue was frozen and lyophilised to afford 3-[(1-benzyl-4-piperidyl)oxy]propanoic acid (269 mg) as an off-white solid.

¹H-NMR (d₆-DMSO) δ: 7.30 (5H, m), 3.60 (3H, t), 3.25 (2H, m), 2.60 (2H, m), 2.40 (2H, t), 2.00 (2H, m), 1.80 (2H, m), 1.40 (2H, m).

PREPARATION 36

(Z)-(2S)-N'²-(3-[1-Benzyl-4-piperidinyl)oxy]propanoyloxy)-1-[(cyclohexylmethyl)sulfonyl]-2-piperidinecarboximidamide

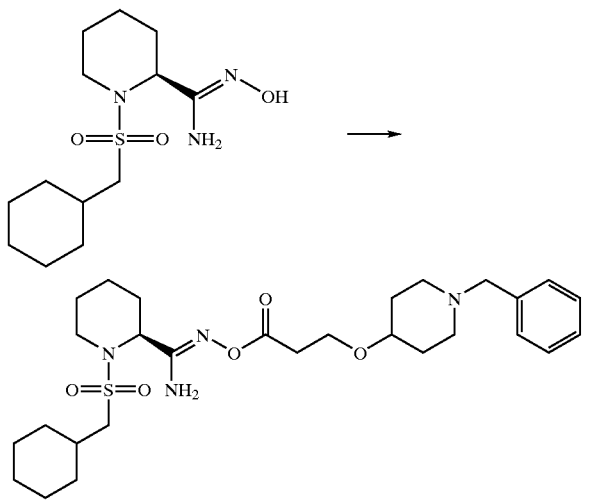

The title compound was prepared by a similar method to Preparation 5 from the compound of Preparation 28 and 3-[(1-benzyl-4-piperidyl)oxy]propanoic acid [see Preparation 35] to afford the title compound as a clear gum.

$^1$H-NMR (CDCl$_3$) δ: 7.30 (5H, m), 5.25 (2H, s), 4.60 (1H, s), 3.80 (3H, m), 3.50 (2H, m), 3.40 (1H, bs), 3.10 (1H, t), 3.00 (2H, m), 2.70 (4H, m), 2.40 (1H, d), 2.10–1.00 (20H, m).

PREPARATION 37

Benzyl N-3-[((Z)-Amino[(1-(1H-1,3-benzimidazol-2-ylsulfonyl)-2-piperidyl]methylideneamino)oxy]-3-oxopropylcarbamate

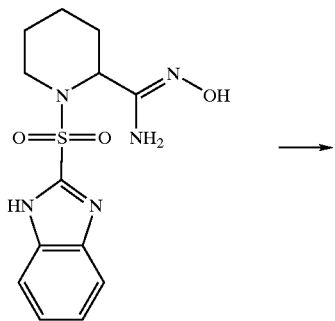

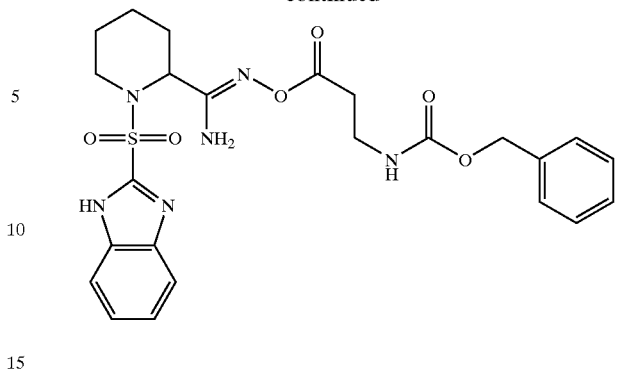

The title compound was prepared by a similar method to Preparation 5 from the compound of Preparation 19 and N-benzyloxycarbonyl-beta-alanine to afford the title compound as an oil.

$^1$H-NMR (d$_6$-DMSO) δ: 7.70 (2H, d), 7.30 (5H, m), 6.65 (2H, s), 5.05 (2H, s), 4.85 (1H, s), 3.70 (1H, d), 3.30 (1H, t), 3.25 (2H, m), 2.55 (2H, m), 2.05 (1H, d), 1.50 (4H, m), 1.20 (1H, m).

PREPARATION 38

(2S)-1-[(4-Fluorophenyl)sulfonyl]-2-piperidinecarboxylic Acid

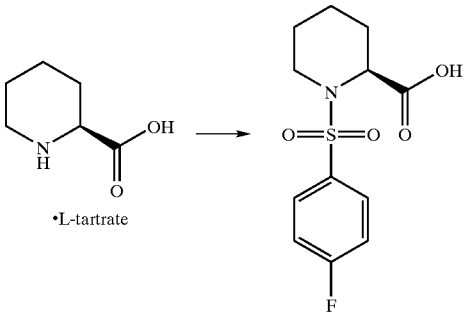

(2S)-2-Piperidinecarboxylic acid L-tartrate (10 g) [see Preparation 1] was dissolved in 1N aqueous sodium hydroxide solution (107.4 ml) and diethylisopropylamine (9.35 ml) was added followed by a solution of 4-fluorobenzenesulphonyl chloride (10.45 g) in acetone (107 ml) at 0° C. The reaction mixture was warmed to room temperature and stirred for 18 hours after which time the solvent was removed under reduced pressure and the residue diluted with 1N aqueous sodium hydroxide solution. The aqueous solution was washed with diethyl ether and acidified with concentrated hydrochloric acid. The product was extracted with ethyl acetate, the organic layers dried over magnesium sulphate and the solvent was removed under reduced pressure to afford (2S)-1-[(4-fluorophenyl)sulfonyl]-2-piperidinecarboxylic acid (9.89 g).

$^1$H-NMR (d$_6$-DMSO) δ: 7.80 (2H, d), 7.40 (2H, d), 4.50 (1H, s), 3.60 (1H, d), 3.20 (1H, t), 2.00 (1H, d), 1.55 (3H, m), 1.20 (2H, m).

PREPARATION 39

N'2-Acetyl-(2S)-1-[(4-fluorophenyl)sulfonyl]-2-piperidinecarbohydrazide

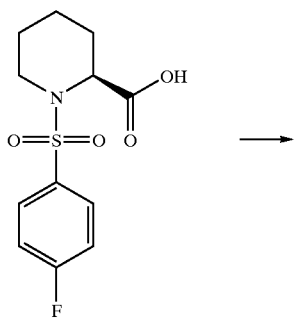

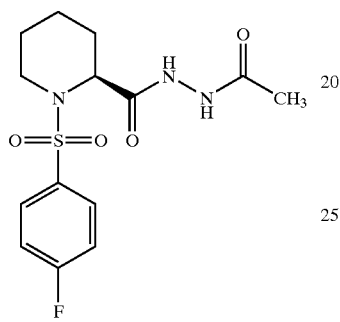

1-Hydroxybenzotriazole hydrate (162 mg), acethydrazide (81 mg), N-methylmorpholine (275 µl) and 1-(3-dimethylaminopropyl)-3-ethylcarbodiimide (230 mg) were added to a stirred solution of (2S)-1-[(4-fluorophenyl)sulfonyl]-2-piperidinecarboxylic acid [see Preparation 38] (287 mg) in dichloromethane (3 ml). The reaction mixture was stirred for 3 hours after which time the mixture was partitioned between dichloromethane and water. The organic layer was separated, dried over magnesium sulphate and the solvent removed under reduced pressure to afford N'2-acetyl-(2S)-1-[(4-fluorophenyl)sulfonyl]-2-piperidinecarbohydrazide (340 mg) as a white solid.

$^1$H-NMR (CDCl$_3$) δ: 8.00 (2H, d), 7.20 (2H, d), 4.60 (1H, d), 3.90 (1H, d), 3.40 (1H, t), 2.25 (1H, d), 2.05 (3H, s), 1.50–1.00 (5H, m).

PREPARATION 40

(2S)-1-[(4-Fluorophenyl)sulfonyl]-2-piperidinecarboxamide

The title compound was prepared by a similar method to Preparation 2 from (2S)-1-[(4-fluorophenyl)sulfonyl]-2-piperidinecarboxylic acid [see Preparation 38]. The crude product was purified by column chromatography on silica gel eluting with a solvent gradient of 50:50 changing to 0:100 (in 10% increments), by volume, hexane:ethyl acetate to afford (2S)-1-[(4-fluorophenyl)sulfonyl]-2-piperidinecarboxamide as a white solid.

$^1$H-NMR (CDCl$_3$) δ: 8.00 (2H, d), 7.40 (2H, d), 6.60 (1h, bs), 5.50 (1H, bs), 4.60 (1H, d), 4.00 (1H, d), 3.20 (1H, t), 2.25 (1H, d), 1.50 (3H, m), 1.10 (2H, m). Rotation: [α]$_D^{25}$=–43.01° (c=0.1, methanol).

PREPARATION 41

Ethyl (2S)-1-[(4-Fluorophenyl)sulfonyl]-2-piperidinecarboximidate

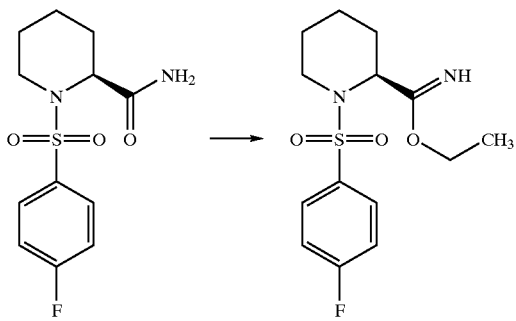

(2S)-1-[(4-Fluorophenyl)sulfonyl]-2-piperidinecarboxamide (286 mg) [see Preparation 40] was added to a solution of triethyloxonium hexafluorophosphate (304 mg) in dichloromethane (5 ml). The reaction mixture was stirred at room temperature for 18 hours after which time the mixture was diluted with dichloromethane and washed with saturated aqueous sodium hydrogen carbonate solution. The organic layer was separated, dried over magnesium sulphate and the solvent was removed under reduced pressure to afford ethyl (2S)-1-[(4-fluorophenyl)sulfonyl]-2-piperidinecarboximidate (290 mg).

$^1$H-NMR (CDCl$_3$) δ: 7.90 (2H, d), 7.20 (2H, d), 4.70 (1H, d), 4.20 (2H, m), 3.80 (1H, d), 3.10 (1H, t), 2.20 (1H, d), 1.60–1.20 (8H, m).

PREPARATION 42

(2S)-1-[(4-Fluorophenyl)sulfonyl]-2-(1H-1,2,4-triazol-3-yl)piperidine

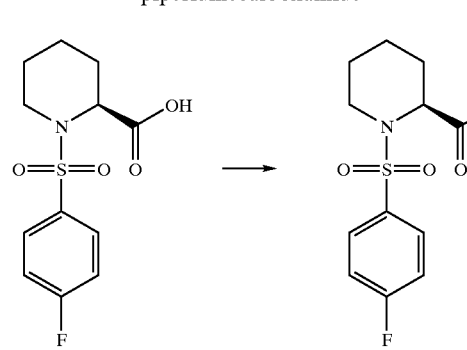

Formylhydrazine (120 mg) was added to a solution of ethyl (2S)-1-[(4-fluorophenyl)sulfonyl]-2-piperidinecarboximidate (295 mg) [see Preparation 41] in toluene (5 ml) and 1,4-dioxane (5 ml). The reaction mixture was stirred at reflux for 26 hours after which time the solvent was removed under reduced pressure. The residue was diluted with ethyl acetate and washed with water. The organic layer was separated, dried over magnesium sulphate and the solvent removed under reduced pressure. The crude product was purified by column chromatography on silica gel eluting with a solvent gradient of 100:0 changing to 0:100 (in 10% increments), by volume, hexane:ethyl acetate to afford (2S)-1-[(4-fluorophenyl)sulfonyl]-2-(1H-1,2,4-triazol-3-yl)piperidine (95 mg) as an off-white foam.

$^1$H-NMR (CDCl$_3$) δ: 8.05 (1H, s), 7.80 (2H, d), 7.10 (2H, t), 5.40 (1H, bs), 3.75 (1H, d), 3.20 (1H, t), 2.30 (1H, d), 1.80–1.40 (5H, m).

PREPARATION 43

N2-Methyl-(2S)-1-[(4-fluorophenyl)sulfonyl]-2-piperidinecarboxamide

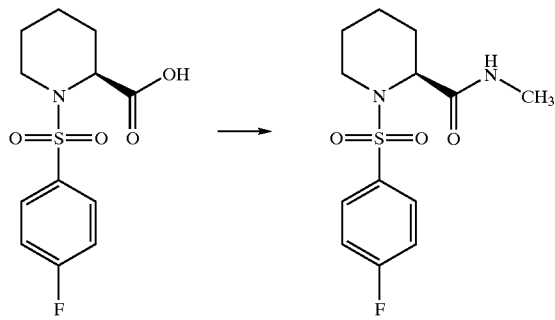

The title compound was prepared by a similar method to Preparation 39 from (2S)-1-[(4-fluorophenyl)sulfonyl]-2-piperidinecarboxylic acid [see Preparation 38] and methylamine to afford N2-methyl-(2S)-1-[(4-fluorophenyl)sulfonyl]-2-piperidinecarboxamide as an oil.

$^1$H-NMR (CDCl$_3$) δ: 7.90 (2H, t), 7.20 (2H, m), 6.60 (1H, bs), 4.45 (1H, s), 3.90 (1H, d), 3.10 (1H, t), 2.85 (3H, s), 2.30 (1H, d), 1.45 (3H, m), 1.10 (2H, m). Rotation: $[α]_D^{25}$=−44.4° (c=0.1, methanol).

PREPARATION 44

N2-Methyl)-2S)-1-[(4-fluorophenyl)sulfonyl]-2-piperidinecarbothioamide

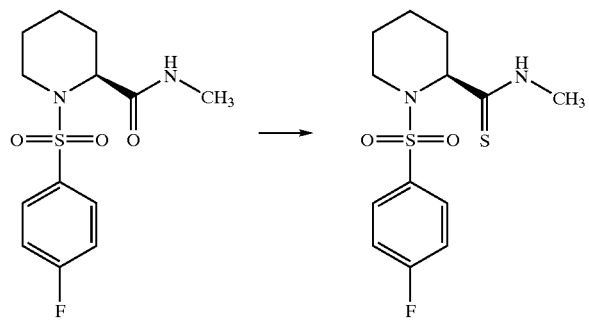

The title compound was prepared by a similar method to Example 20 from N2-methyl-(2S)-1-[(4-fluorophenyl) sulfonyl]-2-piperidinecarboxamide [see Preparation 43] and Lawesson's reagent. The crude product was purified by column chromatography on silica gel eluting with a solvent gradient of 0:100 changing to 25:75 (in 5% increments), by volume, ethyl acetate:hexane, to afford N2-methyl-(2S)-1-[(4-fluorophenyl)sulfonyl]-2-piperidinecarbothioamide as a white solid.

$^1$H-NMR (CDCl$_3$) δ: 8.60 (1H, bs), 7.90 (2H, t), 7.30 (2H, m), 4.65 (1H, s), 3.95 (1H, d), 3.30 (3H, d), 2.95 (2H, d), 1.45 (3H, m), 1.10 (2H, m).

PREPARATION 45

2-((2S)-1-[(4-Fluorophenyl)sulfonyl]-2-piperidylcarbonyl)-1-hydrazinecarbothioamide

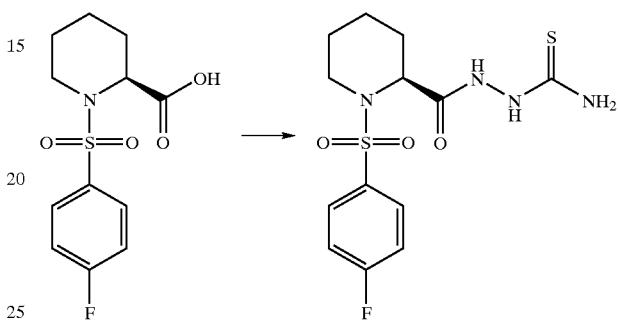

1,1'-Carbonyldimidazole (195 mg) was added to a solution of (2S)-1-[(4-fluorophenyl)sulfonyl]-2-piperidinecarboxylic acid (287 mg) [see Preparation 38] in tetrahydrofuran (5 ml). The reaction mixture was stirred and heated under reflux for 1 hour and then evaporated under reduced pressure to afford a yellow gum. The gum was dissolved in 1,4-dioxane (5 ml) and thiosemicarbazide (182 mg) was added. The reaction mixture was heated under reflux for 1.25 hour. After this time the cooled mixture was purified by column chromatography on MCI (trade mark) reverse phase gel eluting with a solvent gradient of 30:70 changing to 70:30, by volume, methanol:water to afford 2-((2S)-1-[(4-fluorophenyl)sulfonyl]-2-piperidylcarbonyl)-1-hydrazinecarbothioamide (178 mg) as a white foam.

$^1$H-NMR (d$_6$-DMSO) δ: 9.90 (1H, bs), 9.20 (1H, bs), 7.80 (2H, d), 7.40 (2H, d), 4.60 (1H, s), 3.60 (1H, m), 3.40 (1H, m), 2.10 (1H, d), 1.60–1.00 (5H, m).

PREPARATION 46

Methyl (2S)-1-[(4-Fluorophenyl)sulfonyl]-2-piperidinecarboxylate

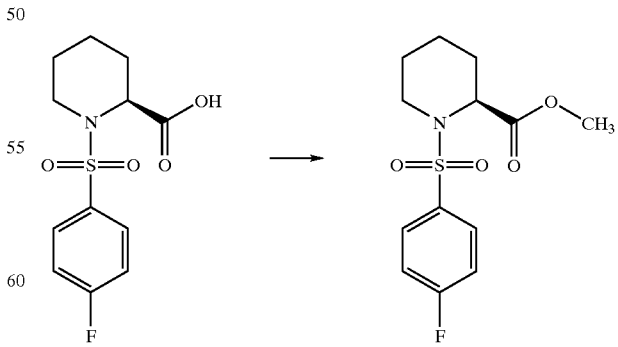

4-Dimethylaminopyridine (61 mg), methanol (45 μl) and 1-(3-dimethylaminopropyl)-3-ethylcarbodiimide hydrochloride (192 mg) were added to a solution of (2S)-1-[(4- fluorophenyl)sulfonyl]-2-piperidinecarboxylic acid (287 mg) [see Preparation 38] in dichloromethane (6 ml). The reaction mixture was stirred at room temperature for 56 hours after which time it was diluted with dichloromethane and washed with 1N aqueous hydrochloric acid solution followed by saturated aqueous sodium hydrogen carbonate solution. The organic layer was dried over magnesium sulphate and the solvent removed under reduced pressure. The crude product was purified by column chromatography on silica gel eluting with a solvent gradient of 90:10 changing to 50:50, by volume, hexane:ethyl acetate, to afford methyl (2S)-1-[(4-fluorophenyl)sulfonyl]-2-piperidinecarboxylate (239 mg) as an oil.

$^1$H-NMR (CDCl$_3$) δ: 7.80 (2H, t), 7.10 (2H, t), 4.70 (1H, d), 3.70 (1H, d), 3.50 (3H, s), 3.20 (1H, t), 2.10 (1H, d), 1.80–1.20 (5H, m).

PREPARATION 47

1-(2S)-1-[(4-Fluorophenyl)sulfonyl]-2-piperidyl-1,3-butanedione 3-Oxime

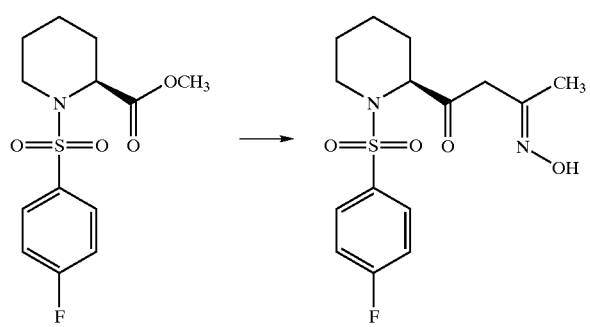

n-Butyllithium (1.98 ml) [1.6M in hexane] was added dropwise to a solution of acetone oxime (116 mg) in tetrahydrofuran (5 ml) at 0° C. The reaction mixture was stirred for 1 hour at 0° C. and a solution of methyl (2S)-1-[(4-fluorophenyl)sulfonyl]-2-piperidinecarboxylate (239 mg) [see Preparation 46] in tetrahydrofuran (1.5 ml) was added. The mixture was stirred for 4 hours after which time saturated aqueous ammonium chloride solution (3 ml) was added. The mixture was partitioned between dichloromethane and aqueous ammonium chloride solution, the aqueous phase was separated and acidified with 1N aqueous hydrochloric acid solution and the product was extracted with dichloromethane. The organic layer was separated, dried over magnesium sulphate, and the solvent removed under reduced pressure to afford the title compound (211 mg). The crude product was used without further purification.

PREPARATION 48

Benzyl (2S)-1-[(4-Fluorophenyl)sulfonyl]-2-pyrrolidinecarboxylate

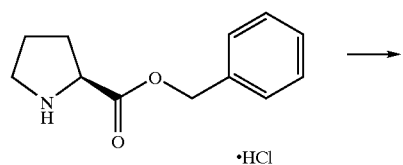

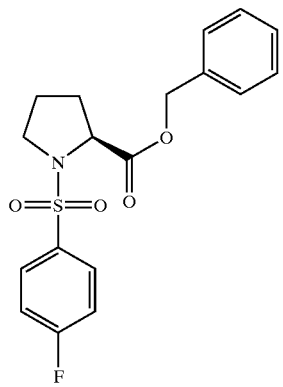

The title compound was prepared by a similar method to Example 1 from L-proline benzyl ester hydrochloride and 4-fluorobenzenesulphonyl chloride. The crude product was purified by column chromatography on silica gel eluting with dichloromethane to afford benzyl (2S)-1-[(4-fluorophenyl)sulfonyl]-2-pyrrolidinecarboxylate as a clear oil.

$^1$H-NMR (CDCl$_3$) δ: 7.90 (2H, m), 7.40 (5H, m), 7.20 (2H, t), 5.10 (2H, s), 4.45 (1H, m), 3.40 (2H, m), 2.20–1.80 (4H, m). Rotation: $[α]_D^{25}$=−93.62° (c=0.1, methanol).

PREPARATION 49

(2S)-1-[(4-Fluoronphenyl)sulfonyl]-2-pyrrolidinecarboxylic Acid

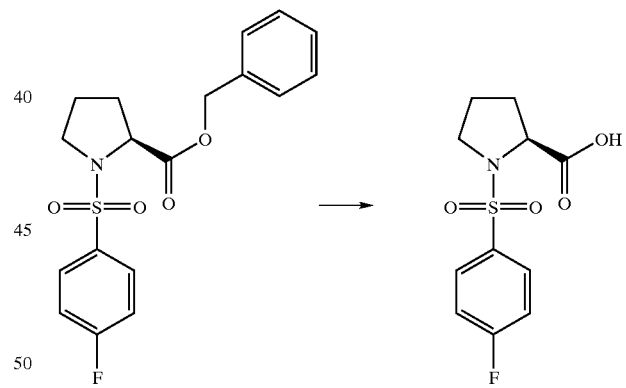

Benzyl (2S)-1-[(4-fluorophenyl)sulfonyl]-2-pyrrolidinecarboxylate (10.03 g) [see Preparation 48] was dissolved in ethanol (200 ml) and hydrogenated over 10% w/w palladium-on-charcoal (2.0 g) at 60 psi (414 kPa) for 18 hours. The reaction mixture was then filtered through a plug of ARBOCEL (trade mark) filter aid and the filtrate evaporated under reduced pressure. The residue was azeotroped with dichloromethane to afford (2S)-1-[(4-fluorophenyl)sulfonyl]-2-pyrrolidinecarboxylic acid (5.50 g) as a white solid.

$^1$H-NMR (CDCl$_3$) δ: 8.00 (2H, t), 7.20 (2H, t), 4.40 (1H, s), 3.50 (1H, m), 3.30 (1H, m), 2.20–2.00 (3H, m), 1.80 (1H, m). Rotation: $[α]_D^{25}$=−92.62° (c=0.1 methanol).

PREPARATION 50

(2S)-1-[(4-Fluorophenyl)sulfonyl]-2-pyrrolidinecarboxamide

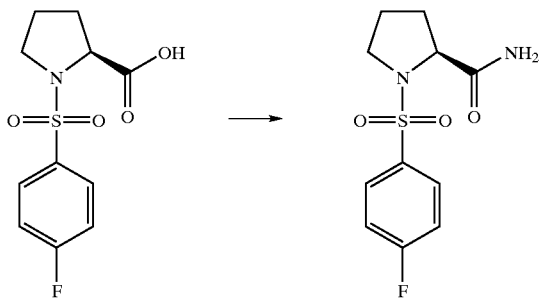

The title compound was prepared by a similar method to Preparation 2 from (2S)-1-[(4-fluorophenyl)sulfonyl]-2-pyrrolidinecarboxylic acid [see Preparation 49] to afford (2S)-1-[(4-fluorophenyl)sulfonyl]-2-pyrrolidinecarboxamide as an oil.

$^1$H-NMR (CDCl$_3$) δ: 7.85 (2H, m), 7.20 (2H, t), 6.80 (1H, bs), 5.60 (1H, bs), 4.00 (1H, t), 3.60 (1H, m), 3.10 (1H, m), 2.20 (1H, m), 1.80 (1H, m), 1.60 (2H, m).

PREPARATION 51

(2S)-1-[(4-Fluorophenyl)sulfonyl]-2-pyrrolidinecarbonitrile

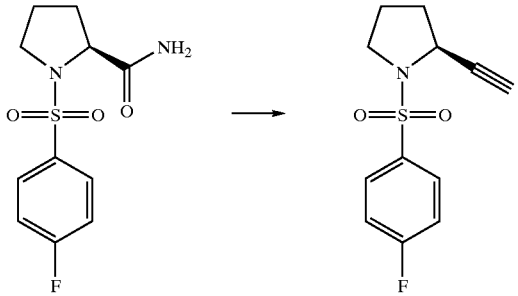

The title compound was prepared by a similar method to Preparation 3 from (2S)-1-[(4-fluorophenyl)sulfonyl]-2-pyrrolidinecarboxamide [see Preparation 50] and oxalyl chloride. The crude product was purified by column chromatography on silica gel eluting with dichloromethane to afford (2S)-1-[(4-fluorophenyl)sulfonyl]-2-pyrrolidinecarbonitrile as a white solid.

$^1$H-NMR (CDCl$_3$) δ: 7.90 (2H, m), 7.20 (2H, t), 4.60 (1H, m), 3.40 (1H, m), 3.25 (1H, m), 2.25–2.00 (4H, m). Rotation: $[α]_D^{25}$=−118° (c=0.1, methanol).

PREPARATION 52

(Z)-(2S)-1-[(4-Fluorophenyl)sulfonyl]-N'$^2$-hydroxy-2-pyrrolidinecarboximidamide

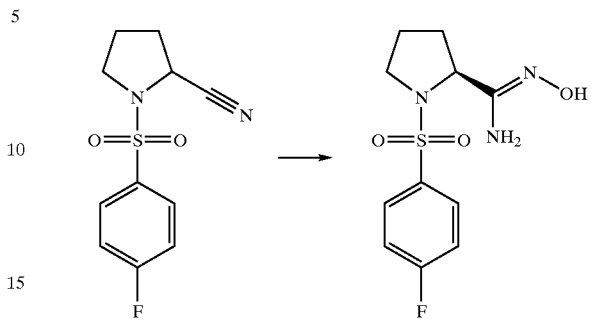

The title compound was prepared by the method of Preparation 4 from (2S)-1-[(4-fluorophenyl)sulfonyl]-2-pyrrolidinecarbonitrile [see Preparation 51] and hydroxylamine hydrochloride to afford the title compound as a white solid.

$^1$H-NMR (CDCl$_3$) δ: 7.90 (2H, m), 7.30 (2H, t), 6.50 (1H, bs), 5.00 (2H, bs), 4.10 (1H, m), 3.60 (1H, m), 3.20 (1H, m), 2.20 (1H, m), 2.00 (1H, m), 1.60 (2H, m). Rotation: $[α]_D^{25}$=−124.22° (c=0.1, methanol).

PREPARATION 53

(Z)-(2S)-1-[(4-Fluorophenyl)sulfonyl]-N'$^2$-(2-phenylacetyl)oxy]-2-pyrrolidinecarboximidamide

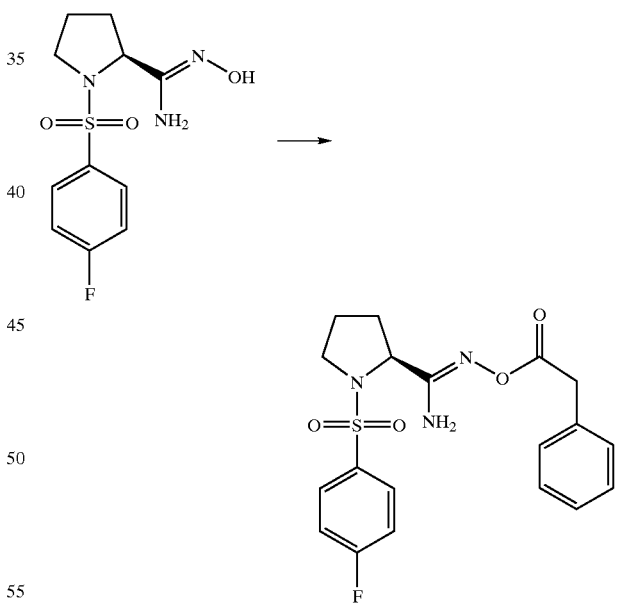

Saturated aqueous sodium hydrogen carbonate solution (10 ml) was added to a solution of the compound of Preparation 52 (250 mg) in dichloromethane (10 ml), followed by phenylacetyl chloride (127 μl). The reaction mixture was stirred at room temperature for 1 hour after which time the mixture was diluted with dichloromethane. The organic layer was separated, dried over magnesium sulphate and the solvent removed under reduced pressure. The crude product was purified by column chromatography on silica gel eluting with 90:10 changing to 70:30 (in 10% increments), by volume, dichloromethane:ethyl acetate, to afford the title compound (186 mg) as a white foam.

$^1$H-NMR (CDCl$_3$) δ: 7.90 (2H, m), 7.40–7.10 (7H, m), 5.10 (2H, bs), 4.20 (1H, m), 3.80 (2H, s), 3.60 (1H, m), 3.20 (1H, q), 2.25 (1H, m), 1.90 (1H, m), 1.80–1.60 (2H, m).

PREPARATION 54

2-[4-(2-[Benzyloxycarbonylamino]ethoxy)phenyl] acetic Acid

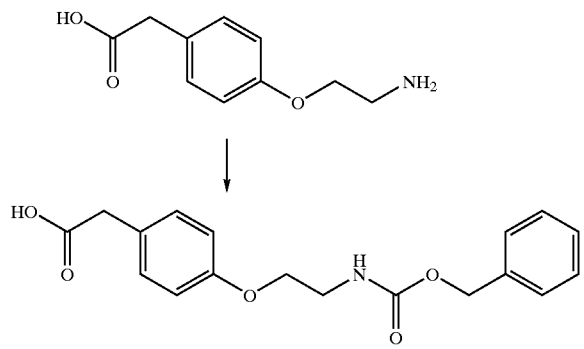

Sodium hydroxide (222 mg) was added to a solution of 2-[4-(2-aminoethoxy)-phenyl]acetic acid (394 mg) (see DE-A-2250400) in 1,4-dioxane: water (1:1, by volume) (20 ml) at 0° C. The reaction mixture was stirred for 20 minutes then benzyl chloroformate (319 mg) was added to the mixture and the solution was stirred for 4 hours. Additional benzyl chloroformate (70 mg) was added to the reaction mixture and it was stirred for a further 1 hour. The solvent was removed under reduced pressure. The resulting solid was dissolved in water and washed with diethyl ether. The aqueous layer was acidified with 2N aqueous hydrochloric acid solution and the product was extracted with ethyl acetate. The organic solution was dried over magnesium sulphate and the solvent removed under reduced pressure to afford 2-[4-(2-[benzyloxycarbonylamino]ethoxy)phenyl] acetic acid (375 mg) as a solid.

$^1$H-NMR (CDCl$_3$) δ: 7.40 (5H, m), 7.20 (2H, d), 6.90 (2H, d), 5.25 (1H, bs), 5.15 (2H, s), 4.05 (2H, s), 3.60 (4H, s).

PREPARATION 55

Benzyl N-[2-(4-2-[((Z)-Amino[1-(1H-1,3-benzimidazol-2-ylsulfonyl)-2-piperidyl] methylideneamino)oxy]-2-oxoethylphenoxy)ethyl] carbamate

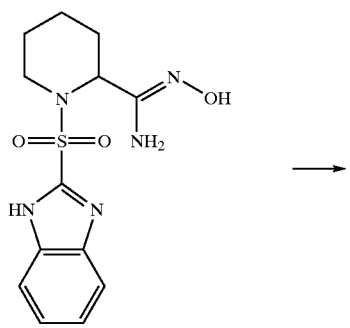

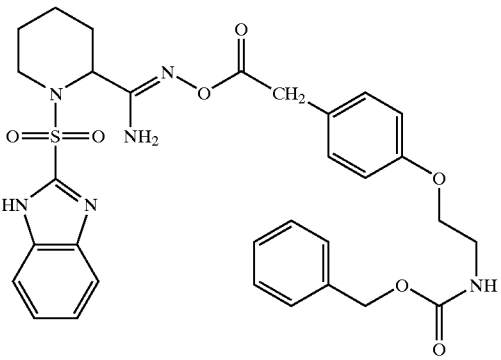

2-[4-(2-(Benzyloxycarbonylamino]ethoxy)phenyl]acetic acid (350 mg) [see Preparation 54] was dissolved in dichloromethane (10 ml) and the compound of Preparation 19 (323 mg) was added followed by 1-(3-dimethylaminopropyl)-3-ethylcarbodiimide hydrochloride (230 mg) and N-methylmorpholine (132 μl). The reaction mixture was stirred for 56 hours after which time the crude mixture was purified by column chromatography on silica gel eluting with 100:0 changing to 60:40, by volume, hexane:ethyl acetate (in 10% increments), to afford the title compound (384 mg) as an oil.

$^1$H-NMR (CDCl$_3$) δ: 7.85 (2H, bs), 7.40–7.20 (9H, m), 6.90 (2H, d), 5.20 (3H, bs), 5.15 (2H, s), 4.90 (1H, m), 4.10 (2H, m), 3.80 (2H, s), 3.65 (2H, q), 3.50 (1H, d), 3.30 (1H, m), 2.10 (1H, m), 1.90 (1H, m), 1.80–1.50 (4H, m).

PREPARATION 56

Benzyl N-(2-[4-(3-[1-(1H-Benzo[d]imidazol-2-ylsulfonyl)-2-piperidyl]-1,2,4-oxadiazol-5-ylmethyl) phenoxy]ethyl)carbamate

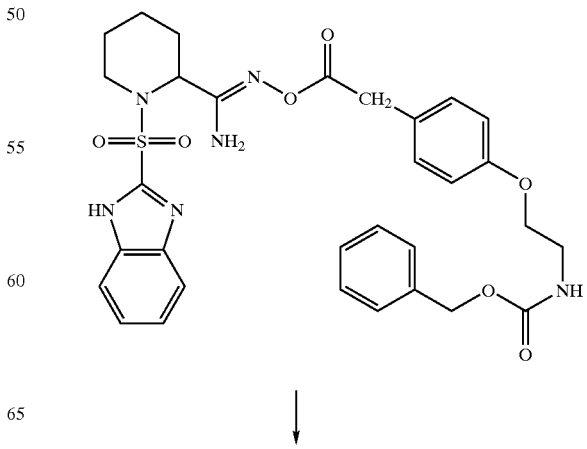

-continued

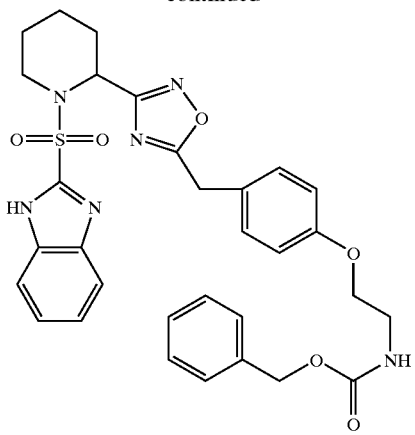

The title compound was prepared by a similar method to Example 16 from the compound of Preparation 55 and pyridine. The crude product was purified by column chromatography on silica gel eluting with 100:0 changing to 60:40, by volume, hexane:ethyl acetate (in 10% increments) to afford benzyl N-(2-[4-(3-[1-(1H-benzo[d]imidazol-2-ylsulfonyl)-2-piperidyl]-1,2,4-oxadiazol-5-ylmethyl)phenoxy]ethyl)carbamate as an oil.

$^1$H-NMR (CDCl$_3$) δ: 7.80 (1H, d), 7.40–7.20 (8H, m), 7.05 (2H, d), 6.80 (2H, d), 5.50 (1H, d), 5.20 (1H, bs), 5.10 (2H, s), 4.00 (3H, m), 3.85 (2H, s), 3.60 (2H, m), 3.20 (1H, m), 2.30 (1H, d), 2.10 (1H, m), 1.80–1.60 (4H, m).

PREPARATION 57

1-[(Benzyloxy)carbonyl]-3-pyrrolidinylmethanesulfonic Acid

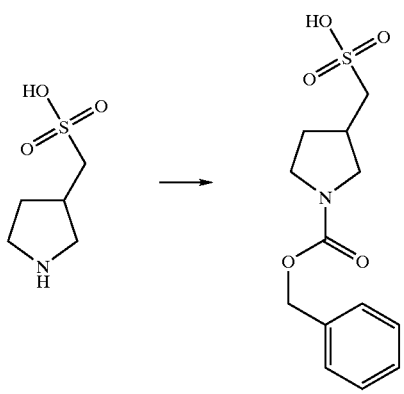

1H-3-Pyrrolidinylmethanesulfonic acid (1.55 g) [Labouta, Ibrahim M, et al Acta Chem Scand, Ser B, (1982), B36(10), 669–74] was dissolved in dioxan (20 ml) and 1N aqueous sodium hydroxide (40 ml) was added followed by benzyl chloroformate (1.62 ml). The reaction mixture was stirred at room temperature for 1 hr, after which time the solvent was removed under reduced pressure and the residue partitioned between dichloromethane and water. The aqueous phase was separated and acidified with conc. aqueous hydrochloric-acid, the product was then extracted with ethyl acetate. The organic layer was dried over magnesium sulphate and the solvent removed under reduced pressure to afford 1-[(benzyloxy)carbonyl]-3-pyrrolidinylmethanesulfonic acid (2.20 g) as a gum.

$^1$H-NMR (D$_2$O) δ: 7.35 (5H, m), 5.05 (2H, s), 3.65 (1H, m), 3.60 (1H, m), 3.30 (1H, m), 3.10 (1H, m), 2.90 (2H, m), 2.55 (1H, m), 2.10 (1H, m), 1.60 (1H, m).

PREPARATION 58

Benzyl 3-(Chlorosulfonylmethyl)-1-pyrrolidinecarboxylate

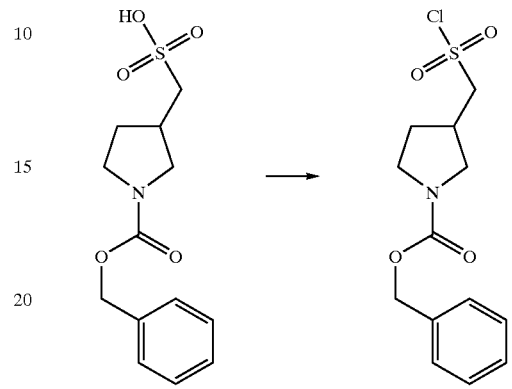

Thionyl chloride (5 ml) was added to a solution of 1-[(benzyloxy)carbonyl]-3-pyrrolidinylmethanesulfonic acid (600 mg) [Preparation 57] in dimethylformamide (50 ml). The reaction mixture was heated to reflux for 20 mins after which time the cooled mixture was evaporated to dryness. The residue was partitioned between ethyl acetate and water. The organic layer was separated, dried over magnesium sulphate and the solvent removed under reduced pressure to afford benzyl 3-(chlorosulfonylmethyl)-1-pyrrolidinecarboxylate (560 mg) as an oil.

$^1$H-NMR (CDCl$_3$) δ: 7.35 (5H, m), 5.15 (2H, s), 3.90 (1H, m), 3.80 (2H, m), 3.60 (1H, m), 3.40 (1H, m), 3.20 (1H, t), 2.90 (1H, m), 2.30 (1H, bs), 1.80 (1H, m).

PREPARATION 59

Benzyl 3-(Hydroxymethyl)-1-piperidinecarboxylate

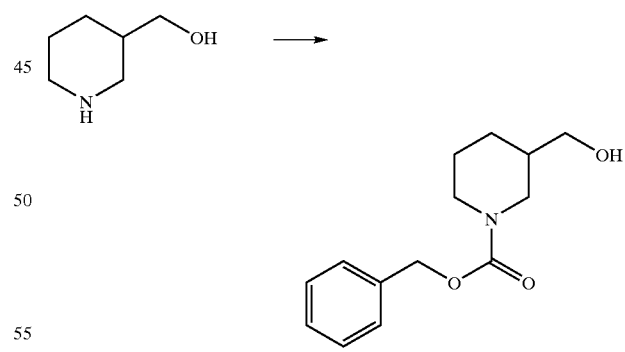

Benzyl chloroformate (7.88 ml) was added over ten minutes to an ice-cold solution of 3-hydroxymethyl piperidine (5.76 g) and ethyldiisopropylamine (9.58 ml) in dichloromethane (300 ml). The reaction mixture was allowed to warm to room temperature and stirred for 1 hr. The reaction was then diluted with dichloromethane (500 ml), washed with 1N aqueous hydrochloric acid (200 ml), dried over magnesium sulphate, and evaporated to afford benzyl 3-(hydroxymethyl)-1-piperidinecarboxylate as an oil (12.4 g).

¹H-NMR (d6-DMSO) δ: 7.30 (5H, m), 5.00 (2H, s), 4.45 (1H, t), 4.00 (1H, d), 3.85 (1H, d), 3.25 (2H, m), 3.15 (1H, m), 2.75 (1H, bs), 1.60 (2H, m), 1.50 (1H, m), 1.30 (1H, m), 1.10 (1H, m).

PREPARATION 60

Benzyl 3-(Bromomethyl)-1-piperidinecarboxylate

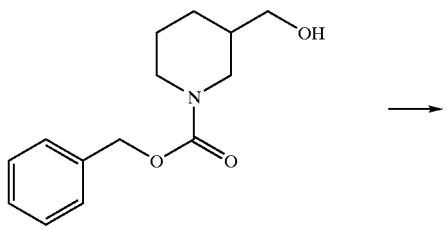

The title compound was prepared by the method of Preparation 9 from benzyl 3-(hydroxymethyl)-1-piperidinecarboxylate [Preparation 59] and carbon tetrabromide. The crude product was purified by column chromatography on silica gel eluting with a solvent gradient of 0:100 changing to 80:20, by volume ethyl acetate:hexane, in 10% increments, to afford benzyl 3-(bromomethyl)-1-piperidinecarboxylate as an oil.

¹H-NMR (d6-DMSO) δ: 7.30 (5H, m), 5.00 (2H, s), 4.05 (1H, d), 3.80 (1H, d), 3.40 (2H, m), 2.80–2.60 (2H, m), 1.80 (1H, m), 1.75 (1H, m), 1.60 (1H, m), 1.40 (1H, m), 1.20 (1H, m).

PREPARATION 61

1-[(Benzyloxy)carbonyl]-3-piperidylmethanesulfonic Acid

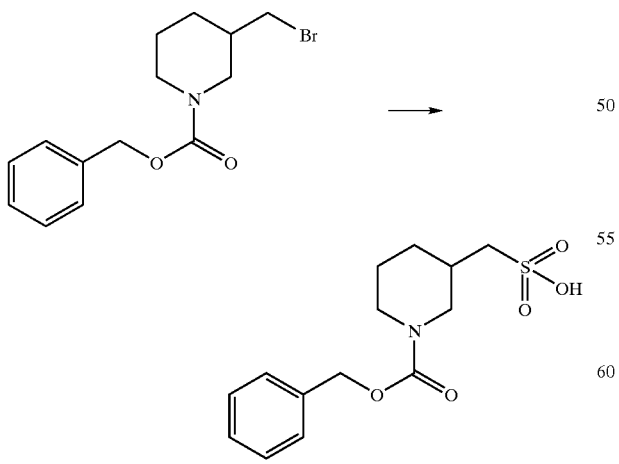

Sodium sulphite (12.6 g) in water (25 ml) was added to a stirred solution of benzyl 3-(bromomethyl)-1-piperidinecarboxylate (7.8 g) [Preparation 60] in dioxan (25 ml). The reaction mixture was stirred at reflux for 18 hrs, after which time the solvent was removed under reduced pressure and the residue partitioned between ethyl acetate and water. The aqueous solution was separated and acidified with 2N aqueous hydrochloric acid. The product was then extracted with ethyl acetate, dried over magnesium sulphate and the solvent removed under reduced pressure to afford 1-[(benzyloxy)carbonyl]-3-piperidylmethanesulfonic acid as a hygroscopic solid (4.5 g).

¹H-NMR (d6-DMSO) δ: 7.30–7.25 (5H, m), 5.00 (2H, s), 4.20 (1H, d), 4.00 (1H, m), 3.80–3.20 (2H, m), 2.80 (1H, m), 2.15 (1H, d), 1.90 (1H, s), 1.80 (1H, m), 1.55 (1H, m), 1.30 (1H, m), 1.10 (1H, m).

PREPARATION 62

Benzyl 3-[(Chlorosulfonyl)methyl]-1-piperidinecarboxylate

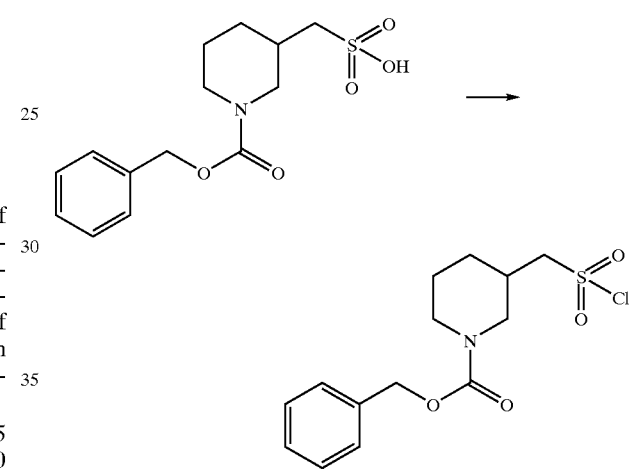

The title compound was prepared by the method of Preparation 58 from 1-[(benzyloxy)carbonyl]-3-piperidylmethanesulfonic acid [see Preparation 61] and thionyl chloride to afford benzyl 3-[(chlorosulfonyl)methyl]-1-piperidinecarboxylate as an oil.

¹H-NMR (CDCl₃) δ: 7.30 (5H, m), 5.10 (2H, s), 4.00 (1H, d), 3.75 (1H, m), 3.70–3.55 (2H, m), 3.20–3.05 (2H, m), 2.45 (1H, m), 2.10 (1H, m), 1.80–1.50 (3H, m).

PREPARATION 63

1-(Bromomethyl)cyclopentane

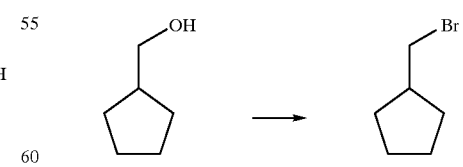

The subtitle compound was prepared by the method of Preparation 9 from cyclopentylmethanol and carbon tetrabromide. The crude product was purified by fractional distillation b.pt. 80° C. @ 30 mmHg to afford 1-(bromomethyl)cyclopentane as a colourless oil.

PREPARATION 64

Sodium Cyclopentylmethanesulfonate

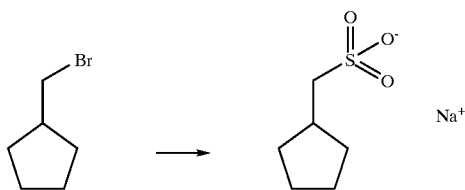

The subtitle compound was prepared by the method of Preparation 61 from 1-(bromomethyl)cyclopentane [Preparation 63] and sodium sulphite. The crude product was purified by recrystallisation from water to afford sodium cyclopentylmethanesulfonate as a white solid.

$^1$H-NMR (D$_2$O) δ: 2.85 (2H, d), 2.10 (1H, m), 1.80 (2H, m), 1.60–1.40 (4H, m), 1.20 (2H, m).

PREPARATION 65

Cyclopentylmethanesulfonyl Chloride

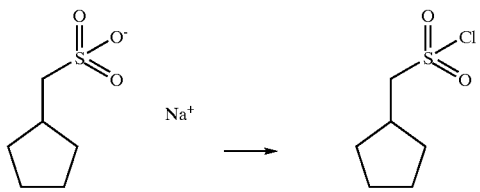

The subtitle compound was prepared by the method of Preparation 58 from sodium cyclopentylmethanesulfonate [Preparation 64] and thionyl chloride, to afford cyclopentylmethanesulfonyl chloride as a solid.

$^1$H-NMR (CDCl$_3$) δ: 3.75 (2H, d), 2.60 (1H, m), 2.05 (2H, m), 1.80–1.60 (4H, m), 1.40 (2H, m).

PREPARATION 66

1-(Bromomethyl)cycloheptane

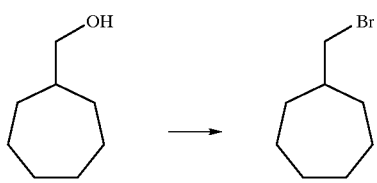

The subtitle compound was prepared by the method of Preparation 9 from cycloheptylmethanol and carbon tetrabromide. The crude product was purified by fractional distillation, b.pt. 115° C.–120° C. @ 30mmHg to afford 1-(bromomethyl)cycloheptane as an oil.

$^1$H-NMR (CDCl$_3$) δ: 3.25 (2H, d), 1.80 (2H, m), 1.70–1.20 (11H, m).

PREPARATION 67

Sodium Cycloheptylmethanesulfonate

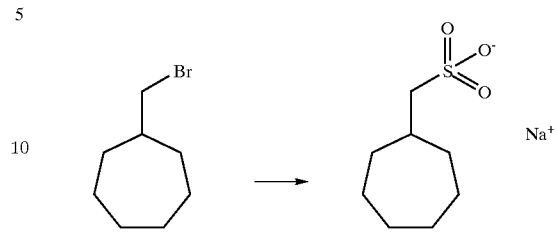

The subtitle compound was prepared by the method of Preparation 61 from 1-(bromomethyl)cycloheptane [Preparation 66] and sodium sulfite. The crude product was purified by recrystallisation from water to afford sodium cycloheptylmethanesulfonate as a white solid.

$^1$H-NMR (D$_2$O) δ: 2.75 (2H, d), 1.90 (1H, m), 1.75 (2H, m), 1.60–1.20 (10 H, m).

PREPARATION 68

Cycloheptylmethanesulfonyl Chloride

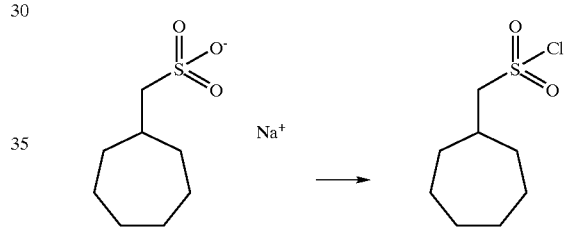

The subtitle compound was prepared by the method of Preparation 58 from sodium cycloheptylmethanesulfonate [Preparation 67] and thionyl chloride, to afford cycloheptylmethanesulfonyl chloride as a colourless oil.

$^1$H-NMR (CDCl$_3$) δ: 3.65 (2H, d), 2.40 (1H, m), 2.00 (2H, m), 1.70–1.40 (10H, m).

PREPARATION 69

(Z)-(2S)-1-[(Cyclohexylmethyl)sulfonyl]-N$^{'2}$-[3-(dimethylamino)propanoyl]oxy-2-piperidinecarboximidamide

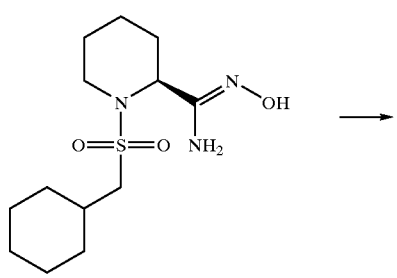

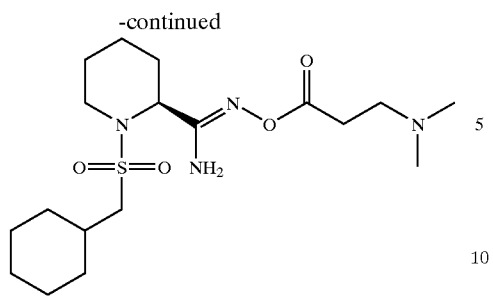

The title compound was prepared by the method of Preparation 5 from (Z)-(2S)-1-[cyclohexylmethylsulfonyl]-N'$^2$-hydroxy-2-piperidinecarboximidamide [see Preparation 28], 3-(dimethylamino)propanoic acid [Papapoulos, et al, WO 9619998A1], N-methyl morpholine, hydroxybenzotriazole hydrate and 1-(3-dimethylaminopropyl)-3-ethylcarbodiimide hydrochloride, to afford (Z)-(2S)-1-[(cyclohexylmethyl)sulfonyl]-N'$^2$-[3-(dimethylamino)propanoyl]oxy-2-piperidinecarboximidamide as an oil.

$^1$H-NMR (CDCl$_3$) δ: 4.60 (1H, d), 3.75 (1H, d), 3.20 (1H, t), 2.90 (2H, m), 2.60 (4H, m), 2.30 (1H, d), 2.25 (6H, s), 2.00 (4H, m), 1.80–1.60 (6H, m), 1.50 (1H, m), 1.35–1.05 (5H, m).

PREPARATION 70

(Z)-(2S)-1-[(Cyclohexylmethyl)sulfonyl]-N'$^2$-(formyloxy)-2-piperidinecarboximidamide

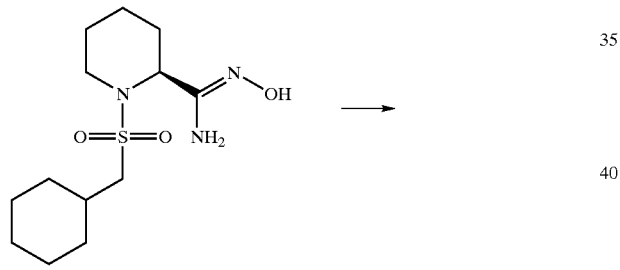

The title compound was prepared by a similar method to Preparation 5 from (Z)-(2S)-1-[cyclohexylmethylsulfonyl]-N'$^2$-hydroxy-2-piperidinecarboximidamide [see Preparation 28], formic acid, N-methyl morpholine, hydroxybenzotriazole hydrate and 1-(3-dimethylaminopropyl)-3-ethylcarbodiimide hydrochloride, to afford (Z)-(2S)-1-[(cyclohexylmethyl)sulfonyl]-N'$^2$-(formyloxy)-2-piperidinecarboximidamide as a colourless oil.

$^1$H-NMR (CDCl$_3$) δ: 8.55 (1H, s), 5.35 (2H, bs), 4.60 (1H, d), 3.80 (1H, d), 3.10 (1H, t), 2.95 (2H, d), 2.35 (1H, d), 2.00 (3H, m), 1.80–1.40 (7H, m), 1.35–1.05 (6H, m).

PREPARATION 71

(Z)-(2S)-N'$^2$-(Acetyloxy)-1-[(cyclohexylmethyl)sulfonyl]-2-piperidinecarboximidamide

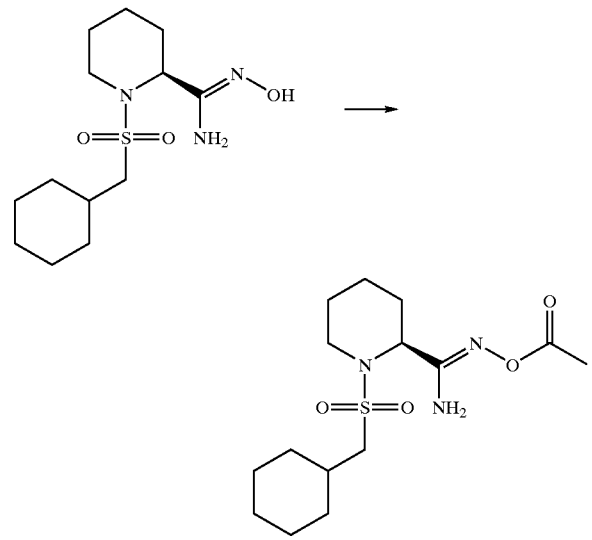

The title compound was prepared by a similar method to Preparation 5 from (Z)-(2S)-1-[cyclohexylmethylsulfonyl]-N'$^2$-hydroxy-2-piperidinecarboximidamide [see Preparation 28], acetic acid, N-methyl morpholine, hydroxybenzotriazole hydrate and 1-(3-dimethylaminopropyl)-3-ethylcarbodiimide hydrochloride, to afford (Z)-(2S)-N'$^2$-(acetyloxy)-1-[(cyclohexylmethyl)sulfonyl]-2-piperidinecarboximidamide as a colourless oil.

$^1$H-NMR (CDCl$_3$) δ: 5.20 (2H, bs), 4.60 (1H, d), 3.80 (1H, d), 3.10 (1H, t), 2.95 (2H, d), 2.40 (1H, d), 2.20 (3H, s), 2.00 (3H, m), 1.90 (1H, m), 1.80–1.40 (7H, m), 1.35–1.05 (5H, m).

PREPARATION 72

(2S)-1-[(4-Fluorophenyl)sulfonyl]-2-piperidylcarbonitrile

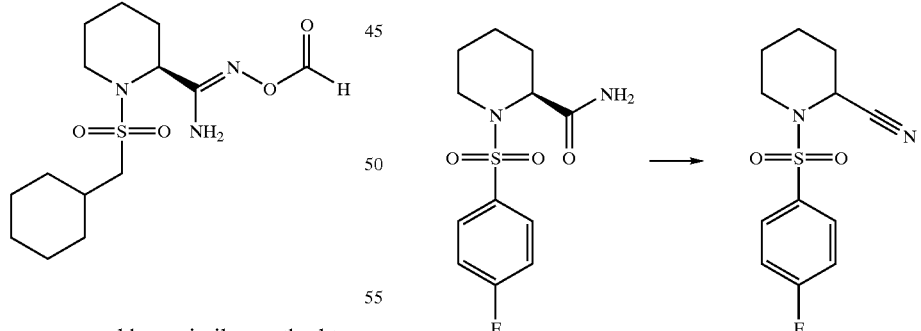

The title compound was prepared by a similar method to Preparation 3 from (2S)-1-[(4-fluorophenyl)sulfonyl]-2-piperidinecarboxamide [see Preparation 40] and oxalyl chloride. The crude product was filtered through a pad of silica eluting with dichloromethane to afford (2S)-1-[(4-fluorophenyl)sulfonyl]-2-piperidylcarbonitrile as an oil.

$^1$H-NMR (CDCl$_3$) δ: 7.90 (2H, m), 7.30 (2H, m), 5.00 (1H, s), 3.85 (1H, d), 2.75 (1H, t), 2.00–1.50 (6H, m). Rotation: $[\alpha]_D^{25}$=−111.40° (c=0.1, methanol).

PREPARATION 73

(Z)-(2S)-1-[(4-Fluorophenyl)sulfonyl]-N'¹-hydroxy-2-piperidylcarboximidamide

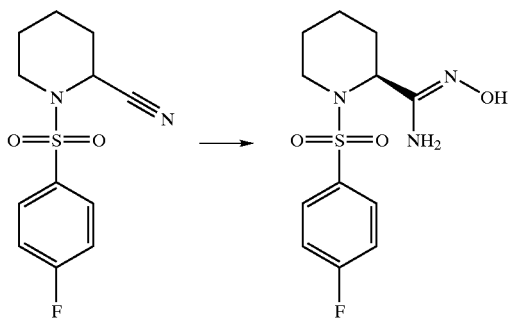

The title compound was prepared by a similar method to Preparation 4 from (2S)-1-[(4-fluorophenyl)sulfonyl]-2-piperidylcarbonitrile [see Preparation 72] and hydroxylamine, to afford (Z)-(2S)-1l-[(4-fluorophenyl)sulfonyl]-N'¹-hydroxy-2-piperidylcarboximidamide as an oil.

$^1$H-NMR (CDCl$_3$) δ: 7.90 (2H, m), 7.25 (2H, m), 6.45 (1H, bs), 5.00 (2H, bs), 4.60 (1H, d), 3.90 (1H, d), 3.10 (1H, m), 2.00 (1H, d), 1.80 (1H, m), 1.50 (2H, m), 1.20 (2H, m).

PREPARATION 74

(Z)-(2S)-1-[(4-Fluorophenyl)sulfonyl]-N'¹-[(2-phenylacetyl)oxy]-2-piperidylcarboximidamide

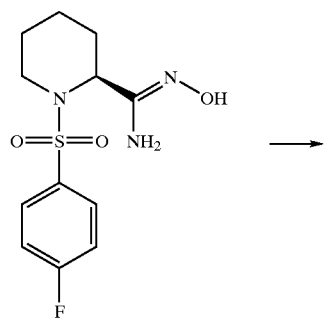

The title compound was prepared by a similar method to Preparation 53 from (Z)-(2S)-1-[(4-fluorophenyl)sulfonyl]-N'¹-hydroxy-2-piperidylcarboximidamide [see Preparation 73] and phenylacetyl chloride, to afford (Z)-(2S)-1-[(4-fluorophenyl)sulfonyl]-N'¹-[(2-phenylacetyl)oxy]-2-piperidylcarboximidamide, which was used immediately without isolation.

PREPARATION 75

(Z)-(2S)-1-[(4-Fluoronphenyl)sulfonyl]-N'¹-(2-[4-(hydroxymethyl)phenoxy]acetyloxy)-2-piperidylcarboximidamide

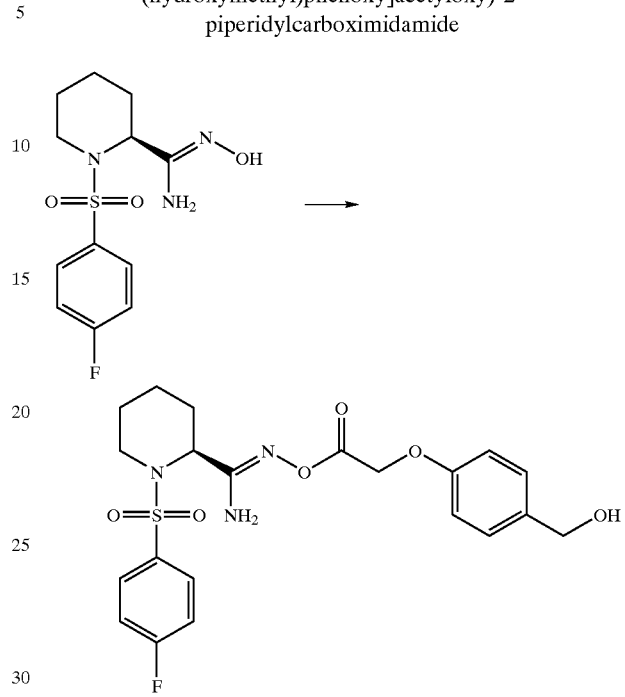

The title compound was prepared by a similar method to Preparation 5 from (Z)-(2S)-1-[(4-fluorophenyl)sulfonyl]-N'¹-hydroxy-2-piperidylcarboximidamide [see Preparation 73], 4-(hydroxymethyl)phenoxyacetic acid, N-methyl morpholine, hydroxybenzotriazole hydrate, and 1-(3-dimethylaminopropyl-3-ethylcarbodiimide hydrochloride, to afford (Z)-(2S)-1-[(4-fluorophenyl)sulfonyl]-N'¹-(2-[4-(hydroxymethyl)phenoxy]acetyloxy)-2-piperidylcarboximidamide as a white solid.

$^1$H-NMR (CDCl$_3$) δ: 7.85 (2H, m), 7.25 (2H, m), 6.85 (2H, m), 6.80 (2H, m), 5.15 (3H, m), 4.80 (2H, s), 4.60 (2H, m), 3.80 (1H, d), 3.10 (1H, t), 2.15 (1H, d), 1.80 (1H, m), 1.50 (2H, m), 1.20 (2H, m).

PREPARATION 76

(Z)-(2S)-N'¹-(Benzoyloxy)-1-[(4-fluorophenyl)sulfonyl]-2-piperidylcarboximidamide

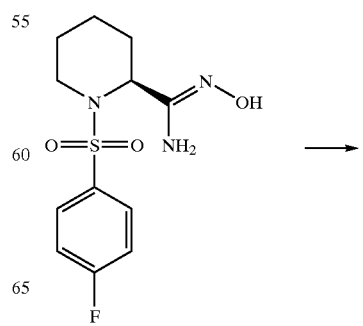

-continued

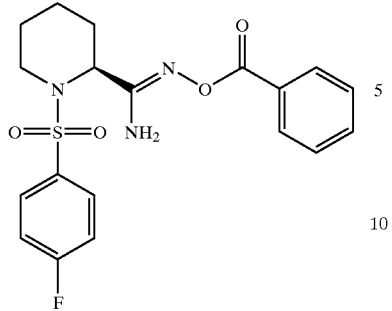

The title compound was prepared by a similar method to Preparation 5 from (Z)-(2S)-1-[(4-fluorophenyl)sulfonyl]-N'1-hydroxy-2-piperidylcarboximidamide [see Preparation 73], benzoic acid, N-methyl morpholine, hydroxybenzotriazole hydrate and 1-(3-dimethylaminopropyl)-3-ethylcarbodiimide hydrochloride, to afford (Z)-(2S)-N'1-(benzoyloxy)-1-[(4-fluorophenyl)sulfonyl]-2-piperidylcarboximidamide as a white solid.

$^1$H-NMR (CDCl$_3$) δ: 8.05 (2H, d), 7.90 (2H, t), 7.60 (1H, m), 7.45 (2H, m), 7.25 (2H, m), 5.25 (2H, m), 4.60 (1H, d), 3.85 (1H, d), 3.20 (1H, t), 2.30 (1H, d), 1.90 (1H, m), 1.50 (2H, m), 1.20 (2H, m).

PREPARATION 77

(2S)-1-[(4-Fluorophenyl)sulfonyl]-N'1-(2-phenylacetyl)-2-piperidylcarbohydrazide

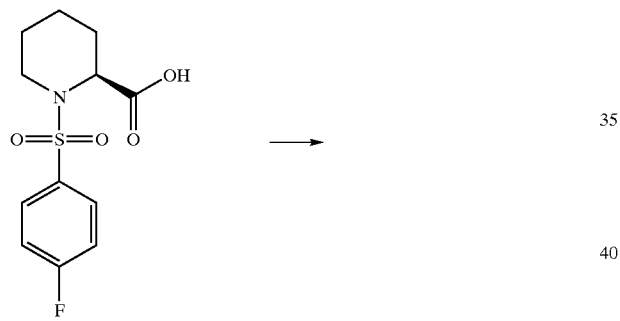

The title compound was prepared by a similar method to Preparation 39 from (2S)-1-[(4-fluorophenyl)sulfonyl]-2-piperidinecarboxylic acid [see Preparation 38], phenylacetic acid hydrazide, N-methyl morpholine, hydroxybenzotriazole hydrate and 1-(3-dimethylaminopropyl)-3-ethylcarbodiimide hydrochloride, to afford (2S)-1-[(4-fluorophenyl)sulfonyl]-N'1-(2-phenylacetyl)-2-piperidylcarbohydrazide as a white foam.

$^1$H-NMR (CDCl$_3$) δ: 7.90 (2H, m), 7.70 (1H, bs), 7.40–7.20 (7H, m), 4.60 (1H, d), 3.90 (1H, d), 3.65 (2H, s), 3.40 (1H, t), 2.20 (1H, d), 1.60–1.40 (3H, m), 1.30–1.10 (2H, m).

PREPARATION 78

(2S)-1-[(4-Fluorophenyl)sulfonyl]-N'1-(3-phenylpropanoyl)-2-piperidylcarbohydrazide

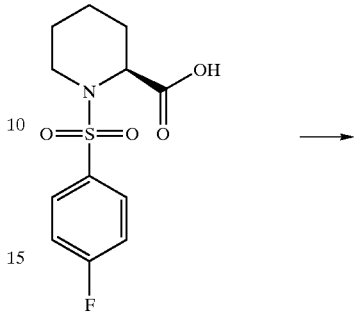

The title compound was prepared by a similar method to Preparation 39 from (2S)-1-[(4-fluorophenyl)sulfonyl]-2-piperidinecarboxylic acid [see Preparation 38], 3-phenylpropanohydrazide, N-methyl morpholine, hydroxybenzotriazole hydrate and 1-(3-dimethylaminopropyl)-3-ethylcarbodiimide hydrochloride, to afford (2S)-1-[(4-fluorophenyl)sulfonyl]-N'1-(3-phenylpropanoyl)-2-piperidylcarbohydrazide as a colourless gum.

$^1$H-NMR (CDCl$_3$) δ: 8.60 (1H, bs), 7.95 (2H, m), 7.65 (1H, bs), 7.40–7.20 (7H, m), 4.65 (1H, s), 3.95 (1H, d), 3.40 (1H, t), 3.00 (2H, t), 2.60 (2H, t), 2.25 (1H, d), 1.60–1.40 (3H, m), 1.30–1.15 (2H, m).

PREPARATION 79

(2S)-1-[(4-Fluorophenyl)sulfonyl]-2-(2H-1,2,3,4-tetraazol-5-yl)piperidine

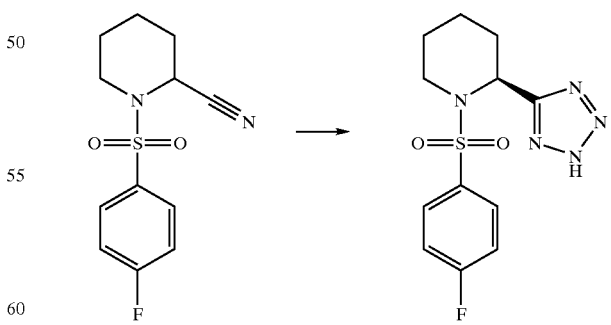

Trimethylsilyl azide (0.66 ml) and dibutyltin oxide (62 mg) were added to a solution of (2S)-1-[(4-Fluorophenyl)sulfonyl]-2-piperidylcarbonitrile (670 mg) [see Preparation 72] in toluene (10 ml). The reaction mixture was heated to reflux and stirred for 18 hrs, after which time the cooled reaction mixture was purified by coloumn chromatography on silica gel eluting with a solvent gradient of 100:0 changing to 98:2, by volume, dichloromethane: methanol followed by 98:1.98:0.02 changing to 95:4.95:0.05, by volume, dichloromethane:methanol acetic acid. The fractions containing the product were evaporated under reduced pressure and the residue partitioned between diethyl ether and saturated sodium bicarbonate solution. The aqueous layer was separated and acidified with conc. aqueous hydrochloric acid and the product extracted with dichloromethane, dried over magnesium sulphate and the solvent removed under reduced pressure to afford (2S)-1-[(4-fluorophenyl)sulfonyl]-2-(2H-1,2,3,4-tetraazol-5-yl)piperidine (735 mg) as a white foam.

$^1$H-NMR (CDCl$_3$) δ: 7.90 (2H, m), 7.25 (2H, m), 5.20 (1H, s), 3.80 (1H, d), 2.95 (1H, t), 2.55 (1H, d), 1.80–1.60 (4H, m), 1.40 (1H, m). Rotation: $[\alpha]_D^{25}$=−43.46° (c=0.1, methanol).

PREPARATION 80

(2S)-1-[(4-Fluorophenyl)sulfonyl]-N$^2$-(2-hydroxypropyl)-2-piperidinecarboxamide

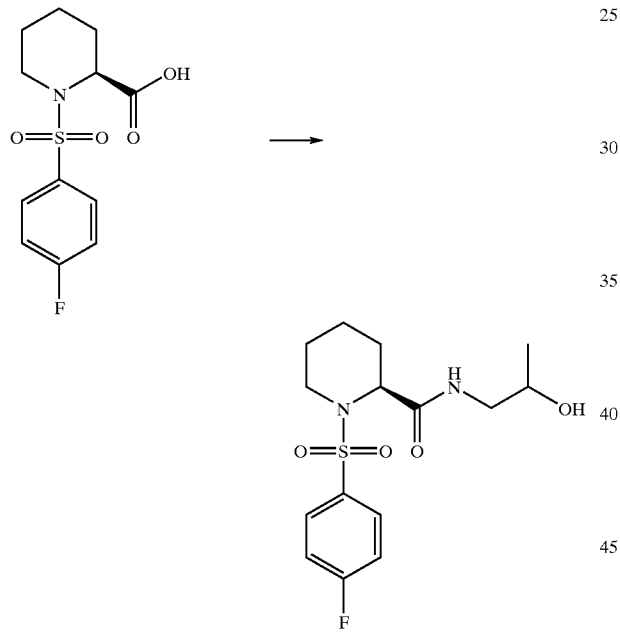

Hydroxybenzotriazole hydrate (297 mg), (3-dimethylminopropyl)-3-ethylcarbodiimide (421 mg) and N-methylmorpholine (241 ml) were added to a solution of (2S)-1-[(4-fluorophenyl)sulfonyl]-2-piperidinecarboxylic acid (575 mg) [see Preparation 38]. The reaction mixture was stirred for 15 mins, then 2-aminopropanol (170 ml) was added and stirring continued for 18 hrs at room temperature. The mixture was then diluted with ethyl acetate and washed with 2M aqueous hydrochloric acid, saturated sodium hydrogen carbonate and water. The organic layer was separated, dried over magnesium sulphate and the solvent removed under reduced pressure to afford (2S)-1-[(4-fluorophenyl)sulfonyl]-N$^2$-(2-hydroxypropyl)-2-piperidinecarboxamide (555 mg) as an oil.

$^1$H-NMR (CDCl$_3$) δ: 7.90 (2H, m), 7.30 (2H, m), 6.95 (1H, bs), 4.55 (1H, m), 3.90 (2H, m), 3.50 (1H, m), 3.20 (2H, m), 2.30 (1H, d), 1.50 (3H, m), 1.20 (5H, s).

PREPARATION 81

(2S)-1-[(4-Fluorophenyl)sulfonyl]-N$^2$-(2-oxopropyl)-2-piperidinecarboxamide

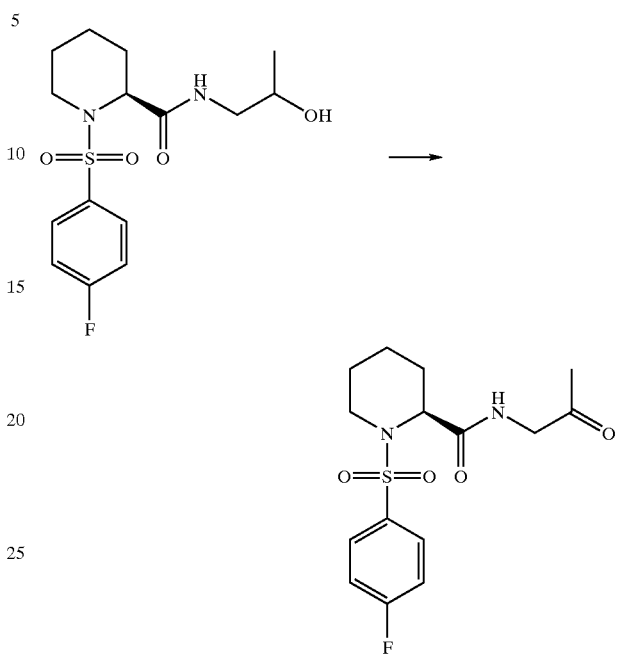

Dess-Martin reagent (814 mg) was added to a stirred solution of (2S)-1-[(4-fluorophenyl)sulfonyl]-N$^2$-(2-hydroxypropyl)-2-piperidinecarboxamide (548 mg) [see Preparation 80) and triethylamine (0.89 ml) in dichloromethane (20 ml). The reaction mixture was stirred for 1 hr after which time the mixture was filtered through a pad of basic alumina and washed through with dichloromethane to afford (2S)-1-[(4-fluorophenyl)sulfonyl]-N$^2$-(2-oxopropyl)-2-piperidinecarboxamide (300 mg).

PREPARATION 82

N$^{\prime 1}$-[((2S)-1-[(4-Fluorophenyl)sulfonyl]-2-piperidylcarbonyl)oxy]ethanimidamide

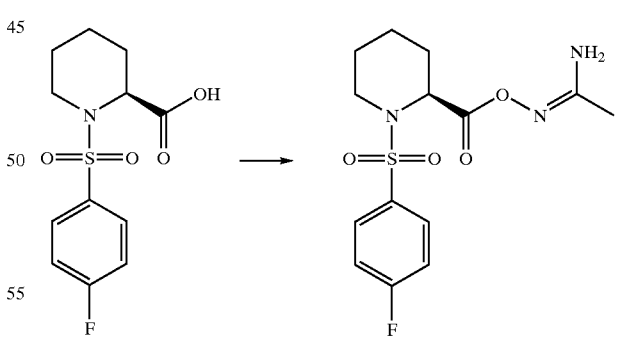

The title compound was prepared by a similar method to Preparation 39 from (2S)-1-[(4-fluorophenyl)sulfonyl]-2-piperidinecarboxylic acid [see Preparation 38], N$^{\prime 1}$-hydroxyethanimidamide [La Manna, et al, Theochem (1990), 69, 161–68], N-methyl morpholine, hydroxybenzotriazole hydrate and 1-(3-dimethylaminopropyl)-3-ethylcarbodiimide hydrochloride, to afford N$^{\prime 1}$-[((2S)-1-[(4-fluorophenyl)sulfonyl]-2-piperidylcarbonyl)oxy] ethanimidamide as a colourless gum.

¹H-NMR (CDCl₃) δ: 7.90 (2H, m), 7.20 (2H, t), 4.90 (1H, bs), 3.50 (1H, d), 3.20 (1H, t), 2.00 (3H, s), 1.70 (4H, m), 1.50 (1H, m), 1.30 (1H, m).

PREPARATION 83

N²-Cyclohexyliden-5-(2S)-1-[(4-fluorophenyl)sulfonyl]-2-piperidyl-1,3,4-oxadiazol-2-amine

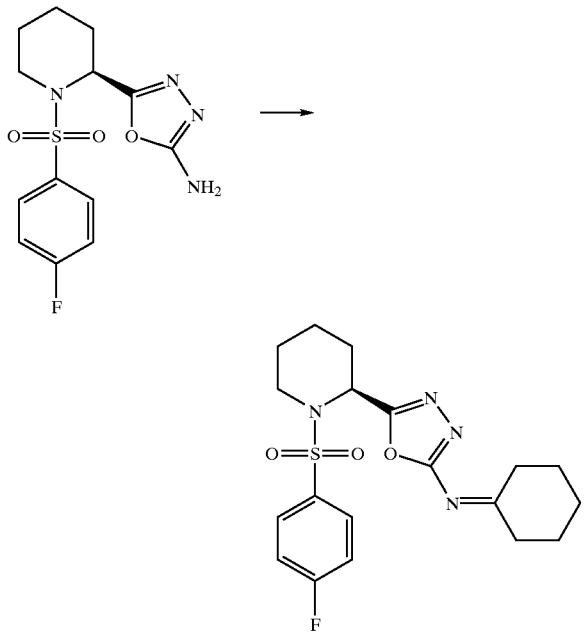

Tosic acid (2.0 mg) was added to a solution of 5-(2S)-1-[(4-fluorophenyl)sulfonyl]-2-piperidyl-1,3,4-oxadiazol-2-amine (245 mg) [see Example 32] and cyclohexanone (155 ml) in toluene (20 ml). The reaction mixture was fitted with a dean-stark tube and heated to reflux for 22 hrs, after which time the mixture was evaporated under reduced pressure to a low volume and used immediately for Example 48.

PREPARATION 84 tert-Butyl N-2-[((Z)-Amino[1-(1H-benzo[d]imidazol-2-ylsulfonyl)-2-piperidyl]methylideneamino)oxy]-2-oxoethylcarbamate

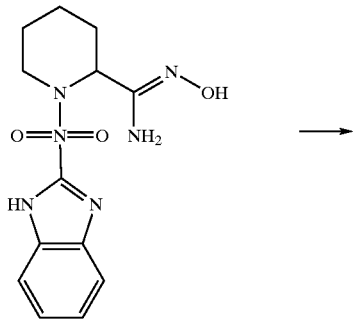

-continued

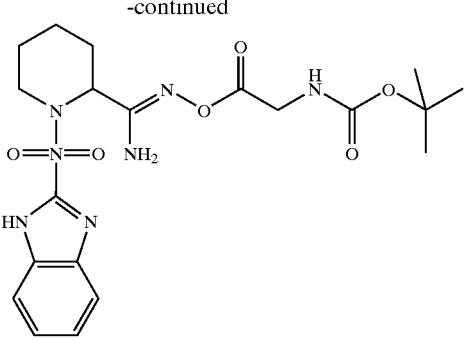

The subtitle compound was prepared by a similar method to Preparation 5 from (Z)-1-(1H-benzo[d]imidazol-2-ylsulfonyl)-N'²-hydroxy-2-piperidinecarboximidamide [see Preparation 19], 4-(hydroxymethyl)phenoxyacetic acid, N-methyl morpholine, hydroxybenzotriazole hydrate and 1-(3-dimethylaminopropyl)-3-ethylcarbodiimide hydrochloride, to afford, tert-butyl N-2-[((Z)-amino[1-(1H-benzo[d]imidazol-2-ylsulfonyl)-2-piperidyl]methylideneamino)oxy]-2-oxoethylcarbamate as an oil.

¹H-NMR (CDCl₃) δ: 7.70 (2H, d), 7.35 (2H, m), 6.80 (2H, bs), 4.90 (1H, s), 3.85 (2H, d), 3.70 (1H, m), 3.35 (1H, t), 2.10 (1H, m), 1.60 (4H, m), 1.40 (9H, s), 1.25 (1H, m).

PREPARATION 85 tert-Butyl N-(3-[1-(1H-benzo[d]imidazol-2-ylsulfonyl)-2-piperidyl]-1,2,4-oxadiazol-5-ylmethyl)carbamate

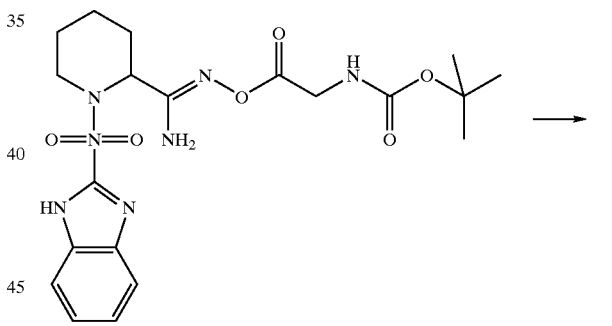

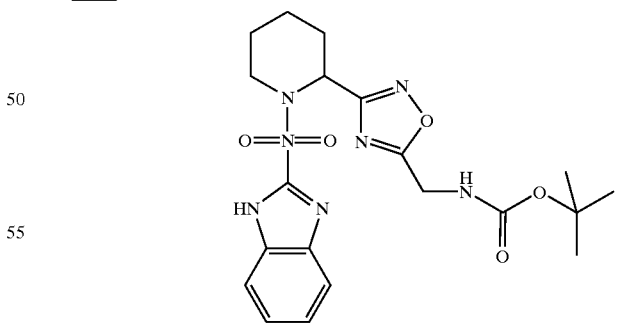

The title compound was prepared by the method of Example 16 from tert-butyl N-2-[((Z)-amino[1-(1H-benzo[d]imidazol-2-ylsulfonyl)-2-piperidyl]methylideneamino)oxy]-2-oxoethylcarbamate [see Preparation 84] and pyridine. The crude product was purified by column chromatography on silica gel eluting with 70:30, by volume, hexane:ethyl acetate, to afford tert-butyl N-(3-[1-(1H-benzo

[d]imidazol-2-ylsulfonyl)-2-piperidyl]-1,2,4-oxadiazol-5-ylmethyl)carbamate as an oil.

¹H-NMR (d6-DMSO) δ: 13.65 (1H, bs), 7.80 (1H, d), 7.60 (2H, m), 7.40–7.30 (2H, m), 5.40 (1H, d), 4.20 (2H, d), 3.95 (1H, d), 3.40 (1H, m), 2.00 (1H, m), 1.80 (1H, m), 1.60–1.50 (2H, m), 1.40 (9H, s), 1.30–1.20 (2H, m).

PREPARATION 86

3-[1-(1H-Benzo[d]imidazol-2-ylsulfonyl)-2-piperidyl]-1,2,4-oxadiazol-5-ylmethylamine

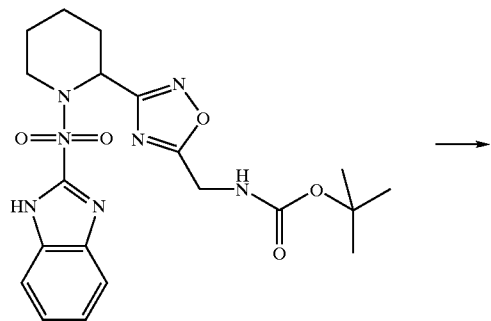

tert-Butyl N-(3-[1-(1H-benzo[d]imidazol-2-ylsulfonyl)-2-piperidyl]-1,2,4-oxadiazol-5-ylmethyl)carbamate (0.88 g) [see Preparation 85] was dissolved in dioxan (20 ml) and cooled to 0° C. Hydrogen chloride gas was then bubbled through for 10 mins. The reaction mixture was then stirred at room temperature for 1 hr. the solvent was then removed under reduced pressure to afford 3-[1-(1H-benzo[d]imidazol-2-ylsulfonyl)-2-piperidyl]-1,2,4-oxadiazol-5-ylmethylamine (0.67 g) as the hydrochloride salt as a white solid.

¹H-NMR (d6-DMSO) δ: 9.00 (3H, bs), 7.70 (2H, d), 7.40 (2H, m), 5.45 (1H, m), 4.40 (2H, s), 3.90 (1H, d), 3.40 (1H, t), 2.05 (1H, bs), 1.80 (1H, m), 1.55 (2H, m), 1.40–1.15 (2H, m).

PREPARATION 87

5-Bromo-1H-benzo[d]imidazole-2-thiol

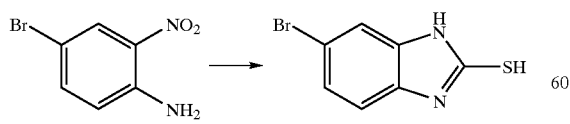

Platinum dioxide (5.7 g) was hydrogenated in ethanol (300 ml) at 50 psi for 30 mins, 4-bromo-2-nitroaniline (15.0 g) was then added and the solution was hydrogenated at 50 psi for a further 3 hrs. The mixture was then filtered through a plug of Arbocel and the ethanolic solution added to a solution of potassium hydroxide (5.8 g) and carbon disulphide (17.51 ml) in water (50 ml). The reaction mixture was then refluxed at 85° C. for 2 hrs, after which time the cooled reaction mixture was diluted with water and acidified with 2M aqueous hydrochloric acid. A green solid formed which was filtered off and washed with water. The solid was dissolved in ethyl acetate and washed with 2M aqueous hydrochloric acid, dried over magnesium sulphate and the solvent was removed under reduced pressure to afford crude product. The filtration mother liquors were then extracted with ethyl acetate, the organic layer was washed with 2M aqueous hydrochloric acid, dried over magnesium sulphate and the solvent was removed under reduced pressure to afford further crude product. The combined crude products were purified by column chromatography on silica gel eluting with a solvent gradient of 70:30 changing to 0:100, by volume, hexane:ethyl acetate, in 10% increments, to afford 5-bromo-1H-benzo[d]imidazole-2-thiol (5.64 g) as a white solid.

¹H-NMR (d6-DMSO) δ: 7.25 (2H, d), 7.05 (1H, d).

PREPARATION 88

5-Bromo-1H-benzo[d]imidazole-2-sulfonyl Chloride

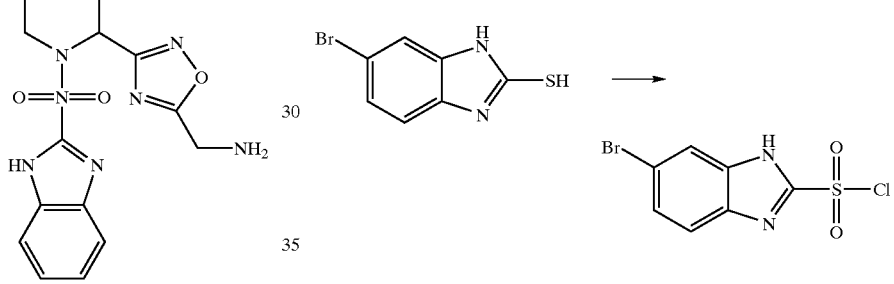

Chlorine gas was bubbled through a solution of 5-bromo-1H-benzo[d]imidazole-2-thiol (4.98 g) [see Preparation 87] in 20% glacial acetic acid (100 ml) at 0° C. for 8 mins. The precipitate formed was quickly filtered and the solid washed with ice cold water to afford 5-bromo-1H-benzo[d]imidazole-2-sulfonyl chloride as a solid which was used immediately for Examples 54 and 55.

PREPARATION 89 tert-Butyl 4-(3-Ethoxy-3-oxopropyl)-1-piperazinecarboxylate

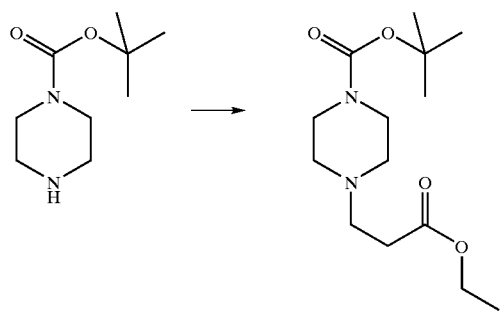

Ethyl-3-bromoproprionate (1.67 ml) was added to a suspension of tert-butyl-1-piperazine carboxylate (2.43 g) and potassium carbonate (2.16 g) in acetonitrile (30 ml). The reaction mixture was stirred for 56 hrs at room temperature, after which time the solvent was removed under reduced pressure and the residue partitioned between dichloromethane and water. The organic layer was separated, dried over magnesium sulphate and the solvent removed under reduced pressure to afford tert-butyl 4-(3-ethoxy-3-oxopropyl)-1-piperazinecarboxylate (2.44 g) as an oil.

$^1$H-NMR (CDCl$_3$) δ: 4.20 (2H, q), 3.40 (4H, m), 2.70 (2H, t), 2.50 (2H, t), 2.40 (4H, m), 1.45 (9H, s), 1.25 (3H, t).

PREPARATION 90

3-[4-(tert-Butoxycarbonyl)piperazino]propanoic Acid

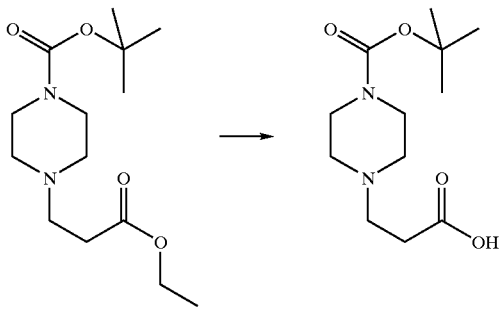

1N Aqueous lithium hydroxide (15.6 ml) was added to a solution of tert-butyl 4-(3-ethoxy-3-oxopropyl)-1-piperazinecarboxylate (2.23 g) [see Preparation 89] in ethanol (95 ml). The reaction mixture was stirred for 18 hrs at room temperature, after which time the solvent was removed under reduced pressure. The crude product was purified by column chromatography on reverse phase MCI gel eluting with 1:1, acetonitrile:water and further purified on Dowex 50W-X8-100 ion-exchange resin eluting with water and then 10% ammonia to afford 3-[4-(tert-butoxycarbonyl) piperazino]propanoic acid (1.33 g) as a white solid.

$^1$H-NMR (d4-CH$_3$OH) δ: 3.55 (2H, m), 3.20 (2H, m), 2.80 (4H, m), 2.50–2.40 (4H, m), 1.45 (9H, s).

PREPARATION 91 tert-Butyl 4-(3-[((Z)-Amino(2S)-1-[(cyclohexylmethyl)sulfonyl]-2-piperidylmethylidene)amino]oxy-3-oxopropyl)-1-piperazinecarboxylate

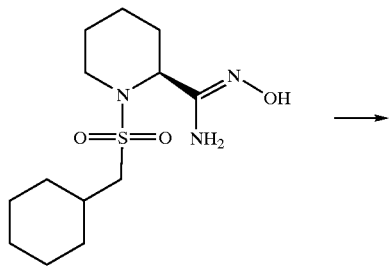

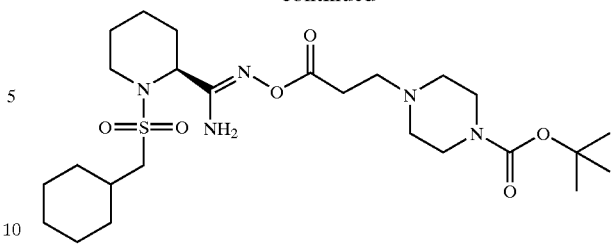

The title compound was prepared by a similar method to Preparation 5 from (Z)-(2S)-1-[cyclohexylmethylsulfonyl]-N'$^2$-hydroxy-2-piperidinecarboximidamide [see Preparation 28] and 3-[4-(tert-butoxycarbonyl)piperazino]propanoic acid [see Preparation 90] to afford tert-butyl 4-(3-[((Z)-amino(2S)-1-[(cyclohexylmethyl)sulfonyl]-2-piperidylmethylidene)amino]oxy-3-oxopropyl)-1-piperazinecarboxylate as a brown oil.

$^1$H-NMR (CDCl$_3$) δ: 5.50 (2H, bs), 4.60 (1H, d), 3.80 (1H, d), 3.45 (6H, m), 3.15 (1H, t), 2.95 (2H, m), 2.75 (3H, m), 2.65 (2H, m), 2.50 (6H, m), 2.00 (4H, m), 1.80–1.60 (4H, m), 1.50 (9H, s), 1.35 (2H, m), 1.20 (2H, m).

PREPARATION 92

2-(1-[(Benzyloxy)carbonyl]-4-piperidyloxy)acetic Acid

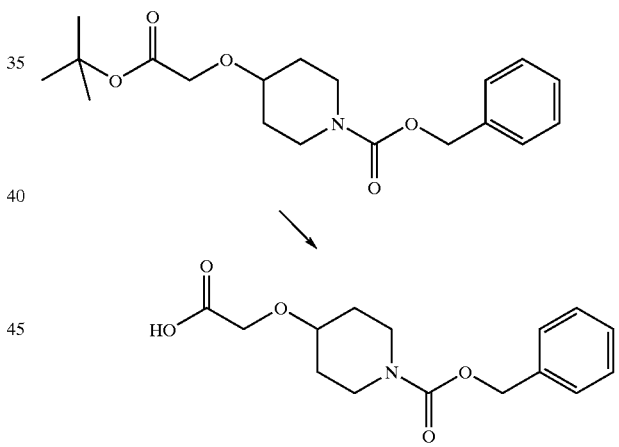

Trifluoroacetic acid (25 ml) was added to a solution of benzyl 4-[2-tert-butoxy)-2-oxoethoxy]-1-piperidinecarboxylate (5.90 g) [J. Med. Chem, (1992), 35(23), 4405] in dichloromethane (50 ml) at 0° C. The reaction mixture was then stirred at room temperature for 2 hrs, after which time the solvent was removed under reduced pressure and the residue partitioned between water and ethyl acetate. The organic layer was separated and washed with 2N aqueous hydrochloric acid, brine, dried over magnesium sulphate and the solvent was removed under reduced pressure to afford 2-(1-[(benzyloxy)carbonyl]-4-piperidyloxy) acetic acid (5.13 g) as a clear oil.

$^1$H-NMR (CDCl$_3$) δ: 9.45 (1H, bs), 7.20 (5H, m), 5.20 (2H, s), 4.20 (2H, s), 3.85 (2H, m), 3.65 (1H, m), 3.30 (2H, m), 1.90 (2H, m), 1.65 (2H, m).

PREPARATION 93 tert-Butyl (Z)-(2S)-2-[Amino([2-(1-[(benzyloxy)carbonyl]-4-piperidyloxy)acetyl]oxyimino)methyl]-1-piperidinecarboxylate

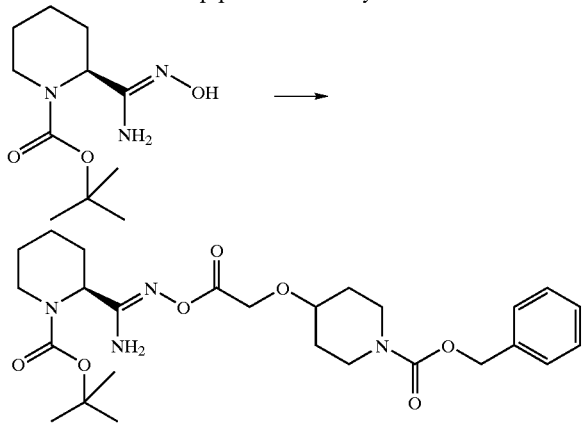

The title compound was prepared by a similar method to Preparation 5 from tert-butyl (Z)-(2S)-2-[amino(hydroxyimino)methyl]-1-piperidinecarboxylate [see Preparation 4] and 2-(1-[(benzyloxy)carbonyl]-4-piperidyloxy)acetic acid [see Preparation 92] to afford tert-butyl (Z)(2S)-2-[amino([2-(1-[(benzyloxy)carbonyl]-4 piperidyloxy)acetyl]oxyimino)methyl]-1-piperidinecarboxylate as a brown oil.

$^1$H-NMR (CDCl$_3$) δ: 7.40 (5H, m), 5.15 (2H, s), 5.05 (2H, bs), 4.95 (1H, d), 4.35 (2H, s), 4.05 (1H, d), 3.80 (2H, m), 3.65 (1H, m), 3.25 (2H, m), 2.80 (1H, t), 2.25 (1H, d), 1.90–1.60 (8H, m), 1.55 (9H, m), 1.40 (1H, m).

PREPARATION 94 tert-Butyl (2S)-2-{5-[(1-[(Benzyloxy)carbonyl]-4-piperidyloxy)methyl]-1,2,4-oxadiazol-3-yl}-1-piperidinecarboxylate

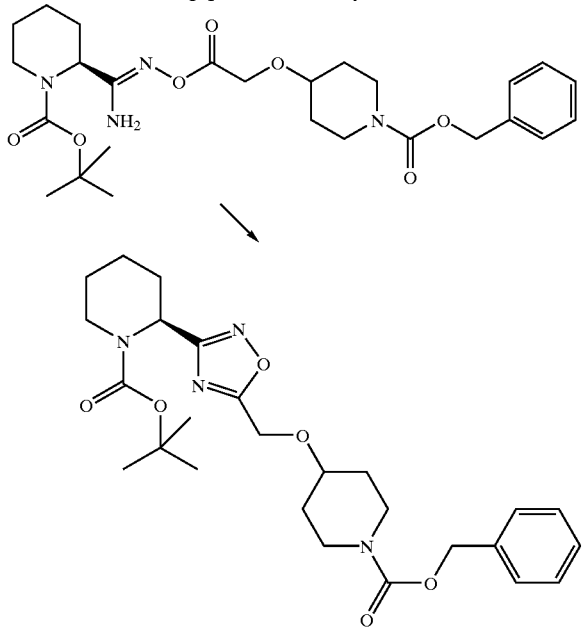

The title compound was prepared by a similar method to Preparation 13 from (Z)-(2S)-2-[amino([2-(1-[(benzyloxy)carbonyl]-4-piperidyloxy)acetyl]oxyimino)methyl]-1-piperidinecarboxylate [see Preparation 93] and pyridine. The crude product was purified by column chromatography on silica gel eluting with a solvent gradient of 80:20, changing to 50:50, by volume, hexane:ethyl acetate, in 5% increments, to afford tert-butyl (2S)-2-{5-[(1-[(benzyloxy)carbonyl]-4-piperidyloxy)methyl]-1,2,4-oxadiazol-3-yl}-1-piperidinecarboxylate.

$^1$H-NMR (CDCl$_3$) δ: 7.40 (5H, m), 5.50 (1H, bs), 5.15 (2H, s), 4.75 (2H, s), 4.10 (1H, m), 3.80 (2H, m), 3.50 (1H, m), 3.30 (2H, m), 3.00 (1H, t), 2.25 (1H, d), 1.90 (3H, m), 1.65 (5H, m), 1.45 (9H, s), 1.40 (1H, m).

PREPARATION 95

Benzyl 4-(3-[(2S)-2-Piperidyl]-1,2,4-oxadiazol-5-ylmethoxy)-1-piperidinecarboxylate

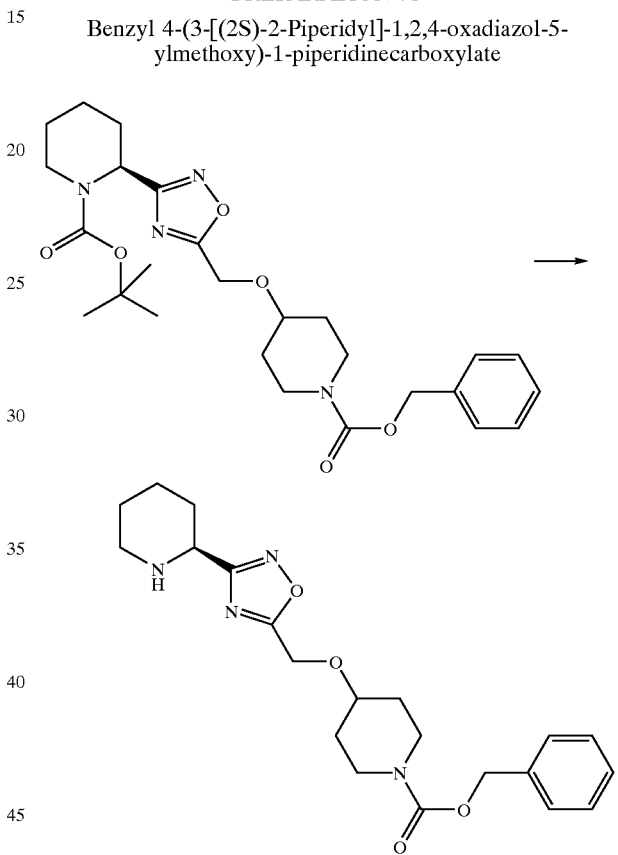

Trifluoroacetic acid (25 ml) was added to a solution of tert-butyl (2S)-2-{5-[(1-[(benzyloxy)carbonyl]-4-piperidyloxy)methyl]-1,2,4-oxadiazol-3-yl}-1-piperidinecarboxylate (1.73 g) [see Preparation 94] in dichloromethane (25 ml) at 0° C. The reaction mixture was stirred for 2 hrs at room temperature, after which time the solvent was removed under reduced pressure and the residue partitioned between ethyl acetate and water. The organic layer was separated and washed with 2N aqueous hydrochloric acid and brine, the combined aqueous layers were then neutralised with saturated sodium hydrogen carbonate and the product re-extracted with ethyl acetate. The organic layer was then separated, dried over magnesium sulphate and the solvent removed under reduced pressure to afford benzyl 4-(3-[(2S)-2-piperidyl]-1,2,4-oxadiazol-5-ylmethoxy)-1-piperidinecarboxylate (1.33 g) as a brown oil.

$^1$H-NMR (CDCl$_3$) δ: 7.40 (5H, m), 5.15 (2H, s), 4.75 (2H, s), 4.00 (1H, d), 3.80 (2H, m), 3.70 (1H, m), 3.30–3.15 (3H, m), 2.80 (1H, t), 2.10 (1H, m), 1.90 (3H, m), 1.80–1.55 (6H, m).

125

PREPARATION 96

Benzyl 4-(3-[(2S)-1-(1H-benzo[d]imidazol-2-ylsulfonyl)-2-piperidyl]-1,2,4-oxadiazol-5-ylmethoxy)-1-piperidinecarboxylate

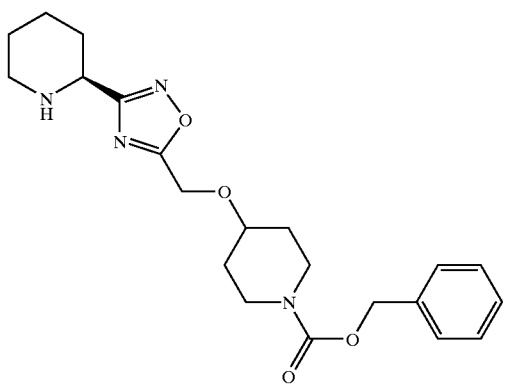

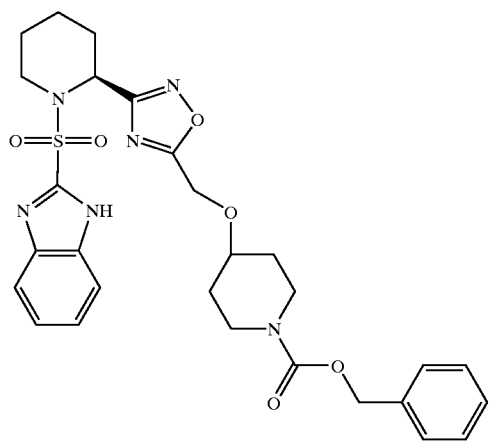

The title compound was prepared by a similar method to Example 1 from benzyl 4-(3-[(2S)-2-piperidyl]-1,2,4-oxadiazol-5-ylmethoxy)-1-piperidinecarboxylate [see Preparation 95] and 1H-benzo[d]imidazol-2-sulfonyl chloride [see Preparation 8]. The crude product was purified by column chromatography on silica gel eluting with a solvent gradient of 80:20 changing to 0:100, by volume, hexane-:ethyl acetate, in 5% increments, to afford benzyl 4-(3-[(2S)-1-(1H-benzo[d]imidazol-2-ylsulfonyl)-2-piperidyl]-1,2,4-oxadiazol-5-ylmethoxy)-1-piperidinecarboxylate as a clear oil.

$^1$H-NMR (CDCl$_3$) δ: 10.65 (1H, bs), 7.85 (1H, d), 7.60 (1H, d), 7.40 (7H, m), 5.60 (1H, d), 5.15 (2H, s), 4.40 (2H, s), 4.00 (1H, d), 3.80 (2H, m), 3.55 (1H, m), 3.20 (3H, m), 2.30 (1H, d), 2.05 (1H, m), 1.85–1.50 (8H, m).

126

PREPARATION 97

(Z)-(2S)-1-[(4-Fluorophenyl)sulfonyl]-N'$^2$-[(2-pyrazinylcarbonyl)oxy]-2-piperidinecarboximidamide

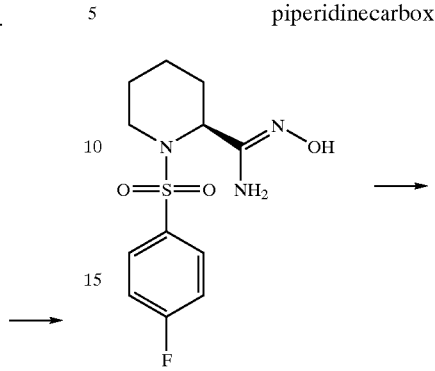

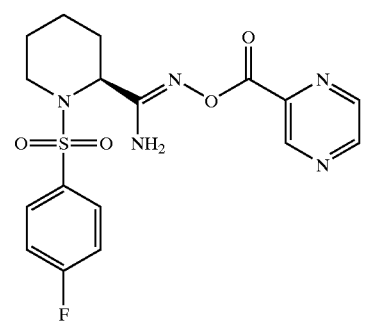

The title compound was prepared by a similar method to Preparation 5 from (Z)-(1S)-2-[(4-fluorophenyl)sulfonyl]-N'$^1$-hydroxy-2-piperidylcarboximidamide [see Preparation 73], 2-pyrazinecarboxylic acid, N-methyl morpholine, hydroxybenzotriazole hydrate, dimethylaminopyridine and 1-(3-dimethylaminopropyl)-3-ethylcarbodiimide hydrochloride, to afford (Z)-(2S)-1-[(4-fluorophenyl)sulfonyl]-N'$^2$-[(2-pyrazinylcarbonyl)oxy]-2-piperidinecarboximidamide as a white solid.

$^1$H-NMR (CDCl$_3$) δ: 9.40 (1H, s), 8.80 (1H, s), 8.75 (1H, s), 7.95 (2H, m), 7.25 (2H, m), 5.50 (2H, bs), 4.70 (1H, m), 3.90 (1H, d), 3.20 (1H, t), 2.30 (1H, d), 1.90 (1H, m), 1.55 (2H, m), 1.20 (2H, m).

PREPARATION 98

5-[(1,3-Dioxo-2,3-dihydro-1H-2-isoindolyl)methyl]-2-furoic Acid

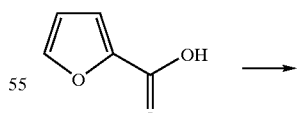

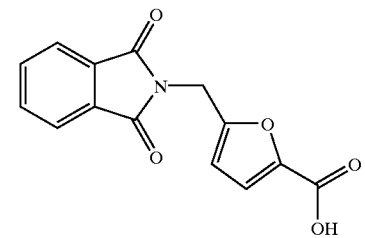

2-Furoic acid (10.0 g) was dissolved in cold concentrated sulphuric acid (50 ml). The mixture was then added to N-hydroxy methylphthalimide (12.0 g) and the reaction mixture allowed to stand for 18 hrs at room temperature. The mixture was then poured into ice and the product extracted with dichloromethane, dried over magnesium sulphate and the solvent removed under reduced pressure. The crude product was triturated with diethyl ether and recrystallised from methanol to afford 5-[(1,3-dioxo-2,3-dihydro-1H-2-isoindolyl)methyl]-2-furoic acid (9.70 g) as a brown solid.

Analysis: Found C, 59.48; H, 3.72; N, 5.03; $C_{14}H_9NO_5 \cdot 0.5H_2O$ requires C, 60.00; H, 3.60; N, 5.04%.

PREPARATION 99

(Z)-(2S)-1-[(Cyclohexylmethyl)sulfonyl]-$N'^2$-[(5-[(1,3-dioxo-2,3-dihydro-1H-2-isoindolyl)methyl]-2-furylcarbonyl)oxy]-2-piperidinecarboximidamide

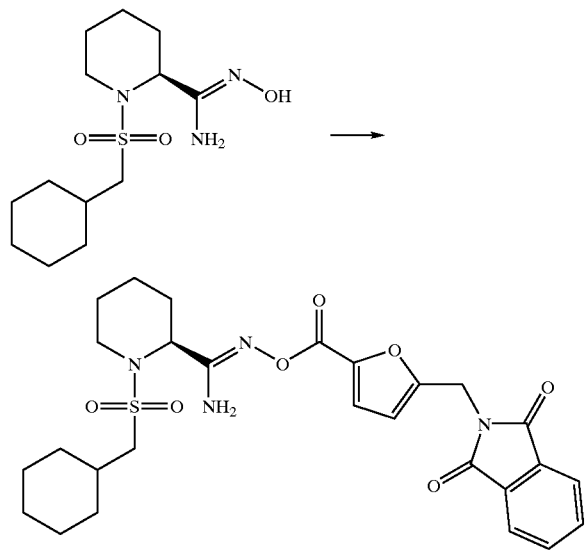

The title compound was prepared by a similar method to Preparation 5 from (Z)-(2S)-1-[(cyclohexylmethyl)sulfonyl]-$N'^2$-hydroxy-2-piperidinecarboximidamide [see Preparation 28] and 5-[(1,3-dioxo-2,3-dihydro-1H-2-isoindolyl)methyl]-2-furoic acid (see Preparation 98], to afford (Z)-(2S)-1-[(cyclohexylmethyl)sulfonyl]-$N'^2$-[(5-[(1,3-dioxo-2,3-dihydro-1H-2-isoindolyl)methyl]-2-furylcarbonyl)oxy]-2-piperidinecarboximidamide as a yellow oil.

$^1$H-NMR (CDCl$_3$) δ: 7.90 (2H, m), 7.80 (2H, m), 7.20 (1H, s), 6.45 (1H, d), 5.30 (2H, bs), 4.95 (2H, s), 4.65 (1H, d), 3.80 (1H, d), 3.20 (1H, t), 2.95 (2H, m), 2.40 (1H, d), 2.00 (4H, m), 1.80–1.60 (7H, m), 1.50 (1H, m), 1.40–1.10 (4H, m).

PREPARATION 100

2-[5-(3-(2S)-1-[(Cyclohexylmethyl)sulfonyl]-2-piperidyl-1,2,4-oxadiazol-5-yl)-2-furyl]methyl-1,3-isoindolinedione

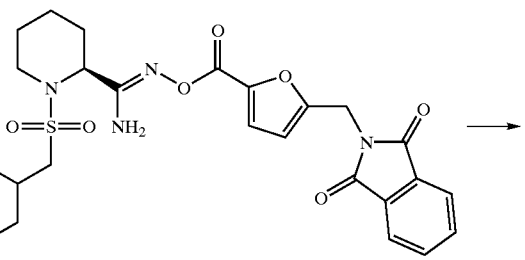

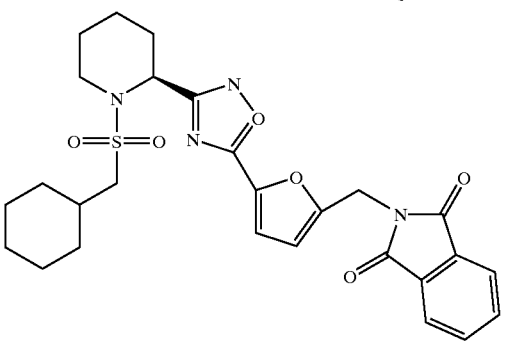

(Z)-(2S)-1-[(Cyclohexylmethyl)sulfonyl]-$N'^2$-[(5-[(1,3-dioxo-2,3-dihydro-1H-2-isoindolyl)methyl]-2-furylcarbonyl)oxy]-2-piperidinecarboximidamide (154 mg) (see Preparation 99) was dissolved in toluene (4 ml) and heated to reflux for 18 hrs. The toluene was removed under reduced pressure and the crude product was purified by column chromatography on silica gel eluting with 2:1, by volume, hexane:ethyl acetate, to afford 2-[5-(3-(2S)-1-[(cyclohexylmethyl)sulfonyl]-2-piperidyl-1,2,4-oxadiazol-5-yl)-2-furyl]methyl-1,3-isoindolinedione (62 mg) as an oil.

$^1$H-NMR (CDCl$_3$) δ: 7.90 (2H, m), 7.75 (2H, m), 7.25 (1H, d), 6.60 (1H, s), 5.40 (1H, d), 5.35 (1H, s), 5.00 (2H, s), 3.80 (1H, d), 3.25 (1H, t), 3.00 (2H, m), 2.30 (1H, d), 2.00 (4H, m) 1.80–1.60 (6H, m), 1.50 (1H, m), 1.40–1.00 (4H, m).

PREPARATION 101 tert-Butyl (2S)-2-[(Z,5R)-1-amino-4,7-dioxo-5,9-diphenyl-3,8-dioxa-2,6-diaza-1-nonen-1-yl]-1-piperidinecarboxylate

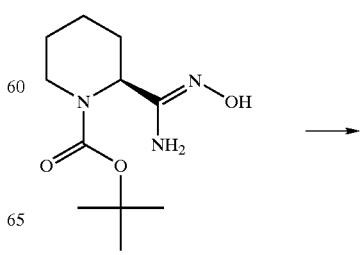

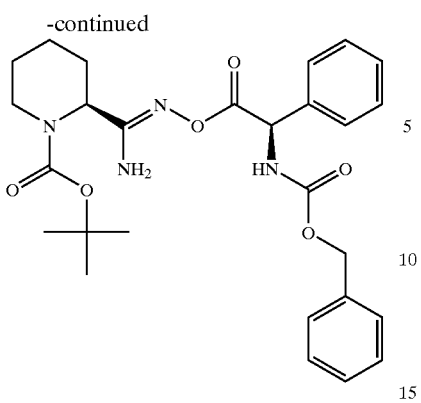

The title compound was prepared by a similar method to Preparation 5 from tert-butyl (Z)-(2S)-2-[amino(hydroxyimino)methyl]-1-piperidinecarboxylate [see Preparation 4] and (2R)-2-{[(benzyloxy)carbonyl]amino}-2-phenylethanoic acid to afford tert-butyl (2S)-2-[(Z,5R)-1-amino-4,7-dioxo-5,9-diphenyl-3,8-dioxa-2,6-diaza-1-nonen-1-yl]-1-piperidinecarboxylate as an oil.

$^1$H-NMR (CDCl$_3$) δ: 8.20 (0.5H, d), 7.35 (10H, m), 6.55 (0.5H, d), 5.90 (1H, m), 5.55 (1H, d), 5.10 (2H, m), 4.90 (2H, m), 3.95 (1H, m), 2.70 (1H, m), 2.40 (1H, m), 2.20 (1H, m), 1.80 (2H, m), 1.60 (2H, m), 1.45 (9H, s).

PREPARATION 102 tert-Butyl (2S)-2-{-[(R)-{[(Benzyloxy)carbonyl]amino}(phenyl)methyl]-1,2,4-oxadiazol-3-yl}-1-piperidinecarboxylate

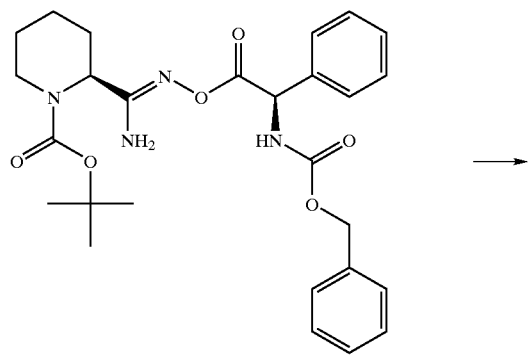

The title compound was prepared by a similar method to Preparation 6 from tert-butyl (2S)-2-[(Z,5R)-1-amino-4,7-dioxo-5,9-diphenyl-3,8-dioxa-2,6-diaza-1-nonen-1-yl]-1-piperidinecarboxylate [see Preparation 10 1] and pyridine to afford tert-butyl (2S)-2-{5-[(R)-{[(benzyloxy)carbonyl]amino}(phenyl)methyl]-1,2,4-oxadiazol-3-yl}-1-piperidinecarboxylate as an oil.

$^1$H-NMR (CDCl$_3$) δ: 7.40 (10H, m), 6.20 (1H, d), 5.85 (1H, s), 5.45 (4H, s), 5.10 (2H, m), 4.00 (1H, d), 2.95 (1H, m), 2.15 (1H, d), 1.85 (1H, m), 1.60 (2H, m), 1.45 (11H, m).

PREPARATION 103

Benzyl (R)-Phenyl{3-[(2S)-piperidyl]-1,2,4-oxadiazol-5-yl}methylcarbamate Hydrochloride

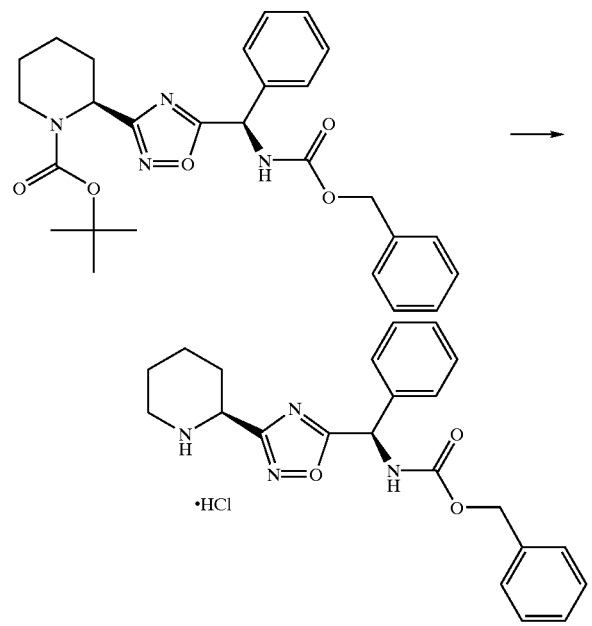

The title compound was prepared by a similar method to Preparation 7 from tert-butyl (2S)-2-{5-[(R)-{[(benzyloxy)carbonyl]amino}(phenyl)methyl]-1,2,4-oxadiazol-3-yl}-1-piperidinecarboxylate [see Preparation 102] and anhydrous hydrogen chloride gas to afford benzyl (R)-phenyl{3-[(2S)-piperidyl]-1,2,4-oxadiazol-5-yl}methylcarbamate hydrochloride as a foam.

$^1$H-NMR (CDCl$_3$) δ: 7.30 (10H, m), 6.25 (1H, s), 6.20 (1H, s), 5.10 (2H, s), 4.40 (1H, s), 3.55 (1H, s), 2.30 (1H, s), 1.95 (5H, m), 1.60 (1H, m).

PREPARATION 104

Benzyl N-[(1S)-2-{[((Z)-amino{(2S)-1-[(cyclohexylmethyl)sulfonyl]piperidyl}methylidene)amino]oxy}-2-oxo-1-phenylethyl]carbamate

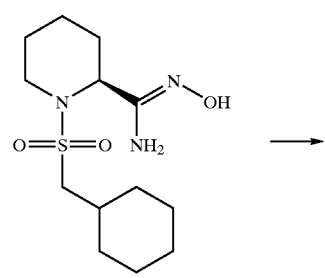

-continued

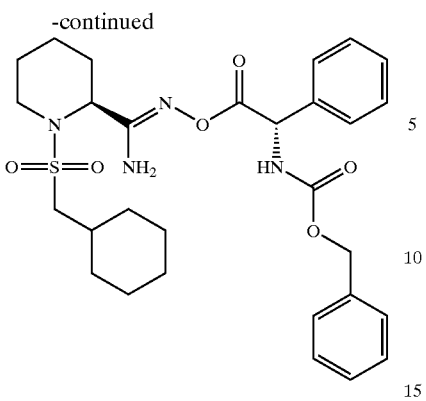

The title compound was prepared by a similar method to Preparation 5 from (Z)-(2S)-1-[cyclohexylmethylsulfonyl]-$N'^2$-hydroxy-2-piperidinecarboximidamide [see Preparation 28] and (2S)-2-{[(benzyloxy)carbonyl]amino}-2-phenylethanoic acid to afford benzyl N-[(1S)-2-{[((Z)-amino{(2S)-1-[(cyclohexylmethyl)sulfonyl]piperidyl}methylidene)amino]oxy}-2-oxo-1-phenylethyl]carbamate as an oil.

$^1$H-NMR (CDCl$_3$) δ: 7.40 (10H, m), 5.90 (2/3H, m), 5.80 (1/3H, m), 5.55 (2/3H, m), 5.40 (1/3H, m), 5.10 (4H, m), 4.55 (1H, s), 3.70 (1H, m), 3.00 (1H, m), 2.90 (2H, m), 2.15 (1H, m), 1.95 (3H, m), 1.70 (6H, m), 1.40 (1H, m), 1.30 (3H, m), 1.05 (3H, m).

PREPARATION 105

1-(1H-Benzo[d]imidazol-2-ylsulfonyl)-$N'^2$-[(2-pyrimidinylcarbonyl)oxy]-2-piperidinecarboximidamide

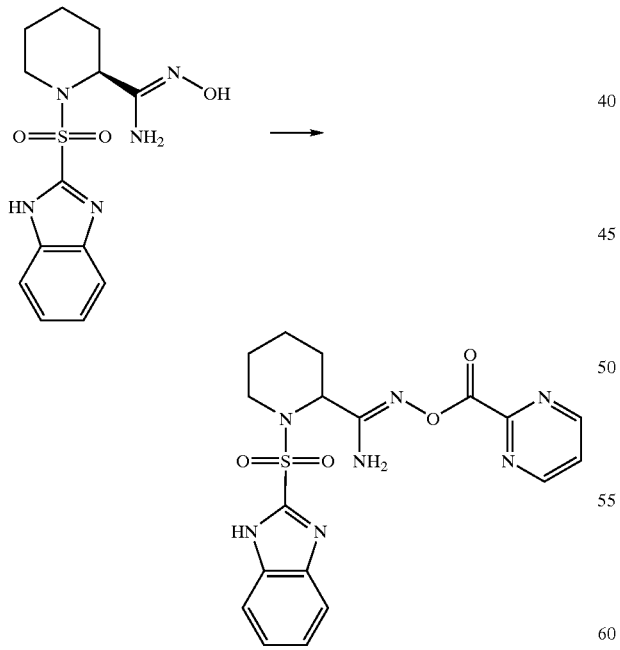

The title compound was prepared by a similar method to Preparation 20 from (Z)-1-(1H-benzo[d]imidazol-2-ylsulfonyl)-$N'^2$-hydroxy-2-piperidinecarboximidamide [see Preparation 19] and pyrimidine-2-carboxylic acid (see Chem. Ind. (London), 1954, 786) to afford 1-(1H-benzo[d]imidazol-2-ylsulfonyl)-$N'^2$-[(2-pyrimidinylcarbonyl)oxy]-2-piperidinecarboximidamide as a gum. The title compound was used directly in Example 65.

It will be appreciated that what will be claimed is as follows:

(i) a compound of the formula (I) or a pharmaceutically acceptable salt or solvate thereof;

(ii) a process for the preparation of a compound of the formula (I) or a pharmaceutically acceptable salt or solvate thereof;

(iii) a pharmaceutical composition comprising a compound of the formula (I) or a pharmaceutically acceptable salt or solvate thereof, together with a pharmaceutically acceptable excipient, diluent or carrier;

(iv) a compound of the formula (I) or a pharmaceutically acceptable salt, solvate or composition thereof, for use as a medicament;

(v) the use of a compound of the formula (I) or of a pharmaceutically acceptable salt, solvate or composition thereof, for the manufacture of a medicament for the treatment of neuronal degeneration;

(vi) the use of a compound of the formula (I) or of a pharmaceutically acceptable salt, solvate or composition thereof, for the manufacture of a medicament for the promotion of neuronal regeneration and outgrowth;

(vii) the use of a compound of the formula (I) or of a pharmaceutically acceptable salt, solvate or composition thereof, for the manufacture of a medicament for the treatment of a neurological disease or disorder such as a neurodegenerative disease;

(viii) use as in (vii) where the neurological disease or disorder is selected from the group consisting of senile dementia (Alzheimer's disease) and other dementias, amyotrophic lateral sclerosis and other forms of motor neuron disease, Parkinson's disease, Huntington's disease, neurological deficits associated with stroke, all forms of degenerative disease affecting the central or peripheral nervous system (e.g. cerebellar-brainstem atrophies, syndromes of progressive ataxias), all forms of muscular dystrophy, progressive muscular atrophies, progressive bulbar muscular atrophy, physical or traumatic damage to the central or peripheral nervous system (e.g. spinal cord), herniated, ruptured or prolapsed intervertebrae disc syndromes, cervical spondylosis, plexus disorders, thoracic outlet syndromes, all forms of peripheral neuropathy (both diabetic and non-diabetic), trigeminal neuralgia, glossopharyngeal neuralgia, Bell's Palsy, all forms of autoimmune related disease resulting in damage of the central or peripheral nervous system (e.g. multiple sclerosis, myasthenia gravis, Guillain-Barré syndrome), AIDS related disorders of the nervous system, dapsone ticks, bulbar and retrobulbar affections of the optic nerve (e.g. retinopathies and retrobulbar neuritis), hearing disorders such as tinnitus, and prion diseases;

(ix) use as (viii) where the neurological disease or disorder is senile dementia (Alzheimer's disease) or another dementia, amyotrophic lateral sclerosis or another form of motor neuron disease, Parkinson's disease, Huntington's disease, a neurological deficit associated with stroke, physical or traumatic damage to the central or peripheral nervous system (e.g. spinal cord), a peripheral neuropathy (either diabetic or non-diabetic), multiple sclerosis or a hearing disorder such as tinnitus;

(x) a method of treatment of a human to treat neuronal degeneration which comprises treating said human with an effective amount of a compound of the formula (I) or with a pharmaceutically acceptable salt, solvate or composition thereof;

(xi) a method of treatment of a human to promote neuronal regeneration and outgrowth which comprises treating said human with an effective amount of a compound of the formula (I) or with a pharmaceutically acceptable salt, solvate or composition thereof;

(xii) a method of treatment of a human to treat a neurological disease or disorder such as a neurodegenerative disease which comprises treating said human with an effective amount of a compound of the formula (I) or with a pharmaceutically acceptable salt, solvate or composition thereof;

(xiii) a method as in (xii) where the neurological disease or disorder is selected from the group consisting of senile dementia (Alzheimer's disease) and other dementias, amyotrophic lateral sclerosis and other forms of motor neuron disease, Parkinson's disease, Huntington's disease, neurological deficits associated with stroke, all forms of degenerative disease affecting the central or peripheral nervous system (e.g. cerebellar-brainstem atrophies, syndromes of progressive ataxias), all forms of muscular dystrophy, progressive muscular atrophies, progressive bulbar muscular atrophy, physical or traumatic damage to the central or peripheral nervous system (e.g. spinal cord), herniated, ruptured or prolapsed intervertebrae disc syndromes, cervical spondylosis, plexus disorders, thoracic outlet syndromes, all forms of peripheral neuropathy (both diabetic and non-diabetic), trigeminal neuralgia, glossopharyngeal neuralgia, Bell's Palsy, all forms of autoimmune related disease resulting in damage of the central or peripheral nervous system (e.g. multiple sclerosis, myasthenia gravis, Guillain-Barré syndrome), AIDS related disorders of the nervous system, dapsone ticks, bulbar and retrobulbar affections of the optic nerve (e.g. retinopathies and retrobulbar neuritis), hearing disorders such as tinnitus, and prion diseases;

(xiv) a method as in (xiii) where the neurological disease or disorder is senile dementia (Alzheimer's disease) or another dementia, amyotrophic lateral sclerosis or another form of motor neuron disease, Parkinson's disease, Huntington's disease, a neurological deficit associated with stroke, physical or traumatic damage to the central or peripheral nervous system (e.g. spinal cord), a peripheral neuropathy (either diabetic or non-diabetic), multiple sclerosis or a hearing disorder such as tinnitus; and (xv) any novel intermediates described herein.

TABLE 6

| EXAMPLE | IC$_{50}$ (nm) FKBP-12 |
|---|---|
| 25 | 81 |
| 14 | 91 |
| 1 | 95 |
| 23 | 336 |
| 65 | 442 |
| 43 | 1675 |
| 42 | 2010 |
| 11 | 685 (FKBP-52, K$_i$) |

What is claimed is:

1. A compound of the formula:

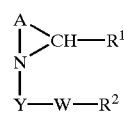

or a pharmaceutically acceptable salt or solvate thereof, wherein

R$^1$ is triazolyl, isoxazolyl, oxadiazolyl, tetraazolyl, thiazolyl or thiadiazolyl, that is linked to the adjacent carbon atom by a ring carbon atom substituted by 1, 2 or 3 substituents each independently selected from C$_1$–C$_6$ alkyl, —X-aryl, X-het, —X—CO$_2$R$^5$ and —X—NR$^3$R$^4$ R$^2$ is H, phenyl or C$_3$–C$_7$cycloalkyl, said phenyl or cycloalkyl being optionally benzo- or C$_3$–C$_7$cycloalkyl fused and optionally substituted, including in the benzo- or cycloalkyl-fused portion, by from 1 to 3 substituents each independently selected from C$_1$–C$_6$alkyl, C$_1$–C$_6$alkoxy, —OH, —(C$_1$–C$_6$alkylene) OH, halo and halo (C$_1$–C$_6$alkylene)—, or R$^2$ is a 5-, 6- or 7-membered ring heterocyclic group containing either 1,2,3 or 4 nitrogen heteroatoms, or 1 oxygen or sulphur heteroatom and, optionally, 1 or 2 nitrogen heteroatoms, said heterocyclic group being saturated or partially or fully unsaturated, optionally benzo-fused and optionally substituted, including in the benzofused portion, by from 1 to 3 substituents each independently selected from C$_1$–C$_6$alkyl, C$_1$–C$_6$alkoxy, halo, halo(C$_1$–C$_6$alkylene- and —CO$_2$R$^5$, said R$^2$ group being attached to W by by any mono- or bicyclic ring carbon atom or heteratom: R$^3$ and R$^4$ are either each independently selected from H, C$_1$–C$_6$alkyl C$_3$–C$_6$cycloalkyl and —(C$_1$–C$_6$alkylene) (C$_3$–C$_6$cycloalkyl), or, when taken together, represent unbranched C$_3$–C$_6$alkylene optionally containing 0 or NR$^5$;

R$^5$ is H, C$_1$–C$_6$alkyl, C$_3$–C$_6$cycloalkyl, —(C$_1$–C$_6$alkyne) (C$_3$–C$_6$cycloalkyl) or —(C$_1$–C$_6$alkylene)aryl;

A is unbranched C$_4$ alkylene optionally substituted by C$_1$–C$_6$alkyl;

W is a direct link, C$_1$–C$_6$alkylene or C$_2$–C$_6$alkenylene;

X is direct link, C$_1$–C$_6$alkylene or (C$_0$–C$_6$alkylene)—Z— (C$_0$–C$_6$alkylene)-;

Y is SO$_2$;

Z is O, S, —CR$^5$NR$^3$R$^4$—, —CR$^5$NR$^5$(CO$_2$R$^5$)—, —CR$^5$(aryl$^1$)—, —NR$^5$—, —NR$^5$CO$_2$, —CONR$^5$— or —NR$^5$CO—;

"aryl" is phenyl optionally substituted by from 1 to 3 substituents each independently selected from C$_1$–C$_6$alkyl, C$_1$–C$_6$alkoxy, —(C$_1$–C$_6$alkylene) (C$_1$–C$_6$alkoxy), halo, halo(C$_1$–C$_6$alkylene)—, —NR$^3$R$^4$, —(C$_1$–C$_6$alkylene)NR$^3$R$^4$, —(C$_1$–C$_6$alkylene)OH, —O(—C$_1$–C$_6$alkylene)NR$^3$R$^4$ and -alkylene)(phthalimido);

"aryl" is phenyl optionally substituted by from 1 to 3 substituents each independently selected from C$_1$–C$_6$alkyl, C$_1$–C$_6$alkoxy, —(C$_1$–C$_6$alkylene) (C$_1$–C$_6$alkoxy), halo and halo(C$_1$–C$_6$alkylene)—; and "het" is a 5-, 6-, or 7-membered ring heterocyclic group containing either 1,2,3 or 4 nitrogen heteroatoms, or 1 oxygen or sulphur heteroatom and, optionally, 1 or 2 nitrogen heteratoms, said heterocyclic group being saturated or partially or fully unsaturated, or "het" is azetidinyl, said "het" being optionally substituted by from 1 to 3 substituted each independently selected from $C_1$–$C_6$alkyl, $C_1$–$C_6$alkoxy, $C_3$–$C_7$ cycloalkyl, —($C_1$–$C_6$alkylene)($C_1$–$C_6$alkoxy), ($C_1$–$C_6$alkylene) ($C_3$–$C_7$cycloaklyl), halo, halo($C_1$–$C_6$alkylene)—, —$NR^3R^4$, —$CO_2R^5$, —($C_1$–$C_6$alkylene)aryl and ($C_1$–$C_6$alkylene)$NR^3R^4$:

with the provisos that (a) the heteroaryl group of $R^1$ is not substituted by $C_0$–$C_6$alkylene)—Z—($C_0$alkylene)(—OH or —$C_1$–$C_4$alkoxy or —CN or —$NR^3R^4$) when Z is O,S, —$NR^5$—, —$CONR^5$—.

2. A compound as claimed in claim 1 having the stereochemical formula (I')

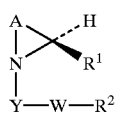

(I')

wherein $R^1$, $R^2$, A, W and Y are as defined in claim 1 formula (I).

3. A compound as claimed in claim 1 wherein X is a directed link, $C_1$–$C_6$ alkylene or —($C_0$–$C_6$alkyene)—Z—($C_0$–$C_6$alkylene—; Z is O, —$CR_5NR_3R_4$, —$CR_5NR_5$ ($CO_2R_5$)—, —NR— or —$NR^5CO_2$—;

wherein said aryl of —X-aryl is phenyl optionally substituted by from 1 to 3 substitutents each independently selected from —($C_1$–$C_6$alkylene)OH, —($C_1$–$C_6$alkylene)$NR_3R_4$, —O($C_1$–$C_6$alkylene) $NR^3R^4$ and —($C_1$–$C_6$alkyene)(phthalimido); and said "het" of -x het is piperidyl, pyrazinyl, furyl, piperazinyl, pyrimidinyl or morphonlinyl, optionally substituted by from 1 to 3 —($C_1$–$C_6$alkylene) ($C_3$–$C_7$cycloaklyl), —($C_1$–$C_6$)alkyl; or ($C_1$–$C_6$alkyene) $NR^3R^4$ where "het" is furyl $R^3$ and $R^4$ are either each independently selected form H and $C_1$–$C_6$alkyl or, when taken together, represent unbranched $C_3$–$C_6$ alkylene; and $R^5$ is H or $C_1$–$C_6$ alkyl.

4. A compound as claimed in claim 1 wherein $R^1$ is 1,2,4-triazolyl, isoxazolyl, 1,2,4-oxadiazolyl, 1,3,4-oxadiazolyl or 1,3,4-thiadiazolyl, that is linked to the adjacent carbon atom by a ring carbon atom and optionally substituted by 1, 2 or 3 substituents each independently selected from methyl, benzyl, α-(amino)benzyl, R or S-'-(amino)benzyl, α-(tert-butoxycarbonylamino)benzyl, benzylamino, benzylaminoethyl, aminomethylphenoxymethyl, methylaminomethylphenoxymethyl, dimethylaminomethylphenoxymethyl, aminomethylphenoxymethyl, hydroxymethylphenoxymethyl, benzylaminoethyl, butoxycarbonylethylpiperazinyl, benzoaminomethyl, pyrrolidinylmethylphenoxymethyl, aminoethoxybenzyl, pyrazinyl, cyclopropylmethylpiperidyloxymethyl, hydroxymethylphenoxymethyl, tertbutyloxycarbonylpiperazinylethyl, pyrimidinyl, (S)-α-(benzyloxycarbonylamino)benzyl, piperazinoethyl, phenylcarbonylaminoethyl, dimethylaminoethyl, hydrogen, phenyl, phenethyl, cyclohexylamino phthalimidomethylphenoxymethyl, piperidyloxymethyl, benzylpiperidyloxymethyl, benzylpiperidyloxyethyl, morpholinomethyl, benzyloxycarbonylaminoethyl, amino, aminoethyl, benzyloxycarbonylpiperidinyloxymethyl, methylaminofuranyl or (R)-α-(benzyloxycarbonylamino) benzyl.

5. A compound as claimed in claim 3 wherein $R_1$ is 5-benzyl-1,2,4-oxadiazol-3-yl, 5-(4-[phthalimidomethyl]phenoxymethyl)-1,2,4-oxadiazol-3-yl, 5-(4-aminomethylphenoxymethyl)-1,2,4-oxadiazol-3-yl, 5-(4-dimethylaminomethylphenoxymethyl)-1,2,4-oxadiazol-3-yl, 5-(4-pyrrolidinomethylphenoxymethyl)-1,2,4-oxadiazol-3-yl, 5-(4-methylaminomethylphenoxymethyl)-1,2,4-oxadiazol-3-yl, 5-(1-benzylpiperid-4-yloxymethyl)-1,2,4-oxadiazol-3-yl, 5-(α-[tert-butoxycarbonylamino]benzyl)-1,2,4-oxadiazol-3-yl, 5-morpholinomethyl-1,2,4-oxadiazol-3-yl, 5-(2-[1-benzylpiperid-4-yloxy]ethyl)-1,2,4-oxadiazol-3-yl, 5-(1H-piperid-4-yloxymethyl)-1,2,4-oxadiazol-3-yl, 5-[α-[amino]benzyl)-1,2,4-oxadiazol-3-yl, 5-(2-[benzyloxycarbonylamino]ethyl)-1,2,4-oxadiazol-3-yl, 5-(2-aminoethyl)-1,2,4-oxadiazol-3-yl, 5-(2-[benzylamino]ethyl)-1,2,4-oxadiazol-3-yl, 5-(4-[2-aminoethoxy]benzyl)-1,2,4-oxadiazol-3-yl, 5-methyl-1,3,4-thiadiazol-2-yl, 1-benzyl-1H-1,2,4-triazol-3-yl, 5-benzyl-4-methyl-4H-1,2,4-triazol-3-yl, 5-amino-1,4-oxadiazol-2-yl, 5-benzylamino-1,3,4-oxadiazol-2-yl, 3-methylisoxazol-5-yl, 5-(pyrazin-2-yl)-1,2,4-oxodiazol-3-yl, 5-(R)-[(α(amino)benzyl]1,2,4-oxadiazol-3-yl, 5-(S)-[α-(amino)benzyl]-1,2,4-oxadiazol-3-yl, 5-(5-methylaminofuran-2-yl)-1,2,4-oxadiazol-3-yl, 5-(1-benzyloxycarbonylpiperid-4-yloxymethyl)-1,2,4-oxadiazol-3-yl, 5-(1-cyclopropylmethylpiperid-4-yloxymethyl)-1,2,4-oxadiazol-3-yl, 5-(4-hydroxymethylphenoxymethyl)-1,2,4-oxadiazol-3-yl, 5[2-(4-tert-butoxycarbonylpiperazin-4-yl)ethyl]-1,2,4-oxadiazol-3-yl, 5-(pyrimidin-2-yl)-1,2,4-oxadiazol-3-yl, 5-methyl-1,2,4-oxadiazol-3-yl, 5-benzylaminoethyl-1,2,4-oxadiazol-3-yl, 5-(S)-(α-[benzyloxycarbonylamino]benzyl)-1,2,4-oxadiazol-3-yl, 5-(R)-(α-[benzyloxycarbonylamino]benzyl)-1,2,4-oxadiazol-3-yl, 5-[2-(4H-piperazin-1-yl)ethyl]-1,2,4-oxadiazol-3-yl, 5[2-(phenylcarbonylamino)ethyl]-1,2,4-oxadiazol-3-yl, 1[2-(dimethylamino)ethyl]-1,2,4-oxadiazol-3-yl, 5-phenyl-1,2,4-oxadiazol-3-yl, 2-benzyl-2H-1,2,3,4-tetraazol-5-yl, 5-benzyl-1,3,4-oxadiazol-2-yl, 5[2-(phenyl)ethyl]-1,3,4-oxadiazol-2-yl,
5-methyl-2H-1,2,3,4-tetraazol-5-yl,
5-cyclohexylamino-1,3,4-oxadiazol-2-yl,
5-methyl-1,3,4-oxadiazol-2-yl, 3-methyl-1,2,4-oxadiazol-3-yl,
5-methyl-1,3-thiazol-2-yl,
5-methyl-1H-1,2,4-tetriazol-3-yl,
5-aminomethyl-1,2,4-oxadiazol-3-yl.

6. A compound according to claim 1 wherein $R^1$ is 1,2,4 or 1,3,4 oxadiazole, that is linked to the adjacent carbon atom by a ring carbon atom which is mono-substituted by one of —X-aryl or —X-het wherein X is selected from —($C_0$–$C_2$ alkylene)—Z—($C_0$–$C_2$ alkylene), where Z is —O—; or X is a direct link or —($C_1$–$C_2$ alkylene); or X is —($C_0$ alkylene)—Z—($C_0$ alkylene) where Z is —$CR^5NR^3R^4$, or —$CR^5NR^5(CO_2R^5)$ where $R^3$ and $R^4$ are selected from H, —($C_1$–$C_3$ alkylene), and $R^5$ is H or —($C_1$–$C_4$ alkylene), or —($C_1$–$C_2$ alkylene)aryl; or X is —($C_1$–$C_2$ alkylene)—Z—($C_1$–$C_2$ alkylene)(aryl) where Z is $NR^5$ and $R^5$ is H or —($C_1$–$C_2$ alkylene)—;
  wherein aryl of —X-aryl is phenyl optionally substituted by from 1 to 3 substituents independently selected from —($C_1$–$C_3$ alkylene)$NR^3R^4$, —($C_1$–$C_6$ alkylene)(phthalimido); —O($C_1$–$C_3$ alkylene)$NR^3R^4$ or —$CO_2R^5$ wherein $R^3$ and $R^4$ are each independently selected from H, $C_1$–$C_3$ alkyl or, when taken together, represent unbranched $C_3$–$C_5$ alkylene; and $R^5$ is H, $C_1$–$C_4$ alkyl or —($C_1$–$C_2$ alkylene)aryl;
  wherein "het" of —X-het is piperidinyl, furyl, pyrazinyl, pyrimidinyl or piperazinyl optionally substituted by —($C_1$–$C_3$ alkylene)(—$C_3$–$C_6$ cycloalkyl), —$CO_2R^5$, —($C_1$–$C_3$ alkylene)$NR_3R_4$ or —($C_1$–$C_2$ alkylene)aryl wherein aryl is phenyl and wherein $R^3$ and $R^4$ are selected from H, —($C_1$–$C_3$ alkylene), more preferably H, —($C_1$–$C_2$ alkylene) and $R^5$ is H or —($C_1$–$C_4$ alkylene), or —($C_1$–$C_2$ alkylene)aryl;
  or X is —($C_1$–$C_2$ alkylene)—Z—($C_1$–$C_2$ alkylene)(aryl) where Z is $NR^5$ and $R^5$ is H or —($C_1$–$C_2$ alkylene)—.

7. A compound as claimed in claim 1 wherein $R^2$ is H, phenyl or $C_3$–$C_7$ cycloalkyl, said phenyl or cycloalkyl being optionally substituted by from 1 to 3 halo substituents, or $R^2$ is a 5- or 6-membered ring heterocyclic group containing either 1 or 2 nitrogen heteroatoms or 1 oxygen heteroatom, said heterocyclic group being saturated or partially or fully unsaturated, optionally benzo-fused and optionally substituted, including in the benzo-fused portion, by from 1 to 3 halo, halo($C_1$–$C_6$ alkyl), $C_1$–$C_6$ alkyl substituents, said $R^2$ group being attached to W by any mono- or bicyclic ring carbon atom or heteroatom.

8. A compound as claimed in claim 7 wherein $R^2$ is H, phenyl, cyclopentyl cyclohexyl or cycloheptyl, said phenyl being optionally substituted by from 1 to 3 fluoro substituents, or $R^2$ is imidazolyl, pyrrolidinyl, piperidinyl or tetrahydrofuranyl, said imidazolyl or tetrahydrofuranyl group being optionally benzo-fused and optionally substituted, including in the benzo-fused portion, by from 1 to 3 methyl, bromine or fluorine substituents, said $R^2$ group being attached to W by any mono- or bicyclic ring carbon atom.

9. A compound as claimed in claim 8 wherein $R^2$ is H, fluorophenyl, cyclopentyl, cyclohexyl, cycloheptyl, methylimidazolyl, benzimidazolyl, bromobenzimidazolyl or furanyl.

10. A compound as claimed in claim 9 wherein $R^2$ is H, 4-fluorophenyl, cyclopentyl, cyclohexyl, cycloheptyl, 1-methyl-1H-imidazol-4-yl, 1H-benzo[d]imidazol-2-yl, 5-bromo-1H-benzo[d]imidazol-2-yl or tetrahydrofuran-3-yl.

11. A compound as claimed in claim 1 wherein W is a direct link, methylene, ethylene or 2,2-dimethyl-1,3-propylene.

12. A compound as claimed in claim 1 wherein —Y—W—$R^2$ are
  5-bromo-1H-benzo[d]imidazolll-2-ylsulphonyl,
  1H-benzo[d]imidazol-2-ylsulphonyl,
  1-methyl-1H-imidazol-4-ylsulphonyl,
  tetrahydrofuran-3-ylmethylsulphonyl,
  cyclohexylmethylsulphonyl,
  4-fluorophenylsulphonyl,
  cyclopentylmethylsulphonyl,
  cycloheptylmethylsulphonyl,
  1-(benzyloxycarbonyl)pyrrolidin-3-ylmethylsulphonyl, or
  1-(benzyloxycarbonyl)piperid-3-ylmethylsulphonyl.

13. A compound as claimed in claim 1 selected from the group consisting of:
  1H-Benzo[d]imidzol-2-yl[2S]-2-(5-benzyl-1,2,4-oxadiazol-3-yl)-1-piperidylsulphone,
  2-[4-(3-[(2S)-1-(1H-Benzo[d]imidazol-2-ylsulfonyl)-2-piperidyl]-1,2,4-oxadiazol-5-ylmethoxy)benzyl]-1,3-isoindolinedione,
  4-(3-[(2S)-1-(1H-Benzo[d]imidazol-2-ylsulfonyl)-2-piperidyl]-1,2,4-oxadiazol-5-ylmethoxy)benzylamine,
  N-[4-(3-[(2S)-1-(1H-Benzo[d]imidazol-2-ylsulfonyl)-2-piperidyl]-1,2,4-oxadiazol-5-ylmethoxy)benzyl]-N,N-dimethylamine,
  3-[1-(1H-Benzo[d]imidazol-2-ylsulfonyl)-2-piperidyl]-5-[4-(1-pyrrolidylmethyl)phenoxy]methyl-1,2,4-oxadiazole,
  N-[4-(3-[1-(1H-Benzo[d]imidazol-2-ylsulfonyl)-2-piperidyl]-1,2,4-oxadiazol-5-ylmethoxy)benzyl]-N-methylamine,
  4-[3-((2S)-1-[Cyclohexylmethylsulfonyl]-2-piperidyl)-1,2,4-oxadiazol-5-ylmethoxy]benzylamine,
  5-[(1-Benzyl4-piperidyl)oxymethyl]-3-[(2S)-1-cyclohexylmethylsulfonyl-2-piperidyl]-1,2,4-oxadiazole,
  3-[(2S)1-Cyclohexylmethylsulfonyl-2-piperidyl]-5-[4-piperidyloxymethyl]-1,2,4-oxadiazole,
  (3-[(2S)-1-Cyclohexylmethylsulfonyl-2-piperidyl]-1,2,4-oxadiazol-5-yl)(phenyl)methylamine,
  5-(3-(2S)-1-[(Cyclohexylmethyl)sulfonyl]-2-piperidyl-1,2,4-oxadiazol-5-yl)-2-furyl]methylamine,
  N-(2-(3-[1-(1H-Benzo[d]imidazol-2-ylsulfonyl)-2-piperidyl]-1,2,4-oxadiazol-5-yl)ethyl)benzylamine,
  2-[4-(3-[1-(1H-Benzo[d]imidazol-2-ylsulfonyl)-2-piperidyl]-1,2,4-oxadiazol-5-ylmethyl)phenoxy]ethylamine,
  N-(3-[1-(1H-benzo[d]imidazol-2-ylsulfonyl)-2-piperidyl]-1,2,4-oxadiazol-5-ylmethyl)-N-benzylamine,
  2-[(2S)-2-5-[(4-Piperidyloxy)methyl]-1,2,4-oxadiazol-3-yl-1-piperidyl]sulfonyl-1H-benzo[d]imidazole,
  2-[(2S)-2-[5-([1-(Cyclopropylmethyl)-4-piperidyl]oxymethyl)-1,2,4-oxadiazol-3-yl]-1-piperidyl]sulfonyl-1H-benzo[d]imidazole,
  2-[(2S)-2-(5-Benzyl-1,2,4-oxadiazol-3-yl)-1-piperidyl]sulfonyl-5-bromo-1H-benzo[d]imidazole,
  2-4-[(3-(2S)-1-[(5-Bromo-1H-benzo[d]imidazol-2-yl)sulfonyl]-2-piperidyl-1,2,4-oxadiazol-5-yl)methoxy]benzyl-1,3-isoindolinedione, 4-[(3-(2S)-1-[(5-Bromo-1H-benzo[d]imidazol-2-yl)sulfonyl]-2-piperidyl-1,2,4-oxadiazol-5-yl)methoxy]benzylamine, tert-Butyl 4-[2-(3-(1S)-2-[(cyclohexylmethyl)sulfonyl]-2-piperidyl-1,2,4-oxadiazol-5-yl)ethyl]-1-piperazinecarboxylate, (R)-(3-{(2S)-1-[(Cyclohexylmethyl)sulfonyl]-2-piperidyl}-1,2,4-oxadiazol-5-yl)(phenyl)methylamine, (S)-(3-{(2S)-1-[(Cyclohexylmethyl)sulfonyl]-2-piperidyl}-1,2,4-oxadiazol-5-yl)(phenyl)methylamine, 2-({2-[5-(2-pyrimidinyl)-1,2,4-oxadiazol-3-yl]-2-piperidyl}sulfonyl)-1H-benzo[d]imidazole, Benzyl 4-(3-[(2S)-1-(1H-benzo[d]imidazol-2-ylsulfonyl)-2-piperidyl]-1,2,4-oxadiazol-5-ylmethoxy)-1-piperidinecarboxylate, (2S)-2-(5-Benzyl-1,2,4-oxadiazol-3-yl)-1-[(cyclopentylmethyl)sulphonylpiperidine, (2S)-2-(5-Benzyl-1,2,4-oxadiazol-3-yl)-1-[(cyclohexylmethyl)sulphonylpiperidine, (2S)-2-(5-Benzyl-1,2,4-oxadiazol-3-yl)-1-[(cycloheptylmethyl)sulphonylpiperidine, tert-Butyl-N-(3{(2S)-1-(cyclohexylmethyl)sulphonyl-2-piperidyl}-1,2,4-oxadiazol 5-yl)(phenyl)methylcarbamate, (2S)-2-(5-{2-[(1-Benzyl-4-piperidyl)oxy]ethyl}-1,2,4-oxadiazol-3-yl)-1-[(cyclohexylmethyl)sulphonyl]piperidine, {4-{3-{2S-1-[4-Fluorophenyl)sulphonyl]piperidyl}-1,2,4-oxadiazol-5-yl)methoxy]phenyl]}methanol, 2-(3-{(2S)-1-[4-Fluorophenyl)sulphonyl]piperidyl}-1,2,4-oxadiazol-5-yl)pyrazine or 1-[2-(3-(1S)-2-[(Cyclohexylmethyl)sulphonyl]-2-piperidyl-1,2,4-oxadiazol-5-yl)ethyl]piperazine.

14. A pharmaceutical composition comprising a compound as claimed in claim 1 or a pharmaceutically acceptable salt or solvate thereof, together with a pharmaceutically acceptable excipient, diluent or carrier.

15. A method of treatment of a human to treat neuronal degeneration which comprises treating said human with an effective amount of a compound as claimed in claim 1 with a pharmaceutically acceptable salt, solvate or composition thereof.

16. A process for the preparation of a compound of formula (I) comprising:

(a) reaction of a compound of the formula:

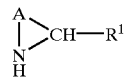

(II)

wherein $R^1$ and A are as defined in claim 1 for a compound of formula (I), with a compound of the formula (III):

(III)

wherein $R^2$, W and Y are as previously defined in claim 1 for a compound of the formula (I) and $L^1$ is a suitable leaving group; or (b) by ring formation of $R^1$ or ring closure of a corresponding open ring structure of $R^1$, in formula (II) wherein A is as defined in claim 1 for a compound of formula (I), and wherein the said open ring corresponds to an optionally substituted heterocycle $R^1$, as is defined in claim 1 for a compound of formula (I), followed by reaction with a compound of formula (III); or (c) by ring formation of $R^1$ or ring closure of a corresponding open ring structure of $R^1$, in formula (I):

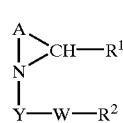

(I)

wherein A is as defined in claim 1 for a compound of formula (I), and wherein the said open ring corresponds to an optionally substituted heterocycle $R^1$, as is defined in claim 1.

* * * * *